(12) United States Patent
Basi et al.

(10) Patent No.: US 9,067,981 B1
(45) Date of Patent: Jun. 30, 2015

(54) HYBRID AMYLOID-BETA ANTIBODIES

(75) Inventors: Guriqbal Basi, Palo Alto, CA (US);
Dale B. Schenk, Burlingame, CA (US);
Hadar Hana Feinberg, Los Altos, CA
(US); William I. Weis, Palo Alto, CA
(US)

(73) Assignees: JANSSEN SCIENCES IRELAND UC
(IE); WYETH LLC, Madison, NJ (US);
**THE BOARD OF TRUSTEES OF
LELAND STANFORD JR.
UNIVERSITY**, Stanford, CA (US)

( * ) Notice: Subject to any disclaimer, the term of this patent is extended or adjusted under 35 U.S.C. 154(b) by 741 days.

(21) Appl. No.: 12/608,869

(22) Filed: Oct. 29, 2009

Related U.S. Application Data

(60) Provisional application No. 61/197,878, filed on Oct. 30, 2008, provisional application No. 61/110,538, filed on Oct. 31, 2008.

(51) Int. Cl.
*C07K 16/18* (2006.01)
*A61K 39/395* (2006.01)

(52) U.S. Cl.
CPC .............. *C07K 16/18* (2013.01); *A61K 39/3955* (2013.01); *C07K 2317/60* (2013.01); *C07K 2317/565* (2013.01); *C07K 2317/24* (2013.01); *C07K 2317/55* (2013.01)

(58) Field of Classification Search
CPC ................... A61K 39/3955; C07K 2317/565; C07K 2317/24; C07K 2317/55; C07K 2317/60
See application file for complete search history.

(56) References Cited

U.S. PATENT DOCUMENTS

| | | | |
|---|---|---|---|
| 4,666,829 A | 5/1987 | Glenner et al. |
| 4,713,366 A | 12/1987 | Stevens |
| 4,816,397 A | 3/1989 | Boss et al. |
| 4,816,567 A | 3/1989 | Cabilly et al. |
| 4,879,213 A | 11/1989 | Fox et al. |
| 4,883,666 A | 11/1989 | Sabel et al. |
| 4,912,206 A | 3/1990 | Goldgaber et al. |
| 4,966,753 A | 10/1990 | McMichael |
| 5,004,697 A | 4/1991 | Pardridge |
| 5,057,540 A | 10/1991 | Kensil et al. |
| 5,096,706 A | 3/1992 | Flint |
| 5,187,153 A | 2/1993 | Cordell et al. |
| 5,192,753 A | 3/1993 | McGeer et al. |
| 5,208,036 A | 5/1993 | Eppstein et al. |
| 5,220,013 A | 6/1993 | Ponte et al. |
| 5,225,539 A | 7/1993 | Winter |
| 5,227,159 A | 7/1993 | Miller |
| 5,231,000 A | 7/1993 | Majocha et al. |
| 5,231,170 A | 7/1993 | Averback |
| 5,245,015 A | 9/1993 | Fung et al. |
| 5,258,498 A | 11/1993 | Huston et al. |
| 5,262,332 A | 11/1993 | Selkoe |
| 5,270,165 A | 12/1993 | Van Nostrand et al. |
| 5,278,049 A | 1/1994 | Baker et al. |
| 5,358,708 A | 10/1994 | Patel |
| 5,385,887 A | 1/1995 | Yim et al. |
| 5,387,742 A | 2/1995 | Cordell |
| 5,417,986 A | 5/1995 | Reid et al. |
| 5,434,170 A | 7/1995 | Andrulis, Jr. |
| 5,441,870 A | 8/1995 | Seubert et al. |
| 5,464,823 A | 11/1995 | Lehrer et al. |
| 5,470,951 A | 11/1995 | Roberts |
| 5,472,693 A | 12/1995 | Gourlie et al. |
| 5,514,548 A | 5/1996 | Krebber et al. |
| 5,530,101 A | 6/1996 | Queen et al. |
| 5,571,499 A | 11/1996 | Hafler et al. |
| 5,571,500 A | 11/1996 | Hafler et al. |
| 5,576,184 A | 11/1996 | Better et al. |

(Continued)

FOREIGN PATENT DOCUMENTS

| | | |
|---|---|---|
| AU | 707083 | 7/1999 |
| EP | 285 159 A1 | 10/1988 |
| EP | 0 391 714 A2 | 10/1990 |
| EP | 451 700 A1 | 10/1991 |
| EP | 506 785 B1 | 10/1992 |
| EP | 276 723 B1 | 12/1993 |
| EP | 613007 A2 | 2/1994 |
| EP | 616 814 A1 | 3/1994 |
| EP | 597 101 A1 | 5/1994 |
| EP | 0 613 007 A2 | 8/1994 |

(Continued)

OTHER PUBLICATIONS

U.S. Appl. No. 09/201,430, Office Action mailed Oct. 1, 2002.
U.S. Appl. No. 09/204,838, Office Action mailed Apr. 18, 2003.
U.S. Appl. No. 09/322,289, Office Action mailed Feb. 7, 2008.
U.S. Appl. No. 09/322,289, Office Action mailed Feb. 24, 2005.
U.S. Appl. No. 09/322,289, Office Action mailed Nov. 4, 2008.
U.S. Appl. No. 09/322,289, Office Action mailed Nov. 17, 2006.
U.S. Appl. No. 09/723,713, Office Action mailed Apr. 19, 2005.
U.S. Appl. No. 09/723,713, Office Action mailed Oct. 24, 2003.
U.S. Appl. No. 09/723,725, Office Action mailed Dec. 9, 2002.
U.S. Appl. No. 09/723,760, Office Action mailed May 4, 2005.

(Continued)

*Primary Examiner* — Kimberly A Ballard
(74) *Attorney, Agent, or Firm* — Alston & Bird LLP

(57) ABSTRACT

The present invention provides crystals including amino acids 1-7 of SEQ ID NO:1 and a Fab fragment of 12A11, 12B4, 10D5 or 3D6, as well as of amino acids 1-40 of SEQ ID NO:1 and a Fab fragment of 12A11 or 3D6, as well as methods for preparing the crystals. The present invention also provides a computer implemented method for analyzing binding of a candidate antibody fragment to a peptide including an epitope of amino acids 1-7 of SEQ ID NO:1, a method for identifying an antibody fragment that can mimic the Fab fragment of 12A11, a method for identifying an antibody fragment that can mimic the Fab fragment of 3D6, a method for identifying a candidate antibody fragment that binds to a peptide including an epitope of amino acids 1-7 of SEQ ID NO:1, and a method for designing a humanized antibody that binds to a peptide comprising an epitope of amino acids 1-7 of SEQ ID NO:1.

2 Claims, 12 Drawing Sheets

(56) References Cited

U.S. PATENT DOCUMENTS

| | | | |
|---|---|---|---|
| 5,583,112 | A | 12/1996 | Kensil et al. |
| 5,585,089 | A | 12/1996 | Queen et al. |
| 5,585,100 | A | 12/1996 | Mond et al. |
| 5,589,154 | A | 12/1996 | Anderson |
| 5,593,846 | A | 1/1997 | Schenk et al. |
| 5,601,827 | A | 2/1997 | Collier et al. |
| 5,605,811 | A | 2/1997 | Seubert et al. |
| 5,612,486 | A | 3/1997 | McConlogue et al. |
| 5,618,920 | A | 4/1997 | Robinson et al. |
| 5,620,844 | A | 4/1997 | Neurath et al. |
| 5,622,701 | A | 4/1997 | Berg |
| 5,624,821 | A | 4/1997 | Winter et al. |
| 5,624,937 | A | 4/1997 | Reel et al. |
| 5,641,473 | A | 6/1997 | Hafler et al. |
| 5,641,474 | A | 6/1997 | Hafler et al. |
| 5,645,820 | A | 7/1997 | Hafler et al. |
| 5,648,260 | A | 7/1997 | Winter et al. |
| 5,652,334 | A | 7/1997 | Roberts |
| 5,677,425 | A | 10/1997 | Bodmer et al. |
| 5,679,348 | A | 10/1997 | Nesburn et al. |
| 5,688,651 | A | 11/1997 | Solomon |
| 5,693,761 | A | 12/1997 | Queen et al. |
| 5,693,762 | A | 12/1997 | Queen et al. |
| 5,702,906 | A | 12/1997 | Rosenthal |
| 5,721,130 | A | 2/1998 | Seubert et al. |
| 5,723,130 | A | 3/1998 | Hancock et al. |
| 5,731,284 | A | 3/1998 | Williams |
| 5,733,547 | A | 3/1998 | Weiner et al. |
| 5,733,548 | A | 3/1998 | Restifo et al. |
| 5,736,142 | A | 4/1998 | Sette et al. |
| 5,744,132 | A | 4/1998 | Warne et al. |
| 5,744,368 | A | 4/1998 | Goldgaber et al. |
| 5,750,349 | A | 5/1998 | Suzuki et al. |
| 5,750,361 | A | 5/1998 | Prusiner et al. |
| 5,753,624 | A | 5/1998 | McMichael et al. |
| 5,766,846 | A | 6/1998 | Schlossmacher et al. |
| 5,770,700 | A | 6/1998 | Webb et al. |
| 5,773,007 | A | 6/1998 | Penney et al. |
| 5,776,468 | A | 7/1998 | Hauser et al. |
| 5,780,587 | A | 7/1998 | Potter |
| 5,786,180 | A | 7/1998 | Konig et al. |
| 5,798,102 | A | 8/1998 | McMichael et al. |
| 5,817,626 | A | 10/1998 | Findeis et al. |
| 5,824,322 | A | 10/1998 | Balasubramanian |
| 5,837,268 | A | 11/1998 | Potter et al. |
| 5,837,473 | A | 11/1998 | Maggio et al. |
| 5,837,672 | A | 11/1998 | Schenk et al. |
| 5,846,533 | A | 12/1998 | Prusiner |
| 5,849,298 | A | 12/1998 | Weiner et al. |
| 5,851,996 | A | 12/1998 | Kline |
| 5,854,204 | A | 12/1998 | Findeis et al. |
| 5,854,215 | A | 12/1998 | Findeis et al. |
| 5,858,981 | A | 1/1999 | Schreiber et al. |
| 5,859,205 | A | 1/1999 | Adair et al. |
| 5,866,129 | A | 2/1999 | Chang et al. |
| 5,869,046 | A | 2/1999 | Presta et al. |
| 5,869,054 | A | 2/1999 | Weiner et al. |
| 5,869,093 | A | 2/1999 | Weiner et al. |
| 5,877,399 | A | 3/1999 | Hsiao et al. |
| 5,891,991 | A | 4/1999 | Wasco et al. |
| 5,895,654 | A | 4/1999 | Hartford et al. |
| 5,910,427 | A | 6/1999 | Mikayama |
| 5,935,927 | A | 8/1999 | Vitek et al. |
| 5,955,079 | A | 9/1999 | Mond et al. |
| 5,955,317 | A | 9/1999 | Suzuki et al. |
| 5,958,883 | A | 9/1999 | Snow |
| 5,985,242 | A | 11/1999 | Findeis et al. |
| 5,989,566 | A | 11/1999 | Cobb et al. |
| 5,994,083 | A | 11/1999 | Felici et al. |
| 6,015,662 | A | 1/2000 | Hackett et al. |
| 6,022,859 | A | 2/2000 | Kiessling et al. |
| 6,054,297 | A | 4/2000 | Carter et al. |
| 6,057,098 | A | 5/2000 | Buechler et al. |
| 6,057,367 | A | 5/2000 | Stamler et al. |
| 6,096,318 | A | 8/2000 | Stevens et al. |
| 6,114,133 | A | 9/2000 | Seubert et al. |
| 6,121,022 | A | 9/2000 | Presta et al. |
| 6,150,091 | A | 11/2000 | Pandolfo et al. |
| 6,165,745 | A | 12/2000 | Ward et al. |
| 6,175,057 | B1 | 1/2001 | Mucke et al. |
| 6,180,370 | B1 | 1/2001 | Queen et al. |
| 6,194,551 | B1 | 2/2001 | Idusogie et al. |
| 6,210,671 | B1 | 4/2001 | Co |
| 6,218,506 | B1 | 4/2001 | Krafft et al. |
| 6,261,569 | B1 | 7/2001 | Comis et al. |
| 6,262,335 | B1 | 7/2001 | Hsiao et al. |
| 6,267,958 | B1 | 7/2001 | Andya et al. |
| 6,270,757 | B1 | 8/2001 | Warne |
| 6,277,375 | B1 | 8/2001 | Ward |
| 6,284,221 | B1 | 9/2001 | Schenk et al. |
| 6,284,533 | B1 | 9/2001 | Thomas |
| 6,294,171 | B2 | 9/2001 | McMichael |
| 6,303,567 | B1 | 10/2001 | Findeis et al. |
| 6,331,440 | B1 | 12/2001 | Nordstedt et al. |
| 6,339,068 | B1 | 1/2002 | Krieg et al. |
| 6,372,716 | B1 | 4/2002 | Bush et al. |
| 6,399,314 | B1 | 6/2002 | Krishnamurthy |
| 6,407,213 | B1 | 6/2002 | Carter et al. |
| 6,417,178 | B1 | 7/2002 | Klunk et al. |
| 6,432,710 | B1 | 8/2002 | Boss, Jr. et al. |
| 6,528,624 | B1 | 3/2003 | Idusogie et al. |
| 6,538,124 | B1 | 3/2003 | Idusogie et al. |
| 6,548,640 | B1 | 4/2003 | Winter |
| 6,562,341 | B2 | 5/2003 | Prusiner et al. |
| 6,582,945 | B1 | 6/2003 | Raso |
| 6,610,493 | B1 | 8/2003 | Citron et al. |
| 6,632,927 | B2 | 10/2003 | Adair et al. |
| 6,639,055 | B1 | 10/2003 | Carter et al. |
| 6,710,226 | B1 | 3/2004 | Schenk |
| 6,713,450 | B2 | 3/2004 | Frangione et al. |
| 6,727,349 | B1 | 4/2004 | LaRosa et al. |
| 6,743,427 | B1 | 6/2004 | Schenk |
| 6,750,324 | B1 | 6/2004 | Schenk et al. |
| 6,761,888 | B1 | 7/2004 | Schenk |
| 6,787,129 | B1 | 9/2004 | Klein et al. |
| 6,787,138 | B1 | 9/2004 | Schenk |
| 6,787,139 | B1 | 9/2004 | Schenk |
| 6,787,140 | B1 | 9/2004 | Schenk |
| 6,787,143 | B1 | 9/2004 | Schenk |
| 6,787,144 | B1 | 9/2004 | Schenk |
| 6,787,523 | B1 | 9/2004 | Schenk |
| 6,787,637 | B1 | 9/2004 | Schenk et al. |
| 6,808,712 | B2 | 10/2004 | Schenk |
| 6,818,218 | B2 | 11/2004 | Schenk |
| 6,824,780 | B1 | 11/2004 | Devaux et al. |
| 6,866,849 | B2 | 3/2005 | Schenk |
| 6,866,850 | B2 | 3/2005 | Schenk |
| 6,875,434 | B1 | 4/2005 | Schenk |
| 6,890,535 | B1 | 5/2005 | Schenk |
| 6,905,686 | B1 | 6/2005 | Schenk |
| 6,913,745 | B1 | 7/2005 | Schenk |
| 6,923,964 | B1 | 8/2005 | Schenk |
| 6,933,368 | B2 | 8/2005 | Co et al. |
| 6,936,698 | B2 | 8/2005 | Taylor |
| 6,946,135 | B2 | 9/2005 | Schenk |
| 6,962,707 | B2 | 11/2005 | Schenk |
| 6,962,984 | B2 | 11/2005 | Ishiwata et al. |
| 6,972,127 | B2 | 12/2005 | Schenk |
| 6,982,084 | B2 | 1/2006 | Schenk |
| 7,014,855 | B2 | 3/2006 | Schenk |
| 7,112,661 | B1 | 9/2006 | Miller |
| 7,147,851 | B1 | 12/2006 | Ponath et al. |
| 7,179,892 | B2 | 2/2007 | Basi et al. |
| 7,189,819 | B2 | 3/2007 | Basi et al. |
| 7,195,761 | B2 | 3/2007 | Holtzman et al. |
| 7,256,273 | B2 | 8/2007 | Basi et al. |
| 7,575,880 | B2 | 8/2009 | Schenk et al. |
| 7,582,733 | B2 | 9/2009 | Basi et al. |
| 7,588,766 | B1 | 9/2009 | Schenk |
| 7,625,560 | B2 | 12/2009 | Basi et al. |
| 7,635,473 | B2 | 12/2009 | Warne et al. |
| 7,790,856 | B2 | 9/2010 | Schenk |
| 7,871,615 | B2 | 1/2011 | Basi et al. |
| 7,893,214 | B2 | 2/2011 | Schenk |

(56) References Cited

U.S. PATENT DOCUMENTS

| | | |
|---|---|---|
| 7,906,626 B2 | 3/2011 | Raso |
| 7,928,203 B2 | 4/2011 | Schenk et al. |
| 2001/0018053 A1 | 8/2001 | McMichael |
| 2001/0021769 A1 | 9/2001 | Prusiner |
| 2002/0009445 A1 | 1/2002 | Du et al. |
| 2002/0058267 A1 | 5/2002 | Ozenberger et al. |
| 2002/0077288 A1 | 6/2002 | Frangione |
| 2002/0086847 A1 | 7/2002 | Chain |
| 2002/0094335 A1 | 7/2002 | Chalifour et al. |
| 2002/0102261 A1 | 8/2002 | Raso |
| 2002/0132268 A1 | 9/2002 | Chang et al. |
| 2002/0133001 A1 | 9/2002 | Gefter et al. |
| 2002/0136718 A1 | 9/2002 | Raso |
| 2002/0160394 A1 | 10/2002 | Wu |
| 2002/0162129 A1 | 10/2002 | Lannfelt |
| 2002/0168377 A1 | 11/2002 | Schaetzl |
| 2002/0187157 A1 | 12/2002 | Jensen et al. |
| 2002/0197258 A1 | 12/2002 | Ghanbari et al. |
| 2003/0009104 A1 | 1/2003 | Hyman et al. |
| 2003/0039645 A1 | 2/2003 | Adair et al. |
| 2003/0054484 A1 | 3/2003 | Fong et al. |
| 2003/0068316 A1 | 4/2003 | Klein et al. |
| 2003/0068325 A1 | 4/2003 | Wang |
| 2003/0073655 A1 | 4/2003 | Chain |
| 2003/0092145 A1 | 5/2003 | Jira et al. |
| 2003/0135035 A1 | 7/2003 | Shannon |
| 2003/0147882 A1 | 8/2003 | Solomon et al. |
| 2003/0165496 A1 | 9/2003 | Basi et al. |
| 2003/0166557 A1 | 9/2003 | Minna et al. |
| 2003/0166558 A1 | 9/2003 | Frangione et al. |
| 2003/0202972 A1 | 10/2003 | Andya et al. |
| 2003/0207828 A1 | 11/2003 | Ishiwata et al. |
| 2004/0043418 A1 | 3/2004 | Holtzman et al. |
| 2004/0081657 A1 | 4/2004 | Schenk |
| 2004/0082762 A1 | 4/2004 | Basi et al. |
| 2004/0087777 A1 | 5/2004 | Basi et al. |
| 2004/0171815 A1 | 9/2004 | Schenk et al. |
| 2004/0171816 A1 | 9/2004 | Schenk et al. |
| 2004/0197324 A1 | 10/2004 | Liu et al. |
| 2004/0213800 A1 | 10/2004 | Seubert et al. |
| 2004/0219146 A1 | 11/2004 | Schenk |
| 2004/0241164 A1 | 12/2004 | Bales et al. |
| 2004/0247590 A1 | 12/2004 | Schenk et al. |
| 2004/0247591 A1 | 12/2004 | Schenk et al. |
| 2004/0247612 A1 | 12/2004 | Wang |
| 2004/0265301 A1 | 12/2004 | Schenk et al. |
| 2004/0265308 A1 | 12/2004 | Schenk |
| 2004/0265919 A1 | 12/2004 | Vanderstichlele et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0090648 A1 | 4/2005 | Tsurushita et al. |
| 2005/0118651 A1 | 6/2005 | Basi et al. |
| 2005/0123534 A1 | 6/2005 | Adair et al. |
| 2005/0123544 A1 | 6/2005 | Schenk et al. |
| 2005/0136054 A1 | 6/2005 | Adair et al. |
| 2005/0142132 A1 | 6/2005 | Schenk et al. |
| 2005/0147613 A1 | 7/2005 | Raso |
| 2005/0152878 A1 | 7/2005 | Solomon et al. |
| 2005/0158304 A1 | 7/2005 | Schenk et al. |
| 2005/0163788 A1 | 7/2005 | Schenk |
| 2005/0169925 A1 | 8/2005 | Bardroff et al. |
| 2005/0191292 A1 | 9/2005 | Schenk |
| 2005/0191314 A1 | 9/2005 | Schenk |
| 2005/0196399 A1 | 9/2005 | Schenk et al. |
| 2005/0214222 A1 | 9/2005 | McKinnon et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0019850 A1 | 1/2006 | Korzenski et al. |
| 2006/0029611 A1 | 2/2006 | Schenk |
| 2006/0034858 A1 | 2/2006 | Schenk |
| 2006/0057701 A1 | 3/2006 | Rosenthal et al. |
| 2006/0099206 A1 | 5/2006 | Sinacore |
| 2006/0121038 A9 | 6/2006 | Schenk et al. |
| 2006/0153772 A1 | 7/2006 | Jacobsen |
| 2006/0160161 A1 | 7/2006 | Pavliakova et al. |
| 2006/0182321 A1 | 8/2006 | Hu et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0210964 A1 | 9/2006 | Hyslop et al. |
| 2006/0234912 A1 | 10/2006 | Wang et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0021454 A1 | 1/2007 | Coburn et al. |
| 2007/0072307 A1 | 3/2007 | Godavarti et al. |
| 2007/0082367 A1 | 4/2007 | Godavarti et al. |
| 2007/0134762 A1 | 6/2007 | Arumugham et al. |
| 2007/0154480 A1 | 7/2007 | Schenk et al. |
| 2007/0161088 A1 | 7/2007 | Arumugham et al. |
| 2007/0196375 A1 | 8/2007 | Tobinick |
| 2007/0238154 A1 | 10/2007 | Basi et al. |
| 2008/0031954 A1 | 2/2008 | Paris et al. |
| 2008/0050367 A1 | 2/2008 | Basi et al. |
| 2008/0096818 A1 | 4/2008 | Schenk et al. |
| 2008/0145373 A1 | 6/2008 | Arumugham |
| 2008/0219931 A1 | 9/2008 | Klunk et al. |
| 2008/0221306 A1 | 9/2008 | Basi |
| 2008/0227718 A1 | 9/2008 | Schenk |
| 2008/0227719 A1 | 9/2008 | Schenk |
| 2008/0279873 A1 | 11/2008 | Seubert |
| 2008/0281082 A1 | 11/2008 | Basi |
| 2008/0292625 A1 | 11/2008 | Schroeter |
| 2008/0299074 A1 | 12/2008 | Arumugham |
| 2009/0069544 A1 | 3/2009 | Basi |
| 2009/0142270 A1 | 6/2009 | Schroeter et al. |
| 2009/0155256 A1 | 6/2009 | Black et al. |
| 2009/0191231 A1 | 7/2009 | Schenk et al. |
| 2009/0297511 A1 | 12/2009 | Schenk |
| 2010/0221187 A1 | 9/2010 | Lieberburg et al. |
| 2010/0266505 A1 | 10/2010 | Black |
| 2011/0142824 A1 | 6/2011 | Burbidge et al. |
| 2011/0229413 A1 | 9/2011 | Lieberburg et al. |

FOREIGN PATENT DOCUMENTS

| | | |
|---|---|---|
| EP | 613 007 A2 | 8/1994 |
| EP | 620 276 A1 | 10/1994 |
| EP | 626 390 A1 | 11/1994 |
| EP | 666 080 A1 | 8/1995 |
| EP | 359 783 B1 | 11/1995 |
| EP | 683 234 A1 | 11/1995 |
| EP | 440 619 B1 | 1/1996 |
| EP | 758 248 B1 | 2/1997 |
| EP | 758 901 B1 | 2/1997 |
| EP | 526 511 B1 | 5/1997 |
| EP | 782 859 A1 | 7/1997 |
| EP | 783 104 A1 | 7/1997 |
| EP | 594 607 B1 | 8/1997 |
| EP | 752 886 B1 | 1/1998 |
| EP | 845 270 A1 | 6/1998 |
| EP | 863 211 A1 | 9/1998 |
| EP | 868 918 A2 | 10/1998 |
| EP | 652 962 B1 | 12/1998 |
| EP | 911 036 A2 | 4/1999 |
| EP | 561 087 B1 | 8/1999 |
| EP | 639 081 B1 | 11/1999 |
| EP | 1 172 378 A1 | 1/2002 |
| EP | 1 481 992 A2 | 12/2004 |
| EP | 1 481 992 A3 | 12/2004 |
| EP | 921 189 B1 | 1/2005 |
| EP | 1 033 998 B1 | 10/2005 |
| EP | 1 185 298 B1 | 6/2009 |
| EP | 1 690 547 B1 | 7/2009 |
| EP | 1 321 166 B1 | 1/2011 |
| EP | 1160256 B2 | 11/2011 |
| EP | 1842859 B1 | 1/2013 |
| GB | 2 220 211 A | 1/1990 |

(56) References Cited

FOREIGN PATENT DOCUMENTS

| | | |
|---|---|---|
| GB | 2 335 192 A | 9/1999 |
| JP | 62-267297 A | 11/1987 |
| JP | 07-132033 A | 5/1995 |
| JP | 7-165799 A | 6/1995 |
| JP | 09/208485 | 8/1997 |
| JP | 9215492 | 8/1997 |
| JP | 9208485 A | 12/1997 |
| JP | 9119929 A | 5/1999 |
| WO | WO 87/02671 A1 | 5/1987 |
| WO | WO 87/06838 A1 | 11/1987 |
| WO | WO 88/10120 A1 | 12/1988 |
| WO | WO 89/01343 A1 | 2/1989 |
| WO | WO 89/03687 A1 | 5/1989 |
| WO | WO 89/06242 A1 | 7/1989 |
| WO | WO 89/06689 A1 | 7/1989 |
| WO | WO 90/05142 A1 | 5/1990 |
| WO | WO 90/07861 A1 | 7/1990 |
| WO | WO 90/12870 A1 | 11/1990 |
| WO | WO 90/12871 A1 | 11/1990 |
| WO | WO 90/14837 A1 | 12/1990 |
| WO | WO 90/14840 A1 | 12/1990 |
| WO | WO 91/08760 A1 | 6/1991 |
| WO | WO 91/09967 A1 | 7/1991 |
| WO | WO 91/10741 A1 | 7/1991 |
| WO | WO 91/12816 A1 | 9/1991 |
| WO | WO 91/16819 A1 | 11/1991 |
| WO | WO 91/16928 A1 | 11/1991 |
| WO | WO 91/17271 A1 | 11/1991 |
| WO | WO 91/19795 A1 | 12/1991 |
| WO | WO 91/19810 A1 | 12/1991 |
| WO | WO 92/01047 A1 | 1/1992 |
| WO | WO 92/01059 A1 | 1/1992 |
| WO | WO 92/05793 A1 | 4/1992 |
| WO | WO 92/06187 A1 | 4/1992 |
| WO | WO 92/06708 A1 | 4/1992 |
| WO | WO 92/07944 A1 | 5/1992 |
| WO | WO 92/13069 A1 | 8/1992 |
| WO | WO 92/15330 A1 | 9/1992 |
| WO | WO 92/19267 A1 | 11/1992 |
| WO | WO 92/22653 A1 | 12/1992 |
| WO | WO 93/02189 A1 | 2/1993 |
| WO | WO 93/04194 A1 | 3/1993 |
| WO | WO 93/12227 A1 | 6/1993 |
| WO | WO 93/14200 A1 | 7/1993 |
| WO | WO 93/15760 A1 | 8/1993 |
| WO | WO 93/16724 A1 | 9/1993 |
| WO | WO 93/21950 A1 | 11/1993 |
| WO | WO 94/00153 A1 | 1/1994 |
| WO | WO 94/01772 A1 | 1/1994 |
| WO | WO 94/03208 A1 | 2/1994 |
| WO | WO 94/03615 A1 | 2/1994 |
| WO | WO 94/05311 A1 | 3/1994 |
| WO | WO 94/09364 A1 | 4/1994 |
| WO | WO 94/09823 A1 | 5/1994 |
| WO | WO 94/10569 A1 | 5/1994 |
| WO | WO 94/16731 A1 | 8/1994 |
| WO | WO 94/17197 A1 | 8/1994 |
| WO | WO 94/21288 A1 | 9/1994 |
| WO | WO 94/28412 A1 | 12/1994 |
| WO | WO 94/29459 A1 | 12/1994 |
| WO | WO 95/04151 A2 | 2/1995 |
| WO | WO 95/05393 A2 | 2/1995 |
| WO | WO 95/05849 A1 | 3/1995 |
| WO | WO 95/05853 A1 | 3/1995 |
| WO | WO 95/06407 A1 | 3/1995 |
| WO | WO 95/07301 A1 | 3/1995 |
| WO | WO 95/07707 A1 | 3/1995 |
| WO | WO 95/08999 A1 | 4/1995 |
| WO | WO 95/11008 A2 | 4/1995 |
| WO | WO 95/11311 A1 | 4/1995 |
| WO | WO 95/11994 A1 | 5/1995 |
| WO | WO 95/12815 A1 | 5/1995 |
| WO | WO 95/17085 A1 | 6/1995 |
| WO | WO 95/23166 A1 | 8/1995 |
| WO | WO 95/23860 A2 | 9/1995 |
| WO | WO 95/31996 A1 | 11/1995 |
| WO | WO 96/01126 A1 | 1/1996 |
| WO | WO 96/03144 A1 | 2/1996 |
| WO | WO 96/08565 A2 | 3/1996 |
| WO | WO 96/14061 A1 | 5/1996 |
| WO | WO 96/15799 A1 | 5/1996 |
| WO | WO 96/18900 A1 | 6/1996 |
| WO | WO 96/22373 A1 | 7/1996 |
| WO | WO 96/25435 A1 | 8/1996 |
| WO | WO 96/28471 A1 | 9/1996 |
| WO | WO 96/29421 A1 | 9/1996 |
| WO | WO 96/33739 A1 | 10/1996 |
| WO | WO 96/37621 A2 | 11/1996 |
| WO | WO 96/39176 A1 | 12/1996 |
| WO | WO 96/39834 A1 | 12/1996 |
| WO | WO 96/40895 A1 | 12/1996 |
| WO | WO 97/03192 A3 | 1/1997 |
| WO | WO 97/05164 A1 | 2/1997 |
| WO | WO 97/08320 A1 | 3/1997 |
| WO | WO 97/10505 A1 | 3/1997 |
| WO | WO 97/13855 A1 | 4/1997 |
| WO | WO 97/17613 A1 | 5/1997 |
| WO | WO 97/18855 A1 | 5/1997 |
| WO | WO 97/21728 A1 | 6/1997 |
| WO | WO 97/36913 A1 | 7/1997 |
| WO | WO 97/28816 A1 | 8/1997 |
| WO | WO 97/32017 A1 | 9/1997 |
| WO | WO 97/36601 A1 | 10/1997 |
| WO | WO 97/37031 A1 | 10/1997 |
| WO | WO 97/40147 A1 | 10/1997 |
| WO | WO 98/02462 A1 | 1/1998 |
| WO | WO 98/04720 A1 | 2/1998 |
| WO | WO 98/05350 A1 | 2/1998 |
| WO | WO 98/07850 A2 | 2/1998 |
| WO | WO 98/08098 A2 | 2/1998 |
| WO | WO 98/08868 A1 | 3/1998 |
| WO | WO 98/22120 A1 | 5/1998 |
| WO | WO 98/33815 A1 | 8/1998 |
| WO | WO 98/39303 A1 | 9/1998 |
| WO | WO 98/44955 A1 | 10/1998 |
| WO | WO 98/46642 A1 | 10/1998 |
| WO | WO 98/56418 A1 | 12/1998 |
| WO | WO 99/00150 A2 | 1/1999 |
| WO | WO 99/06066 A2 | 2/1999 |
| WO | WO 99/06587 A2 | 2/1999 |
| WO | WO 99/10008 A1 | 3/1999 |
| WO | WO 99/27911 A1 | 6/1999 |
| WO | WO 99/27944 A1 | 6/1999 |
| WO | WO 99/27949 A1 | 6/1999 |
| WO | WO 99/06545 A2 | 11/1999 |
| WO | WO 99/58564 A1 | 11/1999 |
| WO | WO 99/60021 A2 | 11/1999 |
| WO | WO 99/60024 A1 | 11/1999 |
| WO | WO 00/20027 A2 | 4/2000 |
| WO | WO 00/23082 A1 | 4/2000 |
| WO | WO 00/26238 A2 | 5/2000 |
| WO | WO 00/43039 A1 | 7/2000 |
| WO | WO 00/43049 A1 | 7/2000 |
| WO | WO 00/68263 A2 | 11/2000 |
| WO | WO 00/72870 A1 | 12/2000 |
| WO | WO 00/72876 A2 | 12/2000 |
| WO | WO 00/72876 A3 | 12/2000 |
| WO | WO 00/72880 A2 | 12/2000 |
| WO | WO 00/72880 A3 | 12/2000 |
| WO | WO 00/77178 A1 | 12/2000 |
| WO | WO 01/05355 A2 | 1/2001 |
| WO | WO 01/10900 A2 | 2/2001 |
| WO | WO 01/18169 A3 | 3/2001 |
| WO | WO 01/39796 A2 | 6/2001 |
| WO | WO 01/42306 A2 | 6/2001 |
| WO | WO 01/62284 A2 | 8/2001 |
| WO | WO 01/62801 A2 | 8/2001 |
| WO | WO 01/77167 A2 | 10/2001 |
| WO | WO 01/78777 A2 | 10/2001 |
| WO | WO 01/90182 A2 | 11/2001 |
| WO | WO 02/03911 A2 | 1/2002 |
| WO | WO 02/21141 A2 | 3/2002 |
| WO | WO 02/34777 A1 | 5/2002 |
| WO | WO 02/34878 A2 | 5/2002 |

(56) References Cited

FOREIGN PATENT DOCUMENTS

| | | |
|---|---|---|
| WO | WO 02/46237 A2 | 6/2002 |
| WO | WO 02/46237 A3 | 6/2002 |
| WO | WO 02/060481 A1 | 8/2002 |
| WO | WO 02/088306 A2 | 11/2002 |
| WO | WO 02/088307 A2 | 11/2002 |
| WO | WO 02/096457 A2 | 12/2002 |
| WO | WO 02/096937 A2 | 12/2002 |
| WO | WO 03/009817 A2 | 2/2003 |
| WO | WO 03/015691 A2 | 2/2003 |
| WO | WO 03/016466 A2 | 2/2003 |
| WO | WO 03/016467 A2 | 2/2003 |
| WO | WO 03/016467 A3 | 2/2003 |
| WO | WO 03/020212 A2 | 3/2003 |
| WO | WO 03/039485 A2 | 5/2003 |
| WO | WO 03/051374 A2 | 6/2003 |
| WO | WO 03/072036 A2 | 9/2003 |
| WO | WO 03/072036 A3 | 9/2003 |
| WO | WO 03/074081 A1 | 9/2003 |
| WO | WO 03/077858 A2 | 9/2003 |
| WO | WO 03/077858 A3 | 9/2003 |
| WO | WO 03/104437 A2 | 12/2003 |
| WO | WO 03/105894 A1 | 12/2003 |
| WO | WO 2004/013172 A2 | 2/2004 |
| WO | WO 2004/013172 A3 | 2/2004 |
| WO | WO 2004/016282 A1 | 2/2004 |
| WO | WO 2004/031400 A2 | 4/2004 |
| WO | WO 2004/044204 A2 | 5/2004 |
| WO | WO 2004/044204 A3 | 5/2004 |
| WO | WO 2004/055164 A2 | 7/2004 |
| WO | WO 2004/069182 A2 | 8/2004 |
| WO | WO 2004/069182 A3 | 8/2004 |
| WO | WO 2004/071408 A2 | 8/2004 |
| WO | WO 2004/080419 A2 | 9/2004 |
| WO | WO 2004/080419 A3 | 9/2004 |
| WO | WO 2004/108895 A2 | 12/2004 |
| WO | WO 2004/108895 A3 | 12/2004 |
| WO | WO 2005/014041 A2 | 2/2005 |
| WO | WO 2005/026211 A2 | 3/2005 |
| WO | WO 2005/026211 A3 | 3/2005 |
| WO | WO 2005/035753 A1 | 4/2005 |
| WO | WO 2005/058940 A2 | 6/2005 |
| WO | WO 2005/058941 A2 | 6/2005 |
| WO | WO 2005/090315 A1 | 9/2005 |
| WO | WO 2006/042158 A2 | 4/2006 |
| WO | WO 2006/066049 A2 | 6/2006 |
| WO | WO 2006/066171 A1 | 6/2006 |
| WO | WO 2006/081587 A2 | 8/2006 |
| WO | WO 2006/081587 A3 | 8/2006 |
| WO | WO 2006/083689 A2 | 8/2006 |
| WO | WO 2006/121656 A2 | 11/2006 |
| WO | WO 2008/011348 A2 | 1/2008 |
| WO | WO 2008/114801 A1 | 9/2008 |
| WO | WO 2008/131298 A2 | 10/2008 |
| WO | WO 2008/131298 A3 | 10/2008 |
| WO | WO 2009/017467 A1 | 2/2009 |
| WO | WO 2009/052439 A2 | 4/2009 |
| WO | WO 2010/033861 A1 | 3/2010 |
| WO | WO 2010/044803 A1 | 4/2010 |
| WO | WO 2011/106732 A1 | 9/2011 |
| WO | WO 2011/133919 A1 | 10/2011 |

OTHER PUBLICATIONS

U.S. Appl. No. 09/723,765, Office Action mailed May 22, 2008.
U.S. Appl. No. 09/723,765, Office Action mailed Aug. 10, 2004.
U.S. Appl. No. 09/723,765, Office Action mailed Dec. 20, 2004.
U.S. Appl. No. 09/724,273, Office Action mailed Jun. 8, 2006.
U.S. Appl. No. 09/724,273, Office Action mailed Jun. 22, 2004.
U.S. Appl. No. 09/724,273, Office Action mailed Dec. 22, 2006.
U.S. Appl. No. 09/724,288, Office Action mailed Mar. 18, 2008.
U.S. Appl. No. 09/724,288, Office Action mailed Apr. 23, 2007.
U.S. Appl. No. 09/724,288, Office Action mailed Jun. 21, 2006.
U.S. Appl. No. 09/724,288, Office Action mailed Oct. 3, 2007.
U.S. Appl. No. 09/724,288, Office Action mailed Dec. 14, 2004.
U.S. Appl. No. 09/724,319, Office Action mailed Jan. 11, 2008.
U.S. Appl. No. 09/724,319, Office Action mailed May 16, 2007.
U.S. Appl. No. 09/724,319, Office Action mailed Aug. 15, 2005.
U.S. Appl. No. 09/724,575, Office Action mailed Mar. 31, 2006.
U.S. Appl. No. 09/724,575, Office Action mailed May 6, 2005.
U.S. Appl. No. 09/724,575, Office Action mailed Oct. 17, 2005.
U.S. Appl. No. 09/980,568, Office Action mailed Nov. 2, 2004.
U.S. Appl. No. 10/010,942, Office Action mailed Jan. 19, 2005.
U.S. Appl. No. 10/010,942, Office Action mailed Mar. 10, 2005.
U.S. Appl. No. 10/232,030, Office Action mailed Jun. 15, 2007.
U.S. Appl. No. 10/429,216, Office Action mailed Jan. 28, 2008.
U.S. Appl. No. 10/429,216, Office Action mailed Mar. 12, 2010.
U.S. Appl. No. 10/429,216, Office Action mailed May 24, 2011.
U.S. Appl. No. 10/429,216, Office Action mailed Sep. 15, 2010.
U.S. Appl. No. 10/544,093, Office Action mailed Jan. 22, 2010.
U.S. Appl. No. 10/625,854, Office Action mailed May 15, 2007.
U.S. Appl. No. 10/703,713, Office Action mailed Jun. 2, 2006.
U.S. Appl. No. 10/777,792, Office Action mailed Apr. 3, 2008.
U.S. Appl. No. 10/828,548, Office Action mailed Sep. 11, 2007.
U.S. Appl. No. 10/858,855, Office Action mailed Dec. 12, 2008.
U.S. Appl. No. 10/858,855, Office Action mailed Dec. 15, 2009.
U.S. Appl. No. 10/889,999, Office Action mailed Aug. 15, 2005.
U.S. Appl. No. 10/890,000, Office Action mailed Mar. 10, 2006.
U.S. Appl. No. 10/890,000, Office Action mailed Sep. 19, 2005.
U.S. Appl. No. 10/890,070, Office Action mailed Sep. 29, 2005.
U.S. Appl. No. 10/923,469, Office Action mailed Mar. 24, 2008.
U.S. Appl. No. 10/923,471, Office Action mailed Mar. 20, 2009.
U.S. Appl. No. 10/923,471, Office Action mailed May 15, 2006.
U.S. Appl. No. 10/923,471, Office Action mailed Jul. 31, 2007.
U.S. Appl. No. 10/923,471, Office Action mailed Aug. 24, 2005.
U.S. Appl. No. 10/923,474, Office Action mailed Jun. 26, 2007.
U.S. Appl. No. 11/244,678, Office Action mailed Sep. 23, 2008.
U.S. Appl. No. 11/245,524, Office Action mailed Apr. 17, 2009.
U.S. Appl. No. 11/245,524, Office Action mailed Jun. 4, 2008.
U.S. Appl. No. 11/245,524, Office Action mailed Dec. 10, 2010.
U.S. Appl. No. 11/245,916, Office Action mailed Jan. 28, 2008.
U.S. Appl. No. 11/245,916, Office Action mailed May 18, 2010.
U.S. Appl. No. 11/245,916, Office Action mailed Oct. 31, 2008.
U.S. Appl. No. 11/245,916, Office Action mailed Dec. 14, 2011.
U.S. Appl. No. 11/342,353, Office Action mailed Jul. 22, 2008.
U.S. Appl. No. 11/809,552, Office Action mailed Feb. 17, 2011.
U.S. Appl. No. 11/841,919, Office Action mailed Mar. 28, 2011.
U.S. Appl. No. 11/842,023, Office Action mailed Aug. 14, 2009.
U.S. Appl. No. 11/842,113, Office Action mailed Aug. 24, 2010.
U.S. Appl. No. 11/893,123, Office Action mailed May 11, 2011.
U.S. Appl. No. 12/037,045, Office Action mailed Apr. 28, 2010.
U.S. Appl. No. 12/106,206, Office Action mailed Jul. 9, 2010.
U.S. Appl. No. 09/580,018, Office Action mailed Mar. 12, 2002.
U.S. Appl. No. 09/724,552, Office Action mailed May 6, 2002.
U.S. Appl. No. 09/723,544, Office Action mailed Sep. 23, 2002.
U.S. Appl. No. 10/625,854, Office Action mailed Nov. 10, 2005.
U.S. Appl. No. 09/724,273, Office Action mailed Jul. 2, 2002.
U.S. Appl. No. 09/724,273, Office Action mailed Nov. 8, 2005.
U.S. Appl. No. 09/724,551, Office Action mailed Jul. 2, 2002.
U.S. Appl. No. 09/724,288, Office Action mailed Mar. 12, 2002.
U.S. Appl. No. 11/305,889, Office Action mailed Jul. 25, 2008.
U.S. Appl. No. 09/724,288, Office Action mailed May 3, 2004.
U.S. Appl. No. 10/777,792, Office Action mailed Mar. 2, 2006.
U.S. Appl. No. 09/723,765, Office Action mailed Mar. 12, 2002.
U.S. Appl. No. 10/822,968, Office Action mailed Mar. 22, 2006.
U.S. Appl. No. 09/724,929, Office Action mailed Mar. 22, 2002.
U.S. Appl. No. 09/724,567, Office Action mailed Mar. 27, 2002.
U.S. Appl. No. 09/724,575, Office Action mailed Mar. 27, 2002.
U.S. Appl. No. 09/724,953, Office Action mailed Mar. 26, 2002.
U.S. Appl. No. 09/979,952, Office Action mailed Aug. 7, 2003.
U.S. Appl. No. 09/980,568, Office Action mailed May 29, 2003.
U.S. Appl. No. 11/245,524, Office Action mailed May 15, 2007.
U.S. Appl. No. 11/245,916, Office Action mailed Jan. 13, 2006.
U.S. Appl. No. 10/934,819, Office Action mailed Oct. 14, 2005.
U.S. Appl. No. 10/923,267, Office Action mailed Jul. 21, 2006.
U.S. Appl. No. 10/923,469, Office Action mailed Mar. 29, 2007.
U.S. Appl. No. 10/429,216, Office Action mailed Dec. 28, 2005.
U.S. Appl. No. 11/304,986, Office Action mailed Jan. 2, 2008.

(56) References Cited

OTHER PUBLICATIONS

U.S. Appl. No. 11/342,353, Office Action mailed Mar. 26, 2008.
U.S. Appl. No. 11/244,678, Office Action mailed Apr. 18, 2007.
U.S. Appl. No. 09/201,430, Office Action mailed Dec. 21, 1999.
U.S. Appl. No. 09/201,430, Office Action mailed May 10, 2000.
U.S. Appl. No. 09/580,019, Office Action mailed Mar. 12, 2002.
U.S. Appl. No. 10/789,273, Office Action mailed Sep. 22, 2006.
U.S. Appl. No. 09/724,495, Office Action mailed Mar. 13, 2003.
U.S. Appl. No. 11/058,757, Office Action mailed Aug. 24, 2005.
U.S. Appl. No. 11/342,353, Office Action mailed Jul. 9, 2008.
U.S. Appl. No. 10/544,093, Office Action mailed Jun. 16, 2008.
U.S. Appl. No. 10/928,926, Office Action mailed Jan. 12, 2007.
U.S. Appl. No. 09/724,921, Office Action mailed Apr. 30, 2002.
U.S. Appl. No. 09/204,838, Office Action mailed Mar. 17, 2000.
U.S. Appl. No. 09/723,766, Office Action mailed Mar. 5, 2002.
U.S. Appl. No. 09/723,766, Office Action mailed Jun. 11, 2002.
U.S. Appl. No. 11/303,478, Office Action mailed Oct. 16, 2008.
U.S. Appl. No. 11/516,724, Office Action mailed Jan. 27, 2009.
U.S. Appl. No. 11/842,120, Office Action mailed Apr. 14, 2009.
U.S. Appl. No. 11/842,085, Office Action mailed Apr. 14, 2009.
U.S. Appl. No. 11/707,639, Office Action mailed Apr. 3, 2009.
U.S. Appl. No. 11/520,438, Office Action mailed Apr. 2, 2009.
U.S. Appl. No. 12/328,740, Office Action mailed Oct. 9, 2009.
U.S. Appl. No. 11/842,113, Office Action mailed Dec. 17, 2009.
U.S. Appl. No. 12/106,206, Office Action mailed Feb. 5, 2010.
U.S. Appl. No. 12/253,929, Office Action mailed Jan. 25, 2010.
U.S. Appl. No. 11/842,116, Office Action mailed Mar. 31, 2010.
U.S. Appl. No. 10/010,942, Office Action mailed Sep. 24, 2003.
U.S. Appl. No. 10/232,030, Office Action mailed Dec. 2, 2004.
U.S. Appl. No. 10/388,389, Office Action mailed Nov. 22, 2005.
U.S. Appl. No. 10/703,713, Office Action mailed Nov. 5, 2004.
U.S. Appl. No. 10/704,070, Office Action mailed Nov. 5, 2004.
U.S. Appl. No. 10/771,174, Office Action mailed Sep. 14, 2006.
U.S. Appl. No. 10/858,855, Office Action mailed Jun. 22, 2006.
U.S. Appl. No. 10/388,214, Office Action mailed May 31, 2005.
U.S. Appl. No. 11/260,047, Office Action mailed Oct. 26, 2006.
U.S. Appl. No. 11/305,889, Office Action mailed May 4, 2007.
U.S. Appl. No. 11/305,899, Office Action mailed Apr. 4, 2008.
U.S. Appl. No. 11/303,478, Office Action mailed Apr. 1, 2008.
U.S. Appl. No. 11/304,072, Office Action mailed Dec. 20, 2006.
U.S. Appl. No. 11/454,772, Office Action mailed Feb. 27, 2007.
U.S. Appl. No. 09/497,553, Office Action mailed Oct. 3, 2003.
U.S. Appl. No. 09/322,289, Office Action mailed Sep. 29, 2000.
U.S. Appl. No. 09/723,760, Office Action mailed Mar. 12, 2002.
U.S. Appl. No. 09/724,319, Office Action mailed Jul. 21, 2003.
U.S. Appl. No. 09/724,495, Office Action mailed Sep. 24, 2002.
U.S. Appl. No. 10/788,666, Office Action mailed Jan. 12, 2005.
U.S. Appl. No. 10/828,548, Office Action mailed Feb. 4, 2005.
U.S. Appl. No. 10/828,548, Office Action mailed Sep. 29, 2005.
U.S. Appl. No. 10/923,474, Office Action mailed Feb. 15, 2005.
U.S. Appl. No. 09/580,015, Office Action mailed Feb. 11, 2002.
U.S. Appl. No. 09/724,940, Office Action mailed Mar. 13, 2003.
U.S. Appl. No. 09/724,961, Office Action mailed Mar. 12, 2002.
U.S. Appl. No. 09/979,701, Office Action mailed Feb. 15, 2005.
U.S. Appl. No. 09/979,701, Office Action mailed Sep. 15, 2005.
U.S. Appl. No. 10/823,463, Office Action mailed Feb. 4, 2005.
U.S. Appl. No. 11/058,757, Office Action mailed May 3, 2005.
U.S. Appl. No. 09/201,430, Notice of Allowance mailed Mar. 26, 2003.
U.S. Appl. No. 09/201,430, Notice of Allowance mailed Sep. 23, 2003.
U.S. Appl. No. 09/322,289, Notice of Allowance mailed Nov. 15, 2010.
U.S. Appl. No. 09/580,018, Notice of Allowance mailed Dec. 3, 2003.
U.S. Appl. No. 09/723,384, Notice of Allowance mailed Mar. 31, 2003.
U.S. Appl. No. 09/723,762, Notice of Allowance mailed May 1, 2003.
U.S. Appl. No. 09/723,927, Notice of Allowance mailed Sep. 23, 2003.
U.S. Appl. No. 09/724,102, Notice of Allowance mailed Aug. 22, 2003.
U.S. Appl. No. 09/724,288, Notice of Allowance mailed Mar. 23, 2009.
U.S. Appl. No. 09/724,477, Notice of Allowance mailed Apr. 30, 2003.
U.S. Appl. No. 09/724,477, Notice of Allowance mailed Sep. 23, 2003.
U.S. Appl. No. 09/724,489, Notice of Allowance mailed Mar. 25, 2003.
U.S. Appl. No. 09/724,489, Notice of Allowance mailed Sep. 22, 2003.
U.S. Appl. No. 09/724,551, Notice of Allowance mailed Dec. 4, 2003.
U.S. Appl. No. 09/724,552, Notice of Allowance mailed Dec. 3, 2003.
U.S. Appl. No. 09/724,567, Notice of Allowance mailed Mar. 3, 2004.
U.S. Appl. No. 09/724,940, Notice of Allowance mailed Oct. 4, 2004.
U.S. Appl. No. 09/724,953, Notice of Allowance mailed Mar. 11, 2004.
U.S. Appl. No. 09/724,961, Notice of Allowance mailed Dec. 3, 2003.
U.S. Appl. No. 09/979,952, Notice of Allowance mailed Nov. 12, 2004.
U.S. Appl. No. 10/010,942, Notice of Allowance mailed May 11, 2006.
U.S. Appl. No. 10/232,030, Notice of Allowance mailed Sep. 4, 2008.
U.S. Appl. No. 10/388,214, Notice of Allowance mailed Mar. 1, 2007.
U.S. Appl. No. 10/388,389, Notice of Allowance mailed May 31, 2006.
U.S. Appl. No. 10/815,353, Notice of Allowance mailed Jul. 1, 2004.
U.S. Appl. No. 10/815,391, Notice of Allowance mailed Jul. 1, 2004.
U.S. Appl. No. 10/815,404, Notice of Allowance mailed Oct. 15, 2004.
U.S. Appl. No. 10/816,022, Notice of Allowance mailed Jul. 1, 2004.
U.S. Appl. No. 10/816,380, Notice of Allowance mailed Dec. 22, 2004.
U.S. Appl. No. 10/816,529, Notice of Allowance mailed Jul. 1, 2004.
U.S. Appl. No. 10/858,855, Notice of Allowance mailed Jul. 12, 2010.
U.S. Appl. No. 10/884,892, Notice of Allowance mailed Mar. 28, 2005.
U.S. Appl. No. 10/923,469, Notice of Allowance mailed Jun. 1, 2011.
U.S. Appl. No. 10/933,559, Notice of Allowance mailed Aug. 17, 2005.
U.S. Appl. No. 10/933,559, Notice of Allowance mailed Sep. 7, 2005.
U.S. Appl. No. 10/933,559, Notice of Allowance mailed Dec. 22, 2004.
U.S. Appl. No. 10/934,609, Notice of Allowance mailed Aug. 17, 2005.
U.S. Appl. No. 10/934,609, Notice of Allowance mailed Dec. 22, 2004.
U.S. Appl. No. 11/304,986, Notice of Allowance mailed Jul. 10, 2009.
U.S. Appl. No. 11/707,639, Notice of Allowance mailed Aug. 20, 2009.
U.S. Appl. No. 11/842,023, Notice of Allowance mailed Oct. 6, 2010.
U.S. Appl. No. 12/181,238, Notice of Allowance mailed Mar. 5, 2010.
U.S. Appl. No. 12/181,238, Notice of Allowance mailed Mar. 11, 2011
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007, Basi.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007, Basi et al.
U.S. Appl. No. 11/893,110, filed Aug. 20, 2007, Basi et al.
U.S. Appl. No. 11/893,103, filed Aug. 20, 2007, Basi et al.

(56) References Cited

OTHER PUBLICATIONS

U.S. Appl. No. 11/893,094, filed Aug. 20, 2007, Basi et al.
U.S. Appl. No. 11/842,101, filed Aug. 20, 2007, Schenk.
U.S. Appl. No. 11/841,950, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/925,228, filed Apr. 18, 2007, Schroeter et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/530,480, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/254,465, filed Dec. 8, 2000, Holtzman et al.
U.S. Appl. No. 60/254,498, filed Dec. 8, 2000, Holtzman et al.
U.S. Appl. No. 60/251,892, filed Dec. 6, 2000, Basi et al.
U.S. Appl. No. 09/724,842, filed Nov. 28, 2000, Chalifour et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,273, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656, filed Jun. 1, 2000, Hirtzer et al.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 60/186,295, filed Mar. 1, 2000, Rasmussen et al.
U.S. Appl. No. 60/184,601, filed Feb. 24, 2000, Holtzman et al.
U.S. Appl. No. 09/497,553, filed Feb. 3, 2000, Schenk.
U.S. Appl. No. 60/169,687, filed Dec. 8, 1999, Chain.
U.S. Appl. No. 60/168,594, filed Nov. 29, 1999, Chalifour et al.
U.S. Appl. No. 09/441,140, filed Nov. 16, 1999, Solomon et al.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 60/080,970, filed Jan. 11, 1999, Schenk.
U.S. Appl. No. 09/204,838, filed Dec. 3, 1998, Weiner.
U.S. Appl. No. 60/079,697, filed Mar. 27, 1998, Weiner et al.
U.S. Appl. No. 60/067,219, filed Dec. 3, 1997, Weiner et al.
U.S. Appl. No. 60/067,740, filed Dec. 2, 1997, Schenk.
"AAB-001 in Patients with Mild to Moderate Alzheimer's Disease" ClinicalTrials.gov last updated Sep. 22, 2009 3 pages.
"Researchers Develop Blood Test to Diagnose Alzheimer's-Type Changes in Mice," downloaded from www.businesswire.com on Dec. 15, 2004.
Agadjanyan et al., "Prototype Alzheimer's Disease Vaccine Using the Immunodominant B Cell Epitope From {beta}-Amyloid and Promiscuous T Cell Epitope Pan HLA DR-Binding Peptide," *J. Immunol.*, 174:1580-1586 (2005).
Aguzzi et al., "Prion research: the next frontiers," *Nature*, 389:795-798 (1997).
Aisen, P., "Inflammation and Alzheimer's Disease: Mechanisms and Therapeutic Strategies," *Gerontology*, 43:143-149 (1997).
Akiyama et al., "Occurrence of the Diffuse Amyloid β-Protein (Aβ) Deposits With Numerous Aβ-Containing Glial Cells in the Cerebral Cortex of Patients With Alzheimer's Disease," *Glia*, 25:324-331 (1999).
Akiyama et al., "The amino-terminally truncated forms of amyloid β-protein in brain macrophages in the ischemic lesions of Alzheimer's disease patients," *Neuroscience Letters*, 219:115-118 (1996).
Akiyama et al., "Inflammation and Alzheimer's disease," *Neurobiology of Aging*, 21:383-421 (2000).
Alberts et al., eds. *Molecular Biology of the Cell*, Third Edition, chapter 23, pp. 1208-1209 (1994).
Alberts et al., eds. *Molecular Biology of the Cell*, Third Edition, chapter 23, pp. 1216-1218 (1994).
Alberts et al., *Molecular Biology of the Cell*, 2nd Edition, pp. 266-267, Garland Publishing Inc., New York (1989).
Allen et al, "Reversible posterior leukoencephalopathy syndrome after bevacizumab/FOLFIRI Regimen for Metastatic Colon Caner," *Arch. Neurol.*, 63(10): 1475-1478 (2006), abstract only.
American Type Culture Collection (ATCC) Search Results for "1KTR, 1ETZ, 1JRH", http://www.atcc.org/, pp. 1-3, Feb. 22, 2007.
Amit et al., "Three-Dimensional Structure of an Antigen-Antibody Complex at 2.8 Å Resolution," *Science*, 233:747-753 (1986).
Andersen et al., "Do nonsteroidal anti-inflammatory drugs decrease the risk for Alzheimer's disease?", *Neurology*, 45:1441-1445 (1995).
Anderson, J. P., "Exact cleavage site of Alzheimer amyloid precursor in neuronal PC-12 cells," *Neuroscience Letters*, 128(1):126-128 (1991).
Anderson, M. W., "Amending the amyloid hypothesis," *The Scientist*, 18(20):28-29 (2004).
Andrew et al., *Current Protocols in Immunology*, 2.7.1-2.9.8, John Wiley & Sons, Inc. (1997).
Ankarcrona et al., "Biomarkers for apoptosis in Alzheimer's disease," *Int. J. Geriatric Psychiatry*, 20:101-105 (2005).
Aquila Press Release, PR Newswire. May 6, 1997.
Ard et al., "Scavenging of Alzheimer's Amyloid β-Protein by Microglia in Culture," *J. Neuroscience Research*, 43:190-202 (1996).
Arendiash et al., "Behavioral assessment of Alzheimer's transgenic mice following long-term Aβ vaccination: Task specificity and correlations between Aβ deposition and spatial memory," *DNA and Cell Biology*, 20(11):737-744 (2001).
Armour et al., "Recombinant human IgG molecules lacking Fcγ receptor I binding and monocyte triggering activites," *J. Immunol*, 29:2613-2624 (1999).
Askelof et al., "Protective immunogenicity of two synthetic peptides selected from the amino acid sequence of *Bordetella pertussis* toxin subunit S1," *PNAS*, 87:1347-1351 (1990).
Associated Press, "Immune cells may promote Alzheimer's, a study finds," *The Boston Globe* (Apr. 13, 1995).
Auclair et al., "Effect of Active Immunization Against Oestriadiol in Developing Ram Lambs on Plasma Gonadotrophin and Testosterone Concentrations, Time of Onset of Puberty and Testicular Blood Flow," *Journal of Reproduction and Fertility*, 104:7-16 (1995).
Auld et al., "Alzheimer's disease and the basal forebrain cholinergic system: relations to β-amyloid peptides, cognition, and treatment strategies," *Progress in Neurobiol.*, 68:209-245 (2002).

(56) References Cited

OTHER PUBLICATIONS

Avis, "Perenteral Preparations," *Remington's Pharmaceutical Sciences*, 17:1518-1519 (1985).

Aylward et al., "Cerebellar Volume in Adults With Down Syndrome," *Arch Neurol.*, 4(2):209-212 (1997). Abstract only.

Bach et al., "Vaccination with AB-Displaying Virus-Like Particles Reduces Soluble and Insoluble Cerebral AB and Lowers Plaque Burden in APP Transgenic Mice," J. Immunol., 2009, 182 7613-7624.

Bacskai et al., "Imaging of amyloid-β deposits in brains of living mice permits direct observation of clearance of plaques with immunotherapy," *Nature Medicine*, 7(3):369-372 (2001).

Bacskai et al., "Non-Fc-mediated mechanisms are involved in clearance of amyloid-β in vivo by immunotherapy," *J. Neurosci.*, 22(18):7873-7878 (2002).

Balbach et al., "Amyloid fibril formation by $A\beta_{16-22}$, a seven-residue fragment of the Alzheimer's β-amyloid peptide, and structural characterization by solid state NMR," *Biochemistry*, 39:13748-13759 (2000).

Bales et al., "Administration of an Anti-Aβ Fab Fragment to $APP^{V717F}$ Transgenic Mice Reduces Neuritic Plaque," Abstract P4-396, presented at Poster Session P4: Therapeutics and Therapeutic Strategies—Therapeutic Strategies, Amyloid-Based, *Neurogiology of Aging*, 25:S587 (2004).

Bales et al., "Cholinergic dysfunction in a mouse model of Alzheimer disease is reversed by an anti-Aβ antibody," *J. Clin. Invest.*, 116(3):825-832 (2006).

Bandlow et al., "Untersuchungen Zum Mechanismus Der Immunologischen Adjvanswirung des Vacciniavirus," *Archiv für due gesamte Virusfoschung*, 38:192-204 (1972). German article.

Bard et al., "Epitope and isotype specificities of antibodies to β-amyloid peptide for protection against Alzheimer's disease-like neuropathology," *PNAS*, 100(4):2023-2028 (2003).

Bard et al., "Peripherally administered antibodies against amyloid β-peptide enter the central nervous system and reduce pathology in a mouse model of Alzheimer disease," *Nature Medicine*, 6(8):916-919 (2000).

Barelli et al., "Characterization of New Polyclonal Antibodies Specific for 40 and 42 Amino Acid-Long Amyloid β Peptides: Their Use to Examine the Cell Biology of Presenilins and the Immunohistochemistry of Sporadic Alzheimer's Disease and Cerebral Amyloid Angiopathy Cases," *Molecular Medicine*, 3(10):695-707 (1997).

Barrow et al., "Solution Conformations and aggregational Properties of Synthetic Amyloid Beta-Peptides of Alzheimer's Disease. Analysis of Circular Dichroism Spectra," *J. Mol. Biol.*, 225(4):1075-1093 (1992).

Bauer et al., "Interleukin-6 and α-2-macroglobulin indicate an acute-phase state in Alzheimer's disease cortices," *FEBS Letters*, 285(1):111-114 (1991).

Beasley, "Alzheimer's traced to proteins caused by aging," Reuters, Apr. 20, 2001 7:56 PM ET.

Begley, "Delivery of Therapeutic Agents to the Central Nervous System: The Problems and the Possibilities," *Pharmacol. Therapy*, 104(1): 29-45 (Oct. 2004).

Bellotti et al., "Application of Monoclonal Anti-idiotypes in the Study of AL Amyloidosi: Therapeutic Implications," *Renal Failure*, 15(3):365-371 (1993). Abstract.

Bendig, "Humanization of Rodent Monoclonal Antibodies by CDR Grafting," *A Companion to Methods in Enzymology*, 8:83-93 (1995).

Benjamini et al., From *Immunology a Short Course*, Second Edition, Chapter 4, Antibody Structure, pp. 49-65, 1991, published by Wiley-Liss, Inc., New York, New York.

Benjamini et al., From *Immunology a Short Course*, Second Edition, pp. 136-138, 143, 73-74, 372-373, and 400-401, 1991, published by Wiley-Liss, Inc., New York, New York.

Benkirane, et al, "Antigenicity and Immunogenicity of Modified Synthetic Peptides Containing D-Amino Acid Residues," *J. Biol. Chem.*, 268(23):26279-26285 (1993).

Ben-Yedidia et al., "Design of peptide and polypeptide vaccines," *Current Opinion in Biotechnology*, 8:442-448 (1997).

Bercovici et al., "Chronic Intravenous Injections of Antigen Induce and Maintain Tolerance in T Cell Receptor-Transgenic Mice," *Eur. J. Immunol.*, 29:345-354 (1999).

Bickel et al., "Development and in Vitro Characterization of a Cationized Monoclonal Antibody against βA4 Protein: A Potential Probe for Alzheimer's Disease," *Bioconjugate Chem.*, 5:119-125 (1994).

Bickel et al., "Site Protected, Cationized Monoclonal Antibody Against Beta Amyloid as a Potential Diagnostic Imaging Technique for Alzheimer's Diseases," *Soc. for Neuroscience Abstracts*, 18:764 (1992).

Biewenga et al., "Cleavage of Protein A-binding IgA1 with IgA1 Protease From *Streptococcus sanguls*," *Immunol Commun.*, 12(5):491-500 (1983), abstract only.

Black et al., "A Single Ascending Dose Study of Bainezumab, A Humanized Monoclonal Antibody to Aβ, in AD," *9th International Geneva/Springfield Symposium on Advances in Alzheimer Therapy*, 1 page (Apr. 20, 2006). Abstract only.

Blasberg et al., "Regional Localization of Glioma-assoicated Antigen Defined by Monoclonal Antibody 81C6 in Vivo: Kinetics and Implications for Diagnosis and Therapy," *Cancer Research*, 47:4432-4443 (1987).

Blass, "Immunologic Treatment of Alzheimer's Disease," *New England J. Medicine*, 341(22):1694 (1999).

Bodmer et al., "Transforming Growth Factor-Beta Bound to Soluble Derivatives of the Beta Amyloid Precursor Protein of Alzheimer's Disease," *Biochem. Biophys. Res. Comm.*, 171(2):890-897 (1990).

Boraschi et al., "Interleukin-1 and Interleukin-1 Fragments a Vaccine Adjuvants", Methods, 1999, 19, pp. 108-113.

Borchelt et al., "Accelerated Amyloid Deposition in the Brains of Transgenic Mice Coexpressing Mutant Presenilin 1 and Amyloid Precursor Proteins," *Neuron*, 19:939-945 (1997).

Borenstein, S., "New Alzheimer's vaccine to be tested on people soon, Early experiments on mice halted condition; considered safe for humans," *Free Press*, Jul. 23, 2001.

Boris-Lawrie et al., "Recent advances in retrovirus vector technology," *Cur. Opin. Genetic Develop.*, 3:102-109 (1993).

Bork et al., "Go hunting in sequence databases but watch out for the traps," *Trends in Genetics*, 12(10):425-427 (1996).

Bork, P., "Powers and Pitfalls in Sequence Analysis: The 70% Hurdle," *Genome Research*, 10:398-400 (2000).

Borras-Cuesta et al., "Engineering of Immunogenic Peptides by Co-Linear Synthesis of Determinants Recognized by B and T Cells," Eur. J. Immunol., 17:1213-1215 (1987).

Brazil et al., "Effects of Incorporation of Immunoglobulin G and Complement Component C1q on Uptake and Degradation of Alzheimer's Disease Amyloid Fibrils by Microglia," *J. Biol. Chem.*, 275(22):16941-16947 (2000).

Brenner, S. E., "Errors in genome annotation," *Trends in Genetics*, 15(4):132-133 (1999).

Brice et al., "Absence of the amyloid precursor protein gene mutation (APP717 : Val->lle) in 85 cases of early onset Alzheimer's disease," *J. Neurology, Neurosurg. Psychiatry*, 56:112-115 (1993).

Brinkman, "Splice Variants as Cancer Biomarkers," *Clinical Biochemisrty*, 37(7):584-594 (2004).

Britt et al., "Formulation of an immunogenic human cytomegalovirus vaccine: responses in mice," *J. Infect. Dis.*, 171:18-25 Abstract (1995).

Broadwell et al., "Serum proteins bypass the blood-brain fluid barriers for extracellular entry to the central nervous system," *Exp. Neurol.*, 120(2):245-263 (1993).

Brookmeyer et al., "Projections of Alzheimer's Disease in the United States and the Public Health Impact of Delaying Disease Onset," *Am. J. Public Health*, 88:1337-1342 (1998).

Burbach et al. "Vessel ultrastructure in APP23 transgenic mice after passive anti-Aβ immunotherapy and subsequent intracerebral hemorrhage" Neurobiology of Aging 28:202-212 (2007).

Burdick et al., "Assembly and aggregartion properties of synthetic Alzheimer's A4/β amyloid peptide antigens," *J. Biol. Chem.*, 267:546-555 (1992).

(56) References Cited

OTHER PUBLICATIONS

Bussiere et al., "Morphological Characterization of Thioflavin-S-Positive Amyloid Plaques in Transgenic Alzheimer Mice and Effect of Passive Aβ Immunotherapy on Their Clearance," *Am. J. Pathology*, 165(3):987-995 (2004).
Buttini et al., "β-Amyloid Immunotherapy Prevents Synaptic Degeneration in a Mouse Model of Alzheimer's Disease," *The Journal of Neuroscience*, 25(40):9096-9101 (2005).
Cameron, "Recent Advances in Transgenic Technology," *Molecular Biotechnology*, 7:253-265 (1997).
Caputo et al., "Therapeutic approaches targeted at the amyloid proteins in Alzheimer's disease," *Clin. Neuropharm.*, 15:414A-414B (1992).
Casadesus et al., "The Estrogen Myth: Potential Use of Gonadotropin-Releasing Hormone Agonists for the Treatment of Alzheimer's Disease," *Drugs R D*, 7(3):187-193 (2006).
Casey, S.O., "Posterior Reversible Encephalopathy Syndrome: Utility of Fluid-attenuated Inversion Recovery MR Imaging in the Detection of Cortical and Subcortical Lesions," *Amer J Neuroradiol*, 21:1199-1206 (2000).
Cassell et al., "Demography and Epidemiology of Age-Associated Neuronal Impairment," chapter 4, pp. 31-50 from *Funcitional Neurobiology of Aging*, Hof et al., eds., Academic Press (2001).
Casset et al., "A Peptide Mimetic of an Anti-CD4 Monoclonal Antibody by Rational Design," *Biochemical and Biophysical Research Commiunications*, 307:198-205 (2003).
Castillo et al., "Amylin / Islet Amyloid Polypeptide: Biochemistry, Physiology, Patho-Physiology," *Diabete & Metabolisme* (Paris), 21:3-25 (1995).
Center for Biologics Evaluation and Research, U.S. Food and Drug Administration, Thimerosal in Vaccines (Mercury in Plasma-Derived Products), web site contents found at : www.fda.gov/cber/vaccine/thimerosal.htm, last updated May 16, 2002.
Chakrabarti et al., "Vaccinia Virus Expression Vector: Coexpression of B-Galactosidas Provides Visual Screening of Recombinant Virus Plaques," *Molecular and Cellular Biology*, 5(12):3403-3409 (1985).
Chang et al., "Adjuvant activity of incomplete Freund's adjuvant," *Advanced Drug Delivery Reviews*, 32:173-186 (1998).
Chao et al., "Transforming Growth Factor-β Protects human Neurons Against β-Amyloid-Induced Injury," *Soc. Neurosci. Abstracts*, 19:513-7 (1993).
Chapman, "Model behavior," *Nature*, 408:915-916 (2000).
Chauhan et al. "Intracerebroventricular Passive Immunization With Anti-Aβ Antibody in Tg2576" J of Neuroscience 74:142-147 (2003).
Check, "Battle of the Mind," *Nature*, 422:370-372 (2003).
Check, "Nerve Inflamtion Halts Trail for Alzheimer's Drugs," Nature, 415:462 (2002).
Chemical Abstract database, Abstract of "Injection of Newborn Mice with Seven Chemical Adjuvants to Help Determine Their Safety in Use in Biologicals," Chemical Abstract database, 75:242 (1971).
Chen et al., "Neurodegenerative Alzheimer-like pathology in PDAPP 717V→F transgenic mice," *Progress in Brain Research*, 117:327-337 (1998).
Chen et al., "A learning deficit related to age and beta-amyloid plaques in a mouse model of Alzheimer's disease," *Nature*, 408(6815):975-979 (2000).
Chen et al., "An Antibody to β Amyloid Precursor Protein Inhibits Cell-substratum Adhesion in Many Mammalian Cell Types," *Neuroscience Letters*, 125:223-226 (1991).
Chen et al., "Selection and Analysis of an Optimized Anti-VEGF Antibody: Crystal Structure of an Affinity-matured Fab in Complex with Antigen," *J. Mol. Biol.*, 293:865-881 (1999).
Chimicon International, "Mouse Anti-Amyloid Beta Protein Monoclonal Antibody," Catalog # MAB1561 (2003-2005).
Chishti et al., "Early-onset Amyloid Deposition and Cognitive Deficits in Transgenic Mice Expressing a Double Mutant Form of Amyloid Precursor Protein 695," *J. Biol.Chem.*, 276(24):21562-70 (2001).

Choi et al., "A Generic Intron Increases Gene Expression in Transgenic Mice," Molecular and Cellular Biology, 11(6):3070-3074 (1991).
Chothia et al., "Domain Association in Immunoglobulin Molecules," *J. Mol. Biol.*, 186:651-663 (1985).
Chromy et al., "Self-assembly of Aβ(1-42) into globular neurotoxins," *Biochemistry*, 42(44):12749-12760 (2003).
Chung et al., "Uptake, Degradation, and Release of Fibrillar and Soluble Forms of Alzheimer's Amyloid β-Peptide by Microglial Cells," *J. Biol. Chem.*, 274(45):32301-32308 (1999).
Cirrito et al., "Amyloid β and Alzheimer disease therapeutics: the devil may be in the details," *J. Clin. Invest.*,112:321-323 (2000).
Citron et al., "Evidence that the 42- and 40-amino acid forms of amyloid-β protein are generated from the β-amyloid precursor protein by different protease activities," *PNAS*, 93(23):13170-13175 (1996).
Citron, M., "Alzheimer's disease: treatments in discovery and development," *Nat. Neurosci.*, 5:1055-1057 (2002).
Clark et al., Chemical Immunology Antibody Engineering IgG Effector Mechanisms, 65:88-110 (1997).
Claudio, "Ultrastructural features of the blood-brain barrier in biopsy tissue for Alzheimer's disease patients." *Acta Neuropathol.* 91:6-14 (1996).
Clayton et al., "Synucleins in Synaptic Plasticity and Neurodegenerative Disorders," *J. Neurosci. Res.*, 58:120-129 (1999).
Co et al., "Chimeric and humanized antibodies with specificity for the CD33 antigen," *J. Immunol.*, 148:1149-1154 (1992).
Coico et al., *Immunology a Short Course*, Fifth Edition, pp. 18-24 (2003).
Colman, "Effects of Amino Acid Sequence Changes on Antibody-Antigen Interactions," *Research in Immunology*, 145:33-36 (1994).
Coloma et al., "Transport Across the Primate Blood-Brain Barrier of a Genetically Engineered Chimeric Monoclonal Antibody to the Human Insulin Receptor," *Pharm. Res.*, 17:266-274 (2000).
Colombian Patent Application No. 98071271, Technical Opinion of Jean Paul Vernot submitted on Jun. 22, 2005 as evidence with the brief amending the nullity action (with English translation) (drafted Nov. 2004).
Comery et al., "Passive Immunization Against β-Amyloid Leads to Acute Cognition Improvement," *Society for Neuroscience*, abstract, Washington DC, Nov. 12-16, 2005.
Constantino, Expert opinion Sep. 17, 2010.
Conway et al., "Acceleration of oligomerization, not fibrillization, is a shared property of both α-synuclein mutations linked to early-onset Parkinson's disease: Implications for pathogenesis and therapy," *PNAS*, 97(2):571-576 (2000).
Corcoran et al., "Overexpression of hAPPswe Impaires Rewarded Alternation and Contextual Fear Conditioning in a Transgenic Mouse Model of Alzheimer's Disease," Learn Mem. 9(5):243-252:2000.
Cordell, B., "β-Amyloid formation as a potential therapeutic target for Alzheimer's disease," *Ann. Rev. Pharmacol. Toxicol.*, 34:69-89 (1994).
Corey-Bloom et al., "Clinical features distinguishing large cohorts with possible AD, probable AD, and mixed dementia," *J. Am. Geriatr. Soc.*, 41(1):31-37 Abstract (1993).
Costa et al., "Immunoassay for transthyretin variants associated with amyloid neuropathy," *Scand. J. Immunol.*, 38:177-182 (1993).
Cox et al., "Adjuvants—a classification and review of their modes of action," *Vaccine*, 15(3):248-256 (1997).
Cribbs et al, "All-D-Erantiomers of Beta-Amyloid Exhibit Similar Biological Properties to All-L-Beta-Amyloids," *J. Biol. Chem.*, 272:7431-7436 (1997).
Cribbs et al., "Adjuvant-dependant modulation of th1 and th2 responses to immunization with B-amyloid", International Immunology, 2003, vol. 15, No. 4, pp. 505-514.
Daly, et al., "Detection of the membrane-retained carboxy-terminal tail containing polypeptides of the amyloid precursor protein in tissue from Alzheimer's Disease brain," *Life Sci.*, 63:2121-2131 (1998).
Das et al., "Amyloid-β Immunization Effectively Reduces Amyloid Deposition in FcRγ Knock-Out-Mice," *J. Neuroscience*, 23(24):8532-8538 (2003).

(56) References Cited

OTHER PUBLICATIONS

Das et al., "Reduced effectiveness of Aβ-42 immunization in APP transgenic mice with significant amyloid deposition," *Neurobiology of Aging*, 22:721-727 (2001).
Database Geneseq, "Nucleotide Sequence of a Variable Heavy Chain of IgG4," EBI Accession No. GSN:ADZ51216 (2005).
Davis, S. S., "Nasal Vaccines," *Advanced Drug Delivery Reviews*, 51:21-42 (2001).
De Felice et al., "β-Amyloid production, aggregation, and clearance as targets for therapy in Alzheimer's disease," *Cell Mol. Neurobiol.*, 22(5/6):545-563 (2002).
De La Cruz et al, "Immumogenicity [sic] and Epitope Mapping of Foreign Sequences via Genetically Engineered Filamentous Phage," *J Biol Chem*, 263(9):4318-4322 (1988).
De Lustig et al., "Peripheral Markers and Diagnostic Criteria in Alzheimer's Disease: Critical Evaluations," *Rev. in Neurosciences*, 5:213-225 (1994).
Declaration of Dr. Mattias Staufenbiel Ph D. Jul. 15, 2011.
Demattos et al., "Brain to plasma amyloid-β efflux: a measure of brain amyoid burden in a mouse model of Alzheimer's disease," *Science*, 295(5563):2264-2267 (2002).
Demattos et al., "Peripheral anti-Aβ antibody alters CNS and plasma clearance and decreases Aβ burden in a mouse model of Alzheimer's disease," *PNAS*, 98(15):8850-8855 (2001).
Demattos et al., "Plaque-associated disruption of CSF and plasma amyloid-β (Aβ) equilibrium in a mouse model of Alzheimer's disease," *J. Neurochem.*, 81:229-236 (2002).
Demattos et al., "Peripheral Anti Aβ Antibody Alters CNS and Plasma Aβ Clearance and Decreases Brain Aβ Burden in a Mouse Model of Alzheimer's Disease," published online before print Jul. 3, 2001 at 10.1073/pnas.151261398; *PNAS*, 98(15):8850-8855 (2001).
Dewitt et al., "Astrocytes regulate microglial phagocytosis of senile plaque cores of Alzheimer's disease," *Experimental Neurology*, 149:329-340 (1998).
Di Martino et al., "Production and Characterization of Antibodies to Mouse Scrapie-Amyloid Protein Elicited by Non-carrier Linked Synthetic Peptide Immunogens," *J. Molecular Recognition*, 4(2-3):85-91 (1991).
Dialog/Derwent, Abstract of WPI Acc No. 1995-261292/199534: Novel monoclonal antibody against human high-affinity IgE receptor—and DNA fragment encoding the MAb, for the specific identification of human Fc-epsilon RI, Derwent WPI database (1995).
Dialog/Derwent, Abstract of WPI Acc No. 1997-054436/199706: Stable vaccine compsns.—comprise a macrocyclic lactone, a milbemycin, an avermectin, an antigen, a dispersing agent, an adjuvant, a water sol. organic solvent and saline or water, Derwent File 351: Derwent WPI database (1997).
Dickey et al., "Duration and specificity of humoral immune responses in mice vaccinated with the Alzheimer's disease-associated β-amyloid 1-42 peptide," *DNA and Cell Biology*, 20(11):723-729 (2001).
Dickson et al., "Neuroimmunology of Alzheimer's disease: a conference report," *Neurobiology of Aging*, 13(6):793-798 (1992), abstract only.
Dictionary.com definition of "prophylactic", pp. 1-3 downloaded from internet Oct. 12, 2005.
Diomede et al., "Activation effects of a prion protein fragment [PrP-(106-126)] on human leucocytes," *Biochem. J.*, 320:563-570 (1996).
Disis et al., "Granulocyte-macrophage colony-stimulating factor: An effective adjuvant for protein and peptide-based vaccines," *Blood*, 88(1):202-210 (1996).
Do et al., "Reprogramming Somatic Gene Activity by Fusion With Pluripotent Cells" *Stem Cell Reviews.*, 2:257-264 (2006).
Dodart et al., "Immunization reverses memory deficits without reducing brain Aβ burden in Alzheimer's disease model," *Nat. Neurosci.*, 5(5):452-457 (2002).
Dodart, "Immunotherapy for Alzheimer's disease: will vaccination work?," *Trends in Molecular Medicine*, 9(3):85-87 (2003).
Dodel et al., "Immunotherapy for Alzheimer's disease," *Lancet Neurol.*, 2(4):215-220 (2003).

Doerks et al., "Protein annotation: detective work for function prediction," *Trends in Genetics*, 14(6):248-250 (1998).
Donnelly, "New Developments in Adjuvants," *Mechanism of Ageing and Development*, 93:171-177 (1997).
Dovey et al., "Functional gamma-secretase inhibitors reduce beta-amyloid peptide levels in brain," *J. Neurochem.*, 76(1):173-181 (2001).
Drew et al., "Vaccination by cholera toxin conjugated to a herpes simplex virus type 2 glycoprotein D peptide," *Journal of General Virology*, 73:2357-2366 (1992).
Du et al., "$\alpha_2$-Macroglobulin as a β-Amyloid Peptide-Binding Plasma Protein," *J. Neurochemistry*, 69(1):299-305 (1997).
Du et al., "Reduced levels of amyloid beta-peptide antibody in Alzheimer disease," *Neurology*, 57(5):801-5 (2001).
Duff et al., "Increased amyloid-β42(43) in brains of mice expressing mutant presenilin 1," *Nature*, 383(6602):710-713 (1996).
Duff et al., "Mouse model made," *Nature*, 373:476-477 (1995).
Dumery et al., "β-Amyloid protein aggregation: its implication in the physiopathology of Alzheimer's disease," *Pathol. Biol.*, 49:72-85 (2001).
Eck et al., *Goodman and Gilman's the pharmacological basis of therapeutics*, Chapter 5, pp. 77-101 (1996).
Ecuador Patent Application No. SP 98-2764, English translation of Expert Report submitted Apr. 19, 2007 in support of the Appeal filed on Jul. 29, 2005.
Ecuadorian Search Report of Jul. 2, 2009 for Ecuador Patent Application No. SP 03-4685.
El-Agnaf et al., "The influence of the central region containing residues 19-25 on the aggregation properties and secondary structure of Alzheimer's beta-amyloid peptide," *Eur. J. Biochem.*, 256(3):560-569 (1998).
Elan Reports First Quarter 2006 Financial Results. Business Wire (May 4, 2006) XP002620724.
Elan Reports First Quarter 2006 Financial Results. Business Wire (May 4, 2006) XP002620725.
Elan, "Elan and AHP Provide an Update on the Phase 2A Clinical Trial of AN-1792," Press Release. (Jan. 18, 2002).
Elan, "Elan and Wyeth Provide Update on Status of Alzheimer's Collaboration," Press Release (Mar. 1, 2002).
Elizan et al., "Antineurofilament antibodies in a postencephalitic and idiopathic Parkinson's disease," *J. Neurol. Sciences*, 59:341-347 (1983).
Eriksen et al., "NSAIDs and enantiomers of flurbiprofen target γ-secretase and lower Aβ42 in vivo," *J. Clin. Invest.*, 112(3):440-449 (2003).
Esiri, "Is an effective immune intervention for Alzheimer's disease in prospect?," *Trends in Pharm, Sci.*, 22:2-3 (2001).
Esler et al., "Point substitution in the central hydrophobic cluster of a human β-amyloid congener disrupts peptide folding and abolishes plaque competence," *Biochemistry*, 35:13914-13921 (1996).
European Examination Report as part of Dec. 8, 2008 communication for European Application 04720353.4.
European Examination Report of Mar. 9, 2007 for European Application 01995364.5-1222.
European Examination Report of Sep. 23, 2008 for European Application 04776252.1-2405.
European Examination Report of Sep. 26, 2007 for European Application 04720353.4-1222.
European Examination Report of Oct. 8, 2007 for European Application 01995364.5-1222.
European Examination Report of Nov. 20, 2008 for European Application 08011409.3.
European Search Report of Feb. 7, 2011 for European Application EP 08 74 6362.6.
European Search Report of Jan. 16, 2007 for European Application 04776252.1-2405.
European Search Report of May 22, 2006 for European Application 06075479.3-2107.
European Search Report of May 22, 2006 for European Application 06075704.4-2107.
Extended European Search Report of Dec. 18, 2008 for European Application 05812436.6-1212.
Family and legal status of EP0613007, Inpadoc Search (2009).

(56) References Cited

OTHER PUBLICATIONS

Felsenstein et al., "Processing of the β-amyloid precursor protein carrying the familial, Dutch-type, and a novel recombinant C-terminal mutation," *Neuroscience Letters*, 152:185-189 (1993).
Felsenstein et al., "Transgenic Rat and In-Vitro Studies of B-Amyloid Precursor Protein Processing;" *Alzheimer's and Parkinson's Diseases*, Hanin et al. Ed., pp. 401-409, Plenum Press, New York, (1995).
Finch et al., "Evolutionary Perspectives on Amyloid and Inflammatory Features of Alzheimer Disease," *Neurobiology of Aging*, 17(5):809-815 (1996).
Findeis et al, "Modified peptide inhibitors of amyloid B-peptide polymerization," *Biochemistry*, 38:6791-6800 (1999).
Findeis, M. A., "Approaches to discovery and characterization of inhibitors of amyloid β-peptide polymerization," *Biochem. Bioghys. Acta*, 1502(1):76-84 (2000).
Fisher et al., "Expression of the amyloid precursor protein gene in mouse oocytes and embryos," *PNAS*, 88:1779-1782 (1991).
Flanders et al., "Altered expression of transforming growth factor-β in Alzheimer's disease," *Neurology*, 45:1561-1569 (1995).
Flood et al., "An amyloid β-Protein fragment, A β [12-28J, equipotently impairs post-training memory processing when injected into different limbic system structures," *Brain Res*, 663(2):271-276 (1994).
Flood, et al, "Topography of a binding site for small amnestic peptides deduced from structure-activity studies: Relation to amnestic effect of amyloid B protein," *PNAS*, 91:380-384 (1994).
Fonseca et al., "The Presence of Isoaspartic Acid in β-Amyloid Plaques Indicates Plaque Age," *Experimental Neurology*, 157(2):277-288 (1999).
Foote et al., "Antibody Framework Residues Affecting the Conformation of the Hypervariable Loops," *J. Mol. Biol.*, 224:487-499 (1992).
Fox et al., "Presymptomatic cognitive deficits in individuals at risk of familial Alzheimer's disease," *Brain*, 121:1631-1639 (1998).
Frangione et al., Familial cerebral amyloid angiopathy related to stroke and dementia. *Amyloid*, 8(Suppl 1):36-42 (2001), abstract only.
Frautschy et al., "Effects of injected Alzheimer β-amyloid cores in rat brain," *PNAS*, 88:8362-8366 (1991).
Frazer et al., "Immunoglobulins: Structure and Function," chapter 3, pp. 37-74 from *Fundamental Immunology*, fourth edition, W.E. Paul, eds., Lippincott-Raven publishers, Philadelphia (1999).
Frenkel et al., "Generation of auto-antibodies towards Alzheimer's disease vaccination," *Vaccine*, 19:2615-2619 (2001).
Frenkel et al., "High affinity binding of monoclonal antibodies to the sequential epitope EFRH of β-amyloid peptide is essential for modulation of fibrillar aggregation," *J. of Neuroimmunology*, 95:136-142 (1999).
Frenkel et al., "Immunization against Alzheimer's β-amyloid plaques via EFRH phage administration," *PNAS*, 97:11455-11459 (2000).
Frenkel et al., "N-terminal EFRH sequence of Alzheimer's β-amyloid peptide represents the epitope of its anti-aggregating antibodies," *J. of Neuroimmunology*, 88:85-90 (1998).
Frenkel et al., "Reduction of β-amyloid plaques in brain of transgenic mouse model of Alzheimer's disease by EFRH-phage immunization," *Vaccine*, 21(11-12):1060-1065 (2003).
Frenkel et al., "Towards Alzheimer's β-amyloid vaccination," *Biologicals*, 29(3-4):243-247 (2001).
Frenkel, et al., "Modulation of Alzheimer's β-amyloid neurotoxicity by site-directed single chain antibody," *J. of Neuroimmunology*, 106:23-31 (2000).
Friedland et al., "Development of an anti-Aβ monoclonal antibody for in vivo imaging of amyloid angiopathy in Alzheimer's disease," *Mol. Neurology*, 9:107-113 (1994).
Friedland, et al., "Neuroimaging of Vessel Amyloid in Alzheimer's Disease," in *Cerebrovascular Pathology in Alzheimer's Disease*, eds. de la Torre and Hachinski, New York Academy of Sciences, New York, New York, 826:242-247 (1997).

Fukutani et al., "Cerebeller pathology in sporadic and familial Alzheimer's disease including APP 717 (Val->lle) mutation cases: A morphometric investigation," *J. Neurologic Sci.*, 149:177-184 (1997).
Furlan et al., "Vaccination with amyloid-β peptide induces autoimmune encephalomyelitis in C57/BL6 mice," *Brain*, 126:285-291 (2003).
Games et al., "Alzheimer-type neuropathology in transgenic mice overexpressing V717F β-amyloid precursor protein," *Nature*, 373(6514):523-527 (1995).
Games et al., "Prevention and Reduction of AD-type Pathology in PDAPP Mice Immunized with $A\beta_{1-42}$," *Annals of the New York Academy of Science*, 920:274-284 (2000).
Gandy et al., "Amyloidogenesis in Alzheimer's disease: some possible therapeutic opportunities," *TiPS*, 13:108-113 (1992).
Gardella et al., "Intact Alzheimer amyloid precursor protein (APP) is present in platelet membranes and is encoded by platelet mRNA," *Biochem. Biophys. Res. Comm.*, 173:1292-1298 (1990).
Gaskin et al., "Human antibodies reactive with beta-amyloid protein in Alzheimer's disease," *J. Exp. Med.*, 177:1181-1186 (1993).
Gauthier et al., "Alzheimer's Disease: Current Knowledge, Management and Research," Can. Med. Assoc. J., 157:1047-1052 (Oct. 15, 1997).
Geddes, "N-terminus truncated β-amyloid peptides and C-terminus truncated secreted forms of amyloid precursor protein: distinct roles in the pathogenesis of Alzheimer's disease," *Neurobiology of Aging*, 20:75-79 (1999).
Gelinas et al., "Immunotherapy for Alzheimer's disease," *PNAS*, 101(suppl. 2):14657-14662 (2004).
Genbank Accession No. AAD00856.1, "Igm Heavy Chain Variable Region [*Homo sapiens*]," Jul. 31, 2001.
Genbank Accession No. AAA69734, Schroeder et al., "Immunoglobulin heavy chain [*Homo sapiens*]", Anti-DNA immunoglobulin light chain IgG [Mus musculus], Jul. 11, 1995.
Genbank Accession No. AAB35009.1, Wang et al., "Antiidiotypic Ig 1F7 Light Chain Variable Region [Human, 1F7 Hybridoma Cells, Peptide Partial, 120aa]," Oct. 28, 1995.
Genbank Accession No. AAB48800, "Anti-DNA immunoglobulin light chain IgG [*Mus musculus*]," Sep. 14, 2001.
Genbank Accession No. AAD26773, "Immunoglobulin heavy chain VH3609-JH3 region [*Mus musculus*]," Apr. 22, 1999.
Genbank Accession No. BAC01733, Akahori et al., "Immunoglobulin kappa light chain VLJ region [*Homo sapiens*]", Jul. 2, 2002.
Genbank Accession No. CAA46659, "IgE antibody light chain(VJ)," Jun. 15, 1993.
Genbank Accession No. X65775.1, "*M.musculus* DNA for IgE antibody light chain (VJ)," Jun. 15, 1993.
Geylis et al., "Immunotherapy of Alzheimer's disease 9AD): From murine models to anti-amyloid beta 9Ab) human monodonal antibodies," *Autoimmunity Rev.*, 5:33-39 (2000).
Ghersi-Egea et al., "Fate of Cerebrospinal Fluid-Borne Amyloid β-Peptide: Rapid Clearance into Blood and Appreciable Accunulation by Cerebral Arteries," *Journal of Neurochemistry*. vol. 67 No. 2:880-883 (1996).
Ghetie et al., "CD4 Peptide-Protein Conjugates, But Not Recombinant Human CD4, Bind to Recombinant gp120 From the Human Immunodeficiency Virus in the Presence of Serum From AIDS Patients.," Proc. Nat. Acad. Sci., 88:5690-5693 (1991).
Ghiso et al., "Epitope map of two polyclonal antibodies that recognize amyloid lesions in patients with Alzheimer's disease," *Biochem. J.*, 282 (Pt 2):517-522 (1992).
Ghochikyan, "Rationale for Peptide and DNA Based Epitope Vaccine for Alzheimer's Disease Immunotherapy", CNS Neurol Disord Drug Targets, 2009: 8(2): 128 1-18.
Gibson et al., "Abnormalities in Alzheimer's Disease Fibroblasts Bearing the APP670/671 Mutation," *Neurobiology of Aging*, 18(6):573-580 (1997).
Gilman, S. et al., "Clinical Effects of Aβ Immunization (AN1792) in Patients with AD in an Interrupted Trial," *Neurology*, 64(9):1553-1562 (2005).

(56) References Cited

OTHER PUBLICATIONS

Giulian et al., "Specific domains of β-amyloid from Alzheimer plaque elicit neuron killing in human microglia," *J Neurosci.*, 16 (19):6021-6037 (1996).
Giulian, et al., "The HHQK Domain of b-Amyloid Provides a Structural Basis for the Immunopathology of Alzheimer's Disease," *J. Biol. Chem..*, 273:29719-29726 (1998).
Glenn et al., "Skin immunization made possible by cholera toxin," *Nature*, 391:851 (1998).
Glenner et al., "Alzheimer's Disease and Downs Syndrome: Sharing of a Unique Cerebrovascular Amyloid Fibril Protein," *Biochem. Biophys. Res. Comm.*, 122(3): 1131-1135 (1984).
Glenner et al., "Alzheimer's Disease: Initial Report of the Purification and Characterization of a Novel Cerebrovascular Amyloid Protein," *Biochem. Biophys. Res. Comm.*, 120(3): 885-890 (1994).
Goate et al., "Segregation of a missense mutation in the amyloid precursor protein gene with familial Alzheimer's disease," Nature, 349:704-706 (1991).
Goldfarb et al., "The Transmissible Spongiform Encephalopathies," *Ann. Rev. Med.*, 46:57-65 (1995).
Golding et al., "Vaccine Strategies: Targeting Helper T Cell Responses," *Annals New York Academy of Sciences*, 31:126-137 (1995).
Goldsby et al., "Vaccines," Chapter 18 from *Immunology, 4th Edition*, W.H. Freeman and Company, New York, pp. 449-465 (2000).
Goldsteins et al., "Éxposure of cryptic epitopes on transthyretin only in amypoid and in amyloidogenic mutants," *PNAS*, 96:3108-3113 (1999).
Gong et al., "Alzheimer's disease-affected brain: presence of oligomeric Aβ ligands (ADDLs) suggests a molecular basis for reversible memory loss," *PNAS*, 100(18):10417-10422 (2003).
Gonzales-Fernandez et al., "Low antigen dose favors selection of somatic mutants with hallmarks of antibody affinity maturation," *Immunology*, 93:149-153 (1998).
Gorevic et al., "Ten to Fourteen Residue Peptides of Alzheimer's Disease Protein are Sufficient for Amyloid Fibril Formation and Its Characteristic X Ray Diffraction Pattern" *Biochem. and Biophy. Res. Commun.*, 147(2):854-862 (1987).
Gortner, *Outlines of Biochemistry*, pp. 322-323, John Wiley & Sons, Inc., New York (1949).
Gozes et al., "Neuroprotective strategy for Alzheimer disease: Intranasal administration of a fatty neuropeptide," *PNAS*, 93:427-432 (1996).
Gravina et al., "Amyloid β Protein (Aβ) in Alzheimer's Disease," *J. Biol. Chem.*, 270(13):7013-7016 (1995).
Greenberg et al. "Amyloid Angiopathy-Related Vascular Congnitive Impairment" Stoke., 35:2616-2619 (2004).
Greenberg et al., "Alzheimer disease's double-edged vaccine," *Nat. Med.*, 9(4):389-390 (2003).
Greisman et al., "A General Strategy for Selecting High-Affinity Zinc finger Proteins for Diverse DNA Target Sites" Science vol. 275:657-661 (1997).
Gross et al., "Microvascular specializations promoting rapid interstitial solute dispersion in nucleus tractus solitarius," *Am J Physiol Regul Integr Comp Physiol*, 259:R1131-R1138 (1990).
Grubeck-Loebenstein, et al., "Immunization with β-amyloid: could T-cell activation have a harmful effect?", *TINS*, 23:114 (2000).
Gupta et al., "Differences in the immunogenicity of native and formalinized cross reacting material ($CRM_{197}$) of diptheria toxin in mice and guinea pigs and their implications on the development and control of diphtheria vaccine based on CRMs," *Vaccine*, 15(12/13): 1341-1343 (1997).
Gupta et al., "Adjuvants for human vaccines—current status, problems, and future prospects," *Vaccine*, 13(14):1263-1275 (1995).
Gustavsson et al., "Mechanisms of Transthyretin Amyloidogenesis Antigenic Mapping of Transthyretin Pruified from Plasma and Amyloid Fibrils and within in Situ Tissue Localizations" American Journal of Pathology 44(6):1301-1311 (1994).
Haass et al. "Amyloid beta-peptide is produced by cultured cells during normal metabolism," *Nature*, 359(6393):322-325 (1992).

Haass et al., "Protofibrils, the unifying toxic molecule of neurodegenerative disorders?," *Nature Neuroscience*, 4(9):859-860 (2001).
Haass, C., "New hope for Alzheimer disease vaccine," *Nat Med.*, 8(11):1195-1196 (2002).
Haga et al., "Synthetic Alzheimer amyloid β/A4 peptides enhance production of complement C3 component by cultured microglial cells," *Brain Research*, 601:88-94 (1993).
Hamilton, "Molecular Engineering: Applications to the Clinical Laboratory," Clin. Chem. 39(9):1988-1997 (1993).
Hanan and Solomon, "Inhibitory effect of monoclonal antibodies on Alzheimer's β-amyloid peptide aggregation," *Int. J. Exp. Clin. Invest.*, 3:130-133 (1996).
Hanes et al., "New advances in microsphere-based single-dose vaccines," *Advanced Drug Delivery Reviews*, 28: 97-119 (1997).
Hara et al., "Development of a safe oral Aβ vaccine using recombinant adeno-associated virus vector for Alzheimer's disease," *J. Alzheimer's Disease*, 6:483-488 (2004).
Hardy, "Amyloid, the presenilins and Alzheimer's disease," *TINS*, 20(4): 154-159 (1997).
Hardy, John, "New Insights into the Genetics of Alzheimer's Disease," *Annals of Med.*, 28:255-258 (1996).
Harigaya, et al., "Modified amyloid β protein ending at 42 or 40 with different solubility accumulates in the brain of Alzheimer's disease," Biochem. Biophys. Res. Comm., 211:1015-1022 (1995).
Harlow et al., eds., *Antibodies: A Laboratory Manual*, p. 98 (1988).
Harlow et al., eds., *Antibodies: A Laboratory Manual*, pp. 139-195 (1988).
Harlow et al., eds., *Antibodies: A Laboratory Manual*, pp. 71-82 (1988).
Harrington et al., "Characterization of an epitope specific to the neuron-specific isoform of human enolase recognized by a monoclonal antibody raised against a synthetic peptide corresponding to the C-terminus of β / A4-protein," *Biochimica Biophysica Acta*, 1158:120-128 (1993).
Hartwig, "Immune ageing and Alzheimer's disease," *NeuroReport*, 6:1274-1276 (1995).
Hazama, et al., "Intranasal Immunization Against Herpes Simplex Virus Infection by Using a Recombinant Glycoprotein D Fused With Immunomodulating Proteins, the B Subunit of *Escherichia coli* Heat-Labile Enterotoxin and Interleukin-2," *Immunology*, 78:643-649 (1993).
He et al., "Humanization and pharmacokinetics of a monoclonal antibody with specificity for both E- and P-selectin," *J. Immunol*, 160:1029-1035 (1998).
Hellman et al., "Allergy Vaccines—A Review of Developments," *Clin. Immunother*, 6(2): 130-142 (Aug. 1996).
Helmuth, "Further Progress on a β-Amyloid Vaccine," *Science*, 289:375 (2000).
Herlyn et al., "Monoclonal antibodies in cell-mediated cytotoxicity against human melanoma and colorectal carcinoma*," *Eur. J. Immunol.*, 9:657-659 (1979).
Hermanson et al., "Amino Acids as Spacers," *Immobilized Affinity Ligand Techniques*, section 3.1.1.5:150-152 (1992).
Hezareh et al., "Effector Function Activities of a Panel of Mutants of a Broadly Neutralizing Antibody against Human Immunodeficiency Virus Type 1," *Journal of Virology*, 24(75):12161-12168 (2001).
Hilbich et al., "Aggregation and secondary structure of synthetic amylold βA4 peptides of Alzheimer's disease," *J. Mol. Biol.*, 218:149-163 (1991).
Hilbich et al., "Human and rodent sequence analogs of Alzheimer's amyloid βA4 share similar properties and can be solubilized in buffers of pH 7.4," Eur. J. Biochem., 201:61-69 (1991).
Hilbich et al., "Substitutions of hydrophobic amino acid reduce the amyloidogenicity of Alzheimer's disease βA4 peptides" *J. Mol. Biol.*, 228:460-473 (1992).
Hillen-Maske et al., "Konichalcit", *Rompp Chemie Lexilkon*, 9th edition, p. 2322 (1990).
Hirschfield et al., "Amylodiosis: new strategies for treatment," *Int. J. Biochem. & Cell Biol.*, 35:1608-1613 (2003).
Hock et al., "Antibodies against β-Amyloid Slow Cognitive Decline in Alzheimer's Disease," *Neuron*, 38:542-554 (2003).

(56) References Cited

OTHER PUBLICATIONS

Hock et al., "Generation of antibodies specific for β-amyloid by vaccination of patients with Alzheimer disease," *Nat. Med.*, 8(11):1270-1275 (2002).
Hogarth, Fc Receptors Are Major Mediators of Antibody Based Inflammation in Autoimmunity, *Current Opinion in Immunology*, 14:798-802 (2002).
Holm et al., "Functional Mapping and Single Chain Construction of the Anti-Cytokeratin 8 Monoclonal Antibody TS1," *Mol. Immunol.*, 44(6):1075-1084 (Feb. 2007).
Holmes et al., "Long-term Effects of Aβ$_{42}$ Immunisation in Alzheimer's Disease: Follow-up of a Randomised, Placebo-controlled Phase I Trial," *Lancet*, 372: 216-223 (2008).
Holtzman et al., "Aβ immunization and anti-Aβ antibodies: potential therapies for the prevention and treatment of Alzheimer's disease," *Advanced Drug Delivery Reviews*, 54:1603-1613 (2002).
Hopp et al., "Prediction of protein antigenic determiniants from amino acid sequences," Proc. Natl. Acad. Sci. USA 78:3824-3828 (1981).
Hsiao et al., "Correlative Memory Deficits, Aβ Elevation, and Amyloid Plaques in Transgenic Mice," *Science*, 274: 99-102 (1996).
Huang et al., "Amyloid β-Peptide Possesses a Transforming Growth Factor-β-Activity," *The Journal of Biological Chemistry*, 273(42):27640-27644 (Oct. 16, 1998).
Huberman et al., "Correlation of cytokine secretion by mononuclear cells of Alzheimer's patients and their disease stage," *J. Neuroimmunology*, 52:147-152 (1994).
Hudson et al., "Antibody as a Probe," *Practical Immunology*, Chapter 2, pp. 34-85 (1989).
Human Immunology & Cancer Program brochure, from the University of Tennessee Medical Center/ Graduate School of Medicine, Knoxville, Tennessee (publication date unknown).
Hussain et al., "Selective Increases in Antibody Isotopes and Immunoglobulin G Subclass Responses to Secreted Antigens in Tuberculosis Patients and Healthy Household Contacts of the Patients," *Clinical and Diagnostic Laboratory Immunology*, 2(6):726-732 (1995).
Hyman et al., "Molecular Epidemiology of Alzheimer's Disease," *N. E. J. Medicine*, 333(19):1283-1284 (1995).
Hyslop et al., "Will Anti-amyloid Therapies Work for Alzheimer's Disease," *Lancet*, 372:180-182 (2008).
Ida et al., "Analysis of Heterogeneous βA4 Peptides in Juman Cerebrospinal Fluid and Blood by a Newly Developed Sensitive Western Blot Assay," *J. Biol. Chem.*, 271(37):22908-22914 (1996).
Idusogie et al., "Mapping of the C1q Binding Site on Rituxan, a Chimeric Antibody with a Human IgG1 Fc," *J. Immunology*, 164:4178-4184 (2000).
Ikeda, et al., "Immunogold labeling of cerebrovascular and neuritic plaque amyloid fibrils in Alzheimer's disease with an anti-β protein monoclonal antibody," Lab. Invest., 57:446-449 (1987).
Irizarry et al., "Alzheimer disease therapeutics," *J. Neuropathol. Exp. Neurol.*, 60(10):923-928 (2001).
Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 17(18):7053-7059 (1997).
Itagaki et al., "Relationship of microglia and astrocytes to amyloid deposits of Alzheimer's disease," *J. Neuroimmunology*, 24:173-182 (1989).
Iwatsubo et al., "Visualization of Aβ42(43) and Aβ40 in Senile Plaques with End-Specific AβMonoclonals: Evidence That an Initially Deposited Species Is Aβ 42(43)," *Neuron*, 13:45-53 (1994).
Jahrling et al., "Opsonization of Alphaviruses in Hamsters," *J. Medical Virology*, 12:1-16 (1983).
Jakes et al., "Characterisation of an Antibody Relevant to the Neuropathology of Alzheimer Disease," *Alzheimer Disease and Associated Disorders*, 9(1):47-51 (1995).
Janeway et al., *Immunobiology*, 3$^{rd}$ edition, pp. 2:7, 2:9, 2:12, 8:16-8:17, 12:43 (1997).
Janeway et al., *Immunobiology*, 3$^{rd}$ edition, pp. 8:18-8:19 (1997).

Jansen et al., "Immunotoxins: Hybrid Molecules Combining High Specificity and Potent Cytotoxicity," *Immun. Rev.*, 62: 185-216 (1982).
Jansen et al., "Use of Highly Encapsulated *Streptococcus pneumoniae* Strains in a Flow-Cytometric Assay for Assessment of the Phagocytic Capacity of Serotype-Specified Antibodies," *Clinical & Diagnostic Lab. Immunol.*, 5(5):703-710 (1998).
Janus et al., "A beta peptide immunization reduces behavioural impairment and plaques in a model of Alzheimer's disease," *Nature*, 408(6815):979-982 (2000).
Janus et al., "Transgenic mouse models of Alzheimer's Disease," *Physiol. Behav.*, 73(5):873-886 (2001).
Jarrett et al., "The Carboxy Terminus of the β Amyloid Protein is Critical for the Seeding of Amyloid Formation: Implications for the Pathogenesis of Alzheimer's Disease," *Biochemistry*, 32:4693-4697 (Nov. 5, 1993).
Jen, et al., "Preparation and purification of antisera against different regions or isoforms of b-amyloid precursor protein," *Brain Research Protocols*, 2:23-30 (1997).
Jennings, "Review of Selected Adjuvants Used in Antibody Production," *ILAR Journal*, 37(3) (1995).
Joachim et al., "Antibodies to Non-beta Regions of the Beta-amyloid Precursor Protein Detect a Subset of Senile Plaques," *Am. J. of Pathology*, 138:373-384 (1991).
Jobling et al., "Analysis of structure and function of the B subunit of cholera toxin by the use of site-directed mutagenesis," *Molecular Microbiology*, 5(7):1755-1767 (1991).
Johnson-Wood et al., "Amyloid precursor protein processing and Aβ42 deposition in a transgenic mouse model of Alzheimer disease," *PNAS*, 94: 1550-1555 (1997).
Johnson-Wood et al., "Amyloid precursor protein processing and Aβ$_{42}$ deposition in a transgenic mouse model of Alzheimer disease," *PNAS*, 94(4):1550-1555 (Feb. 18, 1997).
Johnstone et al., Nuclear and Cytoplasmic Localization of the β-Amyloid Peptide (1-43) in Transfected 293 Cells, *Biochem. Biophys. Res. Comm.*, 220:710-718 (1996).
Jorbeck et al., "Artificial *Salmonella* Vaccines: *Salmonella typhimurium* O-antigen-Specific Oligosaccharide-Protein Conjugates Elicit Opsonizing Antibodies that Enhance Phagocytosis," *Infection and Immunity*, 32(2):497-502 (1981).
Jung et al., "Alzheimer's Beta-amyloid Precursor Protein Is Expressed on the Surface of Immediately Ex Vivo Brain Cells: a Flow Cytometric Study," *J. Neurosci. Res.*, 46(3):336-348 (1996).
Kajkowski et al., "β-Amyloid Peptide-induced Apoptosis Regulated by a Novel Protein Containing a G Protein Activation Module," *J. Biol. Chem.*, 276(22):18748-18756 (2001).
Kalaria, R. N., "Serum amyloid P and related molecules associated with the acute-phase phase response in Alzheimer's disease," *Res. Immunology*, 143:637-641 (1992).
Kalback et al., "APP Transgenic Mice Tg2576 Accumulate Aβ Peptides That Are Distinct from the Chemically Modified and Insoluble Peptides Deposited in Alzheimer's Disease Senile Plaques," *Biochemistry*, 41:922-928 (2002).
Kallberg et al., "Prediction of Amyloid Fibril-Forming Proteins," *The Journal of Biological Chemistry*, 276(16):12945-12950 (Apr. 20, 2001).
Kardana et al., "Serum HCG β-Core Fragment is Masked by Associated Macromolecules," *Journal of Clinical Endocrinology and Metabolism*, 71(5):1393-1395.
Kascsak et al., "Mouse Polyclonal and Monoclonal Antibody to Scrapie-Associated Fibril Proteins," *J. Virology*, 61(12):3688-3693 (1987).
Katzav-Gozansky et al., "Effect of monoclonal antibodies in preventing carboxypeptidase A aggregation," *Biotechnol. Appl. Biochem.*, 23:227-230 (1996).
Kawabata et al., "Amyloid plaques, neurofibrillary tangles and neuronal loss in brains of transgenic mice overexpressing a C-terminal fragment of human amyloid precursor protein," *Nature*, 354:476-478 (1991).
Kayed et al., "Conformational Transitions of Islet Amyloid Polypeptide (IAPP) in Amyloid Formation In Vitro," *J. Mol. Biol.*, 287:781-796 (1999).

(56) References Cited

OTHER PUBLICATIONS

Kelly, J. W., "Alternative conformations of amyloidogenic proteins govern their behavior," *Current Opinion in Structural Biology*, 6:11-17 (1996).
Kettleborough et al., "Humanization of a mouse monoclonal antibody by CDR-grafting: the importance of framework residues on loop conformation," *Protein Engineering*, 4(7):773-783 (1991).
Khan et al., "Immunopotentiation and Delivery Systems for Antigens for Single-Step Immunization: Recent Trends and Progress," *Pharmaceutical Research*, 11(1):2-11 (1994).
Khatoon et al., "Levels of normal and abnormally phosphorylated tau in different cellular and regional compartments of Alzheimer's disease and control brains," *FEBS Letters*, 351:80-84 (1994).
Kida, et al., "Early amyloid-β deposits show different immunoreactivity to the amino- and carboxy-terminal regions of β-peptide in Alzheimer's disease and Down's syndrome brain," Neuroscience Letters, 193:105-108 (1995).
Kim et al., "In Vivo Engineering of a Cellular Immune Response by Coadministration of 1L-12 Expression Vector with a DNA Immunogen," *J. Immunol.*, 158:816-826 (1997).
Kimchi et al., "Analysis of cerebral amyloid angiopathy in a transgenic mouse model of Alzheimer disease using in vivo multiphoton microscopy," *J. Neuropath Exp. Neurol.*, 60(3):274-279 (2001).
Kinnecom et al., "Course of Cerebral Amyloid Angiopathy? Related Inflation," *Neurology*, 68(17):1411-1416 (2007).
Klein et al., "Targeting small Aβ oligomers: the solution to an Alzheimer's disease conundrum?," *Trends in Neurosciences*, 24(4):219-224 (2001).
Klyubin et al., "Anti-Aβ Antibodies Prevent Block of Long-Term Potentiation in the CA1 Area of Rat Hippocampus InVivo by naturally Produced Aβ Oligomers," *Neurobiology of Aging*, 25:S224-S225, abstract P2-004, pp. S224-S225 (2004).
Kofke et al., "Remifentanil-Induced Cerebral Blood Flow Effects in Normal Humans: Dose and ApoE genotype," *Neurosurg Anesthes Neurosci.*, 105(1):167-175 (2007).
Kofler et al., "Immunoglobulin $_\kappa$ Light Chain Variable Region Gene Complex Organization and Immunoglobulin Genes Encoding Anti-DNA Autoantibodies in Lupus Mice," *J. Clin. Invest.*, 82:852-860 (1988).
Kofler et al., "Mechanism of Allergic Cross-Reactions—III. cDNA Cloning and Variable-Region Sequence Analysis of Two IgE Antibodies Specific for Trinitrophenyl," *Mol. Immunology*, 29(2):161-166 (1992).
Koller et al., "Active Immunization of Mice with a Aβ-Hsp70 Vaccine," *Neurodegenerative Disases*, 1:20-28 (2004).
Konig et al., "Development and Characterization of a Monoclonal Antibody 369.2B Specific for the Carboxyl-Terminus of the βA4 Peptide," *Annals of NY Acad. Sci.*, 777:344-355 (1996).
Kotilinek et al., "Reversible memory loss in a mouse transgenic model of Alzheimer's disease," *J. Neurosci.*, 22(15):6331-6335 (2002).
Koudinov et al., "The soluble form of Alzheimer's amyloid beta protein is complexed to high density lipoprotein 3 and very high density lipoprotein in normal human plasma," *Biochem. & Biophys. Res. Comm*, 205:1164-1171 (1994).
Kovács et al., "Mutations of the Prion Protein Gene Phenotypic Spectrum," *J. Neurol.*, 249:1567-1582 (2002).
Krishnan et al., "Correlation Between the Amino Acid Position of Arginine in VH-CDR3 and Specificity for Native DNA Among Autoimmune Antibodies," *J. Immunol.*, 157(6):2430-2439 (1996).
Kuby, J., eds., p. 123 from *Immunology*, Third Edition, W.H. Freeman & co., (1997).
Kuby, J., eds., pp. 108-109, 131-132 from *Immunology*, Third Edition, W.H. Freeman & co., (1997).
Kuo et al., "Comparative Analysis of Amyloid-β Chemical Structure and Amyloid Plaque Morphology of Transgenic Mouse and Alzheimer's Disease Brains," *J. Biol. Chem.*, 276(16):12991-12998 (2001).
Kuo et al., "High levels of circulating Abeta42 are sequestered by plasma proteins in Alzheimer's disease," *Biochem. Biophys. Res. Comm.*, 257(3):787-791 (1999).
Kuo et al., "Water-soluble Aβ (N-40, N-42) Oligomers in Normal and Alzheimer Disease Brains," *J. Biol. Chem.*, 271(8):4077-4081 (1996).
Kurashima et al., "Production of Monoclonal Antibody against Amyloid Fibril Protein and Its InnMunohistochemical Application," *Appl. Pathol.*, 3(1-2):39-54 (1985).
LaDu et al., "Isoform-specific Binding of Apolipoprotein E to β-Amyloid," *J. Biol. Chem.*, 269(38):23403-23406 (1994).
Lambert et al., "Diffusible, nonfibrillar ligands derived from aβ1-42 are potent central nervous system neurotoxins," *PNAS*, 95:6448-6453 (1998).
Lambert et al., "Vaccination with soluble Aβ oligomers generates toxicity-neutralizing antibodies," *J. Neurochem.*, 79:595-605 (2001).
Lampert-Etchells et al., "Regional Localization of Cells Containing Complement C1q and C4 mRNAs in the Frontal Cortex During Alzheimer's Disease," *Neurodegeneration*, 2:111-121 (1993).
Landolfi et al., "The Integrity of the Ball- and Socket Joint Between V and C Domains Is Essential for Complete Activity of a Humanized Antibody," *J. Immunology*, 166(3):1748-1754 (2001).
Langer, "New Methods of Drug Delivery," *Science*, 249:1527-1532 (1990).
Lannfelt et al., "Alzheimer's disease: molecular genetics and transgenic animal models," *Behavioural Brain Res.*, 57:207-213 (1993).
Lansbury, Peter T., "Inhibition of amyloid formation: a strategy to delay the onset of Alzheimer's disease," Curr. Ops. in Chemical Biology, 1:260-267 (1997).
Lavie et al., "EFRH-Phage Immunization of Alzheimer's Disease Animal Model Improves Behavioral Performance in Morris Water Maze Trials," *J. Molecular Neuroscience*, 24:105-113 (2004).
Lee et al., "Aβ immunization: Moving Aβ peptide from brain to blood," *PNAS*, 98(16):8931-8932 (2001).
Lemere et al., "Intranasal immunotherapy for the treatment of Alzheimer's disease: *Escherichia coli* LT and LT(R192G) as mucosal adjuvants," *Neurobiology of Aging*, 23(6):991-1000 (2002).
Lemere et al., "Mucosal Administration of Aβ Peptide Decreases Cerebral Amyloid Burden in Pd-App Transgenic Mice," *Society for Neuroscience Abstracts*, 25(part )I, Abstract 519.6, 29th Annual Meeting, (Oct. 23-28, 1999).
Lemere, "Developing novel immunogens for a safe and effective Alzheimer's disease vaccine" Prog Brain Res. 2009; 175: 83 1-13.
Lemere, et al., "Nasal Aβ treatment induces anti-Aβ antibody production and decreases cerebral amyloid burden in PD-APP mice," Annals of the NY Acad. Sci., 920:328-331 (2000).
Leverone et al., "Aβ1-15 is less immunogenic than Aβ1-40/42 for intranasal immunization of wild-type mice but may be effective for 'boosting'," *Vaccine*, 21:2197-2206 (2003).
Levey, A. I., "Immunization for Alzheimer's disease: A shot in the arm or a whiff?," *Ann. Neurology*, 48(4):553-555 (2000).
Levitt, M., "Molecular dynamics of native protein," *J. Mol . Biol.*, 168:595-620 (1983).
Li et al., "Thermal Stabilization of Carboxypeptidase A as a Function of PH and Ionic Milieu," *Biochem. Mol. Biol. Int.*, 43(3):601-611 (1997).
Licastro et al., "Is immunotherapy an effective treatment for Alzheimer's disease?," *Immunity & Aging*, 1:1-2 (2004).
Linke, "Monoclonal antibodies against amyloid fibril protein AA. Production, specificity, and use for immunohistochemical localization and classification of AA-type amyloidosis," *J. Histochemistry and Cytochemistry*, 32(3):322-328 (1982).
Liu et al., "Amyloid β peptide alters intracellular vesicle trafficking and cholesterol homeostasis," *Proc. Natl. Acad. Sci.*, 95:13266-13271 (1998).
Livingston et al., "The Hepatitis B Virus-Specific CTL Responses Induced in Humans by Lipopeptide Vaccination Are Comparable to Those Elicited by Acute Viral Infection," *J. Immunol.*, 159:1383-1392 (1997).
Lo et al., "High level expression and secretion of Fc-X fusion proteins in mammalian cells," *Protein Engineering*, 11(6):495-500 (1998).

(56) References Cited

OTHER PUBLICATIONS

Lopez et al., "Serum auto-antibodies in Alzheimer's disease," *Acta. Neurol. Scand.*, 84:441-444 (1991).
Lue et al., "Soluble β-amyloid Peptide Concentration as a Predictor of Synaptic Change in Alzheimer's Disease," *Am. J. Pathol.*, 155:853-562 (1999).
MacCallum et al., Antibody-antigen Interactions: *Contact Analysis and Binding Site Topography*, 262:732-745 (1996).
Maggio et al., "Brain Amyloid—A Physicochemical Perspective," *Brain Pathology*, 6:147-162 (1996).
Majocha et al., "Development of a Monoclonal Antibody Specific for β/A4 Amyloid in Alzheimer's Disease Brain for Application to In Vitro Imaging of Amyloid Angiopathy," *The J. of Nuclear Med.*, 33:2184-2189 (1992).
Mak, et al., "Polyclonals to b-amyloid (1-42) identify most plaque and vascular deposits in Alzheimer cortex, but not striatum," *Brain Research*, 667:138-142 (1994).
Mamikonyan et al., "Anti-Aβ$_{1-11}$ Antibody Binds to Different β-Amyloid Species, Inhibits Fibril Formation, and Disaggregates Preformed Fibrils but Not the Most Toxic Oligomers," *J Biol Chem*, 282(31) 22376-22386 (2007).
Mandel et al., "Clinical trials in neurological disorders using AAV vectors: promises and challenges," *Curr. Opin. Mol. Ther.*, 6(5):482-490 (2004).
Mann et al., "Atypical Amyloid (Abeta) Deposition in the cerebellum in Alzheimer's Disease: An Immunohistochemical Study Using End-Specific Abeta Monoclonal Antibodies," *ACTA Neuropathologica*, 91:647-653 (1996).
Mann et al., "Predominant Deposition of Amyloid-B$_{42(43)}$ in Plaques in Cases of Alzheimer's Disease and Hereditary Cerebral Hemorrhage Associated with Mutations in the Amyloid Precursor Protein Gene," *The American Journal of Pathology APR*, 4(148):1257-1266 (1996).
Mann, et al., "The extent of amyloid deposition in brain in patients with Down's syndrome does not depend upon the apolipoprotein E genotype," Neuroscience Letters, 196:105-108 (1995).
Mann, et al., "Amyloid β protein (Aβ) deposition in chromosome 14-linked Alzheimer's disease: Predominance of Aβ$_{42(43)}$," *Annals of Neurology*, 40:149-156 (1996).
Manning et al., "Genetic Immunization with Adeno-Associated Virus Vectors Expressing Herpes Simplex Virus Type 2 Glycoproteins B and D," *Journal of Virology*, 71(10):7960-7962 (1997).
Manoj et al., "Approaches to Enhance the Efficacy of DNA Vaccines," *Critical Rev. Clin. Lab. Sci.*, 41(1):1-39 (2004).
Marhaug et al., "Monoclonal hybridoma antibodies to human amyloid related protein SAA," *Clin. Exp. Immunol.*, 50(2):390-396 (1982).
Marotta et al., "Overexpression of amyloid precursor protein A4 (β-amyloid) immunoreactivity in genetically transformed cells: Implications for a cellular model of Alzheimer amyloidosis," *PNAS*, 86:337-341 (1989).
Marshall, E., "Gene Therapy's Growing Pains," *Science*, 269:1050-1055 (1995).
Masliah et al., "Amyloid Protien Precursor Stimulates Excitatory Amino Acid Transport," *The Journal of Biological Chemisrty*, 273(20):12548-12554 (1998).
Masliah et al., "Comparison of Neurodegenerative Pathology in Transgenic Mice Overexpressing V717F β-Amyloid Precursor Protein and Alzheimer's Disease," *J. Neuroscience*, 16(18):5795-5811 (1996).
Masliah et al., "β-Amyloid peptides enhance α-synuclein accumulation and neuronal deficits in a transgenic mouse model linking Alzheimer's disease and Parkinson's disease," *PNAS*, 98(21):12245-12250 (2001).
Masters et al., "Amyloid Plaque core protein in Alzheimer Disease and Down Syndrome," *PNAS*, 82:4245-4249 (1985).
Mattson et al., "Good and bad amyloid antibodies," *Science*, 301(5641):1845-1849 (2003).

Mattson, "Cellular actions of beta-amyloid precursor protein and its soluble and fibrillogenic derivatives," *Physiol Rev.*, 77(4):1081-132 (1997).
Maury et al., "Immunohistochemical Localization of Amyloid in Finnish Hereditary Amyloidosis with Antibodies to Gelsolin Peptides," *Laboratory Investigation*, 64(3):400-404 (1991).
Mavragani et al., "A Case of Reversible Posterior Leucoencephalopathy Syndrome After Rityximab Infusion," *Rheumatology*, 43(11) 1450-1451 (2006).
McGee et al., "The encapsulation of a model protein in poly (D, L lactide-co-glycolide) microparticles of various sizes: an evaluation of process reproducibility," *J. Micro. Encap.*, 14(2):197-210 (1997).
McGeer, et al., "Immunohistochemical localization of beta-amyloid precursor protein sequences in Alzheimer and normal brain tissue by light and electron microscopy," *J. of Neuroscience Res.*, 31:428-442 (1992).
McLaurin et al., "Therapeutically effective antibodies against amyloid-β peptide target amyloid-β residues and 4-10 and inhibit cytotoxicity and fibrillogenesis," *Nat Med.*, 8(11):1263-1269 (2002).
McLean et al., "Soluble pool of Ab amyloid as a determinant of severity of neurodegeneration in Alzheimer's disease," *Amer. Neurological Assoc*, 46:860-866 (1999).
McNeal et al., "Stimulation of local immunity and protection in mice by intramuscular immunization with triple- or double-layered rotavirus particles and QS-21," *Virology*, 243:158-166 (1998).
Meda et al., "Activation of microglial cells by β-amyloid protein and interferon-γ," *Nature*, 374:647-650 (1995).
Mena, et al., "Monitoring pathological assembly of tau and β-amyloid proteins in Alzheimer's disease," *Acta Neuropathol.*, 89:50-56 (1995).
Merluzzi, et al., "Humanized antibodies as potential drugs for therapeutic use," *Adv Clin Path.*, 4(2):77-85 (2000).
Merriam-Webster online medical dictionary, entry for "cure", accessed Sep. 5, 2006.
Miller et al., "Antigen-driven Bystander Suppression after Oral Administration of Antigens," *J. Exp. Med.*, 174:791-798 (1991).
Misra et al., "Drug Delivery to the Central Nervous System: A review," *J. Pharm Pharm Sci.*, 6(2):252-273 (May 2003). Abstract.
Mitchell et al, "Prevention of Intracerebral Hemorrhage," *Current Drug Targets*, 8(7):832-838 (2007).
Monsonego et al., "Immune hyporesponsiveness to amyloid β-peptide in amyloid precursor protein transgenic mice: Implications for the pathogenesis and treatment of Alzheimer's disease," *PNAS*, 98(18):10273-10278 (2001).
Monsonego et al., "Increased T cell reactivity to amyloid β protein in older humans and patients with Alzheimer's disease," *J. Clin. Invest.*, 112(3):415-422 (2003).
Monsonego et al., "Immunotherapeutic approaches to Alzheimer's disease," *Science*, 302(5646):834-838 (2003).
Morgan et al., "The N-terminal end of the C$_H$2 domain of chimeric human IgG1 anti-HLA-DR is necessary for C1q, FcγRII and FcγRII binding," *Immunology*, 86:319-324 (1995).
Morgan, et al., "A beta peptide vaccination prevents memory loss in an animal model of Alzheimer's disease," *Nature*, 408(6815):982-985 (2000).
Mori et al., "Mass Spectrometry of Purified Amyloid β Protein in Alzheimer's Disease," *J. Biol. Chem.*, 267(24):17082-17088 (1992).
Morris, et al., "The Consortium to Establish a registry for Alzheimer's Disease (CERAD)," *Neurology*, 39:1159-1165 (1989).
Mount et al. "Alzheimer disease: progress or profit?" Market Analysis Nature Medicine 12(7) 780-784 (Jul. 2006).
Movsesyan et al., "Reducing AD-Lide Pathology in 3xTg-AD Mouse Model by DNA epitope Vaccine—A Novel Immunotherapeutic Strategy", PloS ONE, 2008, vol. 3, issue 5, e2124 1-13.
Munch et al., "Potentional neurotoxic inflammatory response to Aβ vaccination in humans," *J. Neural Transm.*, 109:1081-1087 (2002).
Munson eds., *Principals of Pharmacology: Basic Concepts & Clinical Applications*, pp. 47-48, Chapman & Hall, New York, New York (1995).
Murphy et al., "Development of a Monoclonal Antibody Specific for the COOH-Terminal of β-Amyloid 1-42 and Its Immunohistochemical Reactivity in Alzheimer's Disease and Related Disorders," *Am. J. Pathology*, 144(5):1082-1088 (1994).

(56) References Cited

OTHER PUBLICATIONS

Mutschler et al., *Drug Actions: Basic Principles and Therapeutic Aspects* pp. 7, 11-12, Medpharm Scientific Publishers, Stuttgart, Germany (1995).
Mutschler et al., "*Arzneimittel-Wirkungen, Lehrbuch der Pharmakologie und Taxiklogie*," Wissenschftliche Verlagsgesellschaft mbH Stuttgart, 6$^{th}$ edition, pp. 651-656 (1991), (German Article).
Myers et. al., "Targeting Immune Effector Molecules to Human Tumor Cells Through Genetic Delivery of 5T4-Specific SCFV Fusion Protiens," Cancer Gene Therapy, 9(11):884-896 (2002).
Nakamura et al., "Histopathological studies on senile plaques and cerebral Amyloid angiopathy in aged cynomologus monkeys," *Exp. Anim.*, 43:711-718 (1995).
Nakamura, et al., "Carboxyl end-specific monoclonal antibodies to myloid β protein (Aβ) subtypes (Aβ40 and Aβ42(43) differentiate Ab in senile plaques and myloid angiopathy in brains of aged cynomolgus monkeys," *Neuroscience Letters*, 201:151-154 (1995).
Nakayama et al., "Histopathological studies of senile plaques and cerebral amyloidosis in cynomolgus monkeys," *J. of Med. Primatology*, 27:244-252 (1998).
Nalbantoglu, J., "Beta-amyloid protein in Alzheimer's disease," *Can. J. Neurol. Sci.*, 18(3 suppl.):424-427 (1991), abstract only.
Nashar et al., "Current progress in the development of the B subunits of cholera toxin and *Escherichia coli* heat-labile enterotoxin as carries for the oral delivery of herterologous antigens and epitopes," *Vaccine*, 11(2):235-40 (1993), abstract only.
Naslund et al., "Correlation between elevated levels of amyloid b peptide in the brain and cognitive decline," *J. Am. Med. Assoc.*, 283:1571 (2000).
Nathanson et al., "Bovine Spongiform Encephalopathy (BSE): Causes and Consequences of a Common Source Epidemic," *Am. J. Epidemiol.*, 145(11):959-969 (1997).
New York Times National, "Anti-Inflammatory Drugs May Impede Alzheimer's," (Feb. 20, 1994).
Newcombe et al., "Solubility characteristics of isolated amyloid fibrils," Biochim. Biophys. Acta, 104:480-486 (1965).
Ngo et al., "Computational Complexity, Protein Structure Prediction, and the Levinthal Paradox," pp. 492-495 from Chapter 14 of *The Protein Folding Problem and Tertiary Structure Prediction*, Merz et al., eds., Birkhauser Boston (1994).
Nicoll et al., "Neuropathology of human Alzheimer's disease after immunization with amyloid-β peptide: a case report," *Nature Medicine*, 9(4):448-452 (2003).
Niemann, "Transgenic farm animals get off the ground;" *Transgenic Research*, 7:73-75 (1998).
Novartis, "Novartis MF59™—Adjuvanted Influenza Vaccine (Fluad®) Significantly Reduces Hospitalization in Elderly," Novartis Press Release, Oct. 19, 2007.
Novotny et al., "Structural invariants of antigen binding: Comparison of immunoglobulin $V_L$-$V_H$ and $V_L$-$V_L$ domain dimmers," *PNAS*, 82:4592-4596 (1985).
Okie, S., "Promising Vaccine Targets Ravager of Minds," *Washington Post*, p. A01, May 8, 2001.
Okura et al., "Nonviral Aβ DNA vaccine therapy against Alzheimer's disease: Long-term effect and safety," *PNAS*, 103(25):9619-9624 (2006).
Orkin et al., *Report and Recommendations of the Panel to Assess the NIH Investment in Research on Gene Therapy*, Dec. 7, 1995.
Orlandi et al., "Cloning immunoglobulin variable domains for expression by the polymerase chain reaction," *PNAS*, 86:3833-3837 (1989).
Padlan et al., Structure of an Antibody-Antigen Complex: Crystal Structure of the HyHEL-10 Fab-lysozyme Complex, Immunology, 86:5938-5942 (1989).
Paganetti et al., "Amyloid precursor protein truncated at any of the γ-secretase sites is not cleaved to β-amyloid," *J. Neurosci. Res.*, 46(3):283-293 (1996).

Palha et al., "Antibody recognition of amyloidogenic transthyretin variants in serum of patients with familial amyloidiotic polyneuropathy," *J. Mol. Med.*, 78:703-707 (2001).
Pallitto et al., "Recognition sequence design for peptidyl modulators of β-amyloid aggregation and toxicity," *Biochemistry*, 38(12):3570-3578 (1999).
Pan et al., "Antibodies to β-Amyloid Decrease the Blood-to-Brain Transfer of β-Amyloid Peptide," *Exp. Biol. Med.*, 227(8):609-615 (2002).
Pangalos et al., "Disease Modifiying Strategies for the Treatment of Alzheimer's Disease Targeted at Modulating Levels of β-amyloid Peptide," Biochemical Socity Transactions, 33(4):553-558 (2005).
Panka et al., "Variable region framework differences result in decreased or increased affinity of variant anti-digoxin antibodies," *PNAS*, 85:3080-3084 (1998).
Pardridge et al., "Chimeric peptides as a vehicle for peptide pharmaceutical delivery through the blood-brain barrier," *Biochem. Biophys. Res. Comm.*, 146:307-313 (1987).
Pardridge et al., "The Blood-Brain Barrier: Bottleneck in Brain Drug Development," *J. Am. Soc. Exp. Neurotherapeutics*, 2:3-14 (2005).
Paresce et al., "Microglial cells influence aggregates of the Alzheimer's disease amyloid β-protein via a scavenger receptor," Neuron, 17:553-565 (Sep. 1996).
Parnetti et al., "Cognitive Enhancement Therapy for Alzheimer's Disease, The Way Forward," *Drugs*, 53(5):752-768 (1997).
Pascalis et al., "Grafting of "Abbreviated" Complementarity-Determining Containing Specifictiy-Determining Residues Essential for Ligand Contact to Engineer a Less Immunogenic Humanized Monoclonal Antibody," *The Journanal Immunology*, 169:3076-3084 (2002).
Paul et al., "Transdermal immunization with large proteins by means of ultradeformable drug carriers," *Eur. J. Immunol.*, 25: 3521-3524 (1995).
Paul, W. E., eds., *Fundamental Immunology*, Third Edition, pp. 292-295, Raven Press, New York (1993).
PCT International Preliminary Examination Report of Feb. 9, 2004 for application PCT/US01/46587.
PCT International Preliminary Report on Patentability (Chapter I) of Sep. 16, 2005 with Written Opinion of May 9, 2005 for application PCT/US04/007503.
PCT International Preliminary Report on Patentability (Chapter I) of Jul. 31, 2007 with Written Opinion for application PCT/US2006/004741.
PCT International Preliminary Report on Patentability (Chapter I) of Oct. 20, 2009 with Written Opinion of Oct. 3, 2008 for application PCT/US2008/060926.
PCT International Preliminary Report on Patentability (Chapter I) of Feb. 2, 2010 for application PCT/US07/09499.
PCT International Preliminary Report on Patentability (Chapter I) and Written Opinion Completed Dec. 22, 2008 for PCT/US2008/080370.
PCT International Preliminary Report on Patentability (Chapter II) of Apr. 27, 2006 for application PCT/US04/007503.
PCT International Preliminary Report on Patentability (Chapter II) of Dec. 21, 2006 for application PCT/US2006/002837.
PCT Search Report of Jan. 22, 2009 for application PCT/US2008/80370.
PCT Search Report of Mar. 25, 2009 for application PCT/US2008/80382.
PCT Search Report of Oct. 1, 2007 and Written Opinion of Oct. 1, 2007 for application PCT/US07/09499.
PCT Search Report of Oct. 9, 2008 for application PCT/US2008/060926.
PCT Search Report of Apr. 6, 2006 and Written Opinion of Apr. 8, 2006 for application PCT/US04/44093.
PCT Search Report of Aug. 11, 2006 for application PCT/US2006/002837.
PCT Search Report of Aug. 8, 2006 for application PCT/US2005/045515.
PCT Written Opinion of Mar. 8, 2009 for application PCT/US2008/80382.
PCT Written Opinion of Dec. 14, 2004 for application PCT/US04/02856.

(56) References Cited

OTHER PUBLICATIONS

PCT Written Opinion of Dec. 22, 2008 for application PCT/US2008/80370.
PCT Written Opinion of Aug. 11, 2006 for application PCT/US2006/002837.
Peeters et al., "Comparison of four bifunctional reagents for coupling peptides to proteins and the effect of the three moieties on the immunogenicity of the conjugates," *J. Immunological Methods*, 120:133-143 (1989).
Perez et al., "The β-Amyloid Precursor Protein of Alzheimer's Disease Enhances Neuron Viability and Modulates Neuronal Polarity," *J. Neurosci.*, 17(24):9407-9414 (1997)
Persson et al., "IgG subclass-associated affinity differences of specific antibodies in humans," *J. Immunology*, 140(11):3875-3879 (1988), abstract only.
Perutz et al., "Amyloid fibers are water-filed nanotubes," *PNAS*, 99(8):5591-5595 (2002).
Peterson, et al., "Recombinant Antibodies: Alternative Strategies for Developing and Manipulating Murine-Derived Monoclonal Antibodies," *Laboratory Animal Science*, 46(1):8-14 (1996).
Pfeifer et al., "Cerebral hemorrhage after passive anti-Aβ immunotherapy," *Science*, 298(5597):1379 (2002).
Phelps et al., "Development and Characterization of Monoclonal Antibodies Specific for Amylin," *Hybridoma*, 15(5):379-386 (1996).
Philippe, et al. "Generation of a monoclonal antibody to the carboxy-terminal domain of tau by immunization with the amino-terminal domain of the amyloid precursor protein," J. of Neuroscience Res., 46:709-719 (1996).
Piera et al., "Cytokines as adjuvants: effects on the immunogenicity of NeuAc alpha 2-GalNAc alpha-O-Ser/Thr (sialyl-Tn)," *Int. J. Cancer*, 55(1):148-152 (1993).
Plant et al., "The Production of Amyloid β Peptide is a Critical Requirement for the Viability of Central Neurons," *The Journal of Neuroscience*, 23(13):5531-5535, (2003).
Pluckthun, A., "Mono- and Bivalent Antibody Fragments Produced in *Escherichia coli*: Engineering, Folding and Antigen Binding," *Immunological Reviews*, 130:151-188 (1992).
PNAS Information for Authors (revised Jan. 1997), Retrieved Apr. 21, 2008 from web.archive.org/web/19970610092808/www.pnas.org/iforc.shtml.
Poduslo et al., "Macromolecular permeability across the blood-nerve and blood-brain barriers." *Proc. Natl. Acad. Sci USA* . vol. 91 pp. 5705-5709 (1994).
Poduslo et al., "Permeability of proteins at the blood-brain barrier in the normal adult mouse and double transgenic mouse model of Alzheimer's disease," *Neurobiol. Dis.*, 8(4):555-567 (2001).
Prada et al., "Antibody-Mediated Clearance of Amyloid-β Peptide From Cerebral Amyloid Angiopathy Revealed by quantitative in Vivo Imaging," Journal of Neuroscience, 27(8):1973-1980 (2007).
Press Release, "Alzheimer's vaccine developer awarded Potamkin Prize," American Academy of Neurology, May 7, 2001.
Prieels et al., "Synergistic adjuvants for vaccines," *Chemical Abstracts*, 120(8):652, col. 1, abstract 86406t (1994).
Probert et al., "Spontaneous inflammatory demyelinating disease in transgenic mice showing central nervous system-specific expression of tunmor necrosis factor α," *PNAS*, 92:11294-11298 (1995).
Prusiner et al., "Ablation of the prion protein (PrP) gene in mice prevents scrapie and facilitates production of anti-PrP antibodies," *PNAS*, 90:10608-10612 (1993).
Putative CDR determination for SEQ Id Nos. 2 and 4 (pp. 1-2), Jun. 10, 2004.
Qu et al., "Aβ42 gene vaccination reduces brain amyloid plaque burden in transgenic mice," *J. Neurological Sciences*, 244:151-158 (2006).
Qu et al., "Aβ$_{42}$ gene Vaccine Prevents Aβ$_{42}$ deposition in brain of Double Trangenic Mice," *J. Neurological Sciences*, 260:204-213 (2007).
Queen et al., "A humanized antibody that binds to the interieukin 2 receptor," *PNAS*, 86:10029-10033 (1989).
Quon et al., "Formation of β-Amyloid protein deposits in brains of transgenic mice," *Nature*, 352:239-241 (1991).
Racke et al., "Exacerbation of Cerebral Amyloid Angiopathy-Assoiciated Microhemorrhage in Amyloid Precursor Protein Trasngenic Mice by Immunotherapy is Dependent on Antibody Recognition of Deposited Forms of Amyloid β," *J. Neurosci.*, 25(3):629-636 (2005).
Ragusi et al., "Redistribution of Imipramine from Regions of the Brain Under the Influence of Circulating Specific Antibodies," *J. Neurochem.*, 70(5):2099-2105 (1998).
Rammensee, H.G., "Chemistry of peptides associated with MHC class I and class II molecules," *Current Opinion in Immunology* 7:85-96 (1995).
Ramshaw et al., "DNA vaccines for the treatment of autoimmune disease," *Immunology and Cell Biology*, 75:409-413 (1997).
Raso, "Immunotherapy of Alzheimer's Disease," Immunotherapy Weekly, Abstract (Apr. 2, 1998).
Raso, V.A., Grant application # 1 R43 AGI 5746-01 (non-redacted version), "Immunotherapy of Alzheimer's Disease" (publication date unknown).
Raso, V.A., Grant application # 1 R43 AGI 5746-01 (redacted version), "Immunotherapy of Alzheimer's Disease" (publication date unknown).
Research Corporation Technology News, "THP and SangStat Partner to Develop Humanized Polyclonal Antibody Drugs," Nov. 11, 2002.
Riechmann et al., "Reshaping Human Antibodies for Therapy," Nature, 332:323-327 (1988).
Robbins et al., "The Intronic Region of an Imcompletely Spliced gp100 Gene Transcript Encodes an Epitope Recognized by Melanoma-Reactive Tumor-Infiltrarting Lymphocytes," Journal of Immunology, 159(1):303-308 (1997).
Rodriguez et al., "Enfermedad de Azlheimer. Situacion Actual y Estrategias Terapeuticas" (Alzheimer Disease: present situation and therapeutic strategies), *Rev Cubana Med* [online], 38(2):134-142 (1999).
Rogers et al., "Complement activation by β-amyloid in Alzheimer Disease," *PNAS*, 89:1-5 (1992).
Rolph et al., "Recombinant viruses as vaccines and immunological tools," *Immunity to Infection*, 9:517-521 (1997).
Rosenberg, R. N., "The Potamkin Prize for Pick's, Alzheimer's Disease and Related Disorders," pp. 1-5.
Roses, A.D., "Apoplipoprotein E alleles as risk factors in Alzheimer's disease," *Annu. Rev. Med.*, 47:387-400 (1996).
Rossor et al., "Alzheimer's Disease Families with Amyloid Precursor Protein Mutations," *Annals of New York Academy of Sciences*, 695:198-202 (1993).
Rudikoff et al., "Single amino acid substitution altering antigen-binding specificity," *PNAS*, 79:1979-1983 (1982).
Rudinger, "Characteristics of the Amino Acids as Components of a Peptide Hormone Sequence," in *Peptide Hormones*, J.A. Parson, ed. University Park Press, Baltimore, pp. 1-7 (1976).
Saido et al., "Amino- and Carboxyl-Terminal Heterogeneity of β-Amyloid Peptides Deposited in Human Brain," Neuroscience Letters, 215:173-176 (Aug. 8, 1996).
Saido et al., "Autolytic Transition of μ-Calpain Upon Activation as Resolved by Antibodies Distinguishing Between the Pre- and Post-Autolysis Forms," J. Biochem., 111:81-86 (1992).
Saido et al., "Spatial Resolution of Fodrin Proteolysis in Postischemic Brain," *J. Biol. Chem.*, 268(33):25239-25243 (1993).
Saido et al., "Spatial Resolution of the Primary β-Amyloidogenic Process Induced in Postischemic Hippocampus," *J. Biol. Chem.*, 269(21):15253-15257 (1994).
Saito et al., "Vector-mediated delivery of 125I-labeled β-amyloid peptide Ab1-40 through the blood-brain barrier and binding to Alzheimer disease amyloid of the Aβ1-40 vector complex," *PNAS*, 92:10227-10231 (1995).
Saitoh, N. et al., "Immunological analysis of Alzheimer's disease using anti-β-protein monoclonal antibodies," *Sapporo Med. J.*, 60:309-320 (1991).
Saldanha et al., "A single backmutation in the human kIV framework of a previously unsuccessfully humanized antibody restores the binding activity and increases the secretion in cos cells," *Molecular Immunology*, 36:709-719 (1999).

(56) References Cited

OTHER PUBLICATIONS

Sasaki et al., "Human choroid plexus is an uniquely involved area of the brain in amyloidosis: a histochemical, immunohistochemical and ultrastructural study," *Brain Res.*, 755:193-201 (1997).
Schenk et al., "Immunization with amyloid-β attenuates Alzheimer-disease-like pathology in the PDAPP mouse," *Nature*, 400:173-177 (1999).
Schenk et al., "Current progress in beta-amyloid immunotherapy," *Curr. Opin. Immunology*, 16(5):599-606 (2004).
Schenk et al., "Immunotherapy with beta-amyloid for Alzheimer's disease: a new frontier," *DNA Cell Biol.*, 20(11):679-81 (2001).
Schenk et al., "Therapeutic Approaches Related to Amyloid-β Peptide and Alzheimer's Disease," *J. Med. Chem.*, 38(21):4141-4154 (1995).
Schenk et al., "β-peptide immunization," *Arch. Neurol.*, 57:934-936 (2000).
Schenk, D., "Amyloid-β immunotherapy for Alzheimer's disease: the end of the beginning," *Nature Reviews*, 3:824-828 (2002).
Schmid, R. E., "Study suggest Alzheimer vaccine fix," from www.msnbc.com/news, pp. 1-5 (2002).
Schmidt et al., "Monoclonal Antibodies to a 100-kd protein reveal abundant A beta-negative plaques throughout gray matter of Alzheimer's disease brains," *The American Journal of Pathology*, 1(151):69-80 (1997).
Schmitt et al., "Interactions of the alzheimer β amyloid fragment(25-35) with peripheral blood dendritic cells," *Mechanisms of Ageing and Development*, 94:223-232 (1997).
Schroeder et al., "Preferential Utilization of Conserved Immunoglobulin Heavy Chain Variable Gene Segments During Human Fetal Life," *Immunology*, 87:6146-6150 (1990).
Schwarzman et al., "Transthyretin sequesters amyloid b protein and prevents amyloid formation," *PNAS*, 91:8368-8372 (1994).
Seabrook et al., "Species-specific Immune response to Immunization with Human Versus rodent Abeta Peptide," Neuobiology of Aging, 25(9) 1141-1151 (2004).
Seidl et al., "Predominant $V_H$ genes expressed in innate antibodies are associated with distinctive antigen-binding sites," *PNAS*, 96:2262-2267 (1999).
Sela et al, "Different roles of D-amino acids in immune phenomena," *FASEB J*, 11(6):449-456 (1999).
Selkoe, "Alzheimer's Disease: A Central Role for Amyloid," *J. Neuropathol. Exp. Neurol.*, 53(5): 438-447 (1994).
Selkoe, "Physiological production of the β-amyloid protein and the mechanism of Alzheimer's disease," *Trends in Neurosciences*, 16(10): 403-409 (1993).
Selkoe, "The cell biology of beta-amyloid precursor protein and presenilin in Alzheimer's disease," *Trends Cell Biol.*, 8(11):447-53 (1998).
Selkoe, D. J., "Alzheimer's disease is a synaptic failure," *Science*, 298(5594):789-791 (2002).
Selkoe, D.J., "Imaging Alzheimer's Amyloid," *Nat. Biotech.*, 18:823-824 (2000).
Selkoe, Dennis J., "Alzheimer's Disease: Genotypes, Phenotype, and Treatments," *Science*, 275:630-631 (1997).
Selkoe, Dennis J., "Amyloid Protein and Alzheimer's Disease . . . ," *Scientific American*, pp. 68-78 (1991).
Selkoe, Dennis J., "In the Beginning . . . ," *Nature*, 354:432-433 (1991).
Selkoe, Dennis J., "The Molecular pathology of Alzheimer's Disease," *Neuron*, 6:487-498 (1991).
Sergeant et al., "Truncated beta-amyloid peptide species in pre-clinical Alzheimer's disease as new targets for the vaccination approach," *J. Neurochem.*, 85(6):1581-1591 (2003).
Seubert et al., "Antibody Capture of Soluble Aβ does not Reduce Cortical Aβ Amyloidosis in the PDAPP Mouse," *Neurodegenerative Diseases*, 5:65-71 (2008).
Seubert et al., "Isolation and quantification of soluble Alzheimer's β-peptide from biological fluids," *Nature*, 359: 325-327 (1992).

Sheehan et al., "The Utilization of Individual $V_H$ Exons in the Primary Repertoire of Adult BALB/c Mice," The Journal of Immunology, 151(10):5364-5375 (Nov. 15, 1993).
Shepherd et al., "The design of the humanized antibody," Monocolonal Antibodies: A Pratical Approcach 58-66 (2000).
Shinkai et al., "Amyloid β-Proteins 1-40 and 1-42(43) in the Soluble Fraction of Extra- and Intracranial Blood Vessels," *Ann. Neurol.*, 38:421-428 (1995).
Shiosaka, S., "Attempts to make models for Alzheimer's disease," *Neuroscience Res.*, 13:237-255 (1992).
Sidhu, "Page display in pharmaceutical.biotechnology " *Current Opinoin in Biotechnology*, 11:610-616 (2000).
Sigmund, "Viewpoint: Are Studies in Genetically Altered Mice Out of Control," *Arterioscler Thromb Vasc Biol.*, 20:1425-1429 (2000).
Signet Laboratories, Inc., Product data sheet for mouse monoclonal clone 6E10, revised Jul. 13, 2005.
Sigurdsson et al., "A safer vaccine for Alzheimer's disease?," *Neurobiology of Aging*, 23:1001-1008 (2002).
Sigurdsson et al., "Anti-prion antibodies for prophylaxis following prion exposure in mice," *Neurosciences Letters*, 336:185-187 (2003).
Sigurdsson et al., "Immunization Delays the Onset of Prion Disease in Mice," *American Journal of Pathology*, 161:13-17 (2002).
Sigurdsson et al., "Immunization with a Nontoxic/Nonfibrillar Amyloid-β Homologous Peptide Reduces Alzheimer's Disease-Associated Pathology in Trasngenic Mice," *Am. J. Pathology*, 159(2):439-447 (2001).
Sigurdsson, et al., "In vivo reversal of amyloid-β lesions in rat brain," *J Neuropathol Exp Neurol.*, 59(1):11-17 (2000).
Simmons, L., "Secondary Structure of Amyloid β Peptide Correlates with Neurotoxic Activity In Vitro," *Molecular Pharmacology*, 45:373-379 (1994).
Singh, K. S., "Neuroautoimmunity: Pathogenic Implications for Alzheimer's Disease," *Gerontology*, 43:79-94 (1997).
Singh, V. K., "Studies of neuroimmune markers in Alzheimer's disease," *Mol. Neurobiology*, 9(1-3):73-81 (1994), abstract only.
Sinha, et al., "Recent advances in the understanding of the processing of APP to beta amyloid peptide," *Ann N Y Acad Sci.*, 920:206-8 (2000).
Sipe, "Amyloidosis," *Annu. Rev. Biochem.*, 61:947-975 (1992).
Skolnick and Fetrow, "From genes to protein structure and function: novel applications of computational approaches in the genomic era," Trends in Biotech, 18(1):34-39 (2000).
Small et al., "Alzheimer's disease and Abeta toxicity: from top to bottom," *Nat Rev Neurosci.*, 2(8):595-598 (2001).
Small et al., "Cerebral metabolic and cognitive decline in persons at genetic risk for Alzheimer's disease," *PNAS*, 97(11):6037-6042 (2000).
Small, "The Role of the Amyloid Protien Precursors (APP) in Alzheimer's Disease: Does the Normal Function of APP Explain the Topography of Neurodegeneration?," *Neurochemical Research*, 23(5):795-806, (1998).
Smith et al., "Phage Display," *Chemical Reviews, American Chemical Society*, 97(2):391-410 (1997).
Smith et al., "The challenges of genome sequence annotation or 'The devil is in the details,'" *Nature Biotechnology*, 15:1222-1223 (1997).
Smits et al., "Prion Protein and Scrapie Susceptibility," *Vet. Quart.*, 19(3):101-105 (1997).
Solomon and et al., "Modulation of the Catalytic Pathway of Carboxypeptidase A by Conjugation with Polyvinyl Alcohols," *Adv. Mol. Cell Biology*, 15A:33-45 (1996).
Solomon et al., "Activity of monoclonal antibodies in prevention of in vitro aggregation of their antigens," *Immunotechnology*, 2(4):305 (1996).
Solomon et al., "Disaggregation of Alzheimer β-amyloid by site-directed mAb," *PNAS*, 94:4109-4112 (1997).
Solomon et al., "Fast induction of anti-β-amyloid peptide immune response," *Research and Practice in Alzheimer's Disease*, 6:260-264 (2002).
Solomon et al., "Monoclonal antibodies inhibit in vitro fibrillar aggregation of the Alzheimer β-amyloid peptide," *PNAS*, 93:452-455 (1996).

(56) References Cited

OTHER PUBLICATIONS

Solomon et al., "The Amino Terminus of the β-Amyloid Peptide Contains an Essential Epitope for Maintaining Its Solubility," from *Progress in Alzheimer's and Parkinson's Diseases*, edited by Fisher et al., Plenum Press, New York, pp. 205-211 (1995).
Solomon, A., "Pro-Rx (Protein Therapeutics)," University of Tennessee Medical Center (publication date unknown).
Solomon, B., "Generation and brain delivery of anti-aggregating antibodies against β-amyloid plaques using phage display technology," *J. Neural Transm. Suppl.*, 62:321-325 (2002).
Solomon, B., "Immunological approaches as therapy for Alzheimer's disease," *Expert Opin. Biol. Ther.*, 2(8):907-917 (2002).
Solomon, B., "Immunotherapeutic strategies for prevention and treatment of Alzheimer's disease," *DNA and Cell Biology*, 20(11):697-703 (2001).
Sood et al., "Synthetic Peptides: A Modern Approach to Vaccination," *Indian Journal of Experimental Biology*, 34:849-861 (1998).
Soto et al., "The α-helical to β-strand transition in the amino-terminal fragment of the amyloid β-peptide modulates amyloid formation," *J. Biol. Chem*, 270(7):3063-3067 (1995).
Soto et al., "The conformation of Alzheimer's beta peptide determines the rate of amyloid formation and its resistance to proteolysis," Biochem. J., 314:701-707 (1996).
Soto et al., "Beta sheet breaker peptides inhibit fibrillogenesis in a rat brain model of amyloidosis: implications for Alzheimer's therapy," *Nature Medicine.*, 4(7):822-826 (1998).
Souder et al., "Overview of Alzheimer's disease," *Nurs. Clin. N. Am.*, 39:545-559 (2004).
Southwick et al., "Assessment of Amyloid β protein in Cerebrospinal fluid as an Aid in the Diagnosis of Alzheimer's Disease," *J. Neurochemistry*, 66:259-265 (1996).
Spellerberg et al., "DNA Vaccines Against Lymphoma," Journal of Immunology, 159:1885-1892 (1997).
Spooner et al., "The generation and characterization of potentially therapeutic Aβ antibodies in mice: differences according to strain and immunization protocol," *Vaccine*, 21:290-297 (2002).
St. George-Hyslop et al., "Antibody clears senile plaques," *Nature*, 40:116-117 (1999).
Staunton et al., "Primary structures of ICAM-1 demonstrates interaction between members of the immunoglobulin and intergrin supergene families," *Cell* 52(6):925-33 (1988), abstract only.
*Stedman's Medical Dictionary*, 27th Edition, "Vaccine," p. 1922, lines 1-3 (2000).
Stein et al., "Lack of Neurodegeneration in Transgenic Mice Overexpressing Mutant Amyloid Precursor Protein is Associated with Increased Levels of Transthyretin and Activation of Cell Survival Pathways," *The Journal of Neuroscience*, 22(17):7380-7388 (2002).
Stern et al., "Antibodies to the β-amyloid peptide cross-react with conformational epitopes in human fibrinogen subunits from peripheral blood," *FEBS Letters*, 264(1):43-47 (1990).
Stoute et al., "A Preliminary Evaluation of a Recombinant Circumsporozoite Protein Vaccine Against *Plasmodium Falciparum Malaria*", *N. Engl. J. Med.*, 336(2):86-91 (1997).
Strbak et al., "Passive Immunization and Hypothalamic Peptide Secretion", *Neuroendocrinology*, 58:210-217 (1993).
Studnicka et al., "Human-engineered monocilnal antibodies retain full specific binding activity by preserving non-CDR complemenatary-modullating resudes," Protien Eng., 7(6):805-814 (1994), Abstract only.
Sturchler-Pierrat et al., "Two amyloid precursor protein transgenic mouse models with Alzheimer disease-like pathology," PNAS, 94: 13287-13292 (1997).
Su et al., "Intravascular infusions of soluble β-amyloid compromise the blood-brain barrier, activate CNS Glial cells and induce peripheral hemorrhage," *Brain Research*, 818:105-107 (1999).
Suo et al., "Soluble Alzhelmers β-amyloid constricts the cerebral vasculature in vivo" *Neuroscience Letters*, 257:77-80 (1998).
Supplementary Partial European Search Report of Apr. 10, 2007 for European Application 04720353.4-1222.

Szendrei, et al., "The effects of aspartic acid-bond isomerization on in vitro properties of the amyloid β-peptide as modeled with N-terminal decapeptide fragments," Int. J. Peptide Protein Res., 47:289-296 (1996).
Tabaton et al., "Soluble amyloid b-protein is a marker of Alzheimer amyloid in brain but not in cerebrospinal fluid," *Biochem. and Biophys. Res. Comm.*, 200(3):1598-1603 (1994).
Tahtinen et al., "Minimal Size of HIV-1 NEF Antigenic Epitopes Reconzied by Human Sera," Int. Conf. AIDS Jun. 16-21, 1991, Published Jun. 1991, abstract No. W.A. 1334.
Tal et al., "Complete Freund's Adjuvant Immunization Prolongs Survival in Experimental Prion Disease in Mice," *Journal of Neuroscience Research*, 71:286-290 (2003).
Tam, "Synthetic peptide vaccine design: synthesis and properties of a high-density multiple antigenic peptide system", Proc. Natl. Acad. Sci., 1988, vol. 85, pp. 5409-5413.
Tamaokae et al., "Antibodies to amyloid β protein (A β) crossreact with glyceraldehyde-3-phosphate dehyrogenase (GAPDH)," *Neurobiology of Aging*, 3(17):405-414 (1996).
Tan et al., "Amyloidosis," *Histopathology*, 25:403-414 (1994).
Tanaka et al., "NC-1900, an active fragment analog of arginine vasopressin, improves learning and memory deficits induced by beta-amyloid protein in rats," *European J. Pharmacology*, 352:135-142 (1998).
Tang et al., "Genetic immunization is a siple method for eliciting an immune response," *Nature*, 356:152-154 (1992).
Teller et al., "Presence of soluble amyloid b-peptide precedes amyloid plaque formation in Down's syndrome" *Nature Medicine*, 2(1):93-95 (1996).
Tennent et al., "Serum amyloid P component prevents proteolysis of the amyloid fibrils of Alzheimer's disease and systemic amyloidosis," *PNAS*, 92:4299-4303 (1995).
Thorsett, E.D. et al., "Therapeutic approaches to Alzheimer's disease," *Curr. Op. in. Chem. Biology*, 4:377-382 (2000).
Tjernberg et al., "A molecular model for Alzheimer amyloid b-peptide fibril formation," *J. Biol. Chem.*, 274(18):12619-12625 (1999).
Tjernberg et al., "Arrest of β-amyloid fibril formation by a pentapeptide ligand," *J. Biol. Chem.*, 271:8545-8548 (1996).
Tjernberg, et al, "Controlling amyloid β-peptide fibril formation with protease-stable ligands," *J. Biol Chem.*, 272(19):12601-12605 (1997).
Town et al., "Characterization of murine immunoglobulin G antibodies against human amyloid-b1-42" *Neurosci. Lett*, 307:101-104 (2001).
Trang et al., "Pharmacokinetics of a Mouse/Human Chimeric Monoclonal Antibody (C-17-1A) in Metastatic Adencarcinoma Patients," Pharmacutical Research 7(6):587-592 (1990).
Travis, J., "A Vaccine for Alzheimer's Disease?®," *Science News Online*, 156(2) pp. 1-3 downloaded from internet (1999).
Travis, J., "Saving the Mind Faces High Hurdles," *Science*, 309:731-734 (2005).
Trieb et al., "Is Alzheimer beta amyloid precursor protein (APP) an autoantigen? Peptides corresponding to parts of the APP sequence stimulate T lymphocytes in normals, but not in patients with Alzheimer's disease," Immunobiology, 191(2-3):114-115 Abstract C.37, (1994).
Trieb et al., "APP Peptides Stimulate Lymphocyte Proliferation in Normals, But Not in Patients With Alzheimer's Disease," *Neurobiology of Aging*, 17(4):541-547 (1996).
Tsuzuki et al., "Amyloid β protein in rat soleus in choroquine-induced myopthy using end-specific antibodies for Aβ40 and Aβ42: immunohistochemical evidence for amyloid β protein," *Neuroscience Letters*, 2002:77-80 (1995).
U.S. Appl. No. 09/316,387, Declaration of Solomon, Hrncic, and Wall under 37 C.F.R. § 1.131 filed Mar. 6, 2006.
U.S. Appl. No. 09/316,387, Office Action mailed Jun. 20, 2005.
U.S. Appl. No. 09/316,387, Office Action mailed Sep. 10, 2007.
U.S. Appl. No. 09/316,387, Response to Jun. 20, 2005 Office Action filed Dec. 20, 2005.

(56) References Cited

OTHER PUBLICATIONS

Ulvestad et al., "Fc Receptors for IgG on Cultured Human Microglia Mediate Cytotoxicity and Phagocytosis of Antibody-coated Targets," *Journal of Neuropathology and Experimental Neurology*, 53(1):27-36 (1994).
UniProtKB/Swiss-Prot entry P18525, pp. 1-3 downloaded from www.expasy.org/cgi-bin/niceprot.pl/printable?ac=P18525 on Feb. 8, 1997, "HV54_Mouse" (Nov. 1, 1990).
Urmoneit et al., "Cerebrovascular Smooth Muscle Cells Internalize Alzheimer Amyloid Beta Protein via a Lipoprotein Pathway: Implications for Cerebral Amyloid Angiopathy," *Laboratory Investigation*, 77(2):157-166 (1997).
Vajdos et al., "Comprehensive Functional Maps of the Antigen-binging site of an Anti_ErbB2 Antibody Obtained with Shotgun Scanning Mutagenesis," *J. Mol. Biol.*, 320:415-428 (2002).
Valleix et al., "Hereditary renal amyloidosis caused by a new variant lysozyme W64R in a French family," *Kidney International*, 61:907-912 (2002).
Van Den Dobbelsteen et al., "Characteristics of Immune Responses to Native and Protein Conjugated Pneumococcal Polysaccharide Type 14," *Scand. J. Immunol.*, 41:273-280 (1995).
Van Gool et al., "Concentrations of amyloid-β protein in cerebrospinal fluid increase with age in patients free from neurodegenerative disease," Neuroscience Letters, 172:122-124 (1994).
Van Leuven, F., "Single and multiple transgenic mice as models for Alzheimer's disease," *Progress in Neurobiology*, 61:305-312 (2000).
Van Regenmortel et al, "D-peptides as immunogens and diagnostic reagents," *Curr. Opin. Biotechnol.*, 9(4):377-382 (1998).
Vanderstichele et al., "Standardization of Measurement of B-amyloid(1-42) in Cerebrospinal Fluid and Plasma:," *Int. J. Exp. Clin. Invest.*, 7(4):245-258 (2000).
Vastag, "Monoclonals expand into neural disorders" Nature 24:6 p. 595-596 (Jun. 2006).
Vehmas et al., "Beta-Amyloid peptide vaccination results in marked changes in serum and brain Abeta levels in APPswe/PS1 DeltaE9 mice, as detected by SELDI-TOF-based ProteinChip® technology," *DNA Cell Biol.*, (11):713-721 (2001).
Velazquez et al., "Aspartate residue 7 in Amyloid β-protein is critical for classical complement pathway activation: Implications for Alzheimer's disease pathogenesis," *Nature Medicine*, 3(1):77-79 (1997).
Verbeek et al., "Accumulation of Intercellular Adhesion Molecule-1 in Senile Plaques in Brain Tissue of patients with Alzheimer's Disease," *Amer. Journ. Pathology*, 144(1):104-116 (1994).
Verma et al., "Gene therapy—promises, problems and prospects," *Nature*, 389:239-242 (1997).
Vershigora A. E. *Obshchaya Immynologiya*, pp. 35, 229-231 and 152-153 (1990).
Vickers, J. C., "A Vaccine Against Alzheimer's Disease," *Drugs Aging*, 19(7):487-494 (2002).
Vidanovic et al., "Effects of nonionic surfactants on the physical stability of immunoglobulin G in aqueous solution during mechanical agitation," *Die Pharmazie*, 58(6):399-404 (2003).
Viswanathan et al., "Cerebral Microhemorrhage", *Stroke.*, 37:550-555 (2006).
Walker et al., "Labeling of Cerebral Amyloid In Vivo with a Monoclonal Antibody," *J. Neuropath. Exp. Neurology*, 53(4):377-383 (1994).
Walsh et al., "Naturally secreted oligomers of amyloid β protein potently inhibit hippocampal long-term potentiation in vivo," *Nature*, 416(6880):535-539 (2002).
Wang et al, "Site-specific UBITh amyloid-β vaccine for immunotherapy of Alzheimer's disease" *Vaccine* 25 (2007) 3041-3052.
Wang et al., "Soluble oligomers of b amyloid (1-42) inhibit long-term potentiation but not long-term depression in rate dentate gyrus," *Brain Research*, 924:133-140 (2002).
Wang et al., "The levels of soluble versus insoluble brain Aβ distinguish Alzheimer's disease from normal and pathologic aging," *Experimental Neurology*, 158:328-337 (1999).
Wang, W., "Instability, stabilization, and formulation of liquid protein pharmaceuticals," *Int. J. Pharmaceutics*, 185(2):129-188 (1999).
Ward et al., "Spontaneous Deletions in IG Heavy Chain Genes Flaking Seuences Influence Splice Site Selection Nucleic Acids Research," 19(23): 6475-6480 (1991).
Washington University in St. Louis School of Medicine, "Study gives Clues to Working of Anti-Alzheimer Antibody," downloaded from www.medicine.wustl.edu/~wumpa/news on Dec. 15, 2004.
*Webster's New World Dictionary of American English*, Third College Edition, p. 1078 (1988).
*Webster's New World Dictionary*, p. 1387, therapeutic (1988).
Wehner, Declaration May 21, 2007.
Weiner et al., "Nasal administration of amyloid-β peptide decreases cerebral amyloid burden in a mouse model of Alzheimer's disease," *Ann. Neurol.*, 48:567-579 (2000).
Weiner et al., "Oral Tolerance: Immunologic Mechanisms and Treatment of Animal and Human Organ-Specific Autoimmune Diseases by Oral Administration of Autoantigens," *Annu. Rev. Immunol.*, 12:809-837 (1994).
Weiner, H. L., "Oral tolerance: immune mechanisms and treatment of autoimmune diseases," *Immunology Today*, 18:335-343 (1997).
Weinreb et al., "NACP, A Protein Implicated in Alzheimer's Disease and Learning, Is Natively Unfolded," *Biochemistry*, 35(43):13709-13715 (1996).
Weissmann et al., "Bovine spongiform encephalopathy and early onset variant Creutzfeldt-Jakob disease," *Curr. Opin. Neurobiol.*, 7:695-700 (1997).
Weldon et al., "Neurotoxicity of Aβ Peptide: Confocal Imaging of Cellular Changes Induced by—Amyloid in Rat CNS In Vivo," *Society for Neuroscicence Abstracts*, 22(Part 1) (1996).
Welling et al., "Choice of Peptide and Peptide Length for the Generation of Antibodies Reactive With the Intact Protein," *FEBS Letters*, 182(1):81-84 (Mar. 1985).
Wells, J. A., "Additivity of Mutational Effects in Proteins," *Biochemistry*, 29(37):8509-8517 (1990).
Wen, G.Y., "Alzheimer's Disease and Risk Factors," *J. Food Drug Analysis*, 6(2):465-476 (1998).
Wengenack et al., "Targeting Alzheimer amyloid plaques in vivo," *Nature Biotech.*, 18:868-872 (2000).
Whitcomb et al., "Characterization of saturable binding sites for circulating pancreatic polypeptide in rat brain," *Am J Pysiol Gastrointest Liver Physiol*, 259:G687-G691 (1990).
White et al., "Immunotherapy as a therapeutic treatment for neurodegenerative disorders," *J. Neurochem.*, 87(4):801-808 (2003).
Wikipedia definition of "antigen" printed from internet on Apr. 26, 2006.
Wikipedia definition of "epitope" printed from internet on Apr. 26, 2006.
Wikipedia definition of "route of administration including parenteral" printed from internet on Apr. 26, 2006.
Wikipedia entry for Antibody, retrieved Apr. 27, 2009 from en.wikipedia.org/wiki/Antibody.
Wilcock, et al. "Deglycosylated anti-Amyloid-β Antibodies Eliminate Cognitive Deficits and Reduce Parenchymal Amyloid with Minimal Vascular Consequences in Aged Amyloid Precursor Protein Transgenic Mice" Neurobiology of Disease 26(20:5340-5346 (May 17, 2006).
Wilson et al., "Phage display: applications, innovations, and issues in phage and host biology," *Can. J. Microbiol* 44:313-329 (1998).
Winblad et al., "Hints of a therapeutic Vaccine for Alzheimer's?" *Neuron*, 38:517-519 (2003).
Winter et al., "Humanized antibodies" *Immunology Today*, 14(6):243-246 (1996).
Wisconsin Alumni Research Foundation, "Injection of Newborn Mice with Seven Chemical Adjuvants to Help Determine Their Safety in Use in Biologicals", U.S. Govt. Res. Develop. Rep., 70(24), 56 (1969).
Wisniewski et al., "Alzheimer's disease and soluble A beta," *Neurobiol. Aging*, 15(2):143-52 (1994).

(56) References Cited

OTHER PUBLICATIONS

Wisniewski et al., "Therapeutics in Alzheimer's and Prion Diseases," *Biochemical Society Transactions*, 30(4):574-587 (2002).
Wong et al., "Neuritic Plaques and Cerebrovascular Amyloid in Alzheimer Disease are Antigenically Related," *PNAS*, 82:8729-8732 (1985).
Wood et al., "Prolines and amyloidogenicily in fragments of the Alzheimer's peptide β/A4" *Biochemistry*, 34:724-730 (1995).
Wu et al., "An Analysis of the Sequences of the Variable Regions of Bence Jones Proteins and Myeloma Light Chains and their Implications for Antibody Complementarity," *J. Exp. Med.*, 132:211-250 (1970).
Wu et al., "Expression of immunogenic epitopes of hepatitis B surface antigen with hybrid flagellin proteins by a vaccine strain of *Salmonella*," *PNAS*, 86:4726-4730 (1989).
Wu et al., "Humanization of a Murine Monoclonal Antibody by Simultaneous Optimization of Framework and CDR Residues," *J. Mol. Biol.*, 294:151-162 (1999).
Wu, et al., "Drug targeting of a peptide radiopharmaceutical through the primate blood-brain barrier in vivo with a monoclonal antibody to the human insulin receptor," *J. Clin. Invest.*, 100:1804-1812 (1997).
Wyeth, Annual Review 2005: Creating Value . . . Advancing Health (Feb. 27, 2006).
Xiang et al., "Manipulation of the immune response to a plasmid-encoded viral antigen by coinoculation with plasmids expressing cytokines," *Immunity*, 2(2):129-135 Abstract (1995).
Xu et al., "Increased incidence of anti-3-amyloid autoantibodies secreted by Epstein-Barr virus transformed B cell lines from patients with Alzheimer's disease," Mechanisms of Ageing and Development, 94:213-222 1997.
Yamada et al., "Generation and Characterization of Rat Monoclonal Antibodies Against Human Serum Amyloid A," *Scand. J. Immunol.*, 46(2):175-179 (1997).
Yamaguchi et al., Diffuse plaques associated with astroglial amyloid β protein, possibly showing a disappearing stage of senile plaques, *Acta Neuropathol.*, 95:217-222 (1998).
Yanagisawa K et al., "Amyloid Beta-protein (Alpha-Beta) associated with lipid molecules: immunoreactivity distinct from that of soluble Alpha-Beta," FEBS Letters, 1(420): 43-46 (1997).
Yang et al., "Effects of Racemization on the Aggregational Properties of the Amyloid β-Peptide in Alzheimer's Disease," abstract # 255 from American Chemical Society 214th National Meeting (1997).
Yang et al., "Monoclonal Antibody to the C-terminus of Beta-Amyloid," Neuroreport, 16(5):2117-2120 (1994).
Yankner et al., "Neurotrophic and Neurotoxic effects of Amyloid β Protein: Reversal by Tachykinin Neuropeptides," *Science*, 250:279-282 (1990).
Younkin, "Amyloid β vaccination: reduced plaques and improved cognition," *Nature Medicine*, 7:18-19 (2001).
Zameer et al., "Single Chain Fv Antibodies against 25-35 Peptide Fragment of Amyloid-β: Potential Therapeutic for Alzheimer's Disease," Abstract P4-420, p. S593, presented at Poster Session P4:Therapeutics and Therapeutic Strategies—Therapeutic Strategies, Amyloid-Based, also *Neurobiology of Aging*, 25(Suppl. 2): p. S593 (Jul. 2004).
Zhang et al., "A novel recombinant adeno-associated virus vaccine reduces behavioral impairment and β-amyloid plaques in a mouse model of Alzheimer's disease," *Neurobiology of Disease*, 14:365-379 (2003).
Zhang et al., "Specialized Applications, Purification of Recombinant Proteins and Study of Protein Interaction by Epitope Tagging," *Current Protocols in Mol. Biol.*, Supp 41, pp. 10.15.1 through 10.15.9 (1998).
Zlokovic et al., "Blood-Brain Barrier Transport of Circulating Alzheimer's Amyloid β" *Biochemical and Biophysical Research Communications*. vol. 197, No. 3, pp. 1034-1040 (1993).
Zlokovic et al., "Clearance of amyloid β-peptide from brain: transport or metabolism?," *Nature Medicine*, 6(7):718-719 (2000).
Zlokovic et al., "Glycoprotein 330/megalin: probable role in receptor-mediated transport of apolipoprotein J alone and in a complex with Alzheimer disease amyloid beta at the blood-brain and blood-cerebrospinal fluid barriers," *PNAS*, 93(9):4229-4334 (1996) abstract only.
U.S. Appl. No. 09/201,430, Examiner Interview Summary mailed May 30, 2001.
U.S. Appl. No. 09/201,430, Office Action mailed Jan. 17, 2001.
U.S. Appl. No. 09/204,838, Office Action mailed Dec. 21, 2000.
U.S. Appl. No. 09/322,289, Examiner Interview Summary mailed Jun. 27, 2006.
U.S. Appl. No. 09/322,289, Examiner Interview Summary mailed Jan. 15, 2009.
U.S. Appl. No. 09/322,289, Office Action mailed Jun. 19, 2001.
U.S. Appl. No. 09/497,553, Office Action mailed Nov. 29, 2005.
U.S. Appl. No. 09/580,018, Office Action mailed May 20, 2003.
U.S. Appl. No. 09/723,384, Examiner Interview Summary mailed Mar. 28, 2003.
U.S. Appl. No. 09/723,384, Office Action mailed Oct. 9, 2002.
U.S. Appl. No. 09/723,544, Office Action mailed Aug. 11, 2003.
U.S. Appl. No. 09/723,713, Office Action mailed Mar. 26, 2002.
U.S. Appl. No. 09/723,760, Office Action mailed Dec. 19, 2002.
U.S. Appl. No. 09/723,762, Office Action mailed Oct. 2, 2001.
U.S. Appl. No. 09/723,765, Examiner Interview Summary mailed Mar. 18, 2003.
U.S. Appl. No. 09/723,765, Examiner Interview Summary mailed Jan. 25, 2006.
U.S. Appl. No. 09/723,765, Examiner Interview Summary mailed Oct. 8, 2008.
U.S. Appl. No. 09/723,765, Examiner Interview Summary mailed Jan. 16, 2009.
U.S. Appl. No. 09/723,765, Office Action mailed Dec. 3, 2002.
U.S. Appl. No. 09/723,766, Office Action mailed Nov. 1, 2002.
U.S. Appl. No. 09/724,102, Office Action mailed Oct. 3, 2001.
U.S. Appl. No. 09/724,273, Office Action mailed Apr. 21, 2003.
U.S. Appl. No. 09/724,288, Office Action mailed Dec. 11, 2002.
U.S. Appl. No. 09/724,319, Examiner Interview Summary mailed Jul. 19, 2004.
U.S. Appl. No. 09/724,319, Examiner Interview Summary mailed Apr. 9, 2008.
U.S. Appl. No. 09/724,319, Office Action mailed Apr. 26, 2004.
U.S. Appl. No. 09/724,477, Office Action mailed Oct. 2, 2001.
U.S. Appl. No. 09/724,489, Office Action mailed Oct. 2, 2002.
U.S. Appl. No. 09/724,495, Office Action mailed Jan. 16, 2004.
U.S. Appl. No. 09/724,551, Office Action mailed Jun. 3, 2003.
U.S. Appl. No. 09/724,552, Examiner Interview Summary mailed Dec. 3, 2003.
U.S. Appl. No. 09/724,552, Office Action mailed Jun. 3, 2003.
U.S. Appl. No. 09/724,567, Office Action mailed Nov. 15, 2002.
U.S. Appl. No. 09/724,575, Examiner Interview Summary mailed May 6, 2005.
U.S. Appl. No. 09/724,575, Office Action mailed Nov. 21, 2002.
U.S. Appl. No. 09/724,921, Office Action mailed Jan. 28, 2003.
U.S. Appl. No. 09/724,929, Office Action mailed Jul. 22, 2003.
U.S. Appl. No. 09/724,940, Office Action mailed Dec. 24, 2003.
U.S. Appl. No. 09/724,953, Office Action mailed Nov. 27, 2002.
U.S. Appl. No. 09/724,961, Office Action mailed May 16, 2003.
U.S. Appl. No. 09/724,961, Examiner Interview Summary mailed Dec. 3, 2003.
U.S. Appl. No. 09/979,701, Office Action mailed Jan. 10, 2006.
U.S. Appl. No. 09/979,952, Office Action mailed Dec. 30, 2003.
U.S. Appl. No. 09/980,568, Office Action mailed Feb. 23, 2004.
U.S. Appl. No. 10/010,942, Examiner Interview Summary mailed May 10, 2006.
U.S. Appl. No. 10/010,942, Examiner Interview Summary mailed May 11, 2006.
U.S. Appl. No. 10/010,942, Examiner Interview Summary mailed Nov. 18, 2004.
U.S. Appl. No. 10/010,942, Examiner Interview Summary mailed Feb. 22, 2006.
U.S. Appl. No. 10/010,942, Examiner Interview Summary mailed Jan. 19, 2005.
U.S. Appl. No. 10/010,942, Office Action mailed May 26, 2004.

(56) References Cited

OTHER PUBLICATIONS

U.S. Appl. No. 10/232,030, Examiner Interview Summary mailed Feb. 17, 2006.
U.S. Appl. No. 10/232,030, Office Action mailed Oct. 14, 2005.
U.S. Appl. No. 10/388,214, Examiner Interview Summary mailed Oct. 2, 2006.
U.S. Appl. No. 10/388,214, Examiner Interview Summary mailed Nov. 6, 2006.
U.S. Appl. No. 10/388,214, Office Action mailed Jan. 31, 2006.
U.S. Appl. No. 10/388,389, Examiner Interview Summary mailed May 31, 2006.
U.S. Appl. No. 10/388,389, Examiner Interview Summary mailed May 22, 2006.
U.S. Appl. No. 10/429,216, Examiner Interview Summary mailed Mar. 6, 2006.
U.S. Appl. No. 10/429,216, Office Action mailed Apr. 11, 2006.
U.S. Appl. No. 10/544,093, Office Action mailed Feb. 9, 2009.
U.S. Appl. No. 10/625,854, Examiner Interview Summary mailed Jun. 26, 2007.
U.S. Appl. No. 10/625,854, Office Action mailed Feb. 7, 2006.
U.S. Appl. No. 10/703,713, Examiner Interview Summary mailed Feb. 21, 2006.
U.S. Appl. No. 10/703,713, Examiner Interview Summary mailed Mar. 2, 2006.
U.S. Appl. No. 10/703,713, Office Action mailed Sep. 27, 2005.
U.S. Appl. No. 10/704,070, Office Action mailed Sep. 26, 2005.
U.S. Appl. No. 10/771,174, Office Action mailed Nov. 27, 2006.
U.S. Appl. No. 10/777,792, Office Action mailed Aug. 7, 2006.
U.S. Appl. No. 10/788,666, Office Action mailed Dec. 15, 2005.
U.S. Appl. No. 10/823,463, Office Action mailed Sep. 30, 2005.
U.S. Appl. No. 10/828,548, Office Action mailed Feb. 13, 2006.
U.S. Appl. No. 10/858,855, Office Action mailed Mar. 7, 2007.
U.S. Appl. No. 10/889,999, Office Action mailed Jan. 5, 2005.
U.S. Appl. No. 10/890,000, Office Action mailed Apr. 13, 2005.
U.S. Appl. No. 10/890,024, Office Action mailed Nov. 2, 2005.
U.S. Appl. No. 10/890,070, Office Action mailed Apr. 8, 2005.
U.S. Appl. No. 10/890,071, Office Action mailed Dec. 18, 2006.
U.S. Appl. No. 10/923,469, Examiner Interview Summary mailed Apr. 9, 2008.
U.S. Appl. No. 10/923,469, Office Action mailed Jul. 3, 2007.
U.S. Appl No. 10/923,471, Examiner Interview Summary mailed Oct. 20, 2008.
U.S. Appl. No. 10/923,471, Office Action mailed Jan. 5, 2005.
U.S. Appl. No. 10/923,474, Office Action mailed Nov. 17, 2005.
U.S. Appl. No. 10/923,605, Office Action mailed Apr. 12, 2007.
U.S. Appl. No. 10/934,818, Office Action mailed Mar. 26, 2007.
U.S. Appl. No. 10/934,819, Office Action mailed Jan. 24, 2006.
U.S. Appl. No. 11/058,757, Office Action mailed Oct. 20, 2005.
U.S. Appl. No. 11/108,102, Office Action mailed Jan. 11, 2006.
U.S. Appl. No. 11/244,678, Office Action mailed Jul. 13, 2007.
U.S. Appl. No. 11/245,524, Office Action mailed Sep. 27, 2007.
U.S. Appl. No. 11/245,916, Office Action mailed May 19, 2006.
U.S. Appl. No. 11/260,047, Office Action mailed May 15, 2007.
U.S. Appl. No. 11/260,047, Examiner Interview Summary mailed May 15, 2007.
U.S. Appl. No. 11/274,493, Office Action mailed Apr. 23, 2007.
U.S. Appl. No. 11/303,478, Office Action mailed Mar. 18, 2009.
U.S. Appl. No. 11/304,986, Office Action mailed Dec. 31, 2008.
U.S. Appl. No. 11/305,889, Office Action mailed Aug. 14, 2007.
U.S. Appl. No. 11/305,899, Office Action mailed Dec. 10, 2008.
U.S. Appl. No. 11/342,353, Office Action mailed Nov. 14, 2008.
U.S. Appl. No. 11/454,772, Office Action mailed Jun. 27, 2007.
U.S. Appl. No. 11/454,772, Examiner Interview Summary mailed Apr. 13, 2007.
U.S. Appl. No. 11/520,438, Office Action mailed Aug. 6, 2009.
U.S. Appl. No. 11/842,023, Office Action mailed Nov. 13, 2008.
U.S. Appl. No. 11/842,042, Office Action mailed Jun. 24, 2009.
U.S. Appl. No. 11/842,056, Office Action mailed May 6, 2009.
U.S. Appl. No. 11/842,085, Office Action mailed Sep. 30, 2009.
U.S. Appl. No. 11/842,116, Office Action mailed Nov. 26, 2010.
U.S. Appl. No. 12/181,238, Examiner Interview Summary mailed Mar. 5, 2010.
U.S. Appl. No. 12/181,238, Office Action mailed May 28, 2009.
U.S. Appl. No. 12/253,929, Office Action mailed Apr. 28, 2010.
U.S. Appl. No. 12/336,340, Office Action mailed Mar. 4, 2010.
U.S. Appl. No. 09/201,430, Advisory Action mailed Jun. 18, 2002.
U.S. Appl. No. 09/201,430, Office Action mailed Nov. 26, 2001.
U.S. Appl. No. 09/204,838, Office Action mailed Sep. 27, 2001.
U.S. Appl. No. 09/322,289, Office Action mailed Jun. 4, 2009.
U.S. Appl. No. 09/322,289, Office Action mailed Jul. 17, 2007.
U.S. Appl. No. 09/322,289, Office Action mailed Oct. 16, 2005.
U.S. Appl. No. 09/322,289, Office Action mailed Nov. 29, 2005.
U.S. Appl. No. 09/723,713, Advisory Action mailed Dec. 20, 2004.
U.S. Appl. No. 09/723,713, Office Action mailed Jan. 11, 2006.
U.S. Appl. No. 09/723,713, Office Action mailed Feb. 12, 2002.
U.S. Appl. No. 09/723,713, Office Action mailed Jun. 3, 2004.
U.S. Appl. No. 09/723,760, Advisory Action mailed Dec. 16, 2004.
U.S. Appl. No. 09/723,760, Office Action mailed Feb. 23, 2004.
U.S. Appl. No. 09/723,760, Office Action mailed Dec. 29, 2005.
U.S. Appl. No. 09/723,765, Advisory Action mailed Feb. 9, 2004.
U.S. Appl. No. 09/723,765, Office Action mailed May 4, 2005.
U.S. Appl. No. 09/723,765, Office Action mailed Oct. 7, 2003.
U.S. Appl. No. 09/723,765, Office Action mailed Dec. 5, 2008.
U.S. Appl. No. 09/724,273, Advisory Action mailed Mar. 18, 2004.
U.S. Appl. No. 09/724,273, Advisory Action mailed Jun. 16, 2005.
U.S. Appl. No. 09/724,273, Office Action mailed Aug. 22, 2007.
U.S. Appl. No. 09/724,273, Office Action mailed Oct. 16, 2003.
U.S. Appl. No. 09/724,273, Office Action mailed Dec. 28, 2004.
U.S. Appl. No. 09/724,288, Advisory Action mailed Jan. 6, 2004.
U.S. Appl. No. 09/724,288, Advisory Action mailed Mar. 3, 2006.
U.S. Appl. No. 09/724,288, Office Action mailed Jul. 12, 2005.
U.S. Appl. No. 09/724,288, Office Action mailed Sep. 9, 2003.
U.S. Appl. No. 09/724,288, Office Action mailed Dec. 22, 2008.
U.S. Appl. No. 09/724,319, Advisory Action mailed Oct. 28, 2009.
U.S. Appl. No. 09/724,319, Office Action mailed Apr. 8, 2009.
U.S. Appl. No. 09/724,319, Office Action mailed May 2, 2006.
U.S. Appl. No. 09/724,319, Office Action mailed Dec. 21, 2010.
U.S. Appl. No. 09/724,495, Advisory Action mailed May 16, 2006.
U.S. Appl. No. 09/724,495, Office Action mailed Sep. 26, 2005.
U.S. Appl. No. 09/724,567, Office Action mailed Jul. 23, 2003.
U.S. Appl. No. 09/724,575, Advisory Action mailed Feb. 12, 2004.
U.S. Appl. No. 09/724,575, Office Action mailed Jul. 25, 2003.
U.S. Appl. No. 09/724,575, Office Action mailed Oct. 12, 2006.
U.S. Appl. No. 09/724,953, Office Action mailed Jul. 25, 2003.
U.S. Appl. No. 10/232,030, Advisory Action mailed Oct. 30, 2006.
U.S. Appl. No. 10/232,030, Office Action mailed Apr. 1, 2008.
U.S. Appl. No. 10/388,214, Office Action mailed Jul. 28, 2006.
U.S. Appl. No. 10/429,216, Office Action mailed Jan. 3, 2007.
U.S. Appl. No. 10/429,216, Office Action mailed Mar. 6, 2009.
U.S. Appl. No. 10/429,216, Office Action mailed Oct. 16, 2008.
U.S. Appl. No. 10/544,093, Office Action mailed Oct. 13, 2010.
U.S. Appl. No. 10/625,854, Advisory Action mailed Jan. 8, 2008.
U.S. Appl. No. 10/625,854, Office Action mailed Aug. 23, 2006.
U.S. Appl. No. 10/625,854, Office Action mailed Nov. 7, 2007.
U.S. Appl. No. 10/704,070, Office Action mailed Jun. 6, 2006.
U.S. Appl. No. 10/771,174, Office Action mailed Aug. 23, 2007.
U.S. Appl. No. 10/777,792, Advisory Action mailed Mar. 6, 2009.
U.S. Appl. No. 10/777,792, Office Action mailed May 8, 2007.
U.S. Appl. No. 10/777,792, Office Action mailed Nov. 18, 2008.
U.S. Appl. No. 10/828,548, Advisory Action mailed Jun. 8, 2007.
U.S. Appl. No. 10/828,548, Office Action mailed Jun. 4, 2008.
U.S. Appl. No. 10/828,548, Office Action mailed Oct. 24, 2006.
U.S. Appl. No. 10/858,855, Advisory Action mailed Apr. 7, 2008.
U.S. Appl. No. 10/858,855, Office Action mailed Nov. 23, 2007.
U.S. Appl. No. 10/889,999, Office Action mailed Mar. 14, 2006.
U.S. Appl. No. 10/890,000, Advisory Action mailed Jan. 14, 2008.
U.S. Appl. No. 10/890,000, Office Action mailed Nov. 24, 2006.
U.S. Appl. No. 10/890,024, Office Action mailed Jun. 1, 2006.
U.S. Appl. No. 10/890,070, Office Action mailed Jun. 1, 2006.
U.S. Appl. No. 10/923,469, Advisory Action mailed Apr. 16, 2009.
U.S. Appl. No. 10/923,469, Office Action mailed Dec. 29, 2008.
U.S. Appl. No. 10/923,471, Office Action mailed Apr. 24, 2008.
U.S. Appl. No. 10/923,471, Office Action mailed Dec. 24, 2009.

(56) References Cited

OTHER PUBLICATIONS

U.S. Appl. No. 10/923,471, Office Action mailed Dec. 29, 2006.
U.S. Appl. No. 10/923,474, Office Action mailed Aug. 4, 2006.
U.S. Appl. No. 10/923,474, Advisory Action mailed Feb. 22, 2007.
U.S. Appl. No. 11/058,757, Advisory Action mailed Mar. 5, 2007.
U.S. Appl. No. 11/058,757, Office Action mailed Aug. 11, 2006.
U.S. Appl. No. 11/108,102, Office Action mailed Sep. 6, 2006.
U.S. Appl. No. 11/244,678, Office Action mailed Mar. 24, 2008.
U.S. Appl. No. 11/245,524, Office Action mailed Nov. 20, 2009.
U.S. Appl. No. 11/245,916, Advisory Action mailed May 15, 2007.
U.S. Appl. No. 11/245,916, Advisory Action mailed Jun. 10, 2009.
U.S. Appl. No. 11/245,916, Advisory Action mailed Oct. 18, 2007.
U.S. Appl. No. 11/245,916, Office Action mailed Jan. 12, 2007.
U.S. Appl. No. 11/274,493, Office Action mailed Nov. 2, 2007.
U.S. Appl. No. 11/305,889, Office Action mailed May 23, 2008.
U.S. Appl. No. 11/454,772, Office Action mailed Dec. 21, 2007.
U.S. Appl. No. 11/664,865, Office Action mailed Feb. 11, 2011.
U.S. Appl. No. 11/842,042, Office Action mailed Mar. 30, 2010.
U.S. Appl. No. 09/723,765, BPAI Decision on Request for Re-Hearing mailed Oct. 16, 2007.
U.S. Appl. No. 09/723,765, BPAI Order Returning Appeal to Examiner mailed Jun. 27, 2006.
U.S. Appl. No. 09/723,765, Examiner's Answer mailed Jan. 25, 2006.
U.S. Appl. No. 09/723,765, Reply Brief Noted mailed Jun. 16, 2006.
U.S. Appl. No. 10/777,792, BPAI Decision mailed Aug. 30, 2010.
U.S. Appl. No. 10/777,792, BPAI Decision on Request for Reconsideration mailed Nov. 30, 2010.
U.S. Appl. No. 10/777,792, Examiner's Answer mailed Oct. 27, 2009.
U.S. Appl. No. 10/777,792, Reply Brief Noted mailed Jan. 11, 2010.
U.S. Appl. No. 10/923,469, BPAI Decision mailed Feb. 22, 2011.
U.S. Appl. No. 10/923,469, Reply Brief Noted mailed Mar. 9, 2010.
U.S. Appl. No. 10/429,216 , Office Action mailed May 24, 2011.
U.S. Appl. No. 12/037,045 , Office Action mailed Nov. 4, 2011.
U.S. Appl. No. 12/297,636, Office Action mailed Jul. 20, 2011
U.S. Appl. No. 12/297,636, Office Action mailed Oct. 28, 2011.
U.S. Appl. No. 13/123,898, Office Action mailed Nov. 15, 2011.
Abcam, "Anti-beta Amyloid antibody 6F/3D", *Nucleic Acids Res.* 38:D142-D148 (2010).
Aihara, et al., "Immunocytochemical Localization of Immunoglobulins in the Rat Brain: Relationship to the Blood-Brain Barrier", *J of Comparative Neurology* 342:481-496 (1994).
Alzheimer Research Forum, "Drugs in Clinical Trials" Oct. 18, 2010.
Applicants' submission in EP 07012421.9 dated Jun. 16, 2009.
Assignment executed Dec. 8, 2000 in respect of U.S. Appl. No. 60/067,740.
Assignment executed Dec. 8, 2000 in respect of U.S. Appl. No. 60/080,970.
Birmingham et al., "Set back to Alzheimer vaccine studies" Nature Medicine 8(3):199-200 (2002).
Bruggermann, et al. "The Immunogenicity of Chimeric Antibodies" *J. Exp Med.*, 170(2):153-2157 (1989).
Communication in EP 07012421.9 pursuant to Art. 94(3) EPC dated Nov. 5, 2010.
Decision of Opposition Division in EP 1 160 256 dated Feb. 17, 2011.
Declaration of Shyra J. Gardai dated Mar. 2, 2009.
Druckexemplar in EP 1 160 256 dated Jan. 25, 2010.
Extract from EPO patent register of EP 1 160 256 retrieved on Sep. 7, 2011.
Extract from EPO patent register of EP 1 842 859 retrieved on Sep. 7, 2011.
Gambetti, et al., "Human brain amyloidosis," *Nephrology Dialysis Transplantation*, 13(Suppl. 7):33-40, (1998).
GenBank, Accession No. AAA38630.1, "Immunoglobulin gamma-1 chain [*Mus musculus*]" May 5, 1994.
Hampel et al., "Measurement of Phosphorylated Tau epitopes in the Differential Diagnosis of Alzheimer Disease", Arch Gen Psychiatry (2004) 61(1):95-102.

Hyman, et al. "Kunitz Protease Inhibitor-Containing Amyloid β Protein Precursor Immunoreactivity in Alzheimer's Disease", *J. of Neuropathology*, 51(1):76-83 (1992).
Invitrogen Data Sheet, "Mouse anti-β-Amyloid Peptide", Catalog No. 13-0100Z (Rev Oct. 2008) DCC-08-1089.
Jagust et al., "Brain Imaging Evidence of preclinical Alzheimer's disease in normal aging" Ann Neurol, (2006) 59:67-681: abstract p. 676, table 1.
Janeway, et al., *Immunobiology: The Immune System in Health and Disease* 3rd Edition; cover pages and pp. 3.22-3.27 (1997).
Jefferis, "Antibody therapeutic: isotype and glycoform selection", *Expert Opin. Biol. Ther.* 7(9):1401-1413 (2007).
Klafki et al., "Therapeutic approaches to Alzheimer's disease" *Brain* 129:2840-2825 (2006).
Kuby, *Immunology*, 2nd Ed., Freeman pp. 126 and 168-171 (1994).
Marx et al., "Immune recognition of the Alzheimer amyloid β protein" Poster presentation; Autoreactive T. cells P.5.18.03 Jun. 25, 1997.
Moretto, et al., "Conformation-sensitive Antibodies against Alzheimer Amyloid-β by Immunization with a Thioredoxin-constrained B-cell Epitope Peptide", *J of Biological Chemistry*, 282(14):11436-11445 (2007).
Patentee's Grounds of Appeal in EP Patent No. 1 033 996 dated Jul. 18, 2011.
PCT/US2011/026365 International Written Opinion and Search Report mailed Jul. 13, 2011.
PCT/US2011/033649 International Written Opinion and Search Report mailed Aug. 26, 2011.
Ray. "Wyeth Study Finds Alzheimer's Drug Works in ApoE4 Non-Carriers". Poster 2008, [retrieved from the internet 16.06;.2011: <URL: elan2006.blogspot.com/2008/07/elan-wyeth-studfindalzheimerdrug.html>].
Robert et al., Engineered antibody intervention strategies for Alzheimer's disease and related dementias by targeting amyloid and toxic oligomers:, Protein Eng Des Sel. (2009) 22:(2):199-208.
Stern, et al. "Monoclonal Antibodies to a Synthetic Peptide Homologous with the First 28 Amino Acids of Alzheimer's Disease β-Protein Recognize Amyloid and Diverse Glial and Neuronal Cell Types in the Central Nervous System" *Am J of Pathology*, 134(5):973-978 (1989).
Takahashi, et al. "Monoclonal antibody to β peptide, recognizing amyloid deposits, neuronal cells and lipofuscin pigments in systemic organs", *Acta Neuropathol*, 85:159-166 (1993).
Van Dam et al., "Symptomatic effect of donepezil, rivastigmine, galantamine and memantine on cognitive deficits in the APP23 model" *Psychopharmacology* 180:177-190 (2005).
Van Noort, Multiple sclerosis: an altered immune response or an altered stress response?, *J Mol Med* 74:285-296 (1996).
Vanengelen, et al "Immunoglobulin treatment in human and experimental epilepsy" *J of Neuro* (1994); 57 (supplement):72-75.
Wiessler, et al "The Second-Generation Active Aβ Immunotherapy CAD106 Reduces Amyloid Accumulation in APP Transgenic Mice While Minimizing Potential Side Effects", *J. Neurosci.* 31(25):9323-9331 (2011).
Wikipedia entry for "Monoclonal antibody therapy" accessed on Sep. 22, 2011.
Wu et al., "Saponin Adjuvant Enhancement of Antigen-Specific Immune Responses to an Experimental HIV-1 Vaccine" J of Immunology 149:1519-1525 (1992).
Zhao et al., "Macrophage-Mediated Degradation of β-Amyloid via an Apolipoprotein E Isoform-Dependent Mechanism", Neurobiology of disease (Mar. 18, 2009) 29(11):3603-3612.
Zotova et al., "Inflammation in Azheimer's disease: relevance to pathogenesis and therapy" Alzheimer's Research & Therapy 2:1 p. 2-9 (2010).
U.S. Appl. No. 12/977,013, Office Action mailed Jan. 6, 2012.
U.S. Appl. No. 11/893,123, Notice of Allowance mailed Nov. 2, 2011.
U.S. Appl. No. 10/923,471, Office Action mailed Apr. 23, 2013.
U.S. Appl. No. 13/123,898, Office Action mailed Apr. 17, 2013.
Abbott, et al., "Transporting therapeutics across the blood-brain barrier" *Molecular Medicine Today*, pp. 106-113, Mar. 1996.
Annual Report of Johnson and Johnson pp. 1-6 (2012).

(56) References Cited

OTHER PUBLICATIONS

Arriagada, et al., "Neurofibrillary tangles but not senile plaques parallel duration and severity of Alzheimer's disease", *Neurology*, 42:631-639 (1992).
Barbour, et al., Presentation of "Efficacy and Neuropathology of Passively Administered N-Terminal and Midregion Anti-Abeta Antibodies Alone and in Combination in the PDAPP Mouse" Elan Report pp. 1-99 May 2007.
Castillo, "Poor results halt production, studies on promising Alzheimer's drug bapineuzumab" *CBS Interactive Inc.*, Nov. 7, 2012 pp. 1/1.
Centers for Disease Control and Prevention, "Vaccine Safety" Retrieved from www.cdc.gov/vaccinesafety/concerns/adjuants.html (Oct. 18, 2012) p. 1-2.
Check, "Nerve inflammation halts trial for Alzheimer's drug", *Nature*, vol. 415:462 Jan. 2002.
Curriculum Vitae Professor Nancy Joan Abbott, Mar. 2013.
Deane, et al. "IgG-Assisted Age-Dependent Clearance of Alzheimer's Amyloid β Peptide by the Blood-Brain Barrier Neonatal Fc Receptor" *The Journal of Neuroscience*, Dec. 14, 2005 25(50):11495-11503.
Declaration by Dr. Dale Schenk dated Nov. 21, 2011.
Declaration of Dr. Michael John Owen with CV and list of publications May 10, 2013.
Declaration of Georg Friedrich Melchers with CV and list of publications Apr. 6, 2013.
Declaration of Professor Nancy Joan Abbott, Apr. 8, 2013.
Dohi et al., "Reactivity of a Mouse/Human Chimeric Anti-GM2 Antibody KM966 with Brain Tumors" *Anticancer Research*, 14:2577-2582 (1994).
Eli Lilly, "Eli Lilly and Company Announces Top-Line Results on Solanezumab Phase 3 Clinical Trials in Patients with Alzheimer's Disease" Press Release, Aug. 24, 2012.
EP 1160256 B2 Response to Notice of Opposition Jan. 19, 2009.
Extract from EPO patent register of EP1842859 Communication under Rule 71(3) Mar. 28, 2013.
Extract from EPO patent register of EP1842859 Decision to Grant Mar. 28, 2012.
Farlow, et al., "Safety and biomarker effects of solanezumab in patients with Alzheimer's disease" *Alzheimer's & Dementia*, 8:261-271 (2012).
Geeraedts et al., "Superior Immunogenicity of Inactivated Whole Virus H5N1 Influenza Vaccine is Primarily Controlled by Toll-like Receptors Signalling", *PLoS Pathogens*, 2008, 4:1-8.
Gerald, et al., "Alzheimer's disease market: hope deferred", *Nature*, vol. 12:19-20 Jan. 2013.
Gluck et al., "Immunopotentiating Reconstituted Influenza Virus Virosome Vaccine Delivery System for Immunization against Hepatitis A", *J. Clin. Invest.*, (1992) vol. 90:2491-2495.
Gluck, "Immunopotentiating reconstituted influenza virosomes (IRIVs) and other adjuvants for improved presentation of small antigens", *Vaccine*, vol. 10, Issue 13 (1992) 915-919.
Hagen, Declaration Oct. 31, 2011.
Hyslop et al., "Antibody Clears Senile Plaques" *Nature*, vol. 400, Jul. 8, 1999, p. 116-117.
Jacobsen, et al., "Reversal of CM Deficits: A) 2nd Generation of mAbs to central AB epitopes B) PSAPP (18 mo) by 12A11 hv. 1. 0 & m266", *Wyeth Presentation* Apr. 27, 2004.
Janeway et al., Immunobiology, 3rd edition, pp. 8:32-8:36 (1997).
Janeway, et al., *Basic Concepts in Immunology*; pp. 1:21-1:13and 8:1-8:2 (1997).
Johnson & Johnson, "Johnson & Johnson Announces Discontinuation of Phase 3 Development of Bapineuzumab Intravenous (IV) in Mild-to-Moderate Alzheimer's Disease", Press Release, Aug. 6, 2012.
Karran, "Current status of vaccination therapies in Alzheimer's disease" *Journal of Neurochemistry*, 123:647-651 (2012).
Kerchner, et al., "Bapineuzumab", NIH Public Access, Expert Opin Biol Ther., 10(7) 1121-1130 Jul. 2010.

Laino, "Cerebral Edema Common, but Found to Be Manageable, With Bapineuzumab", *Neurology Today*, Aug. 19, 2011.
Lee et al., "Aspects of Immunobiology and Immunotherapy and Uses of Monoclonal Antibodies and Biologic Immune Modifiers in Human Gliomas" *Neurologic Clinics*, vol. 3, No. 4, Nov. 1985, 901-917.
Lemere et al., "Amyloid-Beta Immunotherapy for the Prevention and Treatment of Alzheimer Disease: Lessons from Mice, Monkeys, and Humans", Rejuvenation Research 9(1):77-84 (2006).
Lu, "In Vitro Binding Analysis of LY2062430: Surface Plasmon Resonance and FACS Analysis" Report: bTDR185 Eli Lilly and Company Apr. 2012.
Marx et al., "The Possible Role of the Immune System in Alzheimer's Disease" *Exp Gerontology*, vol. 33, Nos. 7/8 pp. 871-881, 1998.
Miller et al., "Comparative efficacy of two immunocontraceptive vaccines" *Vaccine*, (1997) 15(17-18):1858-1862 (abstract only).
Oh, et al., "Reversible leukoencephalopathy associated with cerebral amyloid angiopathy", *Neurology*, 62 (Feb. 2004) 494-497.
Orgogozo, et al., "Subacute meningoencephalitis in a subset of patients with AD after Aβ42 immunization" *Neurology*, 61:46-54 (2003).
Pfizer Announces Co-Primary Clinical Endpoints Not Met in Second Phase 3 Bapineuzumab Study in Mild-to-Moderate Alzheimer's Disease Patients Who Do Not Carry the Apoe4 Genotype, Press Release, Aug. 6, 2012.
Pfizer Halts Development of AB Antibody, Alzheimer Research Forum, Nov. 2, 2011.
Pfizer, "Pfizer Announces Topline Results of First of Four Studies in Bapineuzumab Phase 3 Program", Press Release, Jul. 23, 2012.
Remes et al., "Hereditary dementia with intracerevbral hemorrhages and cerebral amyloid angiopathy". *Neurology* 63(2):234-240 (2004).
Rieber, et al., "The Effect of Freund's Adjuvants on Blood-Cerebrospinal Fluid Barrier Permeability" *Journal of the Neurological Sciences*, 63:55-61 (1984).
Rivero et al., "Suppression of experimental autoimmune encephalomyelitis (EAE) by intraperitoneal administration of soluble myelin antigens in Wistar rats" *J. Neuroimmunology*, (1997) 72, 3-10.
Roitt, Extracts from Roitt's Essential Immunology, Ninth Edition, (1997).
Solomon, "Alzheimer's Disease and Immunotherapy", *Current Alzheimer Research*, 2004, 1, 149-163.
Solomon, "Beta-Amyloid-Based Immunotherapy as a Treatment of Alzheimer's Disease", *Drugs of Today*, 2007, 43(5):333-342.
Spack, "Antigen-specific therapies for the treatment of multiple sclerosis: a clinical trial update", *Exp. Opin. Invest. Drugs*, (1997) 6(11):1715-1727.
Sperling, et al., "Amyloid-related imaging abnormalities in amyloid-modifying therapeutic trials: Recommendations from the Alzheimer's Association Research Roundtable Workgroup" *Alzheimer's & Dementia*, 7 (2011) 397-385.
Sperling, et al., Presentation and Transcript of "Bapineuzumab Phase 3 trials in mild to moderate Alzheimer's disease dementia in apolipoprotein E ε4 carriers (Study 302) and non-carriers (Study 301)", *American Neurological Association*, Oct. 8, 2012.
Thompson, et al., "Laboratory investigation of cerebrospinal fluid proteins" *Ann Clin Biochem*, 27:425-435 (1990).
Triguero, et al., "Blood-brain barrier transport of cationized immunoglobulin G: Enhanced delivery compared to native protein" *Proc. Natl. Acad. Sci. USA*, vol. 86:4761-4765 Jun. 1989.
Triozzi et al., "Effects of a beta-human chorionic gonadotropin subunit immunogen administered in aqueous solution with a novel nonionic block copolymer adjuvant in patients with advanced cancer", *Clin. Cancer Res.*, (1997) 3(12 pt 1):2355-2362 (abstract only).
Trojano, et al., "Serum IgG to brain microvascular endothelial cells in multiple sclerosis" *Journal of the Neurological Sciences*, 143:107-113 (1996).
Tuomanen, et al., "Reversible opening of the blood-brain barrier by anti-bacterial antibodies" *Proc. Natl. Acad. Sci. USA*, vol. 90:7824-7828 (Aug. 1993).

(56) References Cited

OTHER PUBLICATIONS

Walls, et al., "Autoantibody responses in the cerebrospinal fluid of guinea pigs with chronic relapsing experimental allergic encephalomyelitis", *Acta Neruol. Scan.*, 78:422-428 (1988).

Wick et al., "The Aging Immune System: Primary and Secondary Alterations of Immune Reactivity in the Elderly" *Exp. Geronology*, vol. 32, Nos. 4/5, pp. 401-413, 1997.

Wilcock, et al. "Passive Amyloid Immunotherapy Clears Amyloid and Transiently Activates Microglia in a Transgenic Mouse Model of Amyloid Deposition" *The Journal of Neuroscience*, Jul. 7, 2004 24(27):6144-6151.

Wilcock, et al., "Number of AB Inoculations in APP+PSI Transgenic Mice Influences Antibody Titers, Microglial Activation, and Congophilic Plaque Levels" *DNA and Celll Biology*, vol. 20 No. 11: 731-736 (2001).

U.S. Appl. No. 12/738,396, Office Action mailed Apr. 16, 2013.
U.S. Appl. No. 12/297,636, Office Action mailed Oct. 15, 2012.
U.S. Appl. No. 12/738,396, Office Action mailed Feb. 13, 2012.
U.S. Appl. No. 13/076,379, Office Action mailed Nov. 28, 2012.
U.S. Appl. No. 13/123,898, Office Action mailed Jul. 20, 2012.
U.S. Appl. No. 13/271,081, Office Action mailed Mar. 1, 2013.
U.S. Appl. No. 12/738,396, Office Action mailed Sep. 21, 2012.
U.S. Appl. No. 10/923,471, Notice of Allowance mailed May 21, 2013.
U.S. Appl. No. 12/608,869, Advisory Action mailed Mar. 13, 2013.
U.S. Appl. No. 12/608,869, Office Action mailed Aug. 23, 2012.
U.S. Appl. No. 12/977,013, Office Action mailed Sep. 14, 2012.

Statistics of Fab: Aβ crystals

- Recombinant Fabs
  - Affinity purified from CM of stably transfected CHO cultures on immobilized Aβ1-12 column, followed by SEC and buffer exchange.
  - Purity confirmed by SDS-PAGE, and MS
- Crystals obtained by hanging/sitting drop method

| Fab | 12A11 | | 12B4 | 10D5 | | 3D6 |
|---|---|---|---|---|---|---|
| Ligand | Aβ1-7 | Aβ1-40 | Aβ1-7 | Aβ1-7 | Aβ1-7 | Aβ1-40 |
| Resolution Å | 1.5 | 1.5 | 2.95 | 2.15 | 2.0 | 2.2 |
| $R_{free}$ | 20.6 | 21.2 | 29.91 | 21.8 | 21.3 | 22.83 |
| R | 17.8 | 18.7 | 23.48 | 16.2 | 16.7 | 18.07 |
| Ligand residues in model | Aβ: 1-7 | Aβ:2-7 | Aβ: 2-7 | Aβ: 2-7 | Aβ: 1-6 | Aβ: 1-5 |
| LC Residues in model (219) | 1-218 | 1-219 | 1-218 | 1-218 | 1-218 | 1-204, 208-216 |
| HC Residues in model (222: 12A11, 3D6), (226: 12B4, 10D5) | 1-43, 46-136, 141-220 | 1-133, 141-222 | 2-223 | 1-136, 144-223 | 1-132, 140-219 | 1-100, 103-132, 140-219 |

FIG. 3

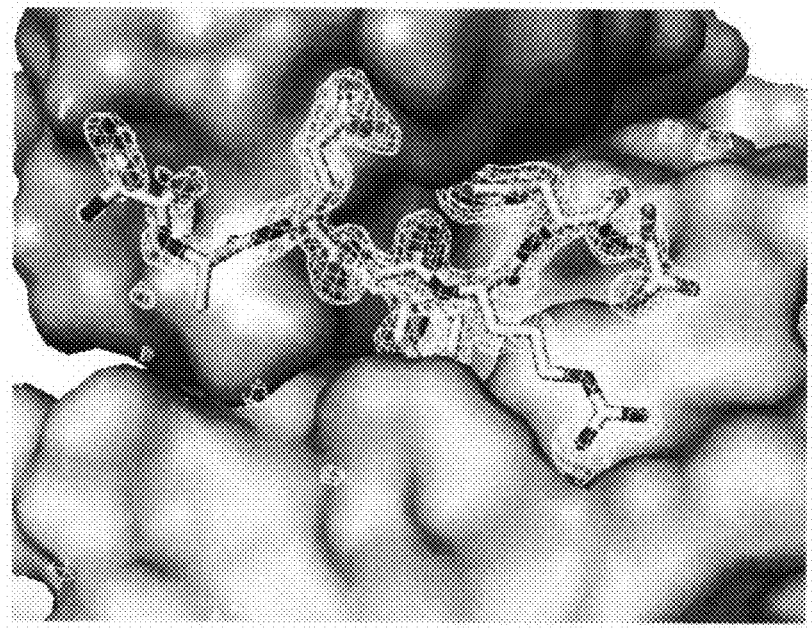
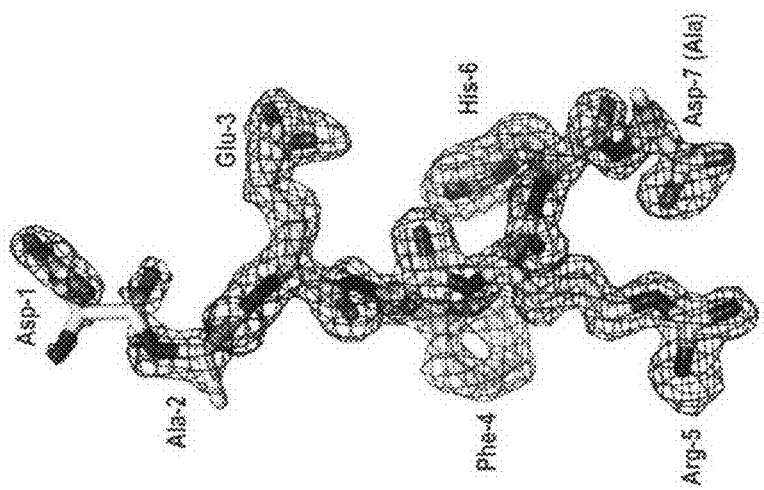
FIG. 4

CDR Homology

| Antibody | L1 | L2 | L3 |
|---|---|---|---|
| 12A11 | RSSQSIVHSNGNTYLE | KVSNRFS | FQGSHVPLT- |
| 12B4 | RSSQNIVHSNGNTYLE | KVSNRFS | FQGSHVPLT- |
| 10D5 | RSSQNIIHSNGNTYLE | KVSNRFS | FQGSHVPLT- |
| PFA1 | ---QSIVHSNGNTY-- | KVS---- | FQGSHVPLTF |
| PFA2 | ---QSIVHSNGNTY-- | KVS---- | FQGSHVPLTF |

CDR residues contacting antigen highlighted in bold, differences underlined
Dash (-) incorporated to enable visual alignment of sequence

FIG. 8A

CDR Homology

| Antibody | H1 | H2 | H3 |
|---|---|---|---|
| 12A11 | TSGMSVG | HIWWDDDKYYNPSLKS | RTTT---ADYFAY |
| 12B4 | TNGMGVS | HIYWDEDKRYNPSLKS | RRIIYDVEDYFDY |
| 10D5 | TSGMGVS | HIYWDDDKRYNPSLKL | RPITPVLVDAMDY |
| PFA1 | TSGMG-- | -IWWDDDR------- | RAHTTVLGDWFAY |
| PFA2 | TSGMG-- | -IWWDDDK------- | RAHNVVLGDWFAY |

CDR residues contacting antigen highlighted in bold, differences underlined
Dash (-) incorporated to enable visual alignment of sequence
• CDR3 of 12A11 VH domain displays unique 3 residue deletion

HYBRID AMYLOID-BETA ANTIBODIES

CROSS-REFERENCES TO RELATED APPLICATIONS

This application claims the benefit under 35 U.S.C. §1.119(e) of U.S. Application Nos. 61/197,878 and 61/110,538, filed Oct. 30, 2008 and Oct. 31, 2008, respectively, each of which is incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 15270CUS.txt is 61,440 bytes and was created on Oct. 28, 2009 for the instant application.

The 3 dimensional protein structure content written in files 3DPCSource_3D6ab17.txt, 3DPCSource_3D6ab140.txt, 3DPCSource_10D5ab17.txt, 3DPCSource_12a11ab1_40.txt, 3DPCSource_12A11ab17.txt, and 3DPCSource_12B4ab17.txt are 585,333 bytes, 569,066 bytes, 1,171,998 bytes, 618,536 bytes 331,745 bytes, and 2,209,226 bytes, respectively, and were all created on Oct. 15, 2008. The information contained each of these files is hereby incorporated by reference.

BACKGROUND OF THE INVENTION

Alzheimer's disease (AD) is a progressive disease resulting in senile dementia. See generally Selkoe, TINS 16:403 (1993); Hardy et al., WO 92/13069; Selkoe, J. Neuropathol. Exp. Neurol. 53:438 (1994); Duff et al., Nature 373:476 (1995); Games et al., Nature 373:523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 µm across with extracellular amyloid deposits at the center filaments twisted about each other in pairs. Senile plaques (i.e., amyloid plaques) are areas of disorganized neuropil up to 150 µm across with extracellular amyloid deposits at the center which are visible by microscopic analysis of sections of brain tissue. The accumulation of amyloid plaques within the brain is also associated with Down's syndrome and other cognitive disorders.

The principal constituent of the plaques is a peptide termed Aβ or B-amyloid peptide. Aβ peptide is a 4-kDa internal fragment of 39-43 amino acids of a larger transmembrane glycoprotein named protein termed amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms associated with this type of neural deterioration characterize Alzheimer's disease.

Several mutations within the APP protein have been correlated with the presence of Alzheimer's disease. See, e.g., Goate et al., Nature 349:704) (1991) (valine$^{717}$ to isoleucine); Chartier Harlan et al. Nature 353:844 (1991)) (valine$^{717}$ to glycine); Murrell et al., Science 254:97 (1991) (valine$^{717}$ to phenylalanine); Mullan et al., Nature Genet. 1:345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, TINS 20: 154 (1997)).

Mouse models have been used to test the effect of various antibodies to Aβ in inhibiting development of Alzheimer's-like indicia (e.g., amyloid burden, gliosis, neuritic dystrophy, synaptic loss, biochemical markers, electrophysiological and behavioral deficits. The results indicate that although many different antibodies show inhibition of at least one indicia of Alzheimer's disease, there are differences between antibodies in indicia inhibited and in the extent of inhibition. Different antibodies also show differences in binding preferences for different forms of Aβ, such as monomeric, oligomeric fibril, and aggregated forms of Aβ. Some of these differences exist even among antibodies binding to the same epitope of Aβ.

BRIEF SUMMARY OF THE INVENTION

The invention provides crystals characterized by unit cell parameters, optionally in isolated form. One crystal comprises amino acids 1-7 of SEQ ID NO:1 and a Fab fragment of 12A11, wherein the crystal is characterized with space group P2$_1$ and has unit cell parameters of a=43.0 Å, b=86.0 Å, c=57.4 Å; α=90°, β=94.7°, γ=90°.

Another crystal comprising amino acids 1-40 of SEQ ID NO:1 and a Fab fragment of 12A11, wherein the crystal is characterized with space group P2$_1$ and has unit cell parameters of a=43.0 Å, b=87.0 Å, c=59.0 Å; α=90°, β=95.8°, γ=90°.

Another crystal comprises amino acids 1-7 of SEQ ID NO:1 and a Fab fragment of 12B4, wherein the crystal is characterized with space group P1 and has unit cell parameters of a=78.9 Å, b=79.2 Å, c=94.1 Å; α=68.7°, β=65.3°, γ=78.5°.

Another crystal comprises amino acids 1-7 of SEQ ID NO:1 and a Fab fragment of 10D5, wherein the crystal is characterized with space group P2$_1$2$_1$2$_1$ and has unit cell parameters of a=96.3 Å, b=100.0 Å, c=104.0 Å; α=90°, β=90°, γ=90°.

Another crystal comprises amino acids 1-7 of SEQ ID NO:1 and a Fab fragment of 3D6, wherein the crystal is characterized with space group C2 and has unit cell parameters of a=126.8 Å, b=69.4 Å, c=61.7 Å; α=90°, β=115.4°, γ=90°.

Another crystal comprises amino acids 1-40 of SEQ ID NO:1 and a Fab fragment of 3D6, wherein the crystal is characterized with space group P222$_1$ and has unit cell parameters of a=40.0 Å, b=84.9 Å, c=175.9 Å; α=90°, β=90°, γ=90°.

The invention further provides a pharmaceutical composition comprising an antibody, or fragment thereof, comprising at least one of the variable light chain CDRs of SEQ ID NO:14, SEQ ID NO:15, and SEQ ID NO:16, and at least one of the variable heavy chain CDRs of SEQ ID NO:17, SEQ ID NO:18, and SEQ ID NO:19, wherein the antibody specifically binds to a peptide comprising an epitope of amino acids 1-7 of SEQ ID NO:1, with the proviso that the antibody is other than 12A11, 12B4, 10D5 and 3D6; and a pharmaceutically acceptable excipient.

The invention further provides a method for crystallizing an antibody fragment and a peptide comprising an epitope within amino acids 1-7 of SEQ ID NO:1 bound by the Fab fragment, the method comprising: contacting the peptide with the Fab fragment and a precipitant; and incubating the mixture from the contacting step over a reservoir solution, under conditions suitable for crystallization, until a crystal of the peptide and the Fab fragment forms. Optionally, the fragment is a Fab fragment.

In some methods, the Fab fragment is a Fab fragment of 12A11; and the reservoir solution comprises about 32% PEG 400 and about 0.1 M Tris, at about pH 9.0. Optionally, the peptide comprises amino acids 1-40 of SEQ ID NO:1; the Fab fragment is a Fab fragment of 12A11; and the reservoir solution comprises about 0.2 M NaCl, about 0.1 M Hepes, and about 25% PEG 4000, at about pH 7.5. Optionally, the Fab fragment is a Fab fragment of 12B4; and the reservoir solution comprises about 30% PEG 8000, about 0.1 M Hepes, and about 0.2 M $(NH_4)_2SO_4$, at about pH 7.0. Optionally, he Fab fragment is a Fab fragment of 10D5; and the reservoir solution comprises about 30% PEG 4000. Optionally, the Fab fragment is a Fab fragment of 3D6; and the reservoir solution comprises about 30% PEG 400, and about 0.1 M Tris, at about pH 9.0. Optionally, the peptide comprises amino acids 1-40 of SEQ ID NO:1; the Fab fragment is a Fab fragment of 3D6; and the reservoir solution comprises about 2.5 M NaCl, about 0.1 M Imidazole, and about 0.2 M $ZnAc_2$, at about pH 8.0.

The invention further provides a computer implemented method for analyzing binding of a candidate antibody to an epitope within amino acids 1-7 of SEQ ID NO:1. The method comprises receiving or generating sequence data for a candidate antibody, fitting the sequence data for the candidate antibody to a model of a complex of a Fab fragment bound to a peptide comprising an epitope of amino acids 1-7 of SEQ ID NO:1. The model is selected from the group consisting of 12A11:Aβ1-7, 12A11:Aβ1-40, 12B4:Aβ1-7, 10D5:Aβ1-7, 3D6:Aβ1-7 and 3D6:Aβ1-40. A representation or measure of the fit of the candidate antibody to the model is generated. Optionally, the candidate antibody is a binding fragment. Optionally, the sequence data comprises amino acid sequences of the light and heavy chain variable regions of the candidate antibody. Optionally, the antibody comprises at least one of the variable light chain CDRs of SEQ ID NO:14, SEQ ID NO:15, and SEQ ID NO:16, and at least one of the variable heavy chain CDRs of SEQ ID NO:17, SEQ ID NO:18, and SEQ ID NO:19. Optionally, the method further comprises fitting the sequence data of the candidate antibody to a plurality of the models. Optionally, the method further comprises displaying the candidate antibody bound to the epitope and/or a measure of the fit. Optionally, the method further comprises administering the antibody to a transgenic animal model of Alzheimer's disease; determining an effect on pathology or cognitive function of the mouse and comparing the effect with an effect of 12A11, 12B4, 10D5 or 3D6 antibody on the pathology or cognitive function.

In some such methods, the model is 12A11:Aβ1-7. In some such methods, the, wherein the model is 3D6:Aβ1-7. In some methods, the candidate antibody comprises a variable light chain of SEQ ID NO:7 or 22 and a variable heavy chain of SEQ ID NO:12 or 13.

The invention further provides a computer implemented method for modeling binding of a candidate antibody to an epitope within amino acids 1-7 of SEQ ID NO:1, the method comprising receiving sequence data for a candidate antibody fragment; providing a model of a complex of a Fab fragment bound to a peptide comprising an epitope of amino acids 1-7 of SEQ ID NO:1, wherein the model is selected from the group consisting of 12A11:Aβ1-7, 12A11:Aβ1-40, 12B4:Aβ1-7, 10D5:Aβ1-7, 3D6:Aβ1-7 and 3D6:Aβ1-40; and adjusting the model to accommodate differences in sequence between the candidate antibody fragment and the antibody of the complex.

The invention further provides a method for identifying an antibody fragment that can mimic the Fab fragment of 12A11, the method comprising providing a three-dimensional structural representation of the Fab fragment of 12A11 having a variable light chain of SEQ ID NO:3 and a variable heavy chain of SEQ ID NO:8, wherein the 12A11 Fab fragment is complexed to a peptide comprising an epitope of amino acids 1-7 of SEQ ID NO:1; and computationally designing an antibody fragment that mimics the binding of the 12A11 Fab fragment to SEQ ID NO:8.

The invention further provides a method for identifying an antibody fragment that can mimic the Fab fragment of 3D6, the method comprising providing a three-dimensional structural representation of the Fab fragment of 3D6 having a variable light chain of SEQ ID NO:6 and a variable heavy chain of SEQ ID NO:11, wherein the 3D6 Fab fragment is complexed to a peptide comprising an epitope of amino acids 1-7 of SEQ ID NO:1; and computationally designing an antibody fragment that mimics the binding of the 3D6 Fab fragment to SEQ ID NO:6.

The invention further provides a method for analyzing binding of a candidate antibody fragment to a peptide comprising an epitope of amino acids 1-7 of SEQ ID NO:1, the method comprising contacting the candidate antibody fragment with the peptide, such that a complex of the antibody fragment and the peptide fauns, wherein the candidate antibody fragment comprises at least one of the variable light chain CDRs of SEQ ID NO:14, SEQ ID NO:15, and SEQ ID NO:16, and at least one of the variable heavy chain CDRs of SEQ ID NO:17, SEQ ID NO:18, and SEQ ID NO:19; and analyzing the complex by X-ray crystallography to identify how the antibody fragment binds to the peptide. Optionally, the peptide comprises amino acids 1-7 of SEQ ID NO:1 or comprises amino acids 1-40 of SEQ ID NO:1. Optionally, the candidate antibody fragment binds to the peptide with an affinity constant of at least $10^{-7}$ M, and wherein the variable light chain has at least 90% identity to the amino acid sequence as set forth in SEQ ID NO:7 or 22 and the variable heavy chain has at least 90% identity to the amino acid sequence as set forth in SEQ ID NO:11, SEQ ID NO:12 or SEQ ID NO:13. Optionally, the candidate antibody fragment comprises at least two of the light chain CDRs of SEQ ID NO:14, SEQ ID NO:15, and SEQ ID NO:16 or at least two of the light chain CDRs of SEQ ID NOS. 23, 24 and 25. Optionally, the candidate antibody fragment comprises at least two of the variable heavy chain CDRs of SEQ ID NO:17, SEQ ID NO:18, and SEQ ID NO:19, or at least two of the heavy chain CDRs of SEQ ID NOS. 26, 27 and 28. Optionally, the candidate antibody fragment comprises at least two of light chain CDRs of SEQ ID NO:14, SEQ ID NO:15, and SEQ ID NO:16 or SEQ ID NOS: 23, 24 and 25, and at least two of the variable heavy chain CDRs of SEQ ID NO:17, SEQ ID NO:18, and SEQ ID NO:19 or 26, 27 and 28. Optionally, the candidate antibody fragment comprises the light chain CDRs of SEQ ID NO:14 and SEQ ID NO:16 or SEQ IS NOS:23 and 25, and the heavy chain CDRs of SEQ ID NO:18 and SEQ ID NO:19 or SEQ ID NOS: 27 and 28. Optionally, the candidate antibody fragment comprises the variable light chain CDRs of SEQ ID NO:14, SEQ ID NO:15, and SEQ ID NO:16 or SEQ ID NOS;

23, 24 and 25, and the heavy chain CDRs of SEQ ID NO:17, SEQ ID NO:18, and SEQ ID NO:19 or SEQ ID NOS: 26, 27 and 28. Optionally, X2 of SEQ ID NO:18 is W or Y.

In some methods, D1 of SEQ ID NO:1 binds to SEQ ID NO:16, when X1, X2, and X5 of SEQ ID NO:16 are occupied by W, G, and R, respectively. In some methods, D1 of SEQ ID NO:1 binds to SEQ ID NO:19, when X1, X10, and X11 of SEQ ID NO:19 are occupied by Y, S, and S, respectively. In some methods, A2 of SEQ ID NO:1 binds to SEQ ID NO:16, when X4 of SEQ ID NO:16 is occupied by V. In some methods, A2 of SEQ ID NO:1 binds to SEQ ID NO:16, when X2 and X3 of SEQ ID NO:16 are occupied by G and T respectively. In some methods, A2 of SEQ ID NO:1 binds to SEQ ID NO:18, when X9 of SEQ ID NO:18 is occupied by R. In some methods, E3 of SEQ ID NO:1 binds to SEQ ID NO:14, when X5 of SEQ ID NO:14 is occupied by H. In some methods, E3 of SEQ ID NO:1 binds to SEQ ID NO:16, when X3 of SEQ ID NO:16 is occupied by S. In some methods, E3 of SEQ ID NO:1 binds to SEQ ID NO:18, when X9 of SEQ ID NO:18 is occupied by R. In some methods, E3 of SEQ ID NO:1 binds to SEQ ID NO:16, when X5 of SEQ ID NO:16 are occupied by R. In some methods, E3 of SEQ ID NO:1 binds to SEQ ID NO:18 when X1, X2, and X9 of SEQ ID NO:18 are occupied by S, R, Y, respectively. In some methods, F4 of SEQ ID NO:1 binds to SEQ ID NO:14 and SEQ ID N016, when X5 of SEQ ID NO:14 is occupied by H, and X2, X3, X4, and X5 of SEQ ID NO 16 are occupied by S, S, V, and L, respectively. In some methods, F4 of SEQ ID NO:1 binds to SEQ ID NO:14 and SEQ ID N016, when X5 of SEQ ID NO:14 is occupied by H, and X2, X3, X4, and X5 of SEQ ID NO 16 are occupied by G, S, V, and L, respectively. In some methods, F4 of SEQ ID NO:1 binds to SEQ ID NO:14 and SEQ ID NO16, when X5 of SEQ ID NO:14 is occupied by H, and X3, X4, and X5 of SEQ ID NO 16 are occupied by S, V, and L, respectively. In some methods, F4 of SEQ ID NO:1 binds to SEQ ID NO:18, when X1 and X2 of SEQ ID NO:18 are occupied by H and W, respectively. In some methods, F4 of SEQ ID NO:1 binds to SEQ ID NO:18, when X1 and X9 of SEQ ID NO18 are occupied by H and Y respectively. In some methods, F4 of SEQ ID NO:1 binds to SEQ ID NO 18 and SEQ ID NO:19, when X1 and X2 of SEQ ID NO 18 are occupied by S and R, respectively, and X1 of SEQ ID NO:19 is occupied by Y. In some methods, R5 of SEQ ID NO:1 binds to SEQ ID NO:18, when X2, X4, X6, and X9 of SEQ ID NO:18 are occupied by W, D, D, and Y, respectively. In some methods, R5 of SEQ ID NO:1 binds to SEQ ID NO:18, when X2, X3, X4, and X9 of SEQ ID NO:18 are occupied by W, W, D, and Y, respectively. In some methods, R5 of SEQ ID NO:1 binds to SEQ ID NO:18, when X2, X3, X4, X6, and X9 of SEQ ID NO:18 are occupied by Y, W, D, D, and R, respectively. In some methods, R5 of SEQ ID NO:1 binds to SEQ ID NO:18, when X2, X3, X4, and X6 of SEQ ID NO:18 are occupied by Y, W, D, and D, respectively. In some methods, R5 of SEQ ID NO:1 binds to SEQ ID NO:14 and SEQ ID NO:16, when X5 of SEQ ID NO:14 is occupied by D and X2 and X3 of SEQ ID NO:16 is occupied by G and T, respectively. In some methods, R5 of SEQ ID NO:1 binds to SEQ ID NO:19, when X1 of SEQ ID NO:19 are occupied by Y. In some methods, H6 of SEQ ID NO:1 binds to SEQ ID NO:14 and SEQ ID NO:16, when X5 and X6 of SEQ ID NO:14 are occupied by H, N, respectively, and X3 of SEQ ID NO:16 is occupied by S. In some methods, H6 of SEQ ID NO:1 binds to SEQ ID NO:14 and SEQ ID NO:16, when X5 of SEQ ID NO:14 is occupied by H and X3 of SEQ ID NO:16 is occupied by G. In some methods, H6 of SEQ ID NO:1 binds to SEQ ID NO:19, when X9 of SEQ ID NO:19 is occupied by D. In some methods, H6 of SEQ ID NO:1 binds to SEQ ID NO:19, when X3, X4, and X9 of SEQ ID NO:19 are occupied by I, T, and D, respectively. In some methods, H6 of SEQ ID NO:1 binds to SEQ ID NO:19, when X4, and X9 of SEQ ID NO:19 are occupied by I, and D, respectively. In some methods, H6 of SEQ ID NO:1 binds to SEQ ID NO:18, when X2 of SEQ ID NO:18 is occupied by R.

In some methods, D7 of SEQ ID NO:1 binds to SEQ ID NO:19, when X7 of SEQ ID NO:19 is occupied by T. In some methods, D7 of SEQ ID NO:1 binds to SEQ ID NO:19, when X4 of SEQ ID NO:19 is occupied by T. In some methods, D7 of SEQ ID NO:1 binds to SEQ ID NO:19, when X4 of SEQ ID NO:19 is occupied by I. In some methods, the variable heavy chain has at least 90% identity to the amino acid sequence as set forth in SEQ ID NO:13. In some methods, the variable heavy chain has at least 90% identity to the amino acid sequence as set forth in SEQ ID NO:11. In some methods, amino acid 2 of SEQ ID NO:1 binds only to the VL region of the antibody fragment.

The invention further provides a method for designing a humanized antibody that binds to a peptide comprising an epitope within amino acids 1-7 of SEQ ID NO:1, the method comprising providing a model of a candidate antibody fragment bound to a peptide comprising an epitope of amino acids 1-7 of SEQ ID NO:1, wherein the model is selected from the group consisting of 12A11:Aβ1-7, 12A11:Aβ1-40, 12B4:Aβ1-7, 10D5:Aβ1-7, 3D6:Aβ1-7 and 3D6:Aβ1-40; varying the model to account for amino acid differences between a mouse antibody of interest and the antibody of the complex to produce a model of the mouse antibody of interest bound to the peptide; identifying the variable region framework residues in the model of the mouse antibody of interest that interact with the CDRs, and producing a humanized form of the mouse antibody in which at least one variable region framework residue identified in the identifying step is substituted.

The invention further provides a computer programmed to display a representation of an antibody binding to an epitope within amino acids 1-7 of SEQ ID NO:1, wherein the model is selected from the group consisting of 12A11:Aβ1-7, 12A11:Aβ1-40, 12B4:Aβ1-7, 10D5:Aβ1-7, 3D6:Aβ1-7 and 3D6:Aβ1-40, and the model is characterized by atomic coordinates of any of the Tables described herein.

The invention further provides an isolated antibody comprising a light chain variable region comprising CDRs L1, L2 and L3 designated SEQ ID NO:14, 15 and 16 respectively and a heavy chain variable region comprising CDRs H1, CDR H2 and CDR H3 designated SEQ ID NOS. 17, 18 and 19, wherein X2, X3 and X4 are absent in CDR H3, and at least one of the CDRs is not a CDR from a 12A11 antibody. Optionally, at least one of the CDRs not from a 12A11 antibody is not CDR H3. Optionally, CDRs L1, L2 and L3 are CDRs L1, L2 and L3 of antibody 10D5, and CDRs H1 and H2 are CDRs H1 and H2 of antibody 10D5 and CDR H3 is either CDR H3 of antibody 12A11 or CDR H3 of antibody 10D5 modified by absence of residues X2, X3 and X4 of SEQ ID NO:19. Optionally, CDRs L1, L2 and L3 are CDRs L1, L2 and L3 of antibody 12B4, and CDRs H1 and H2 are CDRs H1 and H2 of antibody 12B4 and CDR H3 is either CDR H3 of antibody 12A11 or CDR H3 of antibody 12B4 modified by absence of residues X2, X3 and X4 of SEQ ID NO:19. Optionally, CDRs L1, L2 and L3 are CDRs L1, L2 and L3 of antibody PFA1, and CDRs H1 and H2 are CDRs H1 and H2 of antibody PFA1 and CDR H3 is either CDR H3 of antibody 12A11 or CDR H3 of antibody PFA1 modified by Kabat positions 98-100 being unoccupied. Optionally, CDRs L1, L2 and L3 are CDRs L1, L2 and L3 of antibody PFA2, and CDRs H1 and H2 are CDRs H1 and H2 of antibody PFA2 and CDR H3 is either CDR H3 of antibody 12A11 or CDR H3 of antibody PFA2 modified by Kabat positions 98-100 being unoccupied. Optionally, CDRs L1, L2 and L3 are CDRs L1, L2 and L3 of an antibody other than 12A11 that binds to an epitope within residues 3-7 of Aβ, and CDRs H1 and H2 are CDRs H1 and H2 of the antibody other than 12A11 and CDR H3 is either CDR H3 of antibody 12A11 or CDR H3 of the antibody other than 12A11 modified by absence of residues X2, X3 and X4 of SEQ ID NO:19.

The invention further provides an isolated antibody that binds to an epitope within residues 3-7 of Aβ in which positions 98-100 by Kabat numbering in heavy chain CDR H3 are unoccupied and the antibody is not 12A11 or a humanized or chimeric version thereof including CDRs L1, L2, L3, H1, H2 and H3 from a 12A11 antibody. Optionally, the CDR H3 is a CDR H3 of the 12A11 antibody.

Any of the above antibodies can be a humanized or chimeric antibody.

The invention further provides a humanized antibody that binds to an epitope within residues 3-7 of Aβ, comprising a humanized light chain comprising CDRs L1 and L3 from a non-human antibody that binds an epitope within residues 3-7 of Aβ and CDR L2 having an amino acid sequence of a human antibody CDR L2 sequence; and a humanized heavy chain comprising CDRs H2 and H3 from the non-human antibody and CDR H1 having an amino acid sequence that is a human CDR H1 sequence. Optionally, the nonhuman antibody is 10D5, 3D6, 12B4, 12A11, PFA1 or PFA2.

The invention further provides a method of treating or effecting prophylaxis of a disease characterized by amyloid deposits of Aβ in the brain of a patient, comprising administering an effective regime of any of the antibodies described above to the patient. Optionally, the disease is Alzheimer's disease.

The invention further provides a crystal of an antibody that binds to an epitope within residues 3-7 of Aβ in which positions 98-100 of the heavy chain CDR3 by Kabat numbering are unoccupied.

The invention further provides a computer programmed to display a representation of an antibody fragment binding to an epitope within amino acids 1-7 of SEQ ID NO:1, wherein positions 98-100 of the heavy chain CDR3 of the antibody fragment are unoccupied. The invention further provides a method of analyzing antibody binding to an epitope within amino acids 1-7 of SEQ ID NO:1, comprising contacting the antibody and a peptide comprising the epitope to form a complex; crystallizing the complex; determining atomic coordinates of the crystal complex; and displaying a representation of the complex on a computer based on the atomic coordinates, wherein positions 98-100 of the heavy chain CDR3 of the antibody fragment are unoccupied.

The invention further provides an isolated antibody comprising a light chain variable region comprising CDRs L1, L2 and L3 designated SEQ ID NO:23, 24 and 25 respectively and a heavy chain variable region comprising CDRs H1, CDR H2 and CDR H3 designated SEQ ID NOS. 26, 27 and 28, wherein X2, X3 and X4 are absent in CDR H3, and at least one of the CDRs is not a CDR from a 12A11 antibody. Optionally, the at least one of the CDRs not from a 12A11 antibody is not CDR H3. Optionally, CDRs L1, L2 and L3 are CDRs L1, L2 and L3 of antibody 10D5, and CDRs H1 and H2 are CDRs H1 and H2 of antibody 10D5 and CDR H3 is either CDR H3 of antibody 12A11 or CDR H3 of antibody 10D5 modified by absence of residues X2, X3 and X4 of SEQ ID NO:28. Optionally, CDRs L1, L2 and L3 are CDRs L1, L2 and L3 of antibody 12B4, and CDRs H1 and H2 are CDRs H1 and H2 of antibody 12B4 and CDR H3 is either CDR H3 of antibody 12A11 or CDR H3 of antibody 12B4 modified by absence of residues X2, X3 and X4 of SEQ ID NO:28. Optionally, CDRs L1, L2 and L3 are CDRs L1, L2 and L3 of antibody PFA1, and CDRs H1 and H2 are CDRs H1 and H2 of antibody PFA1 and CDR H3 is either CDR H3 of antibody 12A11 or CDR H3 of antibody PFA1 modified by Kabat positions 98-100 being unoccupied. Optionally, CDRs L1, L2 and L3 are CDRs L1, L2 and L3 of antibody PFA2, and CDRs H1 and H2 are CDRs H1 and H2 of antibody PFA2 and CDR H3 is either CDR H3 of antibody 12A11 or CDR H3 of antibody PFA2 modified by Kabat positions 98-100 being unoccupied. Optionally, CDRs L1, L2 and L3 are CDRs L1, L2 and L3 of an antibody other than 12A11 that binds to an epitope within residues 3-7 of Aβ, and CDRs H1 and H2 are CDRs H1 and H2 of the antibody other than 12A11 and CDR H3 is either CDR H3 of antibody 12A11 or CDR H3 of the antibody other than 12A11 modified by absence of residues X2, X3 and X4 of SEQ ID NO:28. Any of the above antibodies can be chimeric or humanized.

The invention further provides a humanized antibody that binds to an epitope within residues 3-7 of Aβ, comprising a humanized light chain comprising CDRs L1 and L3 from a non-human antibody that binds an epitope within residues 3-7 of Aβ and CDR L2 having an amino acid sequence of a human antibody CDR L2 sequence; and a humanized heavy chain comprising CDRs H2 and H3 from the non-human antibody and CDR H1 having an amino acid sequence that is a human CDR H1 sequence. Optionally, the nonhuman antibody is 10D5, 3D6, 12B4, 12A11, PFA1 or PFA2. Optionally, CDRs L1 and L3 have amino acid sequences of SEQ ID NOS. 23 and 15 and CDRs H2 and H3 have amino acid sequences of SEQ ID NOS:27 and 28.

The invention further provides a method of treating or effecting prophylaxis of a disease characterized by amyloid deposits of Aβ in the brain of a patient, comprising administering an effective regime of any of the above antibodies to the patient. Optionally, the disease is Alzheimer's disease.

BRIEF DESCRIPTION OF THE DRAWINGS

FIG. 3 provides statistics of various Fab:Aβ crystals discussed in the Examples.

FIG. 4 shows a three dimensional representation of a 12A11 antibody bound to an Aβ 1-7 peptide. The peptide shown (SEQ ID NO: 41) in ball and stock format occupies a cleft between heavy and light chains of the antibody.

FIGS. 8A and B shows the relationship between light chain (SEQ ID NOS 66, 24, 67, 68, 24, 67, 69, 24, 67 and 29-34, respectively, in order of appearance) (A) and heavy chain (SEQ ID NOS 70-71, 20, 72-77 and 35-40, respectively, in order of appearance) (B) CDRs of five antibodies binding to an epitope within residues 3-7 of Aβ.

BRIEF DESCRIPTION OF THE SEQUENCES

Figure 1:
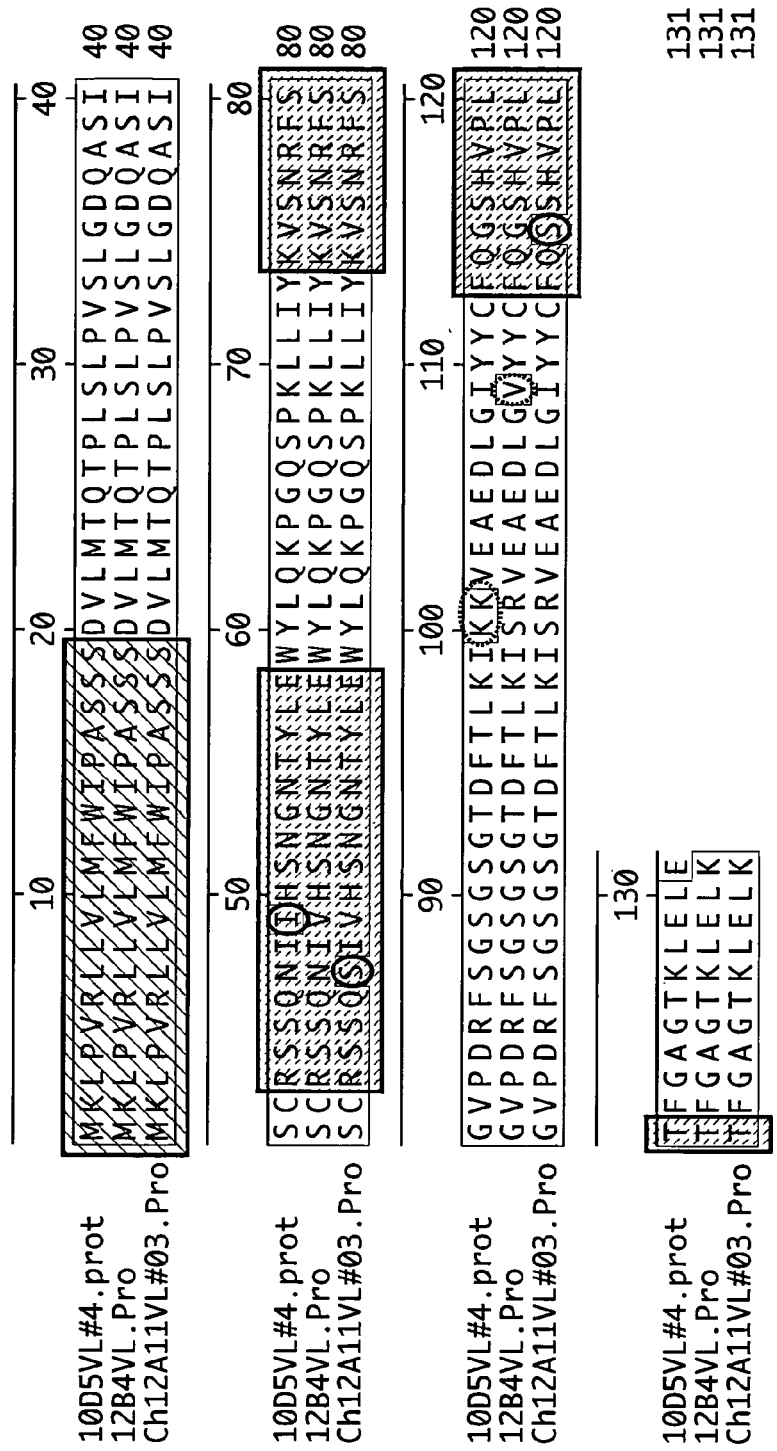
FIG. 1 shows sequence relatedness between the light chain variable regions of 10D5 (SEQ ID NO: 5), 12B4 (SEQ ID NO: 4) and 12A11 (SEQ ID NO: 3) antibodies. CDRs are in shaded boxed and amino acid differences circled.

SEQ ID NO:1 is the amino acid sequence of Aβ40.

SEQ ID NO:2 is the amino acid sequence of Aβ42.

SEQ ID NO:3 is the amino acid sequence of the variable light chain region of the murine 12A11 antibody.

SEQ ID NO:4 is the amino acid sequence of the variable light chain region of the murine 12B4 antibody.

SEQ ID NO:5 is the amino acid sequence of the variable light chain region of the murine 10D5 antibody.

SEQ ID NO:6 is the amino acid sequence of the variable light chain region of the murine 3D6 antibody.

SEQ ID NO:7 is a variable light chain region amino acid consensus sequence based on murine antibodies 12B4, 12A11, 10D5, and 3D6.

SEQ ID NO:8 is the amino acid sequence of the variable heavy chain region of the murine 12A11 antibody.

SEQ ID NO:9 is the amino acid sequence of the variable heavy chain region of the murine 12B4 antibody.

SEQ ID NO:10 is the amino acid sequence of the variable heavy chain region of the murine 10D5 antibody.

SEQ ID NO:11 is the amino acid sequence of the variable heavy chain region of the murine 3D6 antibody.

SEQ ID NO:12 is a variable heavy chain region amino acid consensus sequence based on murine antibodies 12B4, 12A11, 10D5, and 3D6.

SEQ ID NO:13 is a variable heavy chain region amino acid consensus sequence based on murine antibodies 12A11, 12B4, and 10D5.

SEQ ID NO:14 is a variable light chain region CDR1 amino acid consensus sequence based on murine antibodies 12B4, 12A11, 10D5, and 3D6.

SEQ ID NO:15 is a variable light chain region CDR2 amino acid consensus sequence based on murine antibodies 12B4, 12A11, 10D5, and 3D6.

SEQ ID NO:16 is a variable light chain region CDR3 amino acid consensus sequence based on murine antibodies 12B4, 12A11, 10D5, and 3D6.

SEQ ID NO:17 is a variable heavy chain region CDR1 amino acid consensus sequence based on murine antibodies 12B4, 12A11, 10D5, and 3D6.

SEQ ID NO:18 is a variable heavy chain region CDR2 amino acid consensus sequence based on murine antibodies 12B4, 12A11, 10D5, and 3D6.

SEQ ID NO:19 is a variable heavy chain region CDR3 amino acid consensus sequence based on murine antibodies 12B4, 12A11, 10D5, and 3D6.

SEQ ID NO:20 is the amino acid sequence of variable heavy chain region CDR3 sequence of murine 12A11.

SEQ ID NO:21 is the amino acid sequence of the variable heavy chain region CDR3 sequence of murine 3D6.

SEQ ID NO:22 is a variable light chain region amino acid consensus sequence based on murine antibodies 12A11, 12B4, and 10D5.

SEQ ID NO:23 is a variable light chain region CDR1 amino acid consensus sequence based on murine antibodies 12B4, 12A11, and 10D5.

SEQ ID NO:24 is a variable light chain region CDR2 amino acid consensus sequence based on murine antibodies 12B4, 12A11, and 10D5.

SEQ ID NO:25 is a variable light chain region CDR3 amino acid consensus sequence based on murine antibodies 12B4, 12A11, and 10D5.

SEQ ID NO:26 is a variable heavy chain region CDR1 amino acid consensus sequence based on murine antibodies 12B4, 12A11, and 10D5.

SEQ ID NO:27 is a variable heavy chain region CDR2 amino acid consensus sequence based on murine antibodies 12B4, 12A11, and 10D5.

SEQ ID NO:28 is a variable heavy chain region CDR3 amino acid consensus sequence based on murine antibodies 12B4, 12A11, and 10D5.

SEQ ID NO:29 is the amino acid sequence of the variable light chain region CDR1 sequence of murine PFA1.

SEQ ID NO:30 is the amino acid sequence of the variable light chain region CDR2 sequence of murine PFA1.

SEQ ID NO:31 is the amino acid sequence of the variable light chain region CDR3 sequence of murine PFA1.

SEQ ID NO:32 is the amino acid sequence of the variable light chain region CDR1 sequence of murine PFA2.

SEQ ID NO:33 is the amino acid sequence of the variable light chain region CDR2 sequence of murine PFA2.

SEQ ID NO:34 is the amino acid sequence of the variable light chain region CDR3 sequence of murine PFA2.

SEQ ID NO:35 is the amino acid sequence of the variable heavy chain region CDR1 sequence of murine PFA1.

SEQ ID NO:36 is the amino acid sequence of the variable heavy chain region CDR2 sequence of murine PFA1.

SEQ ID NO:37 is the amino acid sequence of the variable heavy chain region CDR3 sequence of murine PFA1.

SEQ ID NO:38 is the amino acid sequence of the variable heavy chain region CDR1 sequence of murine PFA2.

SEQ ID NO:39 is the amino acid sequence of the variable heavy chain region CDR2 sequence of murine PFA2.

SEQ ID NO:40 is the amino acid sequence of the variable heavy chain region CDR3 sequence of murine PFA2.

SEQ ID NO: 41 is the Aβ 1-7 peptide.

SEQ ID NO: 42 is the amino acid sequence for murine 12B4 VL.

SEQ ID NO: 43 is the amino acid sequence for h12B4 VL.

SEQ ID NO: 44 is the amino acid sequence for KABID 005036.

SEQ ID NO: 45 is the amino acid sequence for A19-Germline.

SEQ ID NO: 46 is the amino acid sequence for murine 12B4 VH.

SEQ ID NO: 47 is the amino acid sequence for h12B4 VHv1.

SEQ ID NO: 48 is the amino acid sequence for KABID 000333.

SEQ ID NO: 49 is the amino acid sequence for VH4-39 Germline.

SEQ ID NO: 50 is the amino acid sequence for murine 3D6 VL.

SEQ ID NO: 51 is the amino acid sequence for h3D6VL.

SEQ ID NO: 52 is the amino acid sequence for KABID 019230.

SEQ ID NO: 53 is the amino acid sequence for A19-Germline.

SEQ ID NO: 54 is the amino acid sequence for murine 3D6 VH.

SEQ ID NO: 55 is the amino acid sequence for h3D6 VH.

SEQ ID NO: 56 is the amino acid sequence for KABID 045919.

SEQ ID NO: 57 is the amino acid sequence for VH3-23 Germline.

SEQ ID NO: 58 is the amino acid sequence for murine 12A11 VL.

SEQ ID NO: 59 is the amino acid sequence for h12A11 VL.

SEQ ID NO: 60 is the amino acid sequence for BAC 01733.

SEQ ID NO: 61 is the amino acid sequence for A19-Germline.

SEQ ID NO: 62 is the amino acid sequence for murine 12A11 VH.

SEQ ID NO: 63 is the amino acid sequence for h12A11 VHv1.

SEQ ID NO: 64 is the amino acid sequence for AAA 69734.

SEQ ID NO: 65 is the amino acid sequence for 567123 Germline.

SEQ ID NO: 66 is the amino acid sequence of the variable light chain region CDR1 sequence of murine 12A11.

SEQ ID NO: 67 is a variable light chain region CDR3 amino acid consensus sequence based on murine antibodies 12B4, 12A11, and 10D5.

SEQ ID NO: 68 is the amino acid sequence of the variable light chain region CDR1 sequence of murine 12B4.

SEQ ID NO: 69 is the amino acid sequence of the variable light chain region CDR1 sequence of murine 10D5.

SEQ ID NO: 70 is the amino acid sequence of the variable heavy chain region CDR1 sequence of murine 12A11.

SEQ ID NO: 71 is the amino acid sequence of the variable heavy chain region CDR2 sequence of murine 12A11.

SEQ ID NO: 72 is the amino acid sequence of the variable heavy chain region CDR1 sequence of murine 12B4.

SEQ ID NO: 73 is the amino acid sequence of the variable heavy chain region CDR2 sequence of murine 12B4.

SEQ ID NO: 74 is the amino acid sequence of the variable heavy chain region CDR3 sequence of murine 12B4.

SEQ ID NO: 75 is the amino acid sequence of the variable heavy chain region CDR1 sequence of murine 10D5.

SEQ ID NO: 76 is the amino acid sequence of the variable heavy chain region CDR2 sequence of murine 10D5.

SEQ ID NO: 77 is the amino acid sequence of the variable heavy chain region CDR3 sequence of murine 10D5.

SEQ ID NO: 78 is a partial amino acid sequence of the variable heavy chain region CDR3 sequence of murine 10D5.

SEQ ID NO: 79 is a partial amino acid sequence of the variable heavy chain region CDR3 sequence of murine 12B4.

SEQ ID NO: 80 is a partial amino acid sequence of the variable heavy chain region CDR3 sequence of murine 12A11.

SEQ ID NO: 81 is the amino acid sequence for VH4-61 Germline.

DETAILED DESCRIPTION OF THE INVENTION

I. General

The invention provides crystal structures for complexes between Aβ or a fragment thereof and one of four monoclonal antibodies to Aβ. The four monoclonal antibodies are designated 12A11, 12B4, 10D5 and 3D6. Each of these antibodies has been described in the scientific or patent literature. The 3D6 antibody binds to an epitope formed by residues 1-5 of Aβ. The other three antibodies bind to an epitope formed by residues 3-7 of Aβ. Despite three of these antibodies binding to the same epitope and a fourth binding to an overlapping epitope, significant differences between the antibodies have been observed in their binding capacity to various forms of Aβ and capacity to inhibit development of indicia of Alzheimer's disease in transgenic animal models. For example, the 12A11 antibody is the most effective of the four antibodies in rapid treatment of cognitive deficits. The 3D6 antibody is most effective in reducing amyloid burden.

The crystal structures can be characterized by unit cell parameters defining the crystal structure itself as discussed in further detail below, by a matrix of interacting residues between the Aβ peptide and antibody chains, or by atomic coordinates of the atoms within the crystal structure. The standard parameters for defining a crystal structure provide a concise and quantitative manner of defining a particular crystal structure. The atomic coordinates are a compilation of data indicating the position of individual atoms in a crystal structure. These coordinates are typically stored or loaded into a computer, which can be programmed to display a model of the complex and/or use a model of the complex in various methods of in silico screening. A matrix of interacting residues effectively defines the most important interactions between an antibody and an Aβ peptide derivable from a computerized display of a model. Such a matrixes can be compared between antibodies and are useful in associating interactions with particular functional properties.

The in silico screening methods have a variety of applications. For example, they can be used to predict the properties of other antibodies by comparing their interactions with Aβ with those of one the four modeled antibodies. Similarity of interactions predicts similarity of functional properties. In silico screening methods can also be used to test the effect of varying the sequence of one of the four modeled antibodies. The sequence can be varied in such a way as change the interactions of an antibody with an Aβ peptide (e.g., strengthen the affinity. Alternatively, the sequence can be varied in such a way as reduce immunogenicity or susceptibility to degradation of an antibody but leave the interaction with Aβ unaltered.

II. Definitions

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, 3$^{rd}$ W.H. Freeman & Co., New York (1998). The term also refers to recombinant single chain Fv fragments (scFv).

The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol* :5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

"Specific binding" of an antibody means that the antibody exhibits appreciable affinity for antigen or a preferred epitope and, preferably, does not exhibit significant cross reactivity. Appreciable or preferred binding includes binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$. An antibody that "does not exhibit significant cross reactivity" is one that will not appreciably bind to an undesirable entity (e.g., an undesirable proteinaceous entity). For example, an antibody that specifically binds to Aβ will appreciably bind Aβ but will not significantly react with non-Aβ proteins or peptides (e.g., non-Aβ proteins or peptides included in plaques). An antibody specific for a preferred epitope will, for example, not significantly cross react with remote epitopes on the same protein or peptide. Specific binding can be determined according to any art-recognized means for determining such binding. Preferably, specific binding is determined according to Scatchard analysis and/or competitive binding assays.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region (also known as variable region framework) substantially from a human immunoglobulin or antibody and complementarity determining regions (CDRs) (e.g., at least one CDR, preferably two CDRs, more preferably three CDRs) substantially from a non-human immunoglobulin or antibody (e.g., rodent, and optionally, mouse), and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region (also known as a variable region framework) substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90% (e.g., at least 90%), preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions including donor CDR residues and acceptor framework residues) not found in chimeric immunoglobulins or antibodies, as defined herein.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

An "antigen" is an entity (e.g., a proteinaceous entity or peptide) to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, G. E. Morris, Ed. (1996).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA (Moldenhauer et al., *Scand. J. Immunol.* 32:77 (1990). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

Crystals, antibodies and other entities described herein are optionally provided in isolated form. An entity is in isolated form if it is removed from its natural environment, or exist in at least 50% or 90% w/w purity or is the predominant macromolecular entity present in a composition or any combination of these criteria.

Multiple isoforms of APP exist, for example APP$^{695}$, APP$^{751}$ and APP$^{770}$. Amino acids within APP are assigned numbers according to the sequence of the APP$^{770}$ isoform (see e.g., GenBank Accession No. P05067).

The sequences of Aβ peptides and their relationship to the APP precursor are illustrated by FIG. 1 of Hardy et al., TINS 20, 155-158 (1997). For example, Aβ42 has the sequence:
H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH (SEQ ID NO: 2).

Unless otherwise apparent from the context, reference to Aβ also includes natural allelic variations of the above sequence, particularly those associated with hereditary disease, such as the Arctic mutation, E693G, APP 770 numbering. Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus.

For example, Aβ40 has the sequence:
H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH (SEQ ID NO: 1).

Preferred epitopes or antigenic determinants, as described herein, are located within the N-terminus of the Aβ peptide and include residues within amino acids 1-11 of Aβ, preferably from residues 1-10, 1-3, 1-4, 1-5, 1-6, 1-7, 1-8 or 3-7 of Aβ. Additional preferred epitopes or antigenic determinants include residues 2-4, 5, 6, 7 or 8 of Aβ, residues 3-5, 6, 7, 8 or 9 of Aβ, or residues 4-7, 8, 9 or 10 of Aβ. Aβ can adopt a variety of conformations. Aβ can adopt an extended coil conformation or a compact helix conformation An N-terminal epitope of Aβ means an epitope with residues 1-11. An epitope within a C-terminal region means an epitope within residues 29-43, and an epitope within a central regions means an epitope with residues 12-28.

"Soluble" or "dissociated" Aβ refers to non-aggregating or disaggregated Aβ polypeptide.

"Insoluble" Aβ refers to aggregating Aβ polypeptide, for example, Aβ held together by noncovalent bonds. Aβ (e.g., Aβ42) is believed to aggregate, at least in part, due to the presence of hydrophobic residues at the C-terminus of the peptide (part of the transmembrane domain of APP). One method to prepare soluble Aβ is to dissolve lyophilized peptide in neat DMSO with sonication. The resulting solution is centrifuged to remove any insoluble particulates.

The term "Fc region" refers to a C-terminal region of an IgG antibody, in particular, the C-terminal region of the heavy chain(s) of said IgG antibody. Although the boundaries of the Fc region of an IgG heavy chain can vary slightly, a Fc region is typically defined as spanning from about amino acid residue Cys226 to the carboxyl-terminus of an IgG heavy chain(s).

The term "effector function" refers to an activity that resides in the Fc region of an antibody (e.g., an IgG antibody) and includes, for example, the ability of the antibody to bind effector molecules such as complement and/or Fc receptors, which can control several immune functions of the antibody such as effector cell activity, lysis, complement-mediated activity, antibody clearance, and antibody half-life. Effector function can also be influenced by mutations in the hinge region.

The term "effector molecule" refers to a molecule that is capable of binding to the Fc region of an antibody (e.g., an IgG antibody) including a complement protein or a Fc receptor.

The term "effector cell" refers to a cell capable of binding to the Fc portion of an antibody (e.g., an IgG antibody) typically via an Fc receptor expressed on the surface of the effector cell including, for example, lymphocytes, e.g., antigen presenting cells and T cells.

The term "Kabat numbering" unless otherwise stated, is defined as the numbering of the residues as in Kabat et al. (Sequences of Proteins of Immunological Interest, 5th Ed. Public Health Service, National Institutes of Health, Bethesda, Md. (1991)), incorporated herein by reference.

The term "Fc receptor" or "FcR" refers to a receptor that binds to the Fc region of an antibody. Typical Fc receptors which bind to an Fc region of an antibody (e.g., an IgG antibody) include, for example, receptors of the FcγRI, FcγRII, and FcγRIII subclasses, including allelic variants and alternatively spliced forms of these receptors. Fc receptors are reviewed in Ravetch and Kinet, Armu. Rev. Immunol 9:457-92 (1991); Capel et al., Immunomethods 4:25-34 (1994); and de Haas et al., J. Lab. Clin. Med. 126:330-41 (1995).

"Mutant" refers to a polypeptide or combination of polypeptides characterized by an amino acid sequence that differs from the wild-type sequence(s) by the substitution of at least one amino acid residue of the wild-type sequence(s) with a different amino acid residue and/or by the addition and/or deletion of one or more amino acid residues to or from the wild-type sequence(s). The additions and/or deletions can be from an internal region of the wild-type sequence and/or at either or both of the N- or C-termini. A mutant antibodies or antibody fragments may have, but need not have neutralization activity. Preferably, a mutant displays biological activity that is substantially similar to that of the wild-type Aβ peptide or antibody or antibody fragment.

"Conservative Mutant" refers to a mutant in which at least one amino acid residue from the wild-type sequence(s) is substituted with a different amino acid residue that has similar physical and chemical properties, i.e., an amino acid residue that is a member of the same class or category, as defined above. For example, a conservative mutant may be a polypeptide or combination of polypeptides that differs in amino acid sequence from the wild-type sequence(s) by the substitution of a specific aromatic Phe (F) residue with an aromatic Tyr (Y) or Trp (W) residue.

"Non-Conservative Mutant" refers to a mutant in which at least one amino acid residue from the wild-type sequence(s) is substituted with a different amino acid residue that has dissimilar physical and/or chemical properties, i.e., an amino acid residue that is a member of a different class or category, as defined above. For example, a non-conservative mutant may be a polypeptide or combination of polypeptides that differs in amino acid sequence from the wild-type sequence by the substitution of an acidic Glu (E) residue with a basic Arg (R), Lys (K) or ornithine (Orn) residue.

"Deletion Mutant" refers to a mutant having an amino acid sequence or sequences that differs from the wild-type sequence(s) by the deletion of one or more amino acid residues from the wild-type sequence(s). The residues may be deleted from internal regions of the wild-type sequence(s) and/or from one or both termini.

"Truncated Mutant" refers to a deletion mutant in which the deleted residues are from the N- and/or C-terminus of the wild-type sequence(s).

"Extended Mutant" refers to a mutant in which additional residues are added to the N- and/or C-terminus of the wild-type sequence(s).

"Aβ-antibody complex" refers to an association of Aβ peptide or Aβ peptide fragments and antibody or antibody fragments, as each of these terms is defined herein.

"Crystal" refers to a composition including a Aβ-antibody complex in crystalline form.

"X-ray Diffraction" refers to a type of wave interference created when high energy X-ray radiation interacts with any obstruction in its traveling path. The obstruction is often in the form of a crystal of protein, nucleic acid, or inorganic compound. The electrons that surround the atoms in the crystal, rather than the atomic nuclei, are the entities which physically interact with the incoming X-ray photons. When X-ray radiation hits the atoms in a crystal, they make the electronic clouds of the atoms move as does any electromagnetic wave. The re-emitted X-ray radiation gives rise to constructive or destructive interferences. This phenomenon is called X-ray diffraction. In X-ray crystallography, the X-ray diffraction patterns of closely spaced lattices of atoms in the crystal are recorded and then analyzed to reveal the structural nature of the crystal. For example, the spacing between the crystal lattices can be determined using Bragg's law. X-ray diffraction is widely used in chemistry and biochemistry to determine the structures of an immense variety of molecules, including inorganic compounds, DNA and proteins. X-ray diffraction is commonly carried out using single crystals of a material, but if these are not available, microcrystalline powdered samples may also be used, although this requires different equipment. A detailed discussion on X-ray diffraction may be found in Chapter 4 in "Principles of Protein X-ray Crystallography" by Drenth, second edition 1999, Springer-Verlag Inc.

"Bragg's Law" refers to the principle that defines the diffraction conditions that give rise to constructive interferences. When the phase shift of the incident radiation is proportional to $2\pi$, the condition can be expressed as: $n\lambda=2d \sin(\theta)$, where n is an integer; $\lambda$ is the wavelength of the X-ray radiation, or radiations caused by moving electrons, protons and neutrons; d is the spacing between the planes in the atomic lattice, and $\theta$ is the angle between the incident ray and the scattering planes.

"Crystallization" in the context of protein X-ray crystallography refers to the processes during which soluble proteins are transformed into their crystalline forms. Crystals of a protein can be grown out of its solution state under experimental conditions that allow controlled phase transition. Such experimental conditions include a mixture of multiple solutions that often contain an aqueous solution of the target protein, a solution of one or a mixture of precipitants, and one or more compounds that contribute to the overall pH or ionic strength of the final mixture.

"Mother liquor" refers to the impure or complex residual solution that remains after the crystallization process. Once crystals are formed, they can be preserved in mother liquor when other experimental conditions remain unchanged. Solutions resembling the composition of a mother liquor are often used as carrier solutions for incorporating additional reagents into the already formed crystals, such as introducing heavy atoms or cryoprotectants.

"Diffraction Quality Crystal" refers to a crystal that is well-ordered and of a sufficient size, i.e., at least 10 μm, preferably at least 50 μm, and most preferably at least 100 μm in its smallest dimension such that it produces measurable diffraction to at least 3 Å resolution, preferably to at least 2 Å. resolution, and most preferably to at least 1.5 Å resolution or lower.

"Unit Cell" refers to the smallest and simplest volume element (i.e., parallelpiped-shaped block) of a crystal that is completely representative of the unit or pattern of the crystal, such that the entire crystal can be generated by translation of the unit cell. The dimensions of the unit cell are defined by six numbers: dimensions a, b and c and angles $\alpha$, $\beta$ and $\gamma$ (Blundel et al., 1976, Protein Crystallography, Academic Press). A crystal is an efficiently packed array of many unit cells.

"Triclinic Unit Cell" refers to a unit cell in which a≠b≠c and α≠β≠γ.

"Monoclinic Unit Cell" refers to a unit cell in which a≠b≠c; α=γ=90°; and β≠90°, defined to be ≥90°.

"Orthorhombic Unit Cell" refers to a unit cell in which a≠b≠c; and α=β=γ=90°.

"Tetragonal Unit Cell" refers to a unit cell in which a≠b≠c; and α=β=γ=90°.

"Trigonal/Rhombohedral Unit Cell" refers to a unit cell in which a≠b≠c; and α=β=90°; and γ=120°.

"Trigonal/Hexagonal Unit Cell" refers to a unit cell in which a=b=c; α=β=γ≠90°; and γ=120°.

"Cubic Unit Cell" refers to a unit cell in which a=b=c; and α=β=γ=90°.

"Crystal Lattice" refers to the array of points defined by the vertices of packed unit cells.

"Space Group" refers to the set of symmetry operations of a unit cell. In a space group designation (e.g., C2) the capital letter indicates the lattice type and the other symbols represent symmetry operations that can be carried out on the unit cell without changing its appearance.

"Asymmetric Unit" refers to the largest aggregate of molecules in the unit cell that possesses no symmetry elements that are part of the space group symmetry, but that can be juxtaposed on other identical entities by symmetry operations.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides including the new crystal (Jones et al., 1991, *Acta Crystallogr.* 47:753-70; Brunger et al., 1998, *Acta Crystallogr. D. Biol. Crystallogr.* 54:905-21).

A "pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, diluents, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. 1995, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enterable (e.g., oral, intranasal, rectal, or vaginal) or parenteral (e.g., subcutaneous, intramuscular, intravenous or intraperitoneal injection; or topical, transdeimal, or transmucosal administration).

A "subject" of diagnosis, treatment, or administration is a human or non-human animal, including a mammal, such as a rodent (e.g., a mouse or rat), a lagomorph (e.g., a rabbit), or a primate. A subject of diagnosis, treatment, or administration is preferably a primate, and more preferably a human.

A "therapeutic" treatment is a treatment administered to a subject who exhibits signs of pathology for the purpose of diminishing, slowing the progression, eliminating, or halting those signs.

A "prophylactic" treatment is a treatment administered to a subject who does not exhibit signs of a disease or exhibits only early signs for the purpose of decreasing the risk of developing pathology.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatural amino acids include, for example, azetidinecarboxylic acid, 2-aminoadipic acid, 3-aminoadipic acid, β-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. Each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic amino acids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

As used herein; the term "contacting" refers to the process of bringing into contact at least two distinct species such that they can react. The resulting reaction product can be produced directly from a reaction between the added reagents or from an intermediate from one or more of the added reagents which can be produced in the reaction mixture.

As used herein, the term "precipitant" refers to a compound or mixture that helps the antibody complex precipitate from solution and form a crystal. Precipitants useful in the invention are discussed below.

Transgenic models of Alzheimer's disease are usually characterized by expression of an APP transgene and are disposed to develop one or more indicia of Alzheimer's disease, such as amyloid deposits and/or cognitive deficits. Agents, such as antibodies, are tested in such models by comparing an indicia of Alzheimer's disease in the presence of an agent compared to a control transgenic model not treated with the agent. Such models include, for example, mice bearing a 717 (APP770 numbering) mutation of APP described by Games, *Nature* 373:523 (1995)., supra, and mice bearing a 670/671 (APP770 numbering) Swedish mutation of APP such as described by McConlogue et al., U.S. Pat. No. 5,612,486 and Hsiao et al., *Science*, 274, 99 (1996); Staufenbiel et al., *Proc. Natl. Acad. Sci. USA*, 94:13287-13292 (1997); Sturchler-Pierrat et al., *Proc. Natl. Acad. Sci. USA*, 94:13287-13292 (1997); Borchelt et al., *Neuron*, 19:939-945 (1997)); Richards et al., J. Neurosci. 23:8989-9003, 2003; Cheng, Nat Med. 10(11): 1190-2, 2004 Hwang et al., Exp Neurol. 2004 March Mutations of APP suitable for inclusion in transgenic animals include conversion of the wild-type Val717 (APP770 numbering) codon to a codon for Ile, Phe, Gly, Tyr, Leu, Ala, Pro, Trp, Met, Ser, Thr, Asn, or Gln. A preferred substitution for Val717 is Phe. Another suitable mutation is the arctic mutation E693G (APP 770 numbering). The PSAPP mouse, which has both amyloid precursor protein and presenilin transgenes, is described by Takeuchi et al., American Journal of Pathology. 2000; 157: 331-339. A triple transgenic mouse having amyloid precursor protein, presenilin and tau transgenes is described by LaFerla, (2003), Neuron 39, 409-421. Another useful transgenic mouse has both APP and TGF-β transgenes. Protein encoding sequences in transgenes are in operable linkage with one or more suitable regulatory elements for neural expression. Such elements include the PDGF, prion protein and Thy-1 promoters. Another useful transgenic mouse has an APP transgene with both a Swedish and 717 mutation. Another useful transgenic mouse has an APP transgene with an arctic mutation (E693G).

III. Aβ:Antibody Complexes

A. Antibodies

The invention provide crystal structures for four mouse monoclonal antibodies, 3D6, 10D5, 12A11 and 12B4, all of which bind to Aβ. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and assigned accession number PTA-5130. A cell line producing the 10D5 monoclonal antibody (RB44 10D5.19.21) was deposited with the ATCC on Apr. 8, 2003 under the terms of the Budapest Treaty and assigned accession number PTA-5129.3D6 and 10D5 are effective at mediating phagocytosis of aggregated Aβ and reducing plaque burden and neuritic dystrophy. See, e.g., WO 2002/46237. 3D6 binds specifically to amino acids 1-5 of Aβ while 10D5 binds to amino acids 3-7 of Aβ. Johnson-Wood et al., *Proc. Natl. Acad. Sci. USA* 94: 1550-1555 (1997), Hyman et al., *J. Neuropathol. Exper. Neurology* 51:76-83 (1992).

Humanized and chimeric forms of 3D6 and 10D5 are described in US 20030165496, US 20040087777, WO 02/46237, WO 04/080419, WO 02/088306 and WO 02/088307. 10D5 antibodies are also described in US 20050142131. Additional 3D6 antibodies are described in US 20060198851 and PCT/US05/45614.

12A11 is a murine IgG1 kappa monoclonal antibody that specifically binds an epitope formed by residues 3-7 of Aβ. 12A11 has been shown to (1) have a high avidity for aggregated Aβ 1-42, (2) have the ability to capture soluble Aβ, and (3) mediate phagocytosis of amyloid plaque. See, e.g., WO 2004/108895. 12A11 is also particularly effective in rapid reversal of cognitive deficits. The light and heavy chain variable regions have amino acid sequences designated SEQ ID NOS. 3 and 8 respectively.

12B4 is a murine IgG2a kappa monoclonal antibody that specifically binds to an epitope formed by residues 3-7 of Aβ, and has been shown to mediate phagocytosis of amyloid plaque. See, e.g., WO 03/077858. The light and heavy chain variable regions have amino acid sequences designated SEQ ID NO:4 and 9 respectively.

Figure 2:
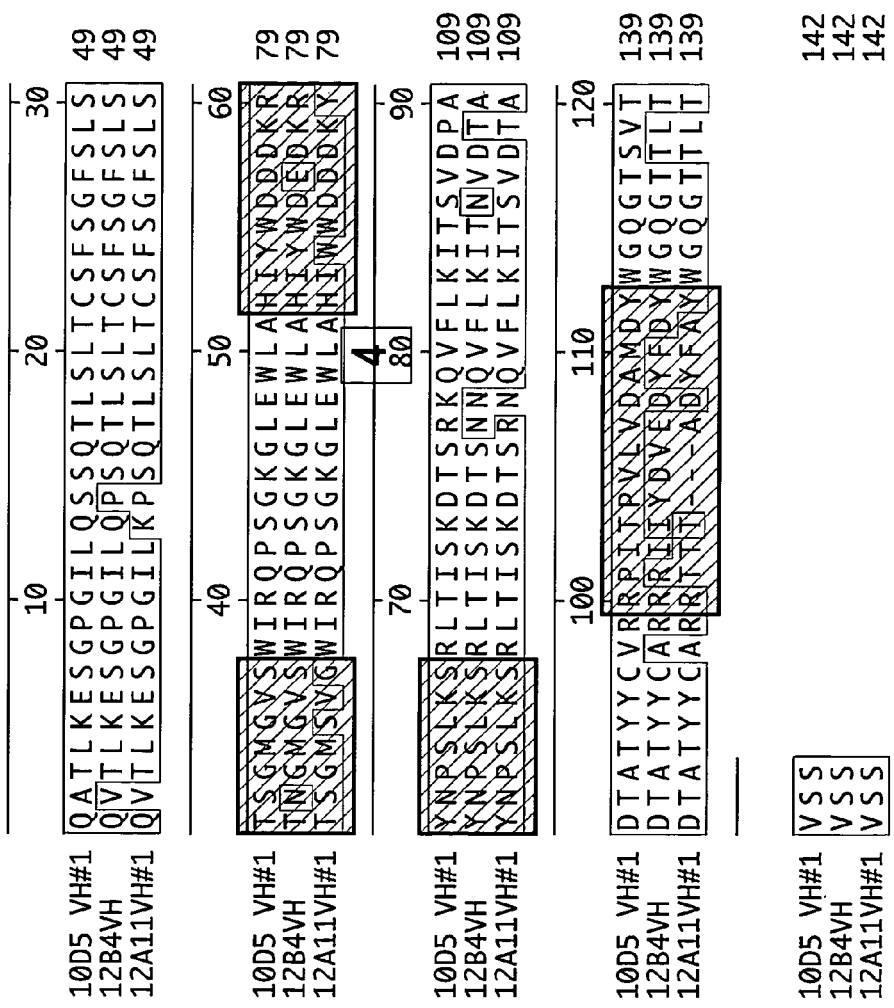
FIG. 2 shows sequence relatedness between the heavy chain variable regions of 10D5 (SEQ ID NO: 10), 12B4 (SEQ ID NO: 9) and 12A11 (SEQ ID NO: 8). CDRs are in shaded boxes, and amino acid differences are shown with lighter boxing.

The complete light and heavy chain variable regions (without signal sequences) of antibodies 12A11, 12B4 and 10D5 are compared in FIGS. 1 and 2 respectively. The CDRs of these antibodies and PFA1 and PFA2 are compared in FIGS. 8A and B.

Table 1 compares various properties of four antibodies that specifically bind to an N-terminal epitope of Aβ.

TABLE 1

| mAb | Epitope | Kd* | Oligomer | CFC Assay |
| --- | --- | --- | --- | --- |
| 12A11 | 3-7 | 8.40 nM | 2,3-mer >> 1-mer | +++ |
| 12B4 | 3-7 | 24.5 nM | 1 > 2,3-mer | − |
| 10D5 | 3-7 | 54.5 nM | 2,3-mer > 1 | + |
| 3D6 | 1-5 | 0.23 nM | 2,3-mer > 1 | + |

*Kd determination by BIACORE binding immobilized Ab1-10, assuming bivalent interaction.

Contextual Fear Conditioning Assays.

Contextual fear conditioning (CFC) is a common form of learning that is exceptionally reliable and rapidly acquired in most animals, for example, mammals. Test animals learn to fear a previously neutral stimulus and/or environment because of its association with an aversive experience. (see, e.g., Fanselow, *Anim. Learn. Behav.* 18:264-270 (1990); Wehner et al., *Nature Genet.* 17:331-334. (1997); Caldarone et al., *Nature Genet.* 17:335-337 (1997)).

Contextual fear conditioning is especially useful for determining cognitive function or dysfunction, e.g., as a result of disease or a disorder, such as a neurodegenerative disease or disorder, an Aβ-related disease or disorder, an amyloidogenic disease or disorder, the presence of an unfavorable genetic alteration effecting cognitive function (e.g., genetic mutation, gene disruption, or undesired genotype), and/or the efficacy of an agent, e.g., an Aβ conjugate agent, on cognitive ability. Accordingly, the CFC assay provides a method for independently testing and/or validating the therapeutic effect of agents for preventing or treating a cognitive disease or disorder, and in particular, a disease or disorder affecting one or more regions of the brains, e.g., the hippocampus, subiculum, cingulated cortex, prefrontal cortex, perirhinal cortex, sensory cortex, and medial temporal lobe (see WO/2006/066118 and US 2008145373).

The crystal structures of 3D6, 10D5, 12A11 and 12B4 are useful in analyzing mutant forms of these antibodies (sometimes referred to as variants). Such mutants include conservative mutants, non-conservative mutants, deletion mutants, addition mutants, truncated mutants, extended mutants, methionine mutants, selenomethionine mutants, cysteine mutants and selenocysteine mutants. A mutant may or may not have wild-type 12A11, 12B4, 10D5 or 3D6 Fab binding affinity and specificity. Preferably, a mutant displays biological activity that is substantially similar to that of the wild-type antibody.

One class of variants of 3D6, 10D5, 12A11 and 12B4 are antibodies that can be screened have shuffled sequences representing a hybrid of sequences of two or more of these antibodies. Such sequences have a light chain variable region conforming to the formula of SEQ ID NO:7 or 22 and a heavy chain variable region conforming to a formula of SEQ ID NO:12 or 13 (SEQ ID NOS 22 and 13 being based on 10D5, 12A11 and 12B4 only). Hybrid sequences can combine distinct useful properties of separate antibodies in the same antibody. Hybrid can be the result of design or a random shuffling process. Variants also include hybrids of the above four antibodies with independently isolated antibodies or hybrids between independently isolated antibodies. Either the light chain variable region or the heavy chain variable region or both can be provided in a hybrid form. One type of hybrid that is particularly useful includes a CDRH3 of 12A11 and one or more other CDRs from 10D4, 12B4, PFA1 or PFA1.

The crystal structures provided herein are also useful for analyzing independently isolated antibodies to Aβ. A variety of antibodies to Aβ have been described in the patent and scientific literature for use in immunotherapy of Alzheimer's disease, some of which are in clinical trials (see, e.g., U.S. Pat. No. 6,750,324). Such antibodies can specifically bind to an N-terminal epitope, a mid (i.e., central)-epitope or a C-terminal epitope as defined above. Some antibodies are N-terminal specific (i.e., such antibodies preferentially to the N-terminus of Aβ over APP). As noted above antibodies binding to epitopes within residues 1-3, 1-4, 1-5, 1-6, 1-7, 1-8, 1-9 or 1-10 of Aβ42 or within residues 2-4, -5, -6, -7, -8, -9 or -10 of Aβ, or within residues 3-5, -6, -7, -8, -9, or -10 of Aβ, or within residues 4-7, 8, 9 or 10 of Aβ42 can be used. Antibodies can also be isolated de novo using Aβ or its fragments as an immunogen. Two examples of independently isolated mouse antibodies binding to an epitope within residues 3-7 of Aβ are designated PFA1 and PFA2. These antibodies are reported by Gardberg et al., PNAS 104, 15659-15664 (2007) and have CDR sequences shown in FIGS. 8A and B.

Although models are provided for mouse antibodies, the models can be used to for analysis of other antibodies of any type including mouse, chimeric, humanized (including veneered antibodies) (see Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539), or human (Lonberg et al., WO 93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991)) EP1481008, Bleck, Bioprocessing Journal 1 (September/October 2005), US 2004132066, US 2005008625, WO 04/072266, WO 05/065348, WO 05/069970, and WO 06/055778.

B Methods of Making Crystals of Aβ:Antibody Complexes

Peptide:antibody complexes can be prepared by a variety of methods, including vapor diffusion, dialysis, batch, microbatch, or liquid bridge crystallization according to methods known in the art ("Crystallization of Biological Macromolecules", A. McPherson, Cold Spring Harbor Laboratory Press, Cold Spring Harbor, N.Y., USA).

In vapor diffusion crystallization, a small volume (i.e., a few microliters) of protein solution is mixed with a solution containing a precipitant. This mixed volume is suspended over a well containing a small amount, i.e., about 1 ml, of precipitant and sometimes about 0.1 microliters for the drop and about 50 microliters for the well. Vapor diffusion between the drop and the well will result in crystal formation in the drop. Examples of precipitants include, for example, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof. Water is removed by controlled evaporation to produce precipitating conditions, which are maintained until crystal growth ceases.

The dialysis method of crystallization utilizes a semipermeable size-exclusion membrane that retains the protein but allows small molecules (i.e., buffers and precipitants) to diffuse in and out. In dialysis, rather than concentrating the protein and the precipitant by evaporation, the precipitant is allowed to slowly diffuse through the membrane and reduce the solubility of the protein while keeping the protein concentration fixed.

The batch method generally involves the slow addition of a precipitant to an aqueous solution of protein until the solution just becomes turbid, at this point the container can be sealed and left undisturbed for a period of time until crystallization occurs. In the batch technique the precipitant and the target molecule solution are simply mixed. Supersaturation is achieved directly rather than by diffusion. Often the batch technique is performed under oil. The oil prevents evaporation and extremely small drops can be used. For this, the term "microbatch" is used. A modification of this technique is not to use paraffin oil (which prevents evaporation completely) but rather use silicone oil or a mixture of silicone and paraffin oils so that a slow evaporation is possible.

The microbatch crystallization method was originally developed to carry out protein crystallization by Douglas Instruments Ltd (Berkshire, United Kingdom) in collaboration with Imperial College, London. The method was developed to allow theoretical studies but can be used for routine large scale crystallization, since it is very rapid and uses only about as little as 0.1 to 1 μl of protein per trial. Like the original batch crystallization methods that were used in the early days of protein crystallization, the microbatch method involves the simple combination of protein with precipitants, buffers, etc., generally without any subsequent concentration step. The ingredients are simply mixed at their final concentrations. Because very small volumes are used, the droplets are generally covered, e.g., with paraffin oil, to prevent evaporation. Vapor Plates designed for batch crystallization available from Douglas Instruments can be used in such methods. These have 96 wells, each holding about 9 μl. Droplets with volumes from about 0.2 to about 2 μl are dispensed at the bottom of the wells. With a special microtip and highly accurate motorized syringes, very small droplets can be dispensed accurately. The dispensing error is generally around 20 nl.

One preferred method of crystallization of Aβ:antibody complexes involves mixing a Aβ:antibody complexes solution with a "reservoir buffer", with a lower concentration of the precipitating agent necessary for crystal formation. For crystal formation, the concentration of the precipitating agent has to be increased, e.g., by addition of precipitating agent, for example by titration, or by allowing the concentration of precipitating agent to balance by diffusion between the crystallization buffer and a reservoir buffer. Under suitable conditions such diffusion of water or volatile precipitating agent occurs along the gradient of precipitating agent, e.g., between the reservoir buffer having a higher concentration of precipitating agent and the crystallization buffer having a lower concentration of precipitating agent. Diffusion may be achieved e.g., by vapor diffusion techniques allowing diffusion of water in the common gas phase. Known techniques are e.g., vapor diffusion methods, such as the "hanging drop" or the "sitting drop" method. In the vapor diffusion method a drop of crystallization buffer containing the protein is hanging above or sitting beside a much larger pool of reservoir buffer. Alternatively, the balancing of the precipitating agent can be achieved through a semi-permeable membrane (dialysis method) that separates the crystallization buffer from the reservoir buffer and prevents dilution of the protein into the reservoir buffer. The invention provides that the crystals are grown by vapor diffusion in hanging and or sitting drops. In this method, the Aβ-antibody complex/precipitant solution is allowed to equilibrate in a closed container with a larger aqueous reservoir having a precipitant concentration optimal for producing crystals.

Exemplified crystallization conditions can be varied by, for example, adjusting pH, protein concentration and/or crystallization temperature, changing the identity or concentration of salt and/or precipitant used, using a different method of crystallization, or introducing additives such as detergents (e.g., TWEEN 20 (monolaurate), LDAO, Brij 30 (4 lauryl ether)), sugars (e.g., glucose, maltose), organic compounds (e.g., dioxane, dimethylformamide), lanthanide ions or polyionic compounds that aid in crystallization. High throughput crystallization assays may also be used to assist in finding or optimizing the crystallization condition.

In some cases, iterative antibody design is carried out by forming successive Aβ:antibody complexes and then crystallizing each new complex. High throughput crystallization assays may be used to find a new crystallization condition or to optimize the original protein crystallization condition for the new complex.

The ratio of Aβ:antibody used in a crystallization can vary. In some methods, the Aβ:antibody complex is prepared with a Aβ:antibody ratio of 1:1. In other methods, the Aβ:antibody complex is prepared with a Aβ:antibody complex ratio of 1:2. In other methods, the Aβ:antibody complex is prepared with a Aβ:antibody ratio of 2:1. In other methods, the Aβ:antibody complex is prepared with a Aβ:antibody ratio of 1:1.1, 1:4.5, 1:1.8. In other methods, the Aβ:antibody ratio of 1:(2 or higher). In other methods, the Aβ:antibody complex is prepared with a Aβ:antibody ratio of 1:(5 or higher). In other methods, the Aβ:antibody complex is prepared with a Aβ:antibody ratio of 1:(10 or higher).

The buffer and pH of the crystallization reaction can also vary. In some methods, the Aβ:antibody complex is prepared in a buffer solution containing 10 mM Hepes, pH 7.5, 75 mM NaCl. In some methods, the Aβ:antibody complex is prepared in a buffer solution with a pH value of 4.0, 5.0, 6.0, 7.0, 8.0, 9.0. In some methods, the Aβ:antibody complex is prepared in a buffer solution with a pH value of less than 4.0, between 4.0 to 5.0, between 5.0 to 6.0, between 6.0 to 7.0, between 8.0 to 9.0, or higher than 9.0. In some methods, the Aβ:antibody complex is prepared in Tris buffer, MES buffer, citrate buffer, acetate buffer, bicine buffer, MOPS buffer, MOPSP buffer, PIPES buffer, or any other buffer suitable for crystallization.

The concentration of the Aβ:antibody complex can also vary. In some methods, the concentration is 1 mg/ml. In other methods, the concentration of the Aβ:antibody complex is 5 mg/ml. In other methods, the concentration of the Aβ:antibody complex is 10 mg/ml. In other methods, the concentration of the Aβ:antibody complex is 15 mg/ml. In other methods, the concentration of the Aβ:antibody complex is 20 mg/ml, or higher. In other methods, the concentration of the Aβ:antibody complex is 5.3 mg/ml, 7.1 mg/ml, 14.3 mg/ml, or 4.1 mg/ml.

In some methods, the Aβ:antibody complex crystals are prepared by mixing the Aβ:antibody complex and reservoir solution in a ratio of 1:1. In other methods, the Aβ:antibody complex crystals are prepared by mixing the Aβ:antibody complex and reservoir solution in a ratio of 1:2. In other methods, the Aβ:antibody complex crystals are prepared by mixing the Aβ:antibody complex and reservoir solution in a ratio of 10:1, 5:1, 4:1, 3:1, 2:1, 1:1, 1:2, 1:3, 1:4, 1:5, or 1:10.

In some methods, the Aβ:antibody complex crystals are prepared by a hanging drop method. In other methods, t the Aβ:antibody complex crystals are prepared by sitting drop method. In some methods, the Aβ:antibody complex crystals were prepared using a robot, which can be for example, a Honeybee robot or a Phoenix robot. In some methods, the Aβ:antibody complex crystallization conditions are screened by high throughput crystallization methods. (See, e.g., *Advanced Drug Delivery Reviews,* 56(3):275-300 (2004).)

The Aβ:antibody complex crystals can be frozen in a freezing solution prior to data collection. The freezing solution can comprise a cryo-protectant, optionally mixed with the reservoir solution.

The invention provides crystals of a peptide including an epitope of amino acids 1-7 of SEQ ID NO:1 with a Fab fragment of 12A11 were frozen in a reservoir solution with an addition of 35% PEG 400. The invention also provides crystals of a peptide including amino acids 1-40 of SEQ ID NO:1 with a Fab fragment of 12A11 were frozen in a reservoir with an addition of 28% PEG 4000. The invention also provides crystals of a peptide including an epitope of amino acids 1-7 of SEQ ID NO:1 with a Fab fragment of 12B4 were frozen directly in the reservoir solution. The invention also provides crystals of a peptide including an epitope of amino acids 1-7 of SEQ ID NO:1 with a Fab fragment of 10D5 were frozen directly in the reservoir solution. The invention also provides crystals of a peptide including an epitope of amino acids 1-7 of SEQ ID NO:1 with a Fab fragment of 3D6 were frozen directly in the reservoir solution. The invention also provides crystals of a peptide including amino acids 1-40 of SEQ ID NO:1 with a Fab fragment of 3D6 were frozen in a reservoir solution with an addition of 20% glycerol.

The invention also provides a crystal complex of an antibody binding to an epitope within residues 3-7 of Aβ in which positions 98-100 of the heavy chain CDR3 by Kabat numbering are unoccupied. These positions are unoccupied in the 12A11 antibody. As explained further below, lack of such residues provides an explanation for the advantageous properties of 12A11 in the CFC assay.

The above-mentioned crystallization conditions and freezing conditions can be varied. Such variations may be used alone or in combination, and include Aβ:antibody complex concentrations between 0.01 mg/ml and 100 mg/ml, pH ranges between 4.0 and 12.0, precipitant concentration between 0.1% and 50% (w/v), salt concentration between 0.1 mM and 500 mM. Other buffer solutions may be used such as Tris buffer, MES buffer, citrate buffer, acetate buffer, bicine buffer, MOPS buffer, MOPSP buffer, PIPES buffer, and the like, as long as the desired pH range is maintained. Such variations can also include an Aβ:Fab ratio between 20:1 to 1:100.

Suitable binding fragments include a scFv fragment, a diabody, a triabody, and a Fab fragment. Exemplary peptides that can be used for crystallization including peptides having Aβ residues amino acids 1-5, 1-6, 1-7, 2-6, 3-5, or 3-7 of SEQ ID NO:1 can be used in the crystallization. Aβ1-40 can also be used.

In general, an Aβ peptide is contacted with an antibody fragment. The mixture is then incubated over a reservoir solution, under conditions suitable for crystallization, until a crystal of the peptide and the antibody fragment forms. For a Fab fragment of 12A11 and a Aβ1-7 peptide, the reservoir solution can include about 32% PEG 400 and about 0.1 M Tris, at about pH 9.0. For an Aβ1-40 peptide, and a Fab fragment of 12A11, the reservoir solution can include about 0.2 M NaCl, about 0.1 M Hepes, and about 25% PEG 4000, at about pH 7.5. For an Aβ1-7 peptide and a Fab fragment of 12B4, and the reservoir solution can include about 30% PEG 8000, about 0.1 M Hepes, and about 0.2 M $(NH_4)_2SO_4$, at about pH 7.0. For an Aβ1-7 peptide and a Fab fragment of 10D5, the reservoir solution can include about 30% PEG 4000. For an Aβ1-7 peptide and a Fab fragment of 3D6, the reservoir solution can include about 30% PEG 400, and about 0.1 M Tris, at about pH 9.0. For, a complex between a including amino acids 1-40 of SEQ ID NO:1, and a Fab fragment of 3D6, the reservoir solution can include about 2.5 M NaCl, about 0.1 M Imidazole, and about 0.2 M $ZnAc_2$, at about pH 8.0.

C. Determination of Crystal Structures

Although the exemplified crystal structures were analyzed by X-ray diffraction, other methods (e.g., Laue, electron or neutron diffraction) can also be used either in reproducing the crystal structures described herein or in producing crystal structures of other antibodies to Aβ by the same strategy and principles.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the be face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. To obtain all three unit cell dimensions, the crystal can be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

D. Data Collection and Determination of Structures Solutions

The diffraction pattern of a crystal is related to the three-dimensional shape of the molecules that constitute the crystal by a Fourier transform. Diffraction patterns of a crystal can result from X-ray diffraction as well as Laue, electron or neutron diffraction. After enough diffraction data are collected for a crystal, the process of determining the solution is in essence a re-focusing of the diffracted X-rays to produce a three-dimensional image of the molecule in the crystal. Since lenses capable of focusing X-ray radiation do not yet exist, the structure determination can be done via mathematical operations that simulate the re-focusing process.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. A complete dataset can be collected using one crystal or more than one crystal of the same type.

Sources of X-rays include a rotating anode X-ray generator such as a Rigaku RU-200 or a beamline at a synchrotron light source, such as the Advanced Photon Source at Argonne National Laboratory, the Advanced Light Source at the Lawrence Berkeley Laboratory, and the Stanford Synchrotron Radiation Laboratory at the Stanford Linear Acceleration Center. Suitable detectors for recording diffraction patterns include, for example, X-ray sensitive film, multiwire area detectors, image plates coated with phosphorus, and CCD cameras. Typically, the detector and the X-ray beam remain stationary so that to record diffraction from different parts of the crystal's sphere of diffraction, the crystal itself is moved via an automated system of moveable circles called a goniostat.

Macromolecular crystals having a high solvent content can degrade in the X-ray beam. To slow the degradation, data is often collected from a crystal at liquid nitrogen temperatures. For a crystal to survive the initial exposure to liquid nitrogen, the formation of ice within the crystal can be prevented by the use of a cryoprotectant. Suitable cryoprotectants include low molecular weight polyethylene glycols, ethylene glycol, sucrose, glycerol, xylitol, and combinations thereof. Crystals may be soaked in a solution including the one or more cryoprotectants prior to exposure to liquid nitrogen, or the one or more cryoprotectants may be added to the crystallization solution. Data collection at liquid nitrogen temperatures may allow the collection of an entire dataset from one crystal.

Once a dataset is collected, the information is used to determine the three-dimensional structure of the molecule in the crystal. However, this cannot be done from a single measurement of reflection intensities because certain information, known as phase information, is lost between the three-dimensional shape of the molecule and its Fourier transform, the diffraction pattern. This phase information can be acquired by methods described below to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, diffraction data for both heavy-atom derivative crystals and native crystals are collected. Differences in diffraction patterns between the native and derivative datasets can be used to determine the positions of heavy atoms bound to the molecules in the heavy-atom derivative crystal. This information can then be used to obtain the phase information necessary to elucidate the three-dimensional structure of the material that constitutes the native crystals (Blundel et al., 1976, Protein Crystallography, Academic Press). In more recent applications of the isomorphous replacement method, manual and automatic (as implemented by the program SHELX) search procedures have been applied to locate the position of the heavy atoms in the derivative crystals (Sheldrick et al., 1993, Acta Cryst. D49:18-23). In other recent applications of the isomorphous replacement method, the inert gas Xenon is introduced into a native crystal to form a heavy atom derivative crystal. Xenon atoms occupy holes in a protein molecule through pure Van der Waals interaction. Examples of isomorphous replacement by Xenon derivatized crystals can be found in Sauer et al., 1997, *J. Appl. Cryst.* 30:476-486 and Panjikar and Tucker, 2002, *Acta Cryst.* D58:1413-1420.

Another method of obtaining phase information is by molecular replacement, which is a method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules including the new crystal. (Lattman, 1985, *Methods in Enzymology* 115:55-77; Rossmann, 1972, "The Molecular Replacement Method," Int. Sci. Rev. Ser. No. 13, Gordon & Breach, New York). The molecular replacement method can be used when a protein with unknown structure shares a certain degree of sequence homology with a protein whose structure is already known. Conventional molecular replacement methods comprise two search algorithms: a rotational search function and a translational search function. Molecular replacement methods can be found in many existing computer programs such as AMoRe (Navaza, 1994, Acta, Cryst. A50:157-163) CNS (Brunger et al., 1998, Acta Cryst. D54: 905-921), as well as many programs in the CCP4 package suites (Collaborative Computational Project, Number 4, 1994).

A third method of phase determination is multi-wavelength anomalous diffraction or MAD. In this method, X-ray diffraction data are collected at several different wavelengths from a single crystal containing at least one heavy atom with absorption edges near the energy of incoming X-ray radiation. The resonance between X-rays and electron orbital leads to differences in X-ray scattering that permits the locations of the heavy atoms to be identified, which in turn provides phase information for a crystal of a polypeptide. MAD analysis uses a radiation source with capacity to adjust its output wavelength. Nearly all synchrotron source around the world are now equipped with the capacity. A detailed discussion of MAD analysis can be found in Hendrickson, 1985, Trans. Am. Crystallogr. Assoc. 21:11; Hendrickson et al., 1990, EMBO J. 9:1665-1672; and Hendrickson, 1991, Science 4:91. In the traditional approach, Se atoms (atomic number 34, in the same group at sulfur), usually in the form of Se-Met, are introduced into native protein prior to crystallization to add anomalous scattering property to the protein crystal (Hendrickson et al, 1990, EMBO J. 9:1665-1672; Leahy et al., 1992, Science, 258:987-991). Incorporating Se-Met into protein is usually achieved by growing recombinant vectors in the presence of medium containing Se-Met supplement (Dyer et al., 2005, Protein Sci. 14:1508-1517).

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, Acta Cryst. D56:431-441. SAD eliminates the requirement for a radiation source with adjustable wavelengths. It is possible to utilize non-synchrotron radiation to determine protein structures by anomalous scattering. For example, the structure of human formylglycine-generating enzyme was determined by de novo calcium and sulfur SAD phasing at a non-synchrotron radiation source (Roeser et al., 2005, Acta Cryst. D61:1057-1066).

A fifth method of determining phase information is single isomorphous replacement with anomalous scattering or SIRAS. This technique combines isomorphous replacement and anomalous scattering techniques to provide phase information for a crystal of a polypeptide. X-ray diffraction data are collected at a single wavelength, usually from a native crystal and a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, Acta Cryst. 18:212-216; Matthews, 1966, Acta Cryst. 20:82-86. It is possible to combine the techniques of MAD and SAD phasing with SIRAS and determine protein structure without synchrotron radiation. For example, the structure of *E. coli* argininosuccinate synthetase was determined using Cu-Kappa radiation in a non-synchrotron source with S-SAD, Se-SAD and S/Se-SIRAS phasing techniques (Lenike et al., 2002, Acta Cryst. D58:2096-2101).

Methods for phase determination have been discussed individually for the purpose of clear illustration. These methods are often combined in practice as previously stated. For example, the methods of MAD, SAD, and SIRAS were all explored when the structure of human mannose-6-phosphate/insulin-like growth factor II receptor was determined (Uson et al., 2002, Acta Cryst. D59:57-66). Also in this study, halide atoms, e.g., bromide and iodide as well as sulfur were used in extract the overall phase information of the molecule instead of the standard Se-Met MAD or SAD phasing techniques.

Once phase information is obtained, it is combined with the diffraction data to produce an electron density map, an image of the electron clouds that surround the molecules in the unit cell. The higher the resolution of the data, the more distinguishable are the features of the electron density map, e.g., amino acid side chains and the positions of carbonyl oxygen atoms in the peptide backbones, because atoms that are closer together are resolvable. A model of the macromolecule is then built into the electron density map with the aid of a computer, using as a guide all available information, such as the polypeptide sequence and the established rules of molecular structure and stereochemistry. Interpreting the electron density map is a process of finding the chemically reasonable conformation that fits the map precisely.

After a model is generated, a structure is refined. Refinement is the process of minimizing the function $\phi$, which is the difference between observed and calculated intensity values (measured by an R-factor), and which is a function of the position, temperature factor, and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the function $\phi$ converges on a minimum wherein the model fits the electron density map and is stereochemically and conformationally reasonable. During refinement, ordered solvent molecules are added to the structure.

"Laue Diffraction" refers to the diffraction pattern obtained from a stationary crystal exposed to a continuous range of wavelengths of X-rays (e.g., polychromatic or "white" radiation). The application of monochromatic X-ray radiation limited the use of Laue diffraction until the availability of synchrotrons that provide fully polychromatic beams with smooth spectral profiles. Synchrotron radiations have high intensity, very small divergence, which renders them ideal sources for Laue diffraction of protein crystals. There are at least two practical variants of the Laue method, the back-reflection and the transmission Laue diffraction. In the back-reflection method, the reflection recorder is placed between the X-ray source and the crystal. The beams that are diffracted in a backward direction are recorded. One side of the cone of Laue reflections is defined by the transmitted beam. The recorder intersects the cone, with the diffraction spots generally lying on a hyperbola. In the transmission Laue diffraction, the reflection recorder is placed behind the crystal to record beams which are transmitted through the crystal. One side of the cone of Laue reflections is defined by the transmitted beam. The recorder intersects the cone, with the diffraction spots generally lying on an ellipse. Under Laue diffraction, protein diffraction pattern at high intensity synchrotron X-ray sources can be taken in times as short as 150 picoseconds (Srajer et al., 1996, Science 274:1726-1729). The greatest advantage of Laue diffraction is its time efficiency under synchrotron radiations. Laue diffraction is extensively discussed in "Time resolved macromolecular crystallography," by Cruickshank et al., 1992, Oxford University Press.

"Neutron Diffraction" refers to a crystallography technique that uses neutrons to determine the atomic structure of a material. Neutrons are particles found in the atomic nucleus. In a nuclear reactor, neutrons can be set free when nuclei decay (fission, radioactivity). All quantum particles can exhibit wave phenomena we typically associate with light or sound. Diffraction is one of these phenomena; it occurs when waves encounter obstacles whose size is comparable with the wavelength. If the wavelength of a quantum particle is short enough, atoms or their nuclei can serve as diffraction obstacles. When neutrons from a reactor are slowed down and selected properly, their wavelength lies near one angstrom (0.1 nanometer), the typical separation between atoms in a solid material. A neutron diffraction measurement typically uses a neutron source (e.g., a nuclear reactor or spallation source), a target (the material to be studied), and a detector. Other components may be needed to select the desired neutron wavelength. Some parts of the setup may also be movable. Since neutrons are not charged, they do not interact with the electron cloud surrounding the atom (unlike X-ray or electron diffraction). The neutrons will only interact with the nucleus of the atom. Thus, neutron diffraction reveals the atomic structure but not the charge distribution around the atom, although the two are usually very similar. Neutron diffraction reveals structural details of the target material, which are measured by recording the way in which neutrons are deflected. Neutrons can also change their speed during the scattering experiment; this can be used to study the types of vibrations that can occur in a solid. An important difference between neutron and X-ray diffraction is that neutrons are sensitive to magnetic forces in the material. The application of neutron diffraction in protein structure determination, in particular in determining the hydration level of protein crystals, is discussed in detail in articles by Cheng and Schoenborn, 1990, Acta Cryst. B46: 195-208; Langan et al., 2004, J. Appl. Cryst. 37:24-31; and Steinbach and Brooks, 1993, Proc. Natl. Acad. Sci. USA 90:9135-9139.

"Electron Diffraction" refers the diffractions where the incident radiation is created by fast-moving electrons. The electrons are deflected not as particles but as waves, as in classical diffraction. The technique is typically used on crystal samples that have a regularly spaced atomic lattice. Most electron diffraction is performed with high energy electrons whose wavelengths are orders of magnitude smaller than the interplanar spacing in most crystals. For example, for 100 keV electrons, their wavelength .lamda. will be shorter than 3.7.times.10.sup.-12 m. Typical lattice parameters for crystals are around 0.3 nanometers. The electrons are scattered by interaction with the positively charged atomic nuclei. Electrons are charged particles that interact very strongly with solids, so their penetration of crystals is very limited. Low-energy Electron Diffraction (LEED) and Reflection High-Energy Electron. Diffraction (RHEED) are therefore considered to be surface science techniques, whereas transmission electron diffraction is usually performed on specimens less than 1 mm thick. In recent studies, however, electron diffraction has been applied to detect structural changes in the photo cycle of bacteriorhodopsin (Subramaniam et al., 1993, EMBO J. 12:1-8).

"Crystallographically-Related Dimer" refers to a dimer of two molecules wherein the symmetry axes or planes that relate the two molecules including the dimer coincide with the symmetry axes or planes of the crystal lattice.

"Non-Crystallographically-Related Dimer" refers to a dimer of two molecules wherein the symmetry axes or planes that relate the two molecules including the dimer do not coincide with the symmetry axes or planes of the crystal lattice.

"Isomorphous Replacement" refers to the method of using heavy-atom derivative crystals to obtain the phase information necessary to elucidate the three-dimensional structure of a crystallized polypeptide (Blundel et al., 1976, Protein Crystallography, Academic Press).

E. Crystals of Aβ:Antibody Complexes
1. Unit Cell Parameters

The dimensions of a unit cell of a crystal are defined by six numbers, the lengths of three unique edges, a, b, and c, and three unique angles, α, β, and γ. The type of unit cell that comprises a crystal is dependent on the values of these variables.

The invention provides crystals of a peptide including an epitope of amino acids 1-7 of SEQ ID NO:1 and a Fab fragment of 12A11, 12B4, 10D5 or 3D6.

One such crystal includes amino acids 1-7 of SEQ ID NO:1 and a Fab fragment of 12A11, and has a space group of P2$_1$, with unit cell parameters of a=43.0 Å, b=86.0 Å, c=57.4 Å; α=90°, β=94.7°, γ=90°.

Another crystal includes amino acids 1-40 of SEQ ID NO:1 and a Fab fragment of 12A11, and has a space group of P2$_1$, with unit cell parameters of a=43.0 Å, b=87.0 Å, c=59.0 Å; α=90°, β=95.8°, γ=90°.

Another crystal includes amino acids 1-7 of SEQ ID NO:1 and a Fab fragment of 12B4, and has a space group of P1, with unit cell parameters of a=78.9 Å, b=79.2 Å, c=94.1 Å; α=68.7°, β=65.3°, γ=78.5.

Another crystal includes amino acids 1-7 of SEQ ID NO:1 and a Fab fragment of 10D5, and having a space group of P2$_1$2$_1$2$_1$, with unit cell parameters of a=96.3 Å, b=100.0 Å, c=104.0 Å; α=90°, β=90°, γ=90.

Another crystal includes amino acids 1-7 of SEQ ID NO:1 and a Fab fragment of 3D6, and having a space group of C2, with unit cell parameters of a=126.8 Å, b=69.4 Å, c=61.7 Å; α=90°, β=115.4°, γ=90.

The invention also a crystal including amino acids 1-40 of SEQ ID NO:1 and a Fab fragment of 3D6, and having a space group of P222$_1$, with unit cell parameters of a=40.0 Å, b=84.9 Å, c=175.9 Å; α=90°, β=90°, γ=90. The substantial similarity of unit cell parameters between crystals formed from Aβ1-7 and Aβ1-40 shows that Aβ1-7 binds to the tested antibodies in a similar manner whether alone or part of Aβ1-40.

The unit cell parameters of crystals may vary slightly, depending on the different batches of protein purification, the purity of the protein or peptide, variation of the temperature, variation in the pH value of the buffer used, different crystallization methods used. Reference to a particular unit cell parameter should be construed as encompassing a margin of experimental error inherent in measuring the parameter.

2. Atomic Coordinates

The atomic structure coordinates of the Aβ:antibody complexes of the present invention are described in the attached tables. The tables of atomic structure coordinates provide the atom number (column 2), atom type (column 3), residue type (column 4), Chain identifier (column 5), residue number (column 6), x coordinate of atom (Å, column 7), y coordinate of atom (Å, column 8), z coordinate of atom (Å, column 9), occupancy (column 10), B-factor (Å$^2$, column 11) and atom (column 12). For water molecules, column 4 reads "HOH", column 5 reads W, column 6 is the number of the water molecule, and the atomic coordinates of the columns 7-9 are the coordinates of the water oxygen atoms. The atomic structure coordinates in the attached tables can be used in molecular modeling and design, as described more fully below. The structure coordinates and other information, e.g., amino acid sequence, connectivity tables, vector-based representations, temperature factors can be used to generate three-dimensional structural representations of the Aβ:antibody complexes for use in the software programs described below and other software programs. For water molecules, column 4 reads "HOH", column 5 reads W, column 6 is the number of the water molecule, and the atomic coordinates of the columns 7-9 are the coordinates of the water oxygen atoms. Reference to a particular unit atomic cell coordinate should be construed as encompassing a margin of experimental error inherent in measuring the coordinates.

The invention encompasses machine-readable media embedded with atomic coordinates and/or other data as described above, or three-dimensional structures derived from such co-ordinates or data. "Machine-readable medium" refers to any medium that can be read and accessed directly by a computer or scanner. Such media include, for example, magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into magnetic or optical storage media with an OCR.

A variety of data storage structures are available for creating a computer readable medium having recorded thereon the atomic structure coordinates of the invention or portions thereof and/or X-ray diffraction data. The choice of the data storage structure is generally based on the means chosen to access the stored information. In addition, a variety of data processor programs and formats can be used to store the sequence and X-ray data information on a computer readable medium. Such formats include, for example, Protein Data Bank ("PDB") format (Research Collaboratory for Structural Bioinformatics; Cambridge Crystallographic Data Centre format; Structure-data ("SD") file format (MDL Information Systems, Inc.; Dalby et al., 1992, J. Chem. Inf. Comp. Sci. 32:244-255), and line-notation, e.g., as used in SMILES (Weininger, 1988, J. Chem. Inf. Comp. Sci. 28:31-36). Methods of converting between various formats read by different computer software are well known, e.g., BABEL (v. 1.06, Walters & Stahl, ©1992, 1993, 1994). All format representations of the polypeptide coordinates described herein, or portions thereof, are contemplated by the present invention. By providing computer readable medium having stored thereon the atomic coordinates of the invention, one can routinely access the atomic coordinates of the invention, or portions thereof, and related information for use in modeling and design programs, described in detail below.

Although Cartesian coordinates are one way of representing the three-dimensional structure of a polypeptide, other means of representing of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multichain protein in which an atom is located, and connectivity information, which indicates to which atoms a particular atom is bonded, is also useful for representing a three-dimensional molecular structure.

3. Interacting Residues

Complexes of antibody fragments and Aβ peptides can also be characterized by a matrix of interacting residues as in Table 3. Different antibodies can be compared for similarity of binding and hence similarity of functional properties by comparing the number of similar and different interactions with Aβ.

By comparing the interactions from different antibodies several approximate rules associating antibody sequences with capacity to bind particular residues of Aβ emerge. These rules are useful in designing hybrid sequences of 3D6, 10D5, 12A11 and 12B4 or theoretical sequences. Of course, the rules are only an approximation and binding is analyzed further by in silico screening, and optionally functional screening, such as in a transgenic mouse model.

Table 3 and the rules based on it refer to antibody positions by sequential numbering. For antibodies 12B4, 3D6 and 12A11, sequential numbering can be converted to Kabat numbering using the appended tables. Sequential numbering of 10D5 can be converted to Kabat numbering by aligning a 10D5 variable region sequence with a 12B4 variable region sequence (light chain aligned with light chain and heavy chain with heavy chain) and assigning Kabat numbers using the conversion table for 12B4. In other words, aligned residues when two antibody sequences are maximally aligned are assigned the same Kabat numbers. Accordingly, any of the interactions or rules expressed below converted to refer to amino acid positions in an antibody variable region by Kabat numbering is also encompassed by the invention.

D1 of SEQ ID NO:1 binds to SEQ ID NO:16, when X1, X2, and X5 of SEQ ID NO:16 are occupied by W, G, and R, respectively. D1 of SEQ ID NO:1 binds to SEQ ID NO:19, when X1, X10, and X11 of SEQ ID NO:19 are occupied by Y, S, and S, respectively.

A2 of SEQ ID NO:1 binds to SEQ ID NO:16, when X4 of SEQ ID NO:16 is occupied by V. A2 of SEQ ID NO:1 binds to SEQ ID NO:16, when X2 and X3 of SEQ ID NO:16 are occupied by G and T respectively. A2 of SEQ ID NO:1 binds to SEQ ID NO:18, when X9 of SEQ ID NO:18 is occupied by R.

E3 of SEQ ID NO:1 binds to SEQ ID NO:14, when X5 of SEQ ID NO:14 is occupied by H. E3 of SEQ ID NO:1 binds to SEQ ID NO:16, when X3 of SEQ ID NO:16 is occupied by S. E3 of SEQ ID NO:1 binds to SEQ ID NO:18, when X9 of SEQ ID NO:18 is occupied by R. E3 of SEQ ID NO:1 binds to SEQ ID NO:16, when X5 of SEQ ID NO:16 are occupied by R. E3 of SEQ ID NO:1 binds to SEQ ID NO:18, when X1, X2, and X9 of SEQ ID NO:18 are occupied by S, R, Y, respectively.

F4 of SEQ ID NO:1 binds to SEQ ID NO:14 and SEQ ID NO16, when X5 of SEQ ID NO:14 is occupied by H, and X2, X3, X4, and X5 of SEQ ID NO16 are occupied by S, S, V, and L respectively. F4 of SEQ ID NO:1 binds to SEQ ID NO:14 and SEQ ID NO16, when X5 of SEQ ID NO:14 is occupied by H, and X2, X3, X4, and X5 of SEQ ID NO16 are occupied by G, S, V, and L respectively. F4 of SEQ ID NO:1 binds to SEQ ID NO:14 and SEQ ID NO16, when X5 of SEQ ID NO:14 is occupied by H, and X3, X4, and X5 of SEQ ID NO16 are occupied by S, V, and L respectively. F4 of SEQ ID NO:1 binds to SEQ ID NO:18, when X1 and X2 of SEQ ID NO:18 are occupied by H and W, respectively. F4 of SEQ ID NO:1 binds to SEQ ID NO:18, when X1 and X9 of SEQ ID NO:18 are occupied by H and Y, respectively. F4 of SEQ ID NO:1 binds to SEQ ID NO:18 and SEQ ID NO. 19, when X1 and X2 of SEQ ID NO:18 are occupied by S and R, respectively, and X1 of SEQ ID NO:19 is occupied by Y.

R5 of SEQ ID NO:1 binds to SEQ ID NO:18, when X2, X4, X6, and X9 of SEQ ID NO:18 are occupied by W, D, D, and Y, respectively. The R5 of SEQ ID NO:1 binds to SEQ ID NO:18, when X2, X3, X4, and X9 of SEQ ID NO:18 are occupied by W, W, D, and Y, respectively. R5 of SEQ ID NO:1 binds to SEQ ID NO:18, when X2, X3, X4, X6, and X9 of SEQ ID NO:18 are occupied by Y, W, D, D, and R, respectively. The R5 of SEQ ID NO:1 binds to SEQ ID NO:18, when X2, X3, X4, and X6 of SEQ ID NO:18 are occupied by Y, W, D, and D, respectively. R5 of SEQ ID NO:1 binds to SEQ ID NO:14 and SEQ ID NO:16, when X5 of SEQ ID NO:14 is occupied by D and X2 and X3 of SEQ ID NO:16 is occupied by G and T, respectively. R5 of SEQ ID NO:1 binds to SEQ ID NO:19, when X1 of SEQ ID NO:19 is occupied by Y.

H6 of SEQ ID NO:1 binds to SEQ ID NO:14 and SEQ ID NO:16, when X5 and X6 of SEQ ID NO:14 are occupied by H, N, respectively, and X3 of SEQ ID NO:16 is occupied by S. H6 of SEQ ID NO:1 binds to SEQ ID NO:14 and SEQ ID NO:16, when X5 of SEQ ID NO:14 is occupied by H and X3 of SEQ ID NO:16 is occupied by G. H6 of SEQ ID NO:1 binds to SEQ ID NO:19, when X9 of SEQ ID NO:19 is occupied by D. H6 of SEQ ID NO:1 binds to SEQ ID NO:19, when X3, X4, and X9 of SEQ ID NO:19 are occupied by I, T, and D, respectively. H6 of SEQ ID NO:1 binds to SEQ ID NO:19, when X4, and X9 of SEQ ID NO:19 are occupied by I, and D, respectively. H6 of SEQ ID NO:1 binds to SEQ ID NO:18, when X2 of SEQ ID NO:18 is occupied by R.

D7 of SEQ ID NO:1 binds to SEQ ID NO:19, when X7 of SEQ ID NO:19 is occupied by T. D7 of SEQ ID NO:1 binds to SEQ ID NO:19, when X4 of SEQ ID NO:19 is occupied by T. D7 of SEQ ID NO:1 binds to SEQ ID NO:19, when X4 of SEQ ID NO:19 is occupied by I.

III. Assay for Identifying Other Antibodies for Binding Aβ

A. In Silico Screening

Structure information, typically in the form of the atomic structure coordinates, can be used in a variety of computational or computer-based methods to, for example, design, screen for and/or identify antibodies that bind the crystallized polypeptide or a portion or fragment thereof, to intelligently design mutants that have altered biological properties, to intelligently design and/or modify antibodies that have desirable binding characteristics, and the like.

Methods of in silico screening can use the entire set of atomic coordinates for a particular complex or a subset thereof. Subsets of the atomic structure coordinates can be used in any of the above methods. Particularly useful subsets of the coordinates include, for example, coordinates of single domains, coordinates of residues lining an active site, coordinates of residues that participate in important protein-protein contacts at an interface, and Cα coordinates. For example, the coordinates of one domain of a protein that contains the active site may be used to design inhibitors that bind to that site, even though the protein is fully described by a larger set of atomic coordinates. Therefore, a set of atomic coordinates that define the entire polypeptide chain, although useful for many applications, do not necessarily need to be used for the methods described herein.

Specialized computer programs to assist in the process of selecting fragments or chemical groups include:

1. GRID (Goodford, 1985, J. Med. Chem. 28:849-857). GRID is available from Oxford University, Oxford, UK;
2. MCSS (Miranker & Karplus, 1991, Proteins: Structure, Function and Genetics 11:29-34). MCSS is available from Molecular Simulations, Burlington, Mass.;
3. AUTODOCK (Goodsell & Olsen, 1990, Proteins: Structure, Function, and Genetics 8:195-202). AUTODOCK is available from Scripps Research Institute, La Jolla, Calif.; and
4. DOCK (Kuntz et al., 1982, J. Mol. Biol. 161:269-288). DOCK is available in several versions from University of California, San Francisco, Calif.
5. CombiDOCK (Sun et al., 1998, J. Comput. Aided Mol. Des. 12:597-604). CombiDOCK is available from University of California, San Francisco, Calif.).
6. FRED (available from OpenEye Scientific Software, Santa Fe, N. Mex.). Based on an original scientific perspective and efficient computational algorithms, FRED is an accurate and extremely fast docking program. With equivalent resolution settings, FRED will out-perform all known docking programs, typically examining about a dozen ligand conformers in a second. For each, FRED exhaustively examines all possible poses within the protein active site, filtering for shape complementarity and pharmacophoric features before scoring with more traditional functions.
7. ROCS (available from OpenEye Scientific Software, Santa Fe, N. Mex.). ROCS is a shape comparison program, based on the idea that molecules have similar shape if their volumes overlay well and any volume mismatch is a measure of dissimilarity. ROCS uses a smooth Gaussian function to represent the molecular volume, so it is possible to routinely minimize to the best global match. ROCS is capable of processing 600-800 comparisons each second, making it possible to search multi-conformer representations of corporate collections in a day on a single processor to find compounds with similar shape to a lead compound.

Once suitable chemical groups or fragments have been selected, they can be assembled into a single antibody. Assembly may proceed by visual inspection of the relationship of the fragments to each other in the three-dimensional image displayed on a computer screen in relation to the structure coordinates of Aβ. This would be followed by manual model building using software such as QUANTA or SYBYL.

Useful programs to aid in connecting the individual chemical groups or fragments include:

1. CAVEAT (Bartlett et al., 1989, "CAVEAT: A Program to Facilitate the Structure-Derived Design of Biologically Active Molecules," In Molecular Recognition in Chemical and Biological Problems', Special Pub., Royal Chem. Soc. 78:182-196). CAVEAT is available from the University of California, Berkeley, Calif.;
2. 3D Database systems such as MACCS-3D (MDL Information Systems, San Leandro, Calif.). This area is reviewed in Martin, 1992, J. Med. Chem. 35:2145-2154); and
3. HOOK (available from Molecular Simulations, Burlington, Mass.).
4. FILTER (available from OpenEye Scientific Software, Santa Fe, N. Mex.). FILTER is a molecular screening and selection tool that uses a combination of physical-property calculations and functional-group knowledge to assess compound collections. In selection mode, FILTER can be used to choose reagents appropriate for specific syntheses. In filter mode, it quickly removes compounds with undesirable elements, functional groups, or physical properties. FILTER is a command line utility that reads and writes many file formats including SDF, Mol, Mol2, SMILES, and OEBinary. Filter is supported on Linux, Windows and ilux; other platforms are available upon request.

5. SMACK (available from OpenEye Scientific Software, Santa Fe, N. Mex.). SMACK converts and optimizes molecular database queries. SMACK can quickly convert from substructure and reaction queries expressed in MDL file format to SMARTS strings. Additionally, SMACK will automatically optimize each resulting query for pattern-matching performance. Typical transformations simplify redundant atom and bond expressions and reorder atoms for faster matching against medicinal/organic chemistry databases.

Instead of proceeding to build an antibody or antibody fragment in a step-wise fashion one fragment or chemical group at a time, as described above, antibody or antibody fragment may be designed as a whole or "de novo" using either an empty Aβ binding site or optionally including some portion(s) of a known antibody(s). These methods include:

1. LUDI (Bohm, 1992, J. Comp. Aid. Molec. Design 6:61-78). LUDI is available from Molecular Simulations, Inc., San Diego, Calif.;
2. LEGEND (Nishibata & Itai, 1991, Tetrahedron 47:8985). LEGEND is available from Molecular Simulations, Burlington, Mass.; and
3. LeapFrog (available from Tripos, Inc., St. Louis, Mo.).
4. WABE (available from OpenEye Scientific Software, Santa Fe, N. Mex.). WABE is a de similis design program, as opposed to de novo design. Using a graph-invariant replacement algorithm, it quickly generates large numbers of isosteres to a lead molecule. The method resembles the process of chemical substitution, e.g., carboxylate to amide or amidine, used in medicinal chemistry to create molecules having the same physical shape but varying in electrostatics. The similarities between analogs eliminate computationally demanding terms, so WABE can also quickly rank them by electrostatic similarity to a known binder or by protein-ligand binding. WABE is useful for exploring the chemical space around a lead compound to elucidate candidates with improved drug profiles or novel scaffolds to avoid patent coverage.

Some examples of other modeling and simulation computer programs include the following:

1. AMBER (available from University of California, San Francisco). AMBER (Assisted Model Building with Energy Refinement) is a molecular dynamics and energy minimization program.
2. CHARMM (available from Harvard University). CHARMM (Chemistry at HARvard Macromolecular Mechanics) is a program for macromolecular simulations, including energy minimization, molecular dynamics and Monte Carlo simulations.
3. Disulfide by Design (available from Wayne State University). Disulfide by Design is an application for the rational design of disulfide bonds in proteins and for exporting mutant PDB files containing the modeled disulfides for visualization in other molecular modeling software. For a given protein structural model, all residue pairs are rapidly assessed for proximity and geometry consistent with disulfide formation assuming the residues were mutated to cysteines. The output displays residue pairs meeting the appropriate criteria. The input model will typically be a PDB structure for the protein of interest; however, structures developed through homology modeling may also be used. Engineered disulfides have proven useful for increasing the stability of proteins and to assist the investigation of protein dynamics and interactions.
4. FTDOCK (available from the Biomolecular Modelling Laboratory of Cancer Research UK). FTDOCK is a program for carrying out rigid-body docking between biomolecules.
5. GROMOS (available from Laboratory of Physical Chemistry; ETH Honggerberg, HC). GROMOS is a general purpose molecular dynamics computer simulation package for the study of biomolecular systems.
6. GROMACS (an open-source tool freely available on the internet). GROMACS is a complete modeling package for proteins, membrane systems and more, including fast molecular dynamics, normal mode analysis, essential dynamics analysis and many trajectory analysis utilities.
7. ICM (Molsoft LLC, San Diego, Calif.). ICM from Molsoft provides programs and modules for applications including for structure analysis, modeling, docking, homology modeling and virtual ligand screening.
8. JACKAL (available from Columbia University). JACKAL is a suite of tools for model building, structure prediction and refinement, reconstruction, and minimization; for SGI, Linux, and Sun Solaris
9. LOOPP (available from Cornell University). LOOP (Linear Optimization of Protein Potentials) is available form Cornell Theory Center program for potential optimization and alignments of sequences and structures.
10. MAMMOTH (available from New York University). MAMMOTH (MAtching Molecular Models Obtained from Theory) is a program for automated pairwise and multiple structural alignments; for SGI, Linux, and Sun Solaris.
11. MCCE (available from the City College of New York). The MCCE (Multi-Conformation Continuum Electrostatics) software calculates theoretical pKas of residues in proteins and provides the modulating factors of pKas based on the structure in PDB format.
12. MidasPlus (available from University of California, San Francisco) MidasPlus is a program for displaying, manipulating and analysing macromolecules.
13. MODELLER (available from University of California, San Francisco). MODELLER is a program for automated protein homology modeling.
14. MOIL (available from Cornell University). MOIL is another program from the Cornell Theory Center package for molecular dynamics simulation of biological molecules.
15. NAMD (available from the University of Illinois at Urbana-Champaign). NAMD is a parallel object-oriented molecular dynamics simulation program.
16. WAM (available from the University of Bath). WAM (Web Antibody Modeling) provides a server for automated structure modeling from antibody Fv sequences.
17. 123D (Ceres Inc., Malibu, Calif.). 123D is a program which threads a sequence through a set of structures using substitution matrix, secondary structure prediction and contact capacity potential.

Additional molecular modeling techniques may also be employed in accordance with this invention. See, e.g., Cohen et al., 1990, J. Med. Chem. 33:883-894. See also Navia & Murcko, 1992, Cur. Op. Struct. Biol. 2:202-210.

Specific computer software is available to evaluate compound deformation energy and electrostatic interaction. Examples of programs designed for such uses include: Gaussian 92, revision C (Frisch, Gaussian, Inc., Pittsburgh, Pa.

(01992); AMBER, version 4.0 (Kollman, University of California at San Francisco, .COPYRGT.1994); QUANTA/CHARMM (Molecular Simulations, Inc., Burlington, Mass., .COPYRGT.1994); and Insight II/Discover (Biosym Technologies Inc., San Diego, Calif., (1994).

Some methods serve to analyze binding of a candidate antibody (often in the form of binding fragment) to an epitope within residues 1-7 of Aβ. The candidate antibody can have light or heavy chain variable region amino acid sequences that represent a variant or mutated form of one of the exemplified (antibodies 2D6, 10D5, 12B4 or 12A11), or can be sequences of an independently isolated antibody, or can be theoretical sequences. As discussed above, some candidate antibodies have either the light or heavy chain variable region sequence or both representing hybrids of corresponding sequences from two or more of the four exemplified antibodies. In these methods, sequence data for the antibody is received in or generated by the computer. The data can be received for example by user input or from storage on magnetic or computer readable media. The sequence data can also be generated within the computer as by partial randomization of heavy or light chain sequence(s) of a prototypical antibody. The data can be complete or partial sequence of an antibody and can be provided either at the amino acid or DNA level. If provided at the DNA level, the information is converted by the computer to an amino acid sequence. Typically, the information includes the sequence of at least 1 CDR, sometimes at least two CDRs (e.g., CDRs L1 and L3 and/or CDRs H2 and H3) on both heavy and light chains, and sometimes all six CDRs of an antibody. Sometimes the information includes the complete amino acid sequence of the light and heavy chain variable regions (although signal sequences are usually omitted). Having received the sequence information, a computer is programmed to fit an antibody characterized by the sequence information to the binding pocket of one or more of the models provided herein.

The computer can be programmed to display a representation of the fit of the candidate antibody fragment to the binding pocket, optionally superimposed over the antibody (e.g., Fab fragment of 3D6, 10D5, 12B4 or 12A11) used to generate the model. The computer can also be calculated to generate a measure of the fit of the candidate antibody to the binding pocket. The quality of fit of such antibodies to Aβ can be judged for example, by shape complementarity or by estimated interaction energy. See Meng et al., 1992, J. Comp. Chem. 13:505-524. The extent of fit to the binding pocket provides an indication of the extent to which a candidate antibody shares the functional properties of the antibody used to generate the model including the binding pocket. Optionally, the sequence data for the candidate antibody is fitted to the binding pocket of two or more models to identify to which of antibodies 3D6, 10D5, 12B4 or 12A11, the candidate antibody most closely corresponds. The functional properties of a candidate antibody can be predicted as most closely resembling those of the antibody used in the model providing the best fit to the candidate antibody.

In some methods, the goal is to characterize the functional properties of an antibody that has not yet been extensively studied experimentally. Some of the relevant properties of an antibody for treatment can only be tested in a transgenic animal model. Such experiments often take several months to perform and involve sacrifice of the animals. In silico screening provides a means to predict the functional properties before such testing is performed. Although testing in transgenic animals is still often performed after in silico analysis, it can be confined to those antibodies that appear to have desired functional properties from the in silico analysis.

In other methods, the goal is to obtain variants of existing properties with improved properties. The improved properties can include altered (usually increased) affinity, and minor changes in epitope specificity. The improved properties can also include reduced immunogenicity or pharmacokinetics. In such cases, the amino acid sequences of an antibody are altered with a view to reducing immunogenicity or otherwise improving pharmacokinetics without significantly affecting the binding affinity or specificity of an antibody. An exemplary modification is to delete one or more of amino acids 98-100 (Kabat numbering) from heavy chain CDR3 of an antibody.

In some methods, the computer is programmed to calculate and/or display an updated model of an antibody fragment/Aβ complex that takes into account differences between an antibody used to generate an original model and a variant of that antibody. In this way, an expanded collection of models and antibodies can be developed without de novo crystallization of every antibody. The updated models can be used in methods of in silico screening as the original models.

After in silico screening, candidate antibody fragments are often subject to additional screening including in transgenic animal models of Alzheimer's disease. For candidate antibody fragments having theoretical sequences (i.e., the candidate antibody has not hitherto been produced), a candidate antibody or fragment thereof can be expressed by standard recombination procedures.

The invention further provides a method for identifying an antibody fragment that can mimic the Fab fragment of 12A11. An antibody mimic is designed to have at least one structural or functional property in common with a prototypical antibody. In the case of 12A11 an antibody mimic can, for example, share the structural absence of amino acids occupying one or more of Kabat positions 98-100 in the heavy chain and/or the functional properties of binding to soluble oligomeric Aβ and high potency in a CFC assay. The method includes providing a three-dimensional structural representation of the Fab fragment of 12A11 having a variable light chain of SEQ ID NO:3 and a variable heavy chain of SEQ ID NO:8, wherein the 12A11 Fab fragment is complexed to a peptide including an epitope of amino acids 1-7 of SEQ ID NO:1, and computationally designing the antibody fragment that mimics the Fab fragment of 12A11. The invention also provides a method for identifying an antibody fragment that can mimic the Fab fragment of 3D6, where the method includes providing a three-dimensional structural representation of the Fab fragment of 3D6 having a variable light chain of SEQ ID NO:6 and a variable heavy chain of SEQ ID NO:11, wherein the 3D6 Fab fragment is complexed to a peptide including an epitope of amino acids 1-7 of SEQ ID NO:1, and computationally designing the antibody fragment that mimics the Fab fragment of 3D6.

B. In Vitro Screening

The strategy and principles used in preparing and analyzing crystal structures of complexes of the antibody 3D6, 10D5, 12A11 and 12B4 can be applied to other antibodies. Of particular interest are antibodies having light or heavy chain variable regions representing hybrids of the light or heavy chain sequences of two or more of the above antibodies. Fragments of such antibodies, typically Fab fragments are contacted with an Aβ peptide (e.g., Aβ1-7), such that a complex of the antibody fragment and the peptide forms. X-ray crystallography is used to identify how the antibody fragment binds to the peptide. In some methods, the candidate antibody fragment includes at least one of the variable light chain CDRs of SEQ ID NO:14, SEQ ID NO:15, and SEQ ID NO:16, and at least one of the variable heavy chain CDRs of SEQ ID NO:17, SEQ ID NO:18, and SEQ ID NO:19. In some methods, the light chain includes two or three of the CDRs or SEQ ID NOS: 14, 15 and 16 and the heavy chain includes two or three of the CDRs of SEQ ID NO:17, 18 or 19. In some methods, the candidate antibody fragment has a light chain variable region according to SEQ ID NO:7 and a heavy chain variable region according to SEQ ID NO:12 or 13. In any of these methods, SEQ ID NOS. 14, 15 and 16 can be replaced by SEQ ID NOS: 23, 24, and 25 respectively and SEQ ID NOS. 17, 18, and 19 can be replaced by SEQ ID NOS. 26, 27 and 28 respectively. In some methods, the candidate antibody fragment includes a light chain variable region having at least 90% sequence identity to the full length of SEQ ID NO:3, 4, 5 or 6 and a heavy chain variable region having at least 90% sequence identity to the full length of SEQ ID NO:8, 9, 10 or 11. In some methods, the candidate antibody has a heavy chain variable region of SEQ ID NO:19 in which position X2 of SEQ ID NO:18 is W or Y. In some methods, the candidate antibody is an antibody that binds an epitope within residues 3-7 of Aβ in which positions H98-H100 Kabat numbering (equivalent to residues X2, X3 and X4 in SEQ ID NO:19) are unoccupied.

IV. Humanized Antibodies

The term "humanized antibody" refers to an antibody including at least one chain including variable region framework residues substantially from a human antibody sequence (referred to as the acceptor immunoglobulin or antibody) and at least one complementarity determining region substantially from a non-human antibody often a mouse antibody, (referred to as the donor immunoglobulin or antibody). See, Queen et al., Proc. Natl. Acad. Sci. USA 86:10029 10033 (1989), U.S. Pat. No. 5,530,101, U.S. Pat. No. 5,585,089, U.S. Pat. No. 5,693,761, Selick et al., WO 90/07861, and Winter, U.S. Pat. No. 5,225,539 (incorporated by reference in their entirety for all purposes). Usually all three CDRs in heavy and light chains of the donor antibody are grafted into the acceptor sequence. The constant region(s), if present, are also substantially or entirely from a human immunoglobulin, albeit optionally with an Fc mutation, many of which are known in the field.

The humanization process represents a common application of molecular modeling. Humanization starts with a non-human antibody, typically a mouse antibody, referred to as a donor. CDRs of the donor and usually certain variable region framework residues from the donor are grafted into a human variable region framework sequence (acceptor sequence). The acceptor sequence can be, for example, a mature human antibody sequence, a human germline sequence or a consensus sequence of human mature or germline sequences. Acceptor sequences for heavy and light chains can be from the same or different sources. Variable region framework positions selected for substitution are residues that differ at corresponding positions between the donor and acceptor sequences, and for which it is reasonably expected that the amino acid: (1) noncovalently binds antigen directly, (2) is adjacent to a CDR region, (3) otherwise interacts with a CDR region (e.g., is within about 3-6 Å of a CDR region as determined by computer modeling), or (4) participates in the VL-VH interface. The variable region residues from the donor grafted into the human acceptor sequences are sometimes referred to as back mutations in that they effectively represent mutation of a human acceptor residue back to a corresponding residue of the donor antibody.

Residues which "noncovalently bind antigen directly" include amino acids in positions in framework regions which are have a good probability of directly interacting with amino acids on the antigen according to established chemical forces, for example, by hydrogen bonding, Van der Waals forces, hydrophobic interactions, and the like.

Residues that "otherwise interact with a CDR region" include those that are determined by secondary structural analysis to be in a spatial orientation sufficient to affect a CDR region. These residues can be identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions and the like. Such amino acids will generally have a side chain atom within about 3 angstrom units (Å) of some atom in the CDRs and must contain an atom that could interact with the CDR atoms according to established chemical forces, such as those listed above. For atoms that may form a hydrogen bond, the 3 Å is measured between their nuclei, but for atoms that do not form a bond, the 3 Å is measured between their Van der Waals surfaces. Hence, in the latter case, the nuclei must be within about 6 Å (3 Å plus the sum of the Van der Waals radii) for the atoms to be considered capable of interacting. Often, nuclei of interacting atoms are from 4 or 5 to 6 Å apart.

Amino acids that are capable of interacting with amino acids in the CDRs can also be identified by solvent accessible surface area. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971).

CDR and framework regions are as defined by Kabat et al. or Chothia and Lesk JMB 196:901 (1987) or a combination of these definitions. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat or Chothia or a combination of the CDRs from these definitions.

Residues which "participate in the VL-VH interface" or "packing residues" include those residues at the interface between VL and VH as defined, for example, by Novotny and Haber, Proc. Natl. Acad. Sci. USA, 82:4592 66 (1985) or Chothia et al, supra Generally, unusual packing residues should be retained in the humanized antibody if they differ from those in the human frameworks.

The variable region framework residues for backmutation are determined by molecular modeling. A suitable model of a donor antibody can be produced starting from one of the models described herein (e.g., 3D6, 10D5, 12A11 and 12B4) and updating the model to accommodate differences in amino acid sequence between the light and heavy chain variable regions of the donor antibody and those of the antibody used in the original model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

In general, one or more of the amino acids fulfilling the above criteria is substituted and sometimes all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. It is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gin; ser, thr; lys, arg; and phe, tyr. As discussed further below, it is also possible and sometimes advantageous to delete residues 98-100 Kabat numbering from CDRH3. One or more of residues 60-65 (Kabat numbering) in CDR H2 often do not make contacts with an antigen and can optionally be replaced with a residue from the corresponding position of a human acceptor variable region sequence (correspondence being defined by Kabat).

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an a typical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare" indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it is often be preferable to consider only those human sequences in the same subgroup as the acceptor sequence.

Other than the specific amino acid substitutions discussed above, the framework regions of humanized immunoglobulins are usually substantially identical to the variable region frameworks of the human acceptor sequence from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. In both heavy and light chains, the variable region frameworks of humanized antibodies typically have at least 85, 90 or 95% sequence identity to the entire length of the variable region framework sequences of the human acceptor sequence from which they were derived.

The humanized antibodies preferably exhibit a specific binding affinity for antigen of at least $10^7$, $10^8$, $10^9$ or $10^{10}$ $M^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabelled reagents) or competitive binding assays.

In some methods, the donor antibody includes at least one of the variable light chain CDRs of SEQ ID NO:14, SEQ ID NO:15, and SEQ ID NO:16, and at least one of the variable heavy chain CDRs of SEQ ID NO:17, SEQ ID NO:18, and SEQ ID NO:19. In some methods, the donor antibody includes at least two of the variable heavy chain CDRs of SEQ ID NO:17, SEQ ID NO:18, and SEQ ID NO:19. In some methods, the donor antibody comprises at least two of the variable light chain CDRs of SEQ ID NO:14, SEQ ID NO:15, and SEQ ID NO:16, and at least two of the variable heavy chain CDRs of SEQ ID NO:17, SEQ ID NO:18, and SEQ ID NO:19. In some methods, the donor antibody comprises the variable light chain CDRs of SEQ ID NO:14, SEQ ID NO:15, and SEQ ID NO:16, and the variable heavy chain CDRs of SEQ ID NO:17, SEQ ID NO:18, and SEQ ID NO:19. As in other methods, SEQ ID NOS. 14, 15 and 16 can be replaced by SEQ ID NOS: 23, 24 and 25 respectively and SEQ ID NOS. 17, 18 and 19 can be replaced by SEQ ID NOS: 26, 27 and 28. Optionally, the humanized antibody is not an antibody in which all CDRs are obtained from 3D6, 12A11, 10D5 or 12B4, or any other single mouse antibody.

The models disclosed in the present application reveal that in each of the tested antibodies 3D6, 10D5, 12B4, and 12A11, CDRs L1 and L3 from the light chain and CDR2 H2 and H3 from the heavy chain make the principal contacts with the antigen. Accordingly, humanized forms of these and other antibodies binding to an epitope within residues 3-7 of Aβ can be made without transfer of all CDRs from a non-human antibody into human acceptor variable region framework. Specifically, a humanized light chain can be formed by combining CDRs L1 and L3 from a non-human antibody into a human light chain variable region framework sequence. CDR L2 can be provided by any human antibody sequence but is preferably provided by the same human light chain variable region sequence as supplies the light chain variable region frameworks. Likewise a humanized heavy chain can be formed by combining CDRs H2 and H3 from a nonhuman antibody into a human heavy chain variable region framework sequence. CDR H1 can be provided by any human heavy chain variable region framework sequence but is preferably provided by the same human heavy chain variable region sequence as supplies the heavy chain variable region frameworks.

V. Flapless Antibodies

Comparison of the crystal complex of 12A11 with that of 10D5 or 12B4 (FIG. 9) shows that residues 98-100 in heavy chain CDR H3 of 10D5 or 12B4 (corresponding to residues 103-105) by sequential numbering form a loop, which does not make contact with the Aβ peptide. This loop is absent in the complex of 12A11 because residues 98-100 by Kabat numbering are absent in this antibody. Although practice of the invention is not dependent on an understanding of mechanism, it is believed that the extra loop (sometimes referred to as a flap) in 10D5 and 12B4 may obstruct binding of these antibodies to oligomeric forms of Aβ without contributing to binding to monomeric Aβ. The absence of this flap in the 12A11 antibody may thus account for its improved binding to oligomeric Aβ relative to 12B4 and 10D5 and more potent properties in inhibiting cognitive decline.

The invention provides novel antibodies which combine the feature of lack of amino acids at any or all of Kabat positions 98-100 as found in 12A11 with advantageous features of other antibodies that bind within residues 3-7 of Aβ. Such other advantageous features can include improved pharmacokinetics for example relative to 12A11. Some such antibodies are hybrid antibodies combining CDRs from different sources, for example two different antibodies each of which binds to an epitope within residues 3-7 of Aβ. Some such antibodies have a light chain variable region comprising CDRs L1, L2 and L3 designated SEQ ID NOS. 14, 15 and 16 respectively. These SEQ ID NOS. are consensus formulae that represent the variation in CDRs L1, L2 and L3 among antibodies 3D6, 10D5, 12B4 and 12A11. Residues that are common between the antibodies are so indicated. Residues that vary are indicated with an X with the various forms of X in the different antibodies. Such antibodies have a heavy chain variable region comprising CDR H1, CDR H2, and CDR H3 designated SEQ ID NOS. 17, 18 and 19 respectively. These SEQ ID NOS. likewise represent consensus formulae of variation in CDRs H1, H2 and H3 among antibodies 3D6, 10D5, 12B4 and 12AA. Residues X2, X3 and X4 in CDR19 corresponding to Kabat positions 98-100 are absent. Furthermore, at least one of the CDRs is different from a 12A11 CDR (i.e., it is from a different antibody or mutated relative to a CDR of 12A11). Usually, a least one of the CDRs other than CDR H3 is from an antibody other than 12A11 in such hybrid antibodies.

The SEQ ID NOS. provided above represent consensus formulae for the four antibodies 3D6, 10D5, 12B4 and 12A11. Other antibodies are provided in which these consensus formulae are replaced with consensus formulae based on 10D5, 12B4 and 12A11 only.

Some hybrid antibodies represent hybrids of an antibody other than 12A11 that binds an epitope within residues 3-7 of Aβ and 12A11 in which the antibody other than 12A11 provides CDRs L1, L2, L3, H1 and H2. CDRH3 is provided either by 12A11 or represents a mutated form of the CDR of the other antibody in which position 98-100 of the heavy chain (by Kabat numbering) are unoccupied. The other antibody can be 10D5, 12B4, PFA1 or PFA2 for example.

Other hybrid antibodies represent hybrids of an antibody other than 12A11 that binds an epitope within residues 3-7 of Aβ and 12A11 in which the antibody other than 12A11 provides CDRs L1, L3, H2. CDRH3 is provided either by 12A11 or represents a mutated form of the CDR of the other antibody in which position 98-100 of the heavy chain (by Kabat numbering) are unoccupied. The other antibody can be 10D5, 12B4, PFA1 or PFA2 for example. CDRs L2 and H1, which do not make contact with antigen directly can be obtained from any antibody. Usually, CDRs L2 and H1 are obtained from a human antibody sequence that also provides variable framework regions in a humanized antibody.

The invention also provides any antibody other than 12A11 that bind to an epitope within residues 3-7 of Aβ in which positions 98-100 by Kabat numbering in heavy chain CDR are unoccupied. Some such antibodies are hybrid antibodies in which CDR H3 is from the 12A 11 antibody.

The remarks above with respect to antibodies in general apply mutatis mutandis to the antibodies described above. Thus, for example, the antibodies can be provided in isolated form and as monoclonal antibodies. The antibodies can be provided in intact form or as binding fragments. The antibodies can be provided as mouse antibodies, chimeric, humanized or human antibodies. Hybrid antibodies are particularly amenable to the humanized form. In this case, the combinations of CDRs specified above are combined into human variable region frameworks, optionally with backmutations, as generally described above. Backmutations in a hybrid antibody can be to the appropriate residue of either of the antibodies being combined in a hybrid.

VI. Pharmaceutical Compositions

Antibodies resulting from the screening methods described above can be incorporated into pharmaceutical compositions. Some antibodies comprise a light chain having at least one of the variable light chain CDRs of SEQ ID NO:14, SEQ ID NO:15, and SEQ ID NO:16, at least one of the variable heavy chain CDRs of SEQ ID NO:17, SEQ ID NO:18, and SEQ ID NO:19, wherein the antibody specifically binds to a peptide including an epitope of amino acids 1-7 of SEQ ID NO:1. Such antibodies represent hybrid forms of two or more of the 12A11, 12B4, 10D5 and 3D6 antibodies. Pharmaceutical composition of 12A11, 12B4, 10D5 and 3D6 as well as humanized or chimeric forms of these antibodies including all six CDRs of a donor antibody have been described elsewhere and are optionally excluded from the present pharmaceutical compositions.

Some antibodies or binding fragments thereof including at least two of the variable light chain CDRs of SEQ ID NO:14, SEQ ID NO:15, and SEQ ID NO:16. Some antibodies or binding fragments includes at least two of the variable heavy chain CDRs of SEQ ID NO:17, SEQ ID NO:18, and SEQ ID NO:19. Some antibodies or binding fragments include at least two of the variable light chain CDRs of SEQ ID NO:14, SEQ ID NO:15, and SEQ ID NO:16, and at least two of the variable heavy chain CDRs of SEQ ID NO:17, SEQ ID NO:18, and SEQ ID NO:19. Some antibodies or binding fragments include the variable light chain CDRs of SEQ ID NO:14, SEQ ID NO:15, and SEQ ID NO:16, and the variable heavy chain CDRs of SEQ ID NO:17, SEQ ID NO:18, and SEQ ID NO:19

Antibodies can be combined with pharmaceutically acceptable carriers, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, and dispensing agents, depending on the nature of the mode of administration and dosage forms. Such ingredients, including pharmaceutically acceptable carriers and excipients are described in the Handbook of Pharmaceutical Excipients, American Pharmaceutical Association (1986), incorporated herein by reference in its entirety. Examples of pharmaceutically acceptable carriers include water, ethanol, polyols, vegetable oils, fats, waxes polymers, including gel forming and non-gel forming polymers, and suitable mixtures thereof. Examples of excipients include starch, pregelatinized starch, Avicel, lactose, milk sugar, sodium citrate, calcium carbonate, dicalcium phosphate, and lake blend. Examples of disintegrating agents include starch, alginic acids, and certain complex silicates. Examples of lubricants include magnesium stearate, sodium lauryl sulphate, talc, as well as high molecular weight polyethylene glycols. Other different excipients can be used in formulations according to the present invention and the list provided herein is not exhaustive.

The antibodies can also be combined with antioxidants or stabilizers to prevent degradation due to oxidation or other means. Antioxidants include, for example, butylated hydroxytoluene (BHT), ferrous sulfate, ethylenediaminetetra-acetic acid (EDTA), or others. Stabilizers include, for example, amglene, hydroquinone, quinine, sodium metabisulfite or others. Antioxidants and stabilizers can be combined with the compounds directly or blended with the compound formulation such as compound-polymer matrix to reduce conformation change or degradation during manufacturing processes and increase shelf life or storage life of the compounds or compound containing implant. The amount of antioxidants such as BHT in the compounds can range from 0.01% to 10%, preferable from 0.05% to 5% and most preferable from 0.1% to 3%. The amount of stabilizers such as amylene in the compounds can range from 0.01% to 10%, preferably from 0.05% to 5%, most preferably from 0.1% to 1%. Other antioxidants and stabilizers are useful in the present invention.

VI. Computer Systems

Figure 13:
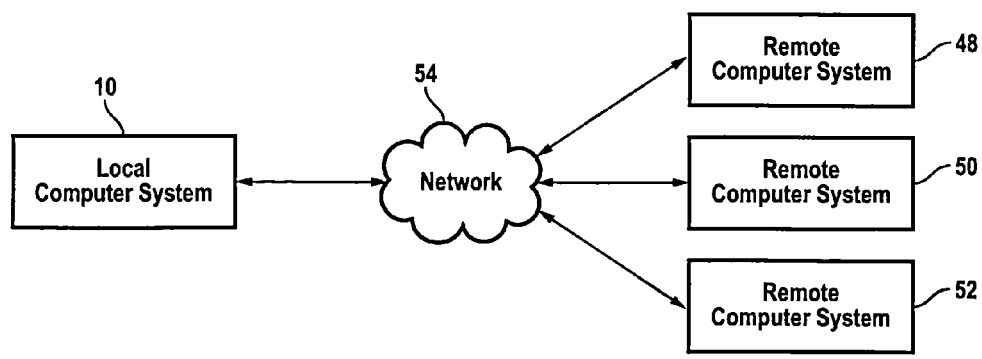
FIG. 13 is an illustration of representative computer system 10 of FIG. 12.

Data of the invention, such as atomic coordinates, can be stored and methods can be performed on standard computer systems. FIG. 13 depicts a representative computer system suitable for implementing the present invention. FIG. 13 shows basic subsystems of a computer system 10 suitable for use with the present invention. In FIG. 13, computer system 10 includes a bus 12 which interconnects major subsystems such as a central processor 14, a system memory 16, an input/output controller 18, an external device such as a printer 20 via a parallel port 22, a display screen 24 via a display adapter 26, a serial port 28, a keyboard 30, a fixed disk drive 32 and a floppy disk drive 33 operative to receive a floppy disk 33A. Many other devices can be connected such as a scanner 60 (not shown) via I/O controller 18, a mouse 36 connected to serial port 28 or a network interface 40. Many other devices or subsystems (not shown) may be connected in a similar manner. Also, it is not necessary for all of the devices shown in FIG. 13 to be present to practice the present invention, as discussed below. The devices and subsystems may be interconnected in different ways from that shown in FIG. 13. The operation of a computer system such as that shown in FIG. 13 is readily known in the art and is not discussed in detail in the present application. Source code to implement the present invention may be operably disposed in system memory 16 or stored on storage media such as a fixed disk 32 or a floppy disk 33A.

Figure 5:
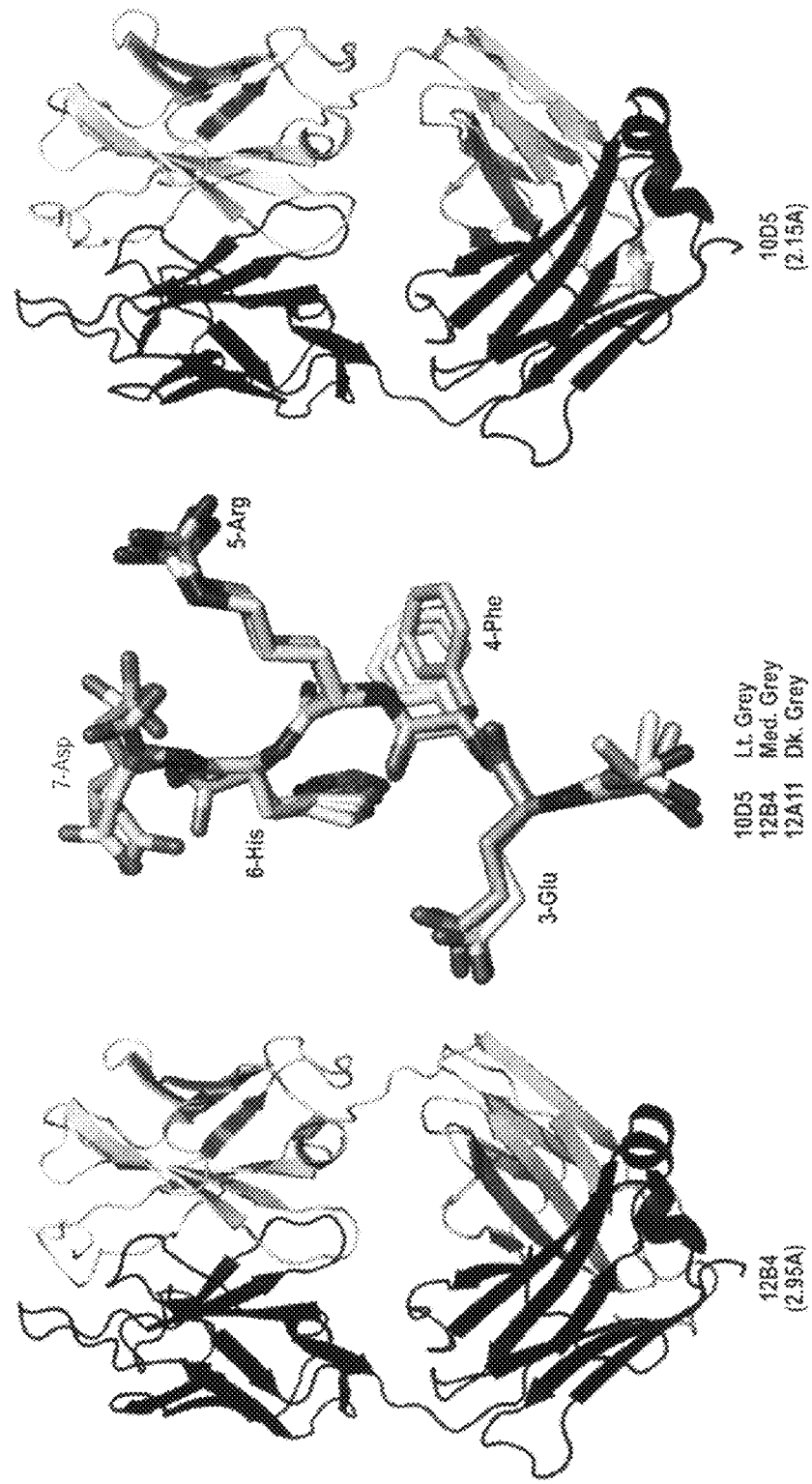
FIG. 5 shows three representations of the 12B4 and 10D5 antibodies. The figure allows shows three superimposed representation of an Aβ 2-7 peptide bound by 10D5, 12B4 and 12A11 respectively. The Aβ 2-7 peptide adopts a similar extended random coil conformation when bound to each antibody.

FIG. 14 is an illustration of representative computer system 10 of FIG. 13 suitable for embodying the methods of the present invention. FIG. 14 depicts but one example of many possible computer types or configurations capable of being used with the present invention. FIG. 5 shows computer system 10 including display screen 24, cabinet 20, keyboard 30, a scanner 60, and mouse 36. Mouse 36 and keyboard 30 illustrate "user input devices." Other examples of user input devices are a touch screen, light pen, track ball, data glove, etc.

In a preferred embodiment, System 10 includes a Pentium® class based computer, running a Windows® operating system by Microsoft Corporation. However, the method is easily adapted to other operating systems without departing from the scope of the present invention.

Mouse 36 may have one or more buttons such as buttons 37. Cabinet 20 houses familiar computer components such as disk drive 33, a processor, storage means, etc. As used in this specification "storage means" includes any storage device used in connection with a computer system such as disk drives, magnetic tape, solid state memory, bubble memory, etc. Cabinet 20 may include additional hardware such as input/output (I/O) interface 18 for connecting computer system 10 to external devices such as a scanner 60, external storage, other computers or additional peripherals. FIG. 14 is representative of but one type of system for embodying the present invention. Many other system types and configurations are suitable for use in conjunction with the present invention.

In prophylactic applications, antibodies or pharmaceutical compositions or medicaments containing the same are administered to a patient susceptible to, or otherwise at risk of, a disease characterized by amyloid deposits of Aβ in the brain, such as Alzheimer's disease, Down's syndrome or mild cognitive impairment, in a regime (amount, and route of administration) sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease in a regime (amount, frequency and route of administration) sufficient to cure, or at least partially arrest, the symptoms of the disease (biochemical, histologic and/or behavioral), including its complications and intermediate pathological phenotypes in development of the disease.

Example 1

Crystallization of Antibody:Aβ Complex

Crystallization conditions are summarized in the table below for each complex. Crystals were grown at 22° C. and frozen in liquid nitrogen for data collection.

TABLE 2

| | Antibody:Aβ Crystallization Conditions | | | | | |
|---|---|---|---|---|---|---|
| | 12A11: Aβ1-7 | 12A11: Aβ1-40 | 3D6: Aβ1-7 | 3D6: Aβ1-40 | 12B4: Aβ1-7 | 10D5: Aβ1-7 |
| Protein concentration (mg/ml) In 10 mM Hepes, pH 7.5 75 mM NaCl | 15 | 5.3 | 7.1 | 14.3 | 4.1 | 15 |

TABLE 2-continued

Antibody:Aβ Crystallization Conditions

| | 12A11: Aβ1-7 | 12A11: Aβ1-40 | 3D6: Aβ1-7 | 3D6: Aβ1-40 | 12B4: Aβ1-7 | 10D5: Aβ1-7 |
|---|---|---|---|---|---|---|
| Protein:peptide molar ratio | 1:1.1* | 1:4.5* | 1:2* | 1:1.8* | 1:1.8 | 1:2 |
| Crystallization method | hanging drop | sitting drop using the Honeybee robot | hanging drop | sitting drop using the Phoenix robot | hanging drop | sitting drop using the Phoenix robot |
| Protein:reservoir ratio (μl:μl) | 1:1 | 0.2:0.2 | 1:2 | 0.25:0.25 | 0.75:0.75 | 0.2:0.2 |
| Reservoir composition | 32% PEG400 0.1M Tris, pH 9.0 | 0.2M NaCl 0.1M Hepes, pH 7.5 25% PEG 4K | 30% PEG 400 0.1M Tris, pH 9.0 | 2.5M NaCl 0.1M Imidazole, pH 8.0 0.2M ZnAc$_2$ | 30% PEG8K 0.1M Hepes, pH 7.0 0.2M (NH$_4$)$_2$SO$_4$ | 30% PEG4K |
| Freezing condition | Reservoir with 35% PEG400 | Reservoir with 28% PEG4K | Reservoir | Reservoir + 20% Glycerol | Reservoir | Reservoir |

*Aβ stock solution (6.5 mM) was prepared in DMSO

Example 2

X-Ray Crystallography of Antibody:Aβ Complex

Data Collection. All data sets were measured at 100 K. Diffraction data for 12A11:Aβ1-7 was collected in two runs using different exposure time to avoid saturating the low resolution diffraction. Diffraction data for 12A11:Aβ1-40 was collected in 3 runs (2 runs to insure completeness of high-resolution data and one run with shorter exposure time to avoid saturating the low resolution diffraction). Diffraction data for 3D6:Aβ1-7 and 3D6:Aβ1-40 were measured using a beam attenuation of 70% and 75% respectively, to avoid large radiation damage to the crystals. For 3D6:Aβ1-40 the small size of the beam allowed to screen different region of the crystals to find the region that gives the best looking diffraction for data collection. Data were processed with MOSFLM and SCALA (Collaborative Computational Project, Number 4. (1994), *Acta Cryst.* D50, 760-763).

Structure Determination. Molecular replacement calculations were performed using the program COMO (Tong, L. (1996) *Acta Cryst.* A52, 782-784). Molecular replacement was done in two stages, first finding the rotation and translation solution of the constant domain and later, while fixing the constant domain, finding the solution for the variable domain. When more than one monomer comprises the asymmetric unit, all the constant domains were found and fixed before moving to the solution of the variable domains. Model building was done using the program Coot (Emsley P, Cowtan, K. (2004) *Acta Cryst.* D60, 2126-2132).

The 12A11+aβ1-7 model was refined using Refmac. Aβ peptide residues P-Asp-1 and P-Asp-7 are not as well defined in the electron density map. P-Asp-7 was modeled as an Ala because no density was visible for the rest of the side chain.

Although the cell and symmetry for the data of 12A11Aβ1-40 are quite similar to the data set of 12A11Aβ1-7, the data sets are not isomorphous to each other as the Fabs have different elbow angles.

In the final model of 3D6+Aβ1-7 the side chain of residue 7 was not visible past Cβ, and hence this residue was refined as Ala.

For 3D6+Aβ1-40, given the presence of 200 mM ZnAc$_2$ in the crystallization medium, several strong difference electron density peaks were modeled as Zn$^{2+}$, based on the geometry of the surrounding ligands and the appearance of strong peaks at these positions in an anomalous difference map. One of these Zn$^{2+}$ occupies the same spatial position as Aβ1-40 and hence can not be present at this site at the same time as the peptide. The peptide and this Zn$^{2+}$ ion were treated as alternative conformations each with 50% occupancy.

12A11Aβ1-40, 3D6Aβ1-7 and 3D6Aβ1-40 were initially refined using Refmac and at later stages using phoenix (Adams, P. D., et al., (2002). *Acta Cryst.* D58, 1948-1954) with individual positional and B-factor refinement and 5 TLS groups (the heavy and light chains were split into two groups each, at the hinge between the constant and the variable domains, and the peptide as a separate group).

In 12B4Aβ1-7, there are 4 non-crystallographic Fab molecules in the cell (symmetry P1). Strict non-crystallographic symmetry, using. CNS (Brunger, A. T., et al., (1998) *Acta Cryst.* D54, 905-921.), was applied during initial model building. In later stages refinement was done using Phenix with restrained NCS using 2 equivalent regions of the Fabs and peptide (the variable domain including the peptide as one group and the constant domain as the second group). Taking into account the resolution of this data (up to 2.95 Å) refinement included individual positional refinement, grouped B-factor and TLS. For the grouped B-factor refinement the heavy and light chains were split into two groups each (at the hinge between the constant and the variable domains) and the peptide as a separate group (5 groups per monomer, 20 groups total). For TLS refinement, 3 groups per monomer were selected (variable domain, constant domain and peptide per monomer, total of 12 groups).

In 10D5Aβ1-7, there are two Fab molecules in the asymmetric unit. Restrained non-crystallographic symmetry was originally applied during initial model building but was removed in later stages. Refinement was done using Phenix with individual positional and B-factor refinement and 3 TLS groups per monomer (variable domain, constant domain and peptide).

The components of each complex, the resolution of the model and residues in the model are summarized in FIG. 2.

Figure 10:
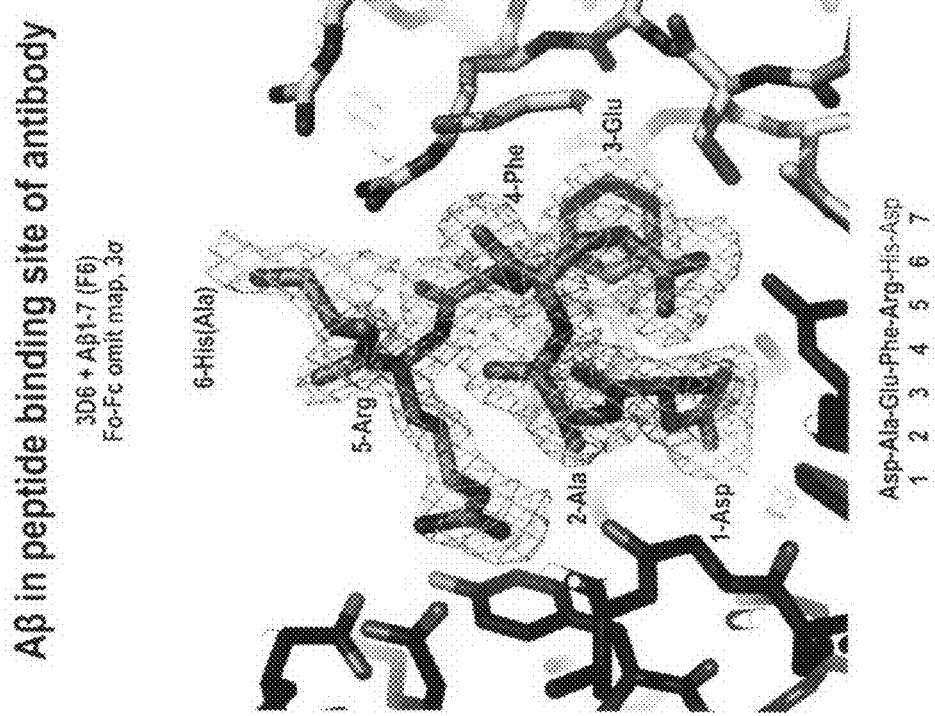
FIG. 10 is a ball and stick representation of 3D6 antibody bound to an Aβ 1-7 peptide (SEQ ID NO: 41). The terminal asp residue is enclosed in a pocket formed by the antibody heavy and light chains.

The interactions between interacting residues in an Aβ peptide and an antibody are summarized in Table 3 below.

is absent from 12A11. FIG. 10 is a ball and stick representation of 3D6 antibody bound to an A| 1-7 peptide. The terminal

TABLE 3

Specific Antibody:β Interactions

Residues in Aβ31-7 and Aβ1-40 that interact with antibodies[1]

| Antibodies | Asp-1 | Ala-2 | Glu-3 | Phe-4 | Arg-5 | His-6 | Asp-7 (SEQ ID NO: 41) |
|---|---|---|---|---|---|---|---|
| 12A11 Aβ1-7 | | L-Val99 | L-His-31<br>L-Ser32<br>L-ser97 | L-His31<br>L-Ser96<br>L-Ser97<br>L-Val99<br>L-Leu101<br>H-His52<br>H-Tyr60 | H-Trp54<br>H-Asp56<br>H-Asp58<br>H-Tyr60 | L-His31<br>L-Asn33<br>L-Tyr37<br>L-Ser96<br>H-Asp105 | |
| 12A11 Aβ1-40 | | L-Val99<br>L-His98 | L-His31<br>L-Ser32<br>L-Ser97 | L-His31<br>L-Ser96<br>L-Ser97<br>L-Val99<br>L-Leu101<br>H-His52<br>H-Tyr60 | H-Trp54<br>H-Trp55<br>H-Asp56<br>H-Tyr60 | L-His31<br>L-Asn33<br>L-Tyr37<br>L-Ser96<br>H-Asp105 | H-Thr102 |
| 10D5 Aβ1-7 | | L-Val99 | L-His-31<br>L-Ser32<br>L-ser97<br>H₂-Arg60[2] | L-His31<br>L-Gly96<br>L-Ser97<br>L-Val99<br>L-Leu101<br>H-His52<br>H-Tyr54 | H-Tyr54<br>H-Trp55<br>H-Asp56<br>H-Asp58<br>H-Arg60 | L-His31<br>L-Tyr37<br>L-Gly96<br>H-Ile102<br>H-Thr103<br>H-Asp108 | H-Thr103 |
| 12B4 Aβ1-7 | | L-Val99<br>H-Arg60 | L-His31<br>L-Ser32<br>L-Ser97<br>H-Arg60 | L-His31<br>L-Ser97<br>L-Val99<br>L-Leu101<br>H-His52<br>H-Tyr54 | H-Tyr54<br>H-Trp55<br>H-Asp56<br>H-Asp58 | L-His31<br>L-Tyr37<br>L-Gly96<br>H-Ile103<br>H-Asp108 | H-Ile103 |
| 3D6 Aβ1-7 | L-Trp94<br>L-Gly96<br>L-Arg101<br>H-Tyr99<br>H-Ser105<br>H-Ser106 | L-Gly96<br>L-Thr97<br>L-His98 | H-Ser 50<br>H-Arg52<br>H-Tyr59<br>L-Arg-101 | H-Gly33<br>H-Ser50<br>H-Arg52<br>H-Tyr99 | L-Asp31<br>L-Tyr37<br>L-Gly96<br>L-Thr97 | H-Arg52 | |
| 3D6 Aβ1-40 | L-Trp94<br>L-Gly96<br>L-Arg101<br>H-Tyr99<br>H-Ser105<br>H-Ser106 | L-Gly96<br>L-Thr97<br>L-His98 | H-Ser50<br>H-Arg52<br>H-Tyr59<br>L-Arg-101 | H-Gly33<br>H-Ser50<br>H-Arg52<br>H-Tyr99<br>H-Ile51<br>H-Ser35<br>L-Arg101 | L-Asp31<br>L-Tyr37<br>L-Gly96<br>L-Thr97<br>H-Tyr99 | | |

[1]L denotes light chain for antibodies; H denotes heavy chain for antibodies.
[2]H₂ is heavy chain in monomer 2 for 10D5.
Arg60 in 10D5 can adopt two conformations.

The atomic coordinates of the crystal complexes can be displayed in three dimensional representations of the antibody:peptide complex in various formats as shown below. Different complexes can be superimposed on one another using, for example, different colors. FIG. 4 shows a three dimensional representation of a 12A11 antibody bound to an Aβ 1-7 peptide. The peptide shown in ball and stock format occupies a cleft between heavy and light chains of the antibody. FIG. 5 shows three dimensional representations of the 12B4 and 10D5 antibodies. The figure allows shows three superimposed representation of an Aβ 2-7 peptide bound by 10D5, 12B4 and 12A11 respectively. The Aβ 2-7 peptide adopts a similar extended random coil conformation when bound to each antibody.

Figure 6:
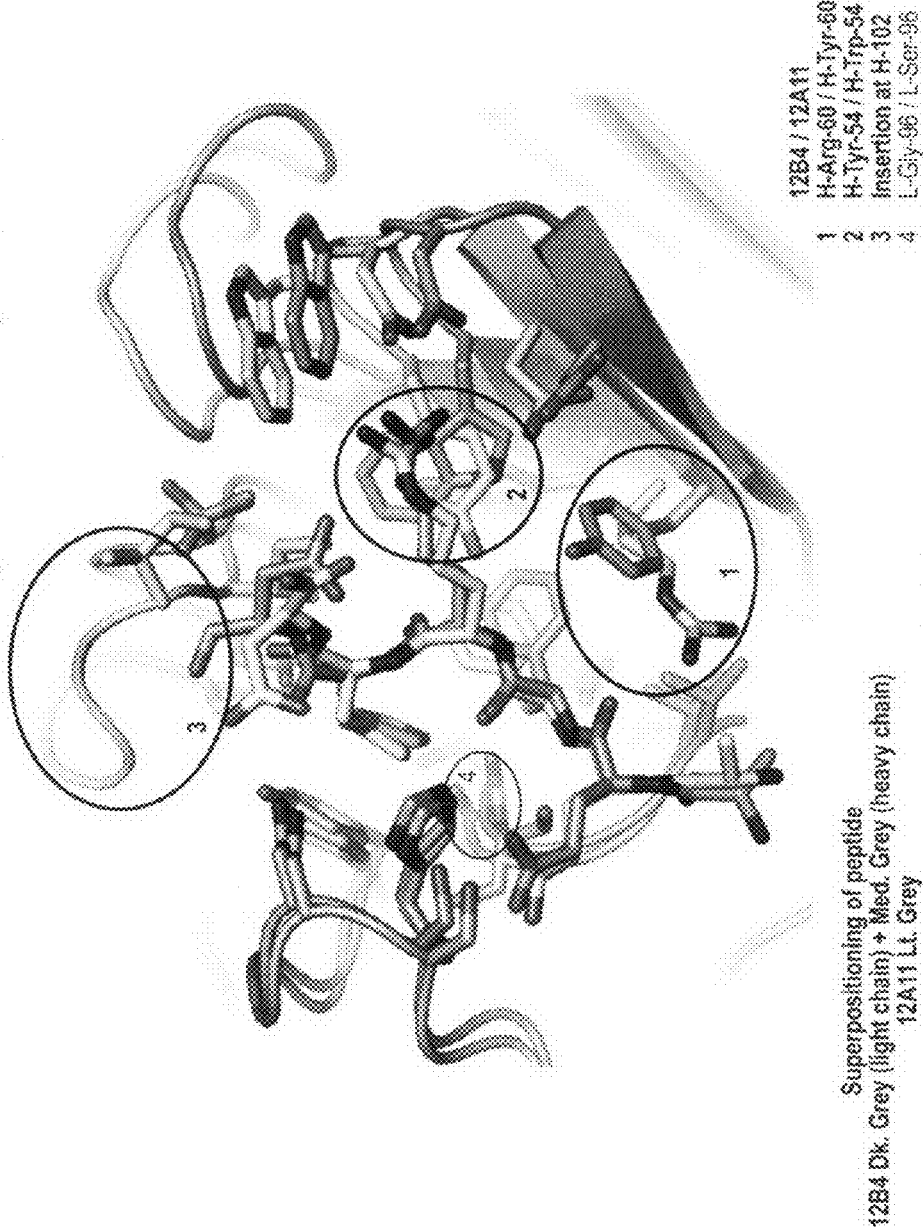
FIG. 6 shows a superimposition of parts of antibodies 12B4 and 12A11 comparing contacts at positions H60, H54, H102 and L96.
Figure 7:
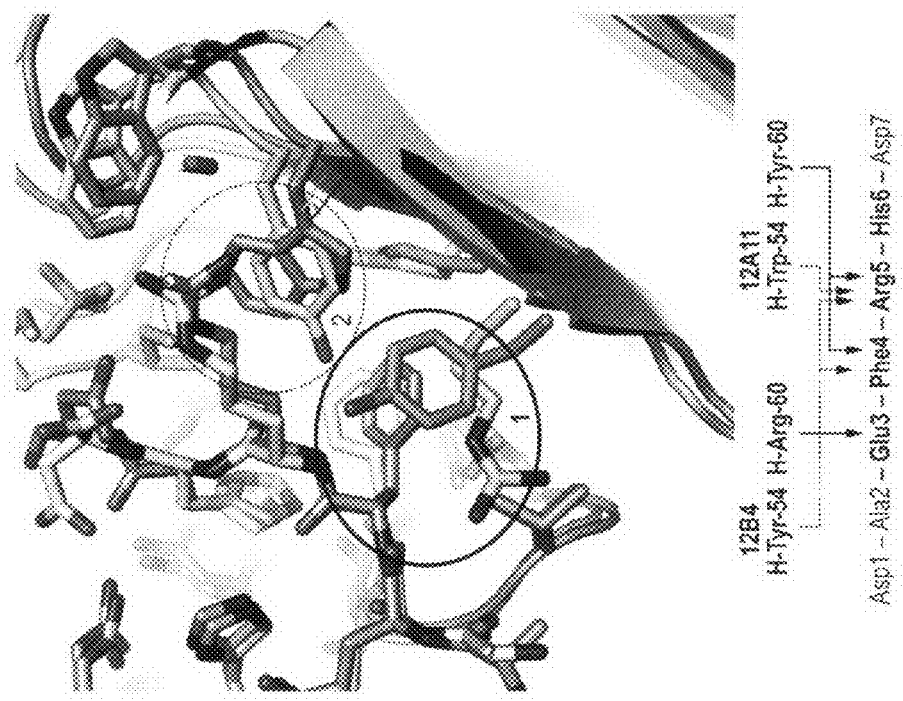
FIG. 7 also shows a superimposition of parts of antibodies 12B4 and 12A11 illustrating differences in contacts in CDR H2. Peptide disclosed as SEQ ID NO: 41.
Figure 9:
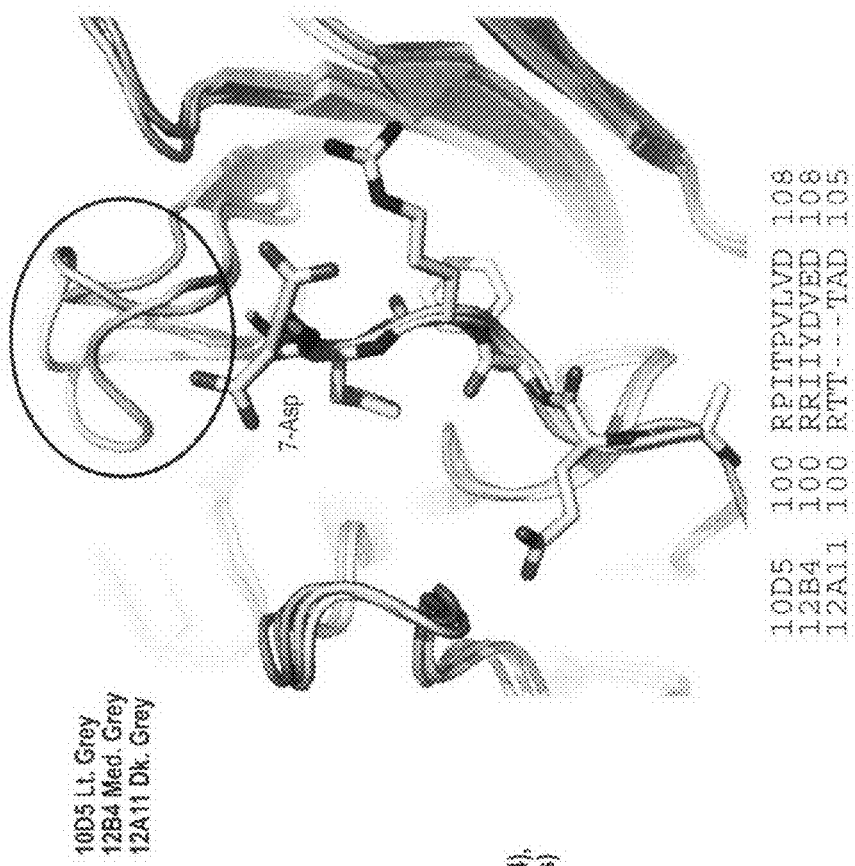
FIG. 9 shows a comparison of CDR H3 for antibodies 10D5 (SEQ ID NO: 78), 12B4 (SEQ ID NO: 79) and 12A11 (SEQ ID NO: 80). Antibodies 12B4 and 10D5 have a flap region (Kabat residues 98-100) circled that is absent from 12A11.
Figure 11:
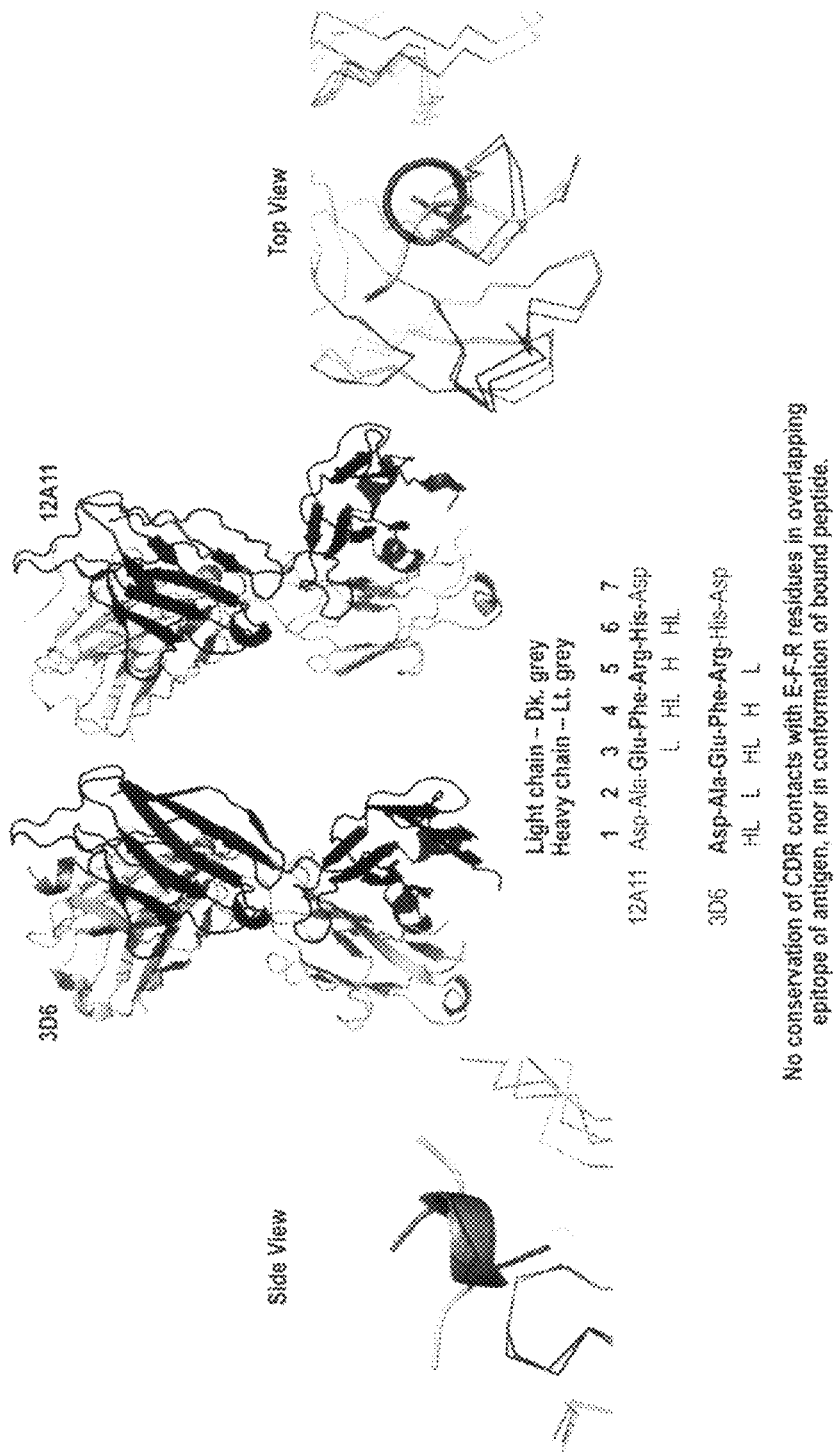
FIG. 11 compares contacts in the region of epitope overlap between antibodies 3D6 and 10D5. Peptides disclosed as SEQ ID NO: 41.
Figure 12:
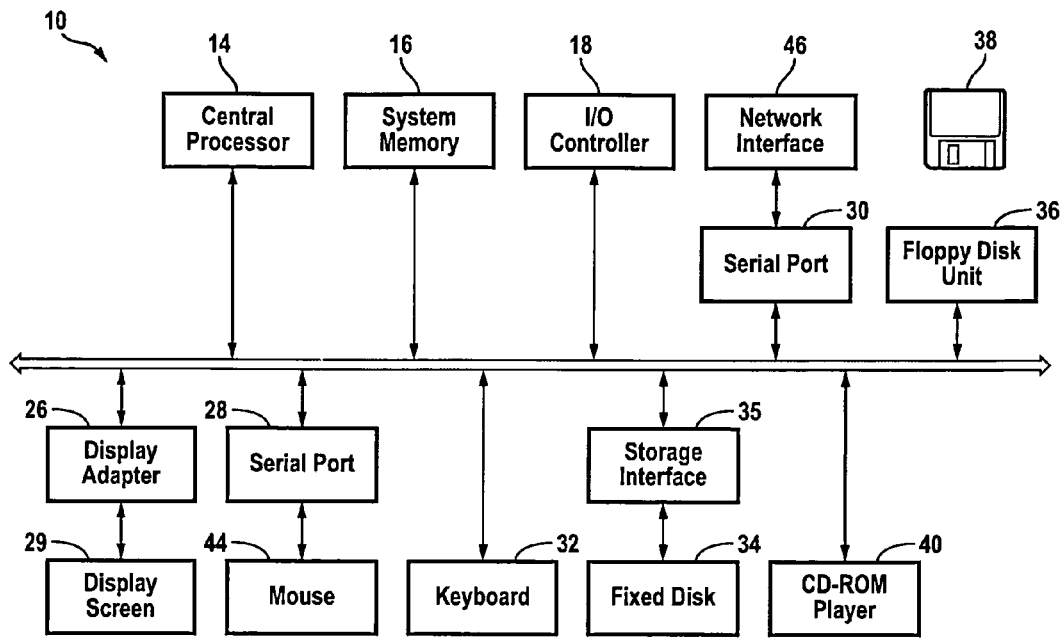
FIG. 12 depicts a representative computer system suitable for implementing the present invention.

FIG. 6 shows a superimposition of parts of antibodies 12B4 and 12A11 comparing contacts at positions H60, H54, H102 and L96. FIG. 7 also shows a superimposition of parts of antibodies 12B4 and 12A11 illustrating differences in contacts in CDR H2. FIG. 9 shows a comparison of CDR H3 for antibodies 10D5, 12B4 and 12A11. antibodies 12B4 and 10D5 have a flap region (Kabat residues 98-100) circled that asp residue is enclosed in a pocket formed by the antibody heavy and light chains. The peptide exists in a helical conformation. FIG. 11 compares contacts in the region of epitope overlap between antibodies 3D6 and 10D5. There is little similarity of CDR contacts between these antibodies.

Although the foregoing invention has been described in some detail by way of illustration and example for purposes of clarity of understanding, certain changes and modifications may be practiced within the scope of the appended claims. In addition, each reference including journal articles, patent filings, sequence identifiers and the like, provided herein is incorporated by reference in its entirety to the same extent as if each reference was individually incorporated by reference.

SUMMARY OF SEQUENCES

SEQ ID NO:1 is the amino acid sequence of Aβ40.

DAEFRHDSGYEVHHQKLVFFAEDVGSNK-
GAIIGLMVGGVV SEQ ID NO:1

SEQ ID NO:2 is the amino acid sequence of Aβ42.

DAEFRHDSGYEVHHQKLVFFAEDVGSNK-
GAIIGLMVGGVVIA SEQ ID NO:2

SEQ ID NO:3 is the amino acid sequence of the variable light chain region of the murine 12A11 antibody.

SEQ ID NO: 3
MKLPVRLLVLMFWIPASSSDVLMTQTPLSLPVSLGDQASISCRSSQSIVH

SNGNTYLEWYLQKPGQSPKLLIYKVSNRFSGVPDRFSGSGSGTDFTLKIS

RVEAEDLGIYYCFQSSHVPLTFGAGTKLELK

SEQ ID NO:4 is the amino acid sequence of the variable light chain region of the murine 12B4 antibody.

SEQ ID NO: 4
MKLPVRLLVLMFWIPASSSDVLMTQTPLSLPVSLGDQASISCRSSQNIVH

SNGNTYLEWYLQKPGQSPKLLIYKVSNRFSGVPDRFSGSGSGTDFTLKIS

RVEAEDLGVYYCFQGSHVPLTFGAGTKLELK

SEQ ID NO:5 is the amino acid sequence of the variable light chain region of the murine 10D5 antibody.

SEQ ID NO: 5
MKLPVRLLVLMFWIPASSSDVLMTQTPLSLPVSLGDQASISCRSSQNIIH

SNGNTYLEWYLQKPGQSPKLLIYKVSNRFSGVPDRFSGSGSGTDFTLKIK

KVEAEDLGIYYCFQGSHVPLTFGAGTKLELE

SEQ ID NO:6 is the amino acid sequence of the variable light chain region of the murine 3D6 antibody.

SEQ ID NO: 6
YVVMTQTPLTLSVTIGQPASISCKSSQSLLDSDGKTYLNWLLQRPGQSPK

RLIYLVSKLDSGVPDRFTGSGSGTDFTLKISRIEAEDLGLYYCWQGTHFP

RTFGGGTKLEIK

SEQ ID NO:7 is a variable light chain region amino acid consensus sequence based on murine antibodies 12B4, 12A11, 10D5, and 3D6.

$X_1VX_2MTQTPLX_3LX_4VX_5X_6GX_7X_8ASISCX_9SSQX_{10}X_{11}X_{12}X_{13}S$ $X_{14}GX_{15}TYLX_{16}WX_{17}LQX_{18}PGQSPKX_{19}LIYX_{20}VSX_{21}X_{22}X_{23}SG$ $VPDRFX_{24}GSGSGTDFTLKIX_{25}X_{26}X_{27}EAEDLGX_{28}YYCX_{29}QX_{30}$ $X_{31}HX_{32}PX_{33}TFGX_{34}GTKLEX_{35}X_{36}$, wherein
$X_1$ is D or V,
$X_2$ is L or V,
$X_3$ is S or T,
$X_4$ is S or P,
$X_5$ is S or T,
$X_6$ is L or I,
$X_7$ is Q or D,
$X_8$ is P or Q,
$X_9$ is K or R,
$X_{10}$ is N or S,
$X_{11}$ is I or L,
$X_{12}$ is V, I, or L,
$X_{13}$ is D or H,
$X_{14}$ is D or N,
$X_{15}$ is K or N,
$X_{16}$ is E or N,
$X_{17}$ is L or Y,
$X_{18}$ is K or R,
$X_{19}$ is L or R,
$X_{20}$ is K or L,
$X_{21}$ is N or K,
$X_{22}$ is R or L,
$X_{23}$ is F or D,
$X_{24}$ is S or T,
$X_{25}$ is S or K,
$X_{26}$ is R or K,
$X_{27}$ is V or I,
$X_{28}$ is V, I, or L,
$X_{29}$ is F or W,
$X_{30}$ is G or S,
$X_{31}$ is S or T,
$X_{32}$ is F or V,
$X_{33}$ is R or L,
$X_{34}$ is A or G,
$X_{35}$ is L or I,
$X_{36}$ is E or K SEQ ID NO:7

SEQ ID NO:8 is the amino acid sequence of the variable heavy chain region of the murine 12A11 antibody.

SEQ ID NO: 8
QVTLKESGPGILKPSQTLSLTCSFSGFSLSTSGMSVGWIRQPSGKGLEWL

AHIWWDDDKYYNPSLKSRLTISKDTSRNQVFLKITSVDTADTATYYCARR

TTTADYFAYWGQGTTLTVSS

SEQ ID NO:9 is the amino acid sequence of the variable heavy chain region of the murine 12B4 antibody.

SEQ ID NO: 9
QVTLKESGPGILQPSQTLSLTCSFSGFSLSTNGMGVSWIRQPSGKGLEWL

AHIYWDEDKRYNPSLKSRLTISKDTSNNQVFLKITNVDTADTATYYCARR

RIIYDVEDYFDYWGQGTTLTVSS

SEQ ID NO:10 is the amino acid sequence of the variable heavy chain region of the murine 10D5 antibody.

SEQ ID NO: 10
QATLKESGPGILQSSQTLSLTCSFSGFSLSTSGMGVSWIRQPSGKGLEWL

AHIYWDDDKRYNPSLKSRLTISKDTSRKQVFLKITSVDPADTATYYCVRR

PITPVLVDAMDYWGQGTSVTVSS

SEQ ID NO:11 is the amino acid sequence of the variable heavy chain region of the murine 3D6 antibody.

SEQ ID NO: 11
EVKLVESGGGLVKPGASLKLSCAASGFTFSNYGMSWVRQNSDKRLEWVAS

IRSGGGRTYYSDNVKGRFTISRENAKNTLYLQMSSLKSEDTALYYCVRYD

HYSGSSDYWGQGTTITVSS

SEQ ID NO:12 is a variable heavy chain region amino acid consensus sequence based on murine antibodies 12B4, 12A11, 10D5, and 3D6.

$X_1X_2X_3LX_4ESGX_5GX_6X_7X_8X_9X_{10}X_{11}X_{12}LX_{13}LX_{14}CX_{15}X_{16}SGF$ $X_{17}X_{18}SX_{19}X_{20}GMX_{21}X_{22}X_{23}WX_{24}RQX_{25}SX_{26}KX_{27}LEWX_{28}IX_{29}$ $X_{30}X_{31}X_{32}X_{33}X_{34}X_{35}X_{36}YX_{37}X_{38}X_{39}X_{40}KX_{41}RX_{42}TISX_{43}X_{44}$ $X_{45}X_{46}X_{47}X_{48}X_{49}X_{50}X_{51}LX_{52}X_{53}X_{54}X_{55}X_{56}X_{57}X_{58}X_{59}DTAX_{60}$ $YYCX_{61}RX_{62}X_{63}X_{64}X_{65}X_{66}X_{67}X_{68}X_{69}X_{70}X_{71}X_{72}X_{73}YWGQGT$ $X_{74}X_{75}TVSS,$ wherein:
X1 is Q or E
X2 is A or V
X3 is T or K
X4 is K or V
X5 is P or G
X6 is I or L
X7 is L or V
X8 is K or Q
X9 is P or S
X10 is S or G
X11 is A or Q
X12 is T or S
X13 is S or K
X14 is T or S
X15 is S or A
X16 is F or A
X17 is S or T
X18 is L or F
X19 is T or N
X20 is S or N
X21 is S, G or absent
X22 is V or absent
X23 is S or G
X24 is I or V
X25 is P or N
X26 is G or D
X27 is G or R
X28 is L or V
X29 is H or S
X30 is W, Y or R
X31 is W or S
X32 is D or G
X33 is D, E or G
X34 is D or G
X35 is K or R
X36 is T or absent
X37 is Y or R
X38 is N or S
X39 is P or D
X40 is S or N
X41 is L or V
X42 is S or G
X43 is L or F
X44 is K or R
X45 is D or E
X46 is T or N
X47 is S or A
X48 is R, N or K
X49 is N or K
X50 is Q or T
X51 is V or L
X52 is F or Y
X53 is K or Q
X54 is I or M
X55 is S or T
X56 is S or N
X57 is V or L
X58 is D or K
X59 is T, P or S
X60 is A or E
X61 is T or L
X62 is A or V
X63 is Y or R
X64 is R, P or absent
X65 is I or absent
X66 is T, Y, P or D
X67 is T, D, V or H
X68 is T, V, L or Y
X69 is A, E, V or S
X70 is D or G
X71 is Y, A or S
X72 is F, M or S
X73 is A or D
X74 is T or S
X75 is L or V SEQ ID NO:12

SEQ ID NO:13 is a variable heavy chain region amino acid consensus sequence based on murine antibodies 12A11, 12B4, and 10D5.

$QX_1TLKESGPGILX_2X_3SQTLSLTCSFSGFSLSTX_4GMX_5VX_6WIRQPSG$ $KGLEWLAHIX_7WDX_8DKX_9YNPSLKSRLTISKDTSX_{10}X_{11}QVFLKITX_{12}$ $VDX_{13}ADTATYYCX_{14}RRX_{15}X_{16}X_{17}X_{18}X_{19}X_{20}X_{22}DX_{22}X_{23}X_{24}YWGQGT$ $X_{25}X_{26}TVSS,$ wherein
X1 is V or A
X2 is K or Q
X3 is P or S
X4 is S or N
X5 is S or G
X6 is S or G
X7 is Y or W
X8 is D or E
X9 is Y or R
X10 is R or N
X11 is N or K
X12 is S or N
X13 is T or P
X14 is A or V
X15 is R, P, or absent
X16 is I or absent
X17 is I, T, or absent
X18 is T, Y, or P
X19 is T, D, or V
X20 is T, V, or L
X21 is A, E, or V
X22 is Y or A
X23 is F or M
X24 is A or D
X25 is T or S
X26 is L or V SEQ ID NO:14 is a variable light chain region CDR1 amino acid consensus sequence based on murine antibodies 12B4, 12A11, 10D5, and 3D6.

$X_1$-S-S-Q-$X_2$-$X_3$-$X_4$-$X_5$-S-$X_6$-G-$X_7$-T-Y-L-$X_8$, wherein

X1 is R or K,
X2 is N or S,
X3 is I or L,
X4 is V, I, or L,
X5 is H or D,
X6 is N or D,
X7 is N or K,
X8 is E or N SEQ ID NO:14

SEQ ID NO:15 is a variable light chain region CDR2 amino acid consensus sequence based on murine antibodies 12B4, 12A11, 10D5, and 3D6.

$X_1$-V-S-$X_2$-$X_3$-$X_4$-S, wherein

X1 is K or L,
X2 is N or K,
X3 is R or L,
X4 is F or D SEQ ID NO:15

SEQ ID NO:16 is a variable light chain region CDR3 amino acid consensus sequence based on murine antibodies 12B4, 12A11, 10D5, and 3D6.

$X_1$-Q-$X_2$-$X_3$-H-$X_4$-P-$X_5$, wherein

X1 is F or W,
X2 is G or S,
X3 is S or T,
X4 is V or F,
X5 is L or R SEQ ID NO:16

SEQ ID NO:17 is a variable heavy chain region CDR1 amino acid consensus sequence based on murine antibodies 12B4, 12A11, 10D5, and 3D6.

$X_1$-$X_2$-G-M-$X_3$-$X_4$-$X_5$, wherein

X1 is T or N,
X2 is S, N, or Y,
X3 is S, G, or absent,
X4 is V or absent,
X5 is G or S SEQ ID NO:17

SEQ ID NO:18 is a variable heavy chain region CDR2 amino acid consensus sequence based on murine antibodies 12B4, 12A11, 10D5, and 3D6.

$X_1$-I-$X_2$-$X_3$-$X_4$-$X_5$-$X_6$-$X_7$-$X_8$-$X_9$-Y-$X_{10}$-$X_{11}$-$X_{12}$-$X_{13}$-K-$X_{14}$, wherein X1 is H or S,
X2 is W, Y, or R,
X3 is W or S,
X4 is D or G,
X5 is D, E, or G,
X6 is D or G,
X7 is K or R,
X8 is T or absent,
X9 is Y or R,
X10 is N or 5,
X11 is P or D,
X12 is S or N,
X13 is L or V,
X14 is S or G SEQ ID NO:18

SEQ ID NO:19 is a variable heavy chain region CDR3 amino acid consensus sequence based on murine antibodies 12B4, 12A11, 10D5, and 3D6.

$X_1$-$X_2$-$X_3$-$X_4$-$X_5$-$X_6$-$X_7$-$X_8$-$X_9$-$X_{10}$-$X_{11}$-$X_{12}$-Y, wherein X1 is R or Y,
X2 is R, P, or absent,
X3 is I or absent,
X4 is I, T, or absent,
X5 is T, Y, P, or D,
X6 is T, D, V, or H,
X7 is T, V, L, or Y,
X8 is A, E, V, or S,
X9 is D or G,
X10 is Y, A, or S,
X11 is F, M, or S,
X12 is A or D SEQ ID NO:19

SEQ ID NO:20 is the amino acid sequence of variable heavy chain region CDR3 sequence of murine 12A11.

RTTTADYFAY SEQ ID NO:20

SEQ ID NO:21 is the amino acid sequence of the variable heavy chain region CDR3 sequence of murine 3D6.

YDHYSGSSDY SEQ ID NO:21

SEQ ID NO:22 is a variable light chain region amino acid consensus sequence based on murine antibodies 12A11, 12B4, and 10D5.

DVLMTQTPLSLPVSLGDQASISCRSSQX$_1$IX$_2$HSNGNTYLEWYLQKPGQS

PKLLIYKVSNRFSGVPDRFSGSGSGTDFTLKIX$_3$X$_4$VEAEDLGX$_5$YYCFQ

X$_6$SHVPLTFGAGTKLELX$_7$, wherein
  $X_1$ is N or S
  $X_2$ is I or V
  $X_3$ is S or K
  $X_4$ is R or K
  $X_5$ is I or V
  $X_6$ is G or S
  $X_7$ is E or K SEQ ID NO:23 is a variable light chain region CDR1 amino acid consensus sequence based on murine antibodies 12B4, 12A11, and 10D5.

RSSQX$_1$IX$_2$HSNGNTYLE, wherein $X_1$ is N or S
  $X_2$ is I or V

SEQ ID NO:24 is a variable light chain region CDR2 amino acid consensus sequence based on murine antibodies 12B4, 12A11, and 10D5.

KVSNRFS

SEQ ID NO:25 is a variable light chain region CDR3 amino acid consensus sequence based on murine antibodies 12B4, 12A11, and 10D5.

FQX$_1$SHVPL, wherein $X_1$ is G or S

SEQ ID NO:26 is a variable heavy chain region CDR1 amino acid consensus sequence based on murine antibodies 12B4, 12A11, and 10D5.

TX$_1$GMX$_2$VX$_3$, wherein $X_1$ is N or S
  $X_2$ is S or G
  $X_3$ is G or S SEQ ID NO:27 is a variable heavy chain region CDR2 amino acid consensus sequence based on murine antibodies 12B4, 12A11, and 10D5.

HIX$_1$WDX$_2$DKX$_3$YNPSLKS, wherein

X₁ is W or Y
X₂ is D or E
X₃ is R or Y

SEQ ID NO:28 is a variable heavy chain region CDR3 amino acid consensus sequence based on murine antibodies 12B4, 12A11, and 10D5.

RX₁X₂X₃X₄X₅X₆X₇DX₈X₉X₁₀Y, wherein

X₁ is R, P, or absent
X₂ is I or absent
X₃ is I, T, or absent
X₄ is T, Y, or P
X₅ is T, D, or V
X₆ is T, V, or L
X₇ is A, E, or V
X₈ is Y or A
X₉ is F or M
X₁₀ is A or D SEQ ID NO:29 is the amino acid sequence of the variable light chain region CDR1 sequence of murine PFA1.

QSIVHSNGNTY SEQ ID NO:29

SEQ ID NO:30 is the amino acid sequence of the variable light chain region CDR2 sequence of murine PFA1.

KVS SEQ ID NO:30

SEQ ID NO:31 is the amino acid sequence of the variable light chain region CDR3 sequence of murine PFA1.

FQGSHVPLTF SEQ ID NO:31

SEQ ID NO:32 is the amino acid sequence of the variable light chain region CDR1 sequence of murine PFA2.

QSIVHSNGNTY SEQ ID NO:32

SEQ ID NO:33 is the amino acid sequence of the variable light chain region CDR2 sequence of murine PFA2.

KVS SEQ ID NO:33

SEQ ID NO:34 is the amino acid sequence of the variable light chain region CDR3 sequence of murine PFA2.

FQGSHVPLTF SEQ ID NO:34

SEQ ID NO:35 is the amino acid sequence of the variable heavy chain region CDR1 sequence of murine PFA1.

TSGMG SEQ ID NO:35

SEQ ID NO:36 is the amino acid sequence of the variable heavy chain region CDR2 sequence of murine PFA1.

IWWDDDR SEQ ID NO:36

SEQ ID NO:37 is the amino acid sequence of the variable heavy chain region CDR3 sequence of murine PFA1.

RAHTTVLGDWFAY SEQ ID NO:37

SEQ ID NO:38 is the amino acid sequence of the variable heavy chain region CDR1 sequence of murine PFA2.

TSGMG SEQ ID NO:38

SEQ ID NO:39 is the amino acid sequence of the variable heavy chain region CDR2 sequence of murine PFA2.

IWWDDDK SEQ ID NO:39

SEQ ID NO:40 is the amino acid sequence of the variable heavy chain region CDR3 sequence of murine PFA2.

RAHNVVLGDWFAY SEQ ID NO:40

SEQ ID NO: 41 is the Aβ 1-7 peptide.

DAEFRHD

SEQ ID NO: 42 is the amino acid sequence for murine 12B4 VL.

DVLMTQTPLSLPVSLGDQASISCRSSQNIVHSNGNTYLEWYLQKPGQSPK
LLIYKVSNRFSGVPDRFSGSGSGTDFTLKISRVEAEDLGVYYCFQGSHVP
LTFGAGTKLELK

SEQ ID NO: 43 is the amino acid sequence for h12B4 VL.

DVVMTQSPLSLPVTPGEPASISCRSSQNIVHSNGNTYLEWYLQKPGQSPQ
LLIYKVSNRFSGVPDRFSGSGSGTDFTLKISRVEAEDVGVYYCFQGSHVP
LTFGQGTKLEIK

SEQ ID NO: 44 is the amino acid sequence for KABID 005036.

DIVMTQSPLSLPVTPGEPASISCRSSQSLLHRYGYNYLDWYLQKPGQSPQ
LLIYLGSNRASGVPDRFSGSGSGTDFTLKISRVEAEDVGVYYCMQALQTP
YTFGQGTKLEIK

SEQ ID NO: 45 is the amino acid sequence for A19-Germline.

DIVMTQSPLSLPVTPGEPASISCRSSQSLLHSNGYNYLDWYLQKPGQSPQ
LLIYLGSNRASGVPDRFSGSGSGTDFTLKISRVEAEDVGVYYCMQALQTP

SEQ ID NO: 46 is the amino acid sequence for murine 12B4 VH.

QVTLKESGPGILQPSQTLSLTCSFSGFSLSTNGMGVSWIRQPSGKGLEWL
AHIYWDEDKRYNPSLKSRLTISKDTSNNQVFLKITNVDTADTATYYCARR
RIIYDVEDYFDYWGQGTTLTVSS

SEQ ID NO: 47 is the amino acid sequence for h12B4 VHv1.

QVQLQESGPGLVKPSETLSLTCTFSGFSLSTNGMGVSWIRQPPGKGLEWL
AHIYWDEDKRYNPSLKSRLTISKDTSKNQVSLKLSSVTAADTAVYYCARR
RIIYDVEDYFDYWGQGTTVTVSS

SEQ ID NO: 48 is the amino acid sequence for KABID 000333.

QLQLQESGPGLVKPSETLSLTCTVSGGSISRGSHYWGWIRQPPGKGLEWI
GSIYYSGNTYFNPSLKSRVTISVDTSKNQFSLKLSSVTAADTAVYYCARL
GPDDYTLDGMDVWGQGTTVTVSS

SEQ ID NO: 49 is the amino acid sequence for VH4-39 Germline.

QLQLQESGPGLVKPSETLSLTCTVSGGSISSSSYYWGWIRQPPGKGLEWI
GSIYYSGSTYYNPSLKSRVTISVDTSKNQFSLKLSSVTAADTAVYYCAR

SEQ ID NO: 50 is the amino acid sequence for murine 3D6 VL.

YVVMTQTPLTLSVTIGQPASISCKSSQSLLDSDGKTYLNWLLQRPGQSPK
RLIYLVSKLDSGVPDRFTGSGSGTDFTLKISRIEAEDLGLYYCWQGTHFP
RTFGGGTKLEIK

SEQ ID NO: 51 is the amino acid sequence for h3D6VL.

YVVMTQSPLSLPVTPGEPASISCKSSQSLLDSDGKTYLNWLLQKPGQSPQ
RLIYLVSKLDSGVPDRFSGSGSGTDFTLKISRVEAEDVGVYYCWQGTHFP
RTFGQGTKVEIK

SEQ ID NO: 52 is the amino acid sequence for KABID 019230.

DIVMTQSPLSLPVTPGEPASISCRSSQSLLHSNGYNYLDWYLQKPGQSPQ
LLIYLGSNRASGVPDRFSGSGSGTDFTLKISRVEAEDVGVYYCMQALQTP
RTFGQGTKVEIK

SEQ ID NO: 53 is the amino acid sequence for A19-Germline.

DIVMTQSPLSLPVTPGEPASISCRSSQSLLHSNGYNYLDWYLQKPGQSPQ
LLIYLGSNRASGVPDRFSGSGSGTDFTLKISRVEAEDVGVYYCMQALQTP

SEQ ID NO: 54 is the amino acid sequence for murine 3D6 VH.

EVKLVESGGGLVKPGASLKLSCAASGFTFSNYGMSWVRQNSDKRLEWVAS
IRSGGGRTYYSDNVKGRFTISRENAKNTLYLQMSSLKSEDTALYYCVRYD
HYSGSSDYWGQGTTVTVSS

SEQ ID NO: 55 is the amino acid sequence for h3D6 VH.

EVQLLESGGGLVQPGGSLRLSCAASGFTFSNYGMSWVRQAPGKGLEWVAS
IRSGGGRTYYSDNVKGRFTISRDNAKNSLYLQMNSLRAEDTALYYCVRYD
HYSGSSDYWGQGTLVTVSS

SEQ ID NO: 56 is the amino acid sequence for KABID 045919.

EVQLLESGGGLVQPGGSLRLSCAASGFTFSSYAVSWVRQAPGKGLEWVSA
ISGSGGSTYYADSVKGRFTISRDNAKNSLYLQMNSLRAEDTALYYCAKDN
YDFWSGTFDYWGQGTLVTVSS

SEQ ID NO: 57 is the amino acid sequence for VH3-23 Germline.

EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAK

SEQ ID NO: 58 is the amino acid sequence for murine 12A11 VL.

DVLMTQTPLSLPVSLGDQASISCRSSQSIVHSNGNTYLEWYLQKPGQSPK
LLIYKVSNRFSGVPDRFSGSGSGTDFTLKISRVEAEDLGIYYCFQSSHVP
LTFGAGTKLELK

SEQ ID NO: 59 is the amino acid sequence for h12A11 VL.

DVVMTQSPLSLPVTPGEPASISCRSSQSIVHSNGNTYLEWYLQKPGQSPQ
LLIYKVSNRFSGVPDRFSGSGSGTDFTLKISRVEAEDVGVYYCFQSSHVP
LTFGQGTKLEIK

SEQ ID NO: 60 is the amino acid sequence for BAC 01733.

DVVMTQSPLSLPVTPGEPASISCRSSQSLLHSNGYNYLDWYLQKPGQSPQ
LLIYLGSNRASGVPDRFSGSGSGTDFTLKISRVEAEDVGVYYCMQALQTP
YTFGQGTKLEIK

SEQ ID NO: 61 is the amino acid sequence for A19-Germline.

DIVMTQSPLSLPVTPGEPASISCRSSQSLLHSNGYNYLDWYLQKPGQSPQ
LLIYLGSNRASGVPDRFSGSGSGTDFTLKISRVEAEDVGVYYCMQALQTP

SEQ ID NO: 62 is the amino acid sequence for murine 12A11 VH.

QVTLKESGPGILKPSQTLSLTCSFSGFSLSTSGMSVGWIRQPSGKGLEWL
AHIWWDDDKYYNPSLKSRLTISKDTSRNQVFLKITSVDTADTATYYCARR
TTTADYFAYWGQGTTLTVSS

SEQ ID NO: 63 is the amino acid sequence for h12A11 VHv1.

QVQLVESGGGVVQPGRSLRLSCAFSGFSLSTSGMSVGWIRQAPGKGLEWL
AHIWWDDDKYYNPSLKSRLTISKDTSKNTVYLQMNSLRAEDTAVYYCARR
TTTADYFAYWGQGTTVTVSS

SEQ ID NO: 64 is the amino acid sequence for AAA 69734.

QVQLVESGGGVVQPGRSLRLSCAASGFTFSSYAMHWVRQAPGKGLEWVAV
ISYDGSNKYYADSVKGRFTISRDNSKNTLYLQMNSLRAEDTAVYYCARDR
HSSSWYYGMDVWGQGTTVTVSS

SEQ ID NO: 65 is the amino acid sequence for 567123 Germline.

QVQLVESGGGVVQPGRSLRLSCAASGFTFSSYAMHWVRQAPGKGLEWVAV
ISYDGSNKYYADSVKGRFTISRDNSKNTLYLQMNSLRAEDTAVYYCARDA
KLLMLLISGAKGQWSPSL

SEQ ID NO: 66 is the amino acid sequence of the variable light chain region CDR1 sequence of murine 12A11.

RSSQSIVHSNGNTYLE

SEQ ID NO: 67 is a variable light chain region CDR3 amino acid consensus sequence based on murine antibodies 12B4, 12A11, and 10D5.

FQGSHVPLT

SEQ ID NO: 68 is the amino acid sequence of the variable light chain region CDR1 sequence of murine 12B4.

RSSQNIVHSNGNTYLE

SEQ ID NO: 69 is the amino acid sequence of the variable light chain region CDR1 sequence of murine 10D5.

RSSQNIIHSNGNTYLE

SEQ ID NO: 70 is the amino acid sequence of the variable heavy chain region CDR1 sequence of murine 12A11.

TSGMSVG

SEQ ID NO: 71 is the amino acid sequence of the variable heavy chain region CDR2 sequence of murine 12A11.

HIWWDDDKYYNPSLKS

SEQ ID NO: 72 is the amino acid sequence of the variable heavy chain region CDR1 sequence of murine 12B4.

TNGMGVS

SEQ ID NO: 73 is the amino acid sequence of the variable heavy chain region CDR2 sequence of murine 12B4.

HIYWDEDKRYNPSLKS

SEQ ID NO: 74 is the amino acid sequence of the variable heavy chain region CDR3 sequence of murine 12B4.

RRIIYDVEDYFDY

SEQ ID NO: 75 is the amino acid sequence of the variable heavy chain region CDR1 sequence of murine 10D5.

TSGMGVS

SEQ ID NO: 76 is the amino acid sequence of the variable heavy chain region CDR2 sequence of murine 10D5.

HIYWDDDKRYNPSLKL

SEQ ID NO: 77 is the amino acid sequence of the variable heavy chain region CDR3 sequence of murine 10D5.

RPITPVLVDAMDY

SEQ ID NO: 78 is a partial amino acid sequence of the variable heavy chain region CDR3 sequence of murine 10D5.

RPITPVLVD

SEQ ID NO: 79 is a partial amino acid sequence of the variable heavy chain region CDR3 sequence of murine 12B4.

RRIIYDVED

SEQ ID NO: 80 is a partial amino acid sequence of the variable heavy chain region CDR3 sequence of murine 12A11.

RTTTAD

SEQ ID NO: 81 is the amino acid sequence for VH4-61 Germline.

QVQLQESGPGLVKPSETLSLTCTVSGGSVSSGGYYWSWIRQPPGKGLEWIG
YIYYSGSTNYNPSLKSRVTISVDTSKNQFSLKLSSVTAADTAVYYCAR

TABLE A

Key to Kabat Numbering for the 12B4 Light Chain Variable Region

| KABAT # | Sequential # | TYPE | murine 12B4 VL (SEQ ID NO: 42) | h12B4 VL (SEQ ID NO: 43) | KABID 005036 (SEQ ID NO: 44) | A19-Germline (SEQ ID NO: 45) | Comment |
|---|---|---|---|---|---|---|---|
| 1 | 1 | FR1 | D | D | D | D | |
| 2 | 2 | | V | V | I | I | canonical - backmutate in v1, v2 and v3 |
| 3 | 3 | | L | V | V | V | |
| 4 | 4 | | M | M | M | M | |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | S | S | S | S | |
| 11 | 11 | | L | L | L | L | |
| 12 | 12 | | P | P | P | P | |
| 13 | 13 | | V | V | V | V | |
| 14 | 14 | | S | T | T | T | |
| 15 | 15 | | L | P | P | P | |
| 16 | 16 | | G | G | G | G | |
| 17 | 17 | | D | E | E | E | |
| 18 | 18 | | Q | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | R | R | R | R | |
| 25 | 25 | | S | S | S | S | |
| 26 | 26 | | S | S | S | S | |
| 27 | 27 | | Q | Q | Q | Q | |
| 27A | 28 | | N | N | S | S | |
| 27B | 29 | | I | I | L | L | |
| 27C | 30 | | V | V | L | L | |

TABLE A-continued

Key to Kabat Numbering for the 12B4 Light Chain Variable Region

| KABAT # | Sequential # | TYPE | murine 12B4 VL (SEQ ID NO: 42) | h12B4 VL (SEQ ID NO: 43) | KABID 005036 (SEQ ID NO: 44) | A19-Germline (SEQ ID NO: 45) | Comment |
|---|---|---|---|---|---|---|---|
| 27D | 31 |  | H | H | H | H |  |
| 27E | 32 |  | S | S | R | S |  |
| 28 | 33 |  | N | N | Y | N |  |
| 29 | 34 |  | G | G | G | G |  |
| 30 | 35 |  | N | N | Y | Y |  |
| 31 | 36 |  | T | T | N | N |  |
| 32 | 37 |  | Y | Y | Y | Y |  |
| 33 | 38 |  | L | L | L | L |  |
| 34 | 39 |  | E | E | D | D |  |
| 35 | 40 | FR2 | W | W | W | W |  |
| 36 | 41 |  | Y | Y | Y | Y |  |
| 37 | 42 |  | L | L | L | L |  |
| 38 | 43 |  | Q | Q | Q | Q |  |
| 39 | 44 |  | K | K | K | K |  |
| 40 | 45 |  | P | P | P | P |  |
| 41 | 46 |  | G | G | G | G |  |
| 42 | 47 |  | Q | Q | Q | Q |  |
| 43 | 48 |  | S | S | S | S |  |
| 44 | 49 |  | P | P | P | P |  |
| 45 | 50 |  | K | Q | Q | Q |  |
| 46 | 51 |  | L | L | L | L |  |
| 47 | 52 |  | L | L | L | L |  |
| 48 | 53 |  | I | I | I | I |  |
| 49 | 54 |  | Y | Y | Y | Y |  |
| 50 | 55 | CDR2 | K | K | L | L |  |
| 51 | 56 |  | V | V | G | G |  |
| 52 | 57 |  | S | S | S | S |  |
| 53 | 58 |  | N | N | N | N |  |
| 54 | 59 |  | R | R | R | R |  |
| 55 | 60 |  | F | F | A | A |  |
| 56 | 61 |  | S | S | S | S |  |
| 57 | 62 | FR3 | G | G | G | G |  |
| 58 | 63 |  | V | V | V | V |  |
| 59 | 64 |  | P | P | P | P |  |
| 60 | 65 |  | D | D | D | D |  |
| 61 | 66 |  | R | R | R | R |  |
| 62 | 67 |  | F | F | F | F |  |
| 63 | 68 |  | S | S | S | S |  |
| 64 | 69 |  | G | G | G | G |  |
| 65 | 70 |  | S | S | S | S |  |
| 66 | 71 |  | G | G | G | G |  |
| 67 | 72 |  | S | S | S | S |  |
| 68 | 73 |  | G | G | G | G |  |
| 69 | 74 |  | T | T | T | T |  |
| 70 | 75 |  | D | D | D | D |  |
| 71 | 76 |  | F | F | F | F |  |
| 72 | 77 |  | T | T | T | T |  |
| 73 | 78 |  | L | L | L | L |  |
| 74 | 79 |  | K | K | K | K |  |
| 75 | 80 |  | I | I | I | I |  |
| 76 | 81 |  | S | S | S | S |  |
| 77 | 82 |  | R | R | R | R |  |
| 78 | 83 |  | V | V | V | V |  |
| 79 | 84 |  | E | E | E | E |  |
| 80 | 85 |  | A | A | A | A |  |
| 81 | 86 |  | E | E | E | E |  |
| 82 | 87 |  | D | D | D | D |  |
| 83 | 88 |  | L | V | V | V |  |
| 84 | 89 |  | G | G | G | G |  |
| 85 | 90 |  | V | V | V | V |  |
| 86 | 91 |  | Y | Y | Y | Y |  |
| 87 | 92 |  | Y | Y | Y | Y |  |
| 88 | 93 |  | C | C | C | C |  |
| 89 | 94 | CDR3 | F | F | M | M |  |
| 90 | 95 |  | Q | Q | Q | Q |  |
| 91 | 96 |  | G | G | A | A |  |
| 92 | 97 |  | S | S | L | L |  |
| 93 | 98 |  | H | H | Q | Q |  |
| 94 | 99 |  | V | V | T | T |  |
| 95 | 100 |  | P | P | P | P |  |
| 96 | 101 |  | L | L | Y |  |  |

TABLE A-continued

Key to Kabat Numbering for the 12B4 Light Chain Variable Region

| KABAT # | Sequential # | TYPE | murine 12B4 VL (SEQ ID NO: 42) | h12B4 VL (SEQ ID NO: 43) | KABID 005036 (SEQ ID NO: 44) | A19-Germline (SEQ ID NO: 45) | Comment |
|---|---|---|---|---|---|---|---|
| 97 | 102 |  | T | T | T |  |  |
| 98 | 103 | FR4 | F | F | F |  |  |
| 99 | 104 |  | G | G | G |  |  |
| 100 | 105 |  | A | Q | Q |  |  |
| 101 | 106 |  | G | G | G |  |  |
| 102 | 107 |  | T | T | T |  |  |
| 103 | 108 |  | K | K | K |  |  |
| 104 | 109 |  | L | L | L |  |  |
| 105 | 110 |  | E | E | E |  |  |
| 106 | 111 |  | L | I | I |  |  |
| 106A | 112 |  | K | K | K |  |  |

TABLE B

Key to Kabat Numbering for the 12B4 Heavy Chain Variable Region

| KABAT # | Sequential # | TYPE | Murine 12B4 VH (SEQ ID NO: 46) | h12B4 VHv1 (SEQ ID NO: 47) | KABID 000333 (SEQ ID NO: 48) | VH4-39 Germline (SEQ ID NO: 49) | VH4-61 Germline (SEQ ID NO: 81) | Comment |
|---|---|---|---|---|---|---|---|---|
| 1 | 1 | FR1 | Q | Q | Q | Q | Q |  |
| 2 | 2 |  | V | V | L | L | V | vernier-backmutate in v1 only |
| 3 | 3 |  | T | Q | Q | Q | Q |  |
| 4 | 4 |  | L | L | L | L | L |  |
| 5 | 5 |  | K | Q | Q | Q | Q. |  |
| 6 | 6 |  | E | E | E | E | E |  |
| 7 | 7 |  | S | S | S | S | S |  |
| 8 | 8 |  | G | G | G | G | G |  |
| 9 | 9 |  | P | P | P | P | P |  |
| 10 | 10 |  | G | G | G | G | G |  |
| 11 | 11 |  | I | L | L | L | L |  |
| 12 | 12 |  | P | P | P | P | P |  |
| 15 | 15 |  | S | S | S | S | S |  |
| 16 | 16 |  | Q | E | E | E | E |  |
| 17 | 17 |  | T | T | T | T | T |  |
| 18 | 18 |  | L | L | L | L | L |  |
| 19 | 19 |  | S | S | S | S | S |  |
| 20 | 20 |  | L | L | L | L | L |  |
| 21 | 21 |  | T | T | T | T | T |  |
| 22 | 22 |  | C | C | C | C | C |  |
| 23 | 23 |  | S | T | T | T | T |  |
| 24 | 24 |  | F | F | V | V | V | canonical - backmutate in v1, v2 and v3 |
| 25 | 25 |  | S | S | S | S | S |  |
| 26 | 26 |  | G | G | G | G | G |  |
| 27 | 27 |  | F | F | G | G | G | canonical - backmutate in v1, v2 and v3 |
| 28 | 28 |  | S | S | S | S | S |  |
| 29 | 29 |  | L | L | I | I | V | canonical - backmutate in v1, v2 and v3 |
| 30 | 30 |  | S | S | S | S | S |  |
| 31 | 31 | CDR1 | T | T | R | S | S |  |
| 32 | 32 |  | N | N | G | S | G |  |
| 33 | 33 |  | G | G | S | S | G |  |
| 34 | 34 |  | M | M | H | Y | Y |  |
| 35 | 35 |  | G | G | Y | Y | Y |  |
| 35A | 36 |  | V | V | W | W | W |  |
| 35B | 37 |  | S | S | G | W | S |  |
| 36 | 38 | FR2 | W | W | W | W | W |  |
| 37 | 39 |  | I | I | I | I | I |  |
| 38 | 40 |  | R | R | R | R | R |  |
| 39 | 41 |  | Q | Q | Q | Q | Q |  |
| 40 | 42 |  | P | P | P | P | P |  |

TABLE B-continued

Key to Kabat Numbering for the 12B4 Heavy Chain Variable Region

| KABAT # | Sequential # | TYPE | Murine 12B4 VH (SEQ ID NO: 46) | h12B4 VHv1 (SEQ ID NO: 47) | KABID 000333 (SEQ ID NO: 48) | VH4-39 Germline (SEQ ID NO: 49) | VH4-61 Germline (SEQ ID NO: 81) | Comment |
|---|---|---|---|---|---|---|---|---|
| 41 | 43 | | S | P | P | P | P | |
| 42 | 44 | | G | G | G | G | G | |
| 43 | 45 | | K | K | K | K | K | |
| 44 | 46 | | G | G | G | G | G | |
| 45 | 47 | | L | L | L | L | L | |
| 46 | 48 | | E | E | E | E | E | |
| 47 | 49 | | W | W | W | W | W | |
| 48 | 50 | | L | L | I | I | I | vernier - backmutate in v1 and v3 only |
| 49 | 51 | | A | A | G | G | G | vernier - backmutate in v1 only |
| 50 | 52 | CDR2 | H | H | S | S | Y | |
| 51 | 53 | | I | I | I | I | I | |
| 52 | 54 | | Y | Y | Y | Y | Y | |
| 53 | 55 | | W | W | Y | Y | Y | |
| 54 | 56 | | D | D | S | S | S | |
| 55 | 57 | | E | E | G | G | G | |
| 56 | 58 | | D | D | N | S | S | |
| 57 | 59 | | K | K | T | T | T | |
| 58 | 60 | | R | R | Y | Y | N | |
| 59 | 61 | | Y | Y | F | Y | Y | |
| 60 | 62 | | N | N | N | N | N | |
| 61 | 63 | | P | P | P | P | P | |
| 62 | 64 | | S | S | S | S | S | |
| 63 | 65 | | L | L | L | L | L | |
| 64 | 66 | | K | K | K | K | K | |
| 65 | 67 | | S | S | S | S | S | |
| 66 | 68 | FR3 | R | R | R | R | R | |
| 67 | 69 | | L | L | V | V | V | vernier - backmutate in v1 only |
| 68 | 70 | | T | T | T | T | T | |
| 69 | 71 | | I | I | I | I | I | |
| 70 | 72 | | S | S | S | S | S | |
| 71 | 73 | | K | K | V | V | V | canonical - backmutate in v1, v2 and v3 |
| 72 | 74 | | D | D | D | D | D | |
| 73 | 75 | | T | T | T | T | T | |
| 74 | 76 | | S | S | S | S | S | |
| 75 | 77 | | N | K | K | K | K | |
| 76 | 78 | | N | N | N | N | N | |
| 77 | 79 | | Q | Q | Q | Q | Q | |
| 78 | 80 | | V | V | F | F | F | vernier - backmutate in v1 and v3 |
| 79 | 81 | | F | S | S | S | S | |
| 80 | 82 | | L | L | L | L | L | |
| 81 | 83 | | K | K | K | K | K | |
| 82 | 84 | | I | L | L | L | L | |
| 82A | 85 | | T | S | S | S | S | |
| 82B | 86 | | N | S | S | S | S | |
| 82C | 87 | | V | V | V | V | V | |
| 83 | 88 | | D | T | T | T | T | |
| 84 | 89 | | T | A | A | A | A | |
| 85 | 90 | | A | A | A | A | A | |
| 86 | 91 | | D | D | D | D | D | |
| 87 | 92 | | T | T | T | T | T | |
| 88 | 93 | | A | A | A | A | A | |
| 89 | 94 | | T | V | V | V | V | |
| 90 | 95 | | Y | Y | Y | Y | Y | |
| 91 | 96 | | Y | Y | Y | Y | Y | |
| 92 | 96 | | C | C | C | C | C | |
| 93 | 97 | | A | A | A | A | A | |
| 94 | 98 | | R | R | R | R | R | |
| 95 | 99 | CDR3 | R | R | L | | | |
| 95A | 100 | | — | — | G | | | |
| 96 | 101 | | R | R | P | | | |
| 97 | 102 | | I | 1 | D | | | |
| 98 | 103 | | I | I | D | | | |
| 99 | 104 | | Y | Y | Y | | | |

TABLE B-continued

Key to Kabat Numbering for the 12B4 Heavy Chain Variable Region

| KABAT # | Sequential # | TYPE | Murine 12B4 VH (SEQ ID NO: 46) | h12B4 VHv1 (SEQ ID NO: 47) | KABID 000333 (SEQ ID NO: 48) | VH4-39 Germline (SEQ ID NO: 49) | VH4-61 Germline (SEQ ID NO: 81) | Comment |
|---|---|---|---|---|---|---|---|---|
| 100 | 105 | | D | D | T | | | |
| 100A | 106 | | V | V | L | | | |
| 100B | 107 | | E | E | D | | | |
| 100C | 108 | | D | D | G | | | |
| 100D | 109 | | Y | Y | — | | | |
| 100E | 110 | | F | F | M | | | |
| 101 | 111 | | D | D | D | | | |
| 102 | 112 | | Y | Y | V | | | |
| 103 | 113 | FR4 | W | W | W | | | |
| 104 | 114 | | G | G | G | | | |
| 105 | 115 | | Q | Q | Q | | | |
| 106 | 116 | | G | G | G | | | |
| 107 | 117 | | T | T | T | | | |
| 108 | 118 | | T | T | T | | | |
| 109 | 119 | | L | V | V | | | |
| 110 | 120 | | T | T | T | | | |
| 111 | 121 | | V | V | V | | | |
| 112 | 122 | | S | S | S | | | |
| 113 | 123 | | S | S | S | | | |

TABLE C

Key to Kabat Numbering for the 3D6 Light Chain Variable Region

| KABAT # | Sequential # | TYPE | murine 3D6 VL SEQ ID NO: 50) | h3D6VL SEQ ID NO: 51) | KABID 019230 SEQ ID NO: 52) | A19- Germline SEQ ID NO: 53) | Comment |
|---|---|---|---|---|---|---|---|
| 1 | 1 | FR1 | Y | Y | D | D | Rare mouse, may contact CDR |
| 2 | 2 | | V | V | I | I | Canonical/CDR contact |
| 3 | 3 | | V | V | V | V | |
| 4 | 4 | | M | M | M | M | |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | T | S | S | S | |
| 11 | 11 | | L | L | L | L | |
| 12 | 12 | | S | P | P | P | |
| 13 | 13 | | V | V | V | V | |
| 14 | 14 | | T | T | T | T | |
| 15 | 15 | | 1 | P | P | P | |
| 16 | 16 | | G | G | G | G | |
| 17 | 17 | | Q | E | E | E | |
| 18 | 18 | | P | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | K | K | R | R | |
| 25 | 25 | | S | S | S | S | |
| 26 | 26 | | S | S | S | S | |
| 27 | 27 | | Q | Q | Q | Q | |
| 27A | 28 | | S | S | S | S | |
| 27B | 29 | | L | L | L | L | |
| 27C | 30 | | L | L | L | L | |
| 27D | 31 | | D | D | H | H | |
| 27E | 32 | | S | S | N | N | |
| 28 | 33 | | D | D | D | N | |
| 29 | 34 | | G | G | G | G | |
| 30 | 35 | | K | K | Y | Y | |
| 31 | 36 | | T | T | N | N | |
| 32 | 37 | | Y | Y | Y | Y | |

TABLE C-continued

Key to Kabat Numbering for the 3D6 Light Chain Variable Region

| KABAT # | Sequential # | TYPE | murine 3D6 VL SEQ ID NO: 50) | h3D6VL SEQ ID NO: 51) | KABID 019230 SEQ ID NO: 52) | A19-Germline SEQ ID NO: 53) | Comment |
|---|---|---|---|---|---|---|---|
| 33 | 38 |  | L | L | L | L |  |
| 34 | 39 |  | N | N | D | D |  |
| 35 | 40 | FR2 | W | W | W | W |  |
| 36 | 41 |  | L | L | Y | Y | Packing residue |
| 37 | 42 |  | L | L | L | L |  |
| 38 | 43 |  | Q | Q | Q | Q |  |
| 39 | 44 |  | R | K | K | K |  |
| 40 | 45 |  | P | P | P | P |  |
| 41 | 46 |  | G | G | G | G |  |
| 42 | 47 |  | Q | Q | Q | Q |  |
| 43 | 48 |  | S | S | S | S |  |
| 44 | 49 |  | P | P | P | P |  |
| 45 | 50 |  | K | Q | Q | Q |  |
| 46 | 51 |  | R | R | L | L | Packing residue |
| 47 | 52 |  | L | L | L | L |  |
| 48 | 53 |  | I | I | I | I |  |
| 49 | 54 |  | Y | Y | Y | Y |  |
| 50 | 55 | CDR2 | L | L | L | L |  |
| 51 | 56 |  | V | V | G | G |  |
| 52 | 57 |  | S | S | S | S |  |
| 53 | 58 |  | K | K | N | N |  |
| 54 | 59 |  | L | L | R | R |  |
| 55 | 60 |  | D | D | A | A |  |
| 56 | 61 |  | S | S | S | S |  |
| 57 | 62 | FR3 | G | G | G | G |  |
| 58 | 63 |  | V | V | V | V |  |
| 59 | 64 |  | P | P | P | P |  |
| 60 | 65 |  | D | D | D | D |  |
| 61 | 66 |  | R | R | R | R |  |
| 62 | 67 |  | F | F | F | F |  |
| 63 | 68 |  | T | S | S | S |  |
| 64 | 69 |  | G | G | G | G |  |
| 65 | 70 |  | S | S | S | S |  |
| 66 | 71 |  | G | G | G | G |  |
| 67 | 72 |  | S | S | S | S |  |
| 68 | 73 |  | G | G | G | G |  |
| 69 | 74 |  | T | T | T | T |  |
| 70 | 75 |  | D | D | D | D |  |
| 71 | 76 |  | F | F | F | F |  |
| 72 | 77 |  | T | T | T | T |  |
| 73 | 78 |  | L | L | L | L |  |
| 74 | 79 |  | K | K | K | K |  |
| 75 | 80 |  | I | I | I | I |  |
| 76 | 81 |  | S | S | S | S |  |
| 77 | 82 |  | R | R | R | R |  |
| 78 | 83 |  | I | V | V | V |  |
| 79 | 84 |  | E | E | E | E |  |
| 80 | 85 |  | A | A | A | A |  |
| 81 | 86 |  | E | E | E | E |  |
| 82 | 87 |  | D | D | D | D |  |
| 83 | 88 |  | L | V | V | V |  |
| 84 | 89 |  | G | G | G | G |  |
| 85 | 90 |  | L | V | V | V |  |
| 86 | 91 |  | Y | Y | Y | Y |  |
| 87 | 92 |  | Y | Y | Y | Y |  |
| 88 | 93 |  | C | C | C | C |  |
| 89 | 94 | CDR3 | W | W | M | M |  |
| 90 | 95 |  | Q | Q | Q | Q |  |
| 91 | 96 |  | G | G | A | A |  |
| 92 | 97 |  | T | T | L | L |  |
| 93 | 98 |  | H | H | Q | Q |  |
| 94 | 99 |  | F | F | T | T |  |
| 95 | 100 |  | P | P | P | P |  |
| 96 | 101 |  | R | R | R |  |  |
| 97 | 102 |  | T | T | T |  |  |
| 98 | 103 | FR4 | F | F | F |  |  |
| 99 | 104 |  | G | G | G |  |  |
| 100 | 105 |  | G | G | Q |  |  |
| 101 | 106 |  | G | G | G |  |  |
| 102 | 107 |  | T | T | T |  |  |
| 103 | 108 |  | K | K | K |  |  |

TABLE C-continued

Key to Kabat Numbering for the 3D6 Light Chain Variable Region

| KABAT # | Sequential # | TYPE | murine 3D6 VL SEQ ID NO: 50) | h3D6VL SEQ ID NO: 51) | KABID 019230 SEQ ID NO: 52) | A19- Germline SEQ ID NO: 53) | Comment |
|---|---|---|---|---|---|---|---|
| 104 | 109 | | L | V | V | | |
| 105 | 110 | | E | E | E | | |
| 106 | 111 | | I | I | I | | |
| 106A | 112 | | K | K | K | | |

TABLE D

Key to Kabat Numbering for the 3D6 Heavy Chain Variable Region

| KABAT # | Sequential # | TYPE | murine 3D6 VH SEQ ID NO: 54) | h3D6 VH SEQ ID NO: 55) | KABID 045919 SEQ ID NO: 56) | VH3-23 Germline SEQ ID NO: 57) | Comment |
|---|---|---|---|---|---|---|---|
| 1 | 1 | FR1 | E | E | E | E | |
| 2 | 2 | | V | V | V | V | |
| 3 | 3 | | K | Q | Q | Q | |
| 4 | 4 | | L | L | L | L | |
| 5 | 5 | | V | L | L | L | |
| 6 | 6 | | E | E | E | E | |
| 7 | 7 | | S | S | S | S | |
| 8 | 8 | | G | G | G | G | |
| 9 | 9 | | G | G | G | G | |
| 10 | 10 | | G | G | G | G | |
| 11 | 11 | | L | L | L | L | |
| 12 | 12 | | V | V | V | V | |
| 13 | 13 | | K | Q | Q | Q | |
| 14 | 14 | | P | P | P | P | |
| 15 | 15 | | G | G | G | G | |
| 16 | 16 | | A | G | G | G | |
| 17 | 17 | | S | S | S | S | |
| 18 | 18 | | L | L | L | L | |
| 19 | 19 | | K | R | R | R | |
| 20 | 20 | | L | L | L | L | |
| 21 | 21 | | S | S | S | S | |
| 22 | 22 | | C | C | C | C | |
| 23 | 23 | | A | A | A | A | |
| 24 | 24 | | A | A | A | A | |
| 25 | 25 | | S | S | S | S | |
| 26 | 26 | | G | G | G | G | |
| 27 | 27 | | F | F | F | F | |
| 28 | 28 | | T | T | T | T | |
| 29 | 29 | | F | F | F | F | |
| 30 | 30 | | S | S | S | S | |
| 31 | 31 | CDR1 | N | N | S | S | |
| 32 | 32 | | Y | Y | Y | Y | |
| 33 | 33 | | G | G | A | A | |
| 34 | 34 | | M | M | V | M | |
| 35 | 35 | | S | S | S | S | |
| 36 | 36 | FR2 | W | W | W | W | |
| 37 | 37 | | V | V | V | V | |
| 38 | 38 | | R | R | R | R | |
| 39 | 39 | | Q | Q | Q | Q | |
| 40 | 40 | | N | A | A | A | Rare mouse, replace w/Hum |
| 41 | 41 | | S | P | P | P | |
| 42 | 42 | | D | G | G | G | Rare mouse, replace w/Hum |
| 43 | 43 | | K | K | K | K | |
| 44 | 44 | | R | G | G | G | |
| 45 | 45 | | L | L | L | L | |
| 46 | 46 | | E | E | E | E | |
| 47 | 47 | | W | W | W | W | |
| 48 | 48 | | V | V | V | V | |
| 49 | 49 | | A | A | S | S | CDR contact/veneer |
| 50 | 50 | CDR2 | S | S | A | A | |
| 51 | 51 | | I | I | I | I | |
| 52 | 52 | | R | R | S | S | |
| 52A | 53 | | S | S | G | G | |

TABLE D-continued

Key to Kabat Numbering for the 3D6 Heavy Chain Variable Region

| KABAT # | Sequential # | TYPE | murine 3D6 VH SEQ ID NO: 54) | h3D6 VH SEQ ID NO: 55) | KABID 045919 SEQ ID NO: 56) | VH3-23 Germline SEQ ID NO: 57) | Comment |
|---|---|---|---|---|---|---|---|
| 53 | 54 | | G | G | S | S | |
| 54 | 55 | | G | G | G | G | |
| 55 | 56 | | G | G | G | G | |
| 56 | 57 | | R | R | S | S | |
| 57 | 58 | | T | T | T | T | |
| 58 | 59 | | Y | Y | Y | Y | |
| 59 | 60 | | Y | Y | Y | Y | |
| 60 | 61 | | S | S | A | A | |
| 61 | 62 | | D | D | D | D | |
| 62 | 63 | | N | N | S | S | |
| 63 | 64 | | V | V | V | V | |
| 64 | 65 | | K | K | K | K | |
| 65 | 66 | | G | G | G | G | |
| 66 | 67 | FR3 | R | R | R | R | |
| 67 | 68 | | F | F | F | F | |
| 68 | 69 | | T | T | T | T | |
| 69 | 70 | | I | I | I | I | |
| 70 | 71 | | S | S | S | S | |
| 71 | 72 | | R | R | R | R | |
| 72 | 73 | | E | D | D | D | |
| 73 | 74 | | N | N | N | N | |
| 74 | 75 | | A | A | A | S | |
| 75 | 76 | | K | K | K | K | |
| 76 | 77 | | N | N | N | N | |
| 77 | 78 | | T | S | S | T | |
| 78 | 79 | | L | L | L | L | |
| 79 | 80 | | Y | Y | Y | Y | |
| 80 | 81 | | L | L | L | L | |
| 81 | 82 | | Q | Q | Q | Q | |
| 82 | 83 | | M | M | M | M | |
| 82A | 84 | | S | N | N | N | |
| 82B | 85 | | S | S | S | S | |
| 82C | 86 | | L | L | L | L | |
| 83 | 87 | | K | R | R | R | |
| 84 | 88 | | S | A | A | A | |
| 85 | 89 | | E | E | E | E | |
| 86 | 90 | | D | D | D | D | |
| 87 | 91 | | T | T | T | T | |
| 88 | 92 | | A | A | A | A | |
| 89 | 93 | | L | L | L | V | |
| 90 | 94 | | Y | Y | Y | Y | |
| 91 | 95 | | Y | Y | Y | Y | |
| 92 | 96 | | C | C | C | C | |
| 93 | 97 | | V | V | A | A | Packing residue, use mouse |
| 94 | 98 | | R | R | K | K | Canonical, use mouse |
| 95 | 99 | CDR3 | Y | Y | D | | |
| 96 | 100 | | D | D | N | | |
| 97 | 101 | | H | H | Y | | |
| 98 | 102 | | Y | Y | D | | |
| 99 | 103 | | S | S | F | | |
| 100 | 104 | | G | G | W | | |
| 100A | 105 | | S | S | S | | |
| 100B | 106 | | S | S | G | | |
| 100C | 107 | | — | — | T | | |
| 100D | 108 | | — | — | F | | |
| 101 | 109 | | D | D | D | | |
| 102 | 110 | | Y | Y | Y | | |
| 103 | 111 | FR4 | W | W | W | | |
| 104 | 112 | | G | G | G | | |
| 105 | 113 | | Q | Q | Q | | |
| 106 | 114 | | G | G | G | | |
| 107 | 115 | | T | T | T | | |
| 108 | 116 | | T | L | L | | |
| 109 | 117 | | V | V | V | | |
| 110 | 118 | | T | T | T | | |
| 111 | 119 | | V | V | V | | |
| 112 | 120 | | S | S | S | | |
| 113 | 121 | | S | S | S | | |

TABLE E

Key to Kabat Numbering for the 12A11 Light Chain Variable Region

| KABAT # | Sequential # | TYPE | Murine 12A11 VL SEQ ID NO: 58) | h12A11 VL SEQ ID NO: 59) | BAC 01733 SEQ ID NO: 56) | A19-Germline SEQ ID NO: 61) | Comment |
|---|---|---|---|---|---|---|---|
| 1 | 1 | FR1 | D | D | D | D | |
| 2 | 2 | | V | V | V | I | canonical |
| 3 | 3 | | L | V | V | V | |
| 4 | 4 | | M | M | M | M | vernier |
| 5 | 5 | | T | T | T | T | |
| 6 | 6 | | Q | Q | Q | Q | |
| 7 | 7 | | T | S | S | S | |
| 8 | 8 | | P | P | P | P | |
| 9 | 9 | | L | L | L | L | |
| 10 | 10 | | S | S | S | S | |
| 11 | 11 | | L | L | L | L | |
| 12 | 12 | | P | P | P | P | |
| 13 | 13 | | V | V | V | V | |
| 14 | 14 | | S | T | T | T | |
| 15 | 15 | | L | P | P | P | |
| 16 | 16 | | G | G | G | G | |
| 17 | 17 | | D | E | E | E | |
| 18 | 18 | | Q | P | P | P | |
| 19 | 19 | | A | A | A | A | |
| 20 | 20 | | S | S | S | S | |
| 21 | 21 | | I | I | I | I | |
| 22 | 22 | | S | S | S | S | |
| 23 | 23 | | C | C | C | C | |
| 24 | 24 | CDR1 | R | R | R | R | |
| 25 | 25 | | S | S | S | S | |
| 26 | 26 | | S | S | S | S | |
| 27 | 27 | | Q | Q | Q | Q | |
| 27A | 28 | | S | S | S | S | |
| 27B | 29 | | I | I | L | L | |
| 27C | 30 | | V | V | L | L | |
| 27D | 31 | | H | H | H | H | |
| 27E | 32 | | S | S | S | S | |
| 28 | 33 | | N | N | N | N | |
| 29 | 34 | | G | G | G | G | |
| 30 | 35 | | N | N | Y | Y | |
| 31 | 36 | | T | T | N | N | |
| 32 | 37 | | Y | Y | Y | Y | |
| 33 | 38 | | L | L | L | L | |
| 34 | 39 | | E | E | D | D | |
| 35 | 40 | FR2 | W | W | W | W | |
| 36 | 41 | | Y | Y | Y | Y | packing |
| 37 | 42 | | L | L | L | L | |
| 38 | 43 | | Q | Q | Q | Q | packing |
| 39 | 44 | | K | K | K | K | |
| 40 | 45 | | P | P | P | P | vernier |
| 41 | 46 | | G | G | G | G | |
| 42 | 47 | | Q | Q | Q | Q | |
| 43 | 48 | | S | S | S | S | |
| 44 | 49 | | P | P | P | P | packing |
| 45 | 50 | | K | Q | Q | Q | |
| 46 | 51 | | L | L | L | L | packing |
| 47 | 52 | | L | L | L | L | vernier |
| 48 | 53 | | I | I | I | I | canonical |
| 49 | 54 | | Y | Y | Y | Y | vernier |
| 50 | 55 | CDR2 | K | K | L | L | |
| 51 | 56 | | V | V | G | G | |
| 52 | 57 | | S | S | S | S | |
| 53 | 58 | | N | N | N | N | |
| 54 | 59 | | R | R | R | R | |
| 55 | 60 | | F | F | A | A | |
| 56 | 61 | | S | S | S | S | |
| 57 | 62 | FR3 | G | G | G | G | |
| 58 | 63 | | V | V | V | V | |
| 59 | 64 | | P | P | P | P | |
| 60 | 65 | | D | D | D | D | |
| 61 | 66 | | R | R | R | R | |
| 62 | 67 | | F | F | F | F | |
| 63 | 68 | | S | S | S | S | |
| 64 | 69 | | G | G | G | G | canonical |
| 65 | 70 | | S | S | S | S | |
| 66 | 71 | | G | G | G | G | vernier |
| 67 | 72 | | S | S | S | S | |
| 68 | 73 | | G | G | G | G | vernier |
| 69 | 74 | | T | T | T | T | vernier |
| 70 | 75 | | D | D | D | D | |
| 71 | 76 | | F | F | F | F | canonical |
| 72 | 77 | | T | T | T | T | |
| 73 | 78 | | L | L | L | L | |
| 74 | 79 | | K | K | K | K | |
| 75 | 80 | | I | I | I | I | |
| 76 | 81 | | S | S | S | S | |
| 77 | 82 | | R | R | R | R | |
| 78 | 83 | | V | V | V | V | |
| 79 | 84 | | E | E | E | E | |
| 80 | 85 | | A | A | A | A | |
| 81 | 86 | | E | E | E | E | |
| 82 | 87 | | D | D | D | D | |
| 83 | 88 | | L | V | V | V | |
| 84 | 89 | | G | G | G | G | |
| 85 | 90 | | I | V | V | V | |
| 86 | 91 | | Y | Y | Y | Y | |
| 87 | 92 | | Y | Y | Y | Y | packing |
| 88 | 93 | | C | C | C | C | |
| 89 | 94 | CDR3 | F | F | M | M | |
| 90 | 95 | | Q | Q | Q | Q | |
| 91 | 96 | | S | S | A | A | |
| 92 | 97 | | S | S | L | L | |
| 93 | 98 | | H | H | Q | Q | |
| 94 | 99 | | V | V | T | T | |
| 95 | 100 | | P | P | P | P | |
| 96 | 101 | | L | L | Y | | |
| 97 | 102 | | T | T | T | | |
| 98 | 103 | FR4 | F | F | F | | packing |
| 99 | 104 | | G | G | G | | |
| 100 | 105 | | A | Q | Q | | |
| 101 | 106 | | G | G | G | | |
| 102 | 107 | | T | T | T | | |
| 103 | 108 | | K | K | K | | |
| 104 | 109 | | L | L | L | | |
| 105 | 110 | | E | E | E | | |
| 106 | 111 | | L | I | I | | |
| 106A | 112 | | K | K | K | | |

TABLE F

Key to Kabat Numbering for the 3D6 Heavy Chain Variable Region

| KABAT # | Sequential # | TYPE | Murine 12A11 VH SEQ ID NO: 62) | h12A11 VHv1 SEQ ID NO: 63) | AAA 69734 SEQ ID NO: 64) | 567123 Germline SEQ ID NO: 65) | Comment |
|---|---|---|---|---|---|---|---|
| 1 | 1 | FR1 | Q | Q | Q | Q | |
| 2 | 2 | | V | V | V | V | vernier |
| 3 | 3 | | T | Q | Q | Q | |
| 4 | 4 | | L | L | L | L | |
| 5 | 5 | | K | V | V | V | |
| 6 | 6 | | E | E | E | E | |
| 7 | 7 | | S | S | S | S | |
| 8 | 8 | | G | G | G | G | |
| 9 | 9 | | P | G | G | G | |
| 10 | 10 | | G | G | G | G | |
| 11 | 11 | | I | V | V | V | |
| 12 | 12 | | L | V | V | V | |
| 13 | 13 | | K | Q | Q | Q | |
| 14 | 14 | | P | P | P | P | |
| 15 | 15 | | S | G | G | G | |
| 16 | 16 | | Q | R | R | R | |
| 17 | 17 | | T | S | S | S | |
| 18 | 18 | | L | L | L | L | |
| 19 | 19 | | S | R | R | R | |
| 20 | 20 | | L | L | L | L | |
| 21 | 21 | | T | S | S | S | |
| 22 | 22 | | C | C | C | C | |
| 23 | 23 | | S | A | A | A | |
| 24 | 24 | | F | F | A | A | canonical for H1 - backmutate in v1 |
| 25 | 25 | | S | S | S | S | |
| 26 | 26 | | G | G | G | G | canonical |
| 27 | 27 | | F | F | F | F | canonical |
| 28 | 28 | | S | S | T | T | vernier, close to H1 - backmutate in v1 |
| 29 | 29 | | L | L | F | F | canonical for H1 - backmutate in v1 |
| 30 | 30 | | S | S | S | S | |
| 31 | 31 | CDR1 | T | T | S | S | |
| 32 | 32 | | S | S | Y | Y | |
| 33 | 33 | | G | G | A | A | |
| 34 | 34 | | M | M | M | M | |
| 35 | 35 | | S | S | H | H | |
| 35A | 36 | | V | V | — | — | |
| 35B | 37 | | G | G | — | — | |
| 36 | 38 | FR2 | W | W | W | W | |
| 37 | 39 | | I | I | V | V | packing - bacmutate in v1 |
| 38 | 40 | | R | R | R | R | |
| 39 | 41 | | Q | Q | Q | Q | packing |
| 40 | 42 | | P | A | A | A | |
| 41 | 43 | | S | P | P | P | |
| 42 | 44 | | G | G | G | G | |
| 43 | 45 | | K | K | K | K | |
| 44 | 46 | | G | G | G | G | |
| 45 | 47 | | L | L | L | L | packing |
| 46 | 48 | | E | E | E | E | |
| 47 | 49 | | W | W | W | W | packing |
| 48 | 50 | | L | L | V | V | vernier (underneath H2) - backmutate in v1 |
| 49 | 51 | | A | A | A | A | |
| 50 | 52 | CDR2 | H | H | V | V | |
| 51 | 53 | | I | I | I | I | |
| 52 | 54 | | W | W | S | S | |
| 53 | 55 | | W | W | Y | Y | |
| 54 | 56 | | D | D | D | D | |
| 55 | 57 | | D | D | G | G | |
| | | | — | — | S | S | |
| 56 | 58 | | D | D | N | N | |
| 57 | 59 | | K | K | K | K | |
| 58 | 60 | | Y | Y | Y | Y | |
| 59 | 61 | | Y | Y | Y | Y | |
| 60 | 62 | | N | N | A | A | |
| 61 | 63 | | P | P | D | D | |
| 62 | 64 | | S | S | S | S | |

TABLE F-continued

Key to Kabat Numbering for the 3D6 Heavy Chain Variable Region

| KABAT # | Sequential # | TYPE | Murine 12A11 VH SEQ ID NO: 62) | h12A11 VHv1 SEQ ID NO: 63) | AAA 69734 SEQ ID NO: 64) | 567123 Germline SEQ ID NO: 65) | Comment |
|---|---|---|---|---|---|---|---|
| 63 | 65 | | L | L | V | V | |
| 64 | 66 | | K | K | K | K | |
| 65 | 67 | | S | S | G | G | |
| 66 | 68 | FR3 | R | R | R | R | |
| 67 | 69 | | L | L | F | F | vernier (underneath H2, possibly interacting with L63) - backmutate in v1 |
| 63 | 70 | | T | T | T | T | |
| 69 | 71 | | I | I | I | I | |
| 70 | 72 | | S | S | S | S | |
| 71 | 73 | | K | K | R | R | canonical for H2 - backmutate in v1 |
| 72 | 74 | | D | D | D | D | |
| 73 | 75 | | T | T | N | N | vernier (edge of binding site, possibly interacting with S30) - backmutate in v1 |
| 74 | 76 | | S | S | S | S | |
| 75 | 77 | | R | K | K | K | |
| 76 | 78 | | N | N | N | N | |
| 77 | 79 | | Q | T | T | T | |
| 78 | 80 | | V | V | L | L | vernier (buried under H1, possibly interacting with V35A) - backmutate in v1 |
| 79 | 81 | | F | Y | Y | Y | |
| 80 | 82 | | L | L | L | L | |
| 81 | 83 | | K | Q | Q | Q | |
| 82 | 84 | | I | M | M | M | |
| 82A | 85 | | T | N | N | N | |
| 82B | 86 | | S | S | S | S | |
| 82C | 87 | | V | L | L | L | |
| 83 | 88 | | D | R | R | R | |
| 84 | 89 | | T | A | A | A | |
| 85 | 90 | | A | E | E | E | |
| 86 | 91 | | D | D | D | D | |
| 87 | 92 | | T | T | T | T | |
| 88 | 93 | | A | A | A | A | |
| 89 | 94 | | T | V | V | V | |
| 90 | 95 | | Y | Y | Y | Y | |
| 91 | 96 | | Y | Y | Y | Y | packing |
| 92 | 97 | | C | C | C | C | |
| 93 | 98 | | A | A | A | A | packing |
| 94 | 99 | | R | R | R | R | canonical |
| | | | — | — | D | D | |
| 95 | 100 | CDR3 | R | R | R | — | |
| 96 | 101 | | T | T | H | — | |
| 97 | 102 | | T | T | S | — | |
| 98 | 103 | | T | T | S | — | |
| 99 | 104 | | A | A | S | A | |
| 100 | 105 | | D | D | W | K | |
| 100A | 106 | | Y | Y | Y | L | |
| 100B | 107 | | F | F | Y | L | |
| 101 | 108 | | A | A | G | M | |
| 102 | 109 | | Y | Y | M | L | |
| | | | — | — | D | L | |
| | | | — | — | V | I | |
| 103 | 110 | | W | W | W | S | packing |
| 104 | 111 | | G | G | G | G | |
| 105 | 112 | | Q | Q | Q | A | |
| 106 | 113 | | G | G | G | K | |
| 107 | 114 | FR4 | T | T | T | G | |
| 108 | 115 | | T | T | T | Q | |
| 109 | 116 | | L | V | V | W | |
| 110 | 117 | | T | T | T | S | |
| 111 | 118 | | V | V | V | P | |
| 112 | 119 | | S | S | S | S | |
| 113 | 120 | | S | S | S | L | |

What is claimed is:

1. An isolated antibody that binds to an epitope within residues 3-7 of Aβ, wherein CDRs L1, L2 and L3 are CDRs L1, L2 and L3 of an antibody other than 12A11 that binds to an epitope within residues 3-7 of Aβ, and CDRs H1 and H2 are CDRs H1 and H2 of the antibody other than 12A11 and CDRs L1, L2, L3, H1 and H2 of the isolated antibody differ from corresponding CDRs of 12A11 and CDR H3 is either CDR H3 of antibody 12A11 or CDR H3 of the antibody other than 12A11 modified by absence of residues X2, X3 and X4 of SEQ ID NO:28, wherein CDRs L1, L2 and L3 are CDRs L1, L2 and L3 of antibody PFA1, and CDRs H1 and H2 are CDRs H1 and H2 of antibody PFA1 and CDR H3 is CDR H3 of antibody 12A11.

2. An isolated antibody that binds to an epitope within residues 3-7 of Aβ, wherein CDRs L1, L2 and L3 are CDRs L1, L2 and L3 of an antibody other than 12A11 that binds to an epitope within residues 3-7 of Aβ, and CDRs H1 and H2 are CDRs H1 and H2 of the antibody other than 12A11 and CDRs L1, L2, L3, H1 and H2 of the isolated antibody differ from corresponding CDRs of 12A11 and CDR H3 is either CDR H3 of antibody 12A11 or CDR H3 of the antibody other than 12A11 modified by absence of residues X2, X3 and X4 of SEQ ID NO:28, wherein CDRs L1, L2 and L3 are CDRs L1, L2 and L3 of antibody PFA2, and CDRs H1 and H2 are CDRs H1 and H2 of antibody PFA2 and CDR H3 is CDR H3 of antibody 12A11.

* * * * *

SEQUENCE LISTING

<160> NUMBER OF SEQ ID NOS: 81

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 131
<212> TYPE: PRT
<213> ORGANISM: Mus sp.

<400> SEQUENCE: 3

Met Lys Leu Pro Val Arg Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Phe Gln Ser Ser His Val Pro Leu Thr Phe Gly Ala Gly Thr Lys Leu
        115                 120                 125

Glu Leu Lys
    130

<210> SEQ ID NO 4
<211> LENGTH: 131
<212> TYPE: PRT
<213> ORGANISM: Mus sp.

```
<400> SEQUENCE: 4

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Asn Ile
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Leu Thr Phe Gly Ala Gly Thr Lys Leu
            115                 120                 125

Glu Leu Lys
    130

<210> SEQ ID NO 5
<211> LENGTH: 131
<212> TYPE: PRT
<213> ORGANISM: Mus sp.

<400> SEQUENCE: 5

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Asn Ile
            35                  40                  45

Ile His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Lys Lys Val Glu Ala Glu Asp Leu Gly Ile Tyr Tyr Cys
                100                 105                 110

Phe Gln Gly Ser His Val Pro Leu Thr Phe Gly Ala Gly Thr Lys Leu
            115                 120                 125

Glu Leu Glu
    130

<210> SEQ ID NO 6
<211> LENGTH: 112
<212> TYPE: PRT
<213> ORGANISM: Mus sp.

<400> SEQUENCE: 6

Tyr Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
```

```
                35                  40                  45
Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Ile Glu Ala Glu Asp Leu Gly Leu Tyr Tyr Cys Trp Gln Gly
                85                  90                  95

Thr His Phe Pro Arg Thr Phe Gly Gly Gly Thr Lys Leu Glu Ile Lys
            100                 105                 110
```

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Asp or Val
<220> FEATURE:
<221> NAME/KEY: MOD_RES
<222> LOCATION: (3)..(3)
<223> OTHER INFORMATION: Leu or Val
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (12)..(12)
<223> OTHER INFORMATION: Ser or Pro
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu or Ile
<220> FEATURE:
<221> NAME/KEY: MOD_RES
<222> LOCATION: (17)..(17)
<223> OTHER INFORMATION: Gln or Asp
<220> FEATURE:
<221> NAME/KEY: MOD_RES
<222> LOCATION: (18)..(18)
<223> OTHER INFORMATION: Pro or Gln
<220> FEATURE:
<221> NAME/KEY: MOD_RES
<222> LOCATION: (24)..(24)
<223> OTHER INFORMATION: Lys or Arg
<220> FEATURE:
<221> NAME/KEY: MOD_RES
<222> LOCATION: (28)..(28)
<223> OTHER INFORMATION: Asn or Ser
<220> FEATURE:
<221> NAME/KEY: MOD_RES
<222> LOCATION: (29)..(29)
<223> OTHER INFORMATION: Ile or Leu
<220> FEATURE:
<221> NAME/KEY: MOD_RES
<222> LOCATION: (30)..(30)
<223> OTHER INFORMATION: Val, Ile or Leu
<220> FEATURE:
<221> NAME/KEY: MOD_RES
<222> LOCATION: (31)..(31)
<223> OTHER INFORMATION: Asp or His
<220> FEATURE:
<221> NAME/KEY: MOD_RES
<222> LOCATION: (33)..(33)
<223> OTHER INFORMATION: Asp or Asn
<220> FEATURE:

```
<221> NAME/KEY: MOD_RES
<222> LOCATION: (35)..(35)
<223> OTHER INFORMATION: Lys or Asn
<220> FEATURE:
<221> NAME/KEY: MOD_RES
<222> LOCATION: (39)..(39)
<223> OTHER INFORMATION: Glu or Asn
<220> FEATURE:
<221> NAME/KEY: MOD_RES
<222> LOCATION: (41)..(41)
<223> OTHER INFORMATION: Leu or Tyr
<220> FEATURE:
<221> NAME/KEY: MOD_RES
<222> LOCATION: (44)..(44)
<223> OTHER INFORMATION: Lys or Arg
<220> FEATURE:
<221> NAME/KEY: MOD_RES
<222> LOCATION: (51)..(51)
<223> OTHER INFORMATION: Leu or Arg
<220> FEATURE:
<221> NAME/KEY: MOD_RES
<222> LOCATION: (55)..(55)
<223> OTHER INFORMATION: Lys or Leu
<220> FEATURE:
<221> NAME/KEY: MOD_RES
<222> LOCATION: (58)..(58)
<223> OTHER INFORMATION: Asn or Lys
<220> FEATURE:
<221> NAME/KEY: MOD_RES
<222> LOCATION: (59)..(59)
<223> OTHER INFORMATION: Arg or Leu
<220> FEATURE:
<221> NAME/KEY: MOD_RES
<222> LOCATION: (60)..(60)
<223> OTHER INFORMATION: Phe or Asp
<220> FEATURE:
<221> NAME/KEY: MOD_RES
<222> LOCATION: (68)..(68)
<223> OTHER INFORMATION: Ser or Thr
<220> FEATURE:
<221> NAME/KEY: MOD_RES
<222> LOCATION: (81)..(81)
<223> OTHER INFORMATION: Ser or Lys
<220> FEATURE:
<221> NAME/KEY: MOD_RES
<222> LOCATION: (82)..(82)
<223> OTHER INFORMATION: Arg or Lys
<220> FEATURE:
<221> NAME/KEY: MOD_RES
<222> LOCATION: (83)..(83)
<223> OTHER INFORMATION: Val or Ile
<220> FEATURE:
<221> NAME/KEY: MOD_RES
<222> LOCATION: (90)..(90)
<223> OTHER INFORMATION: Val, Ile or Leu
<220> FEATURE:
<221> NAME/KEY: MOD_RES
<222> LOCATION: (94)..(94)
<223> OTHER INFORMATION: Phe or Trp
<220> FEATURE:
<221> NAME/KEY: MOD_RES
<222> LOCATION: (96)..(96)
<223> OTHER INFORMATION: Gly or Ser
<220> FEATURE:
<221> NAME/KEY: MOD_RES
<222> LOCATION: (97)..(97)
<223> OTHER INFORMATION: Ser or Thr
<220> FEATURE:
<221> NAME/KEY: MOD_RES
<222> LOCATION: (99)..(99)
<223> OTHER INFORMATION: Phe or Val
<220> FEATURE:
<221> NAME/KEY: MOD_RES
<222> LOCATION: (101)..(101)
<223> OTHER INFORMATION: Arg or Leu
<220> FEATURE:
<221> NAME/KEY: MOD_RES
<222> LOCATION: (105)..(105)
<223> OTHER INFORMATION: Ala or Gly
```

```
<220> FEATURE:
<221> NAME/KEY: MOD_RES
<222> LOCATION: (111)..(111)
<223> OTHER INFORMATION: Leu or Ile
<220> FEATURE:
<221> NAME/KEY: MOD_RES
<222> LOCATION: (112)..(112)
<223> OTHER INFORMATION: Glu or Lys

<400> SEQUENCE: 7

Xaa Val Xaa Met Thr Gln Thr Pro Leu Xaa Leu Xaa Val Xaa Xaa Gly
 1               5                  10                  15

Xaa Xaa Ala Ser Ile Ser Cys Xaa Ser Ser Gln Xaa Xaa Xaa Xaa Ser
            20                  25                  30

Xaa Gly Xaa Thr Tyr Leu Xaa Trp Xaa Leu Gln Xaa Pro Gly Gln Ser
        35                  40                  45

Pro Lys Xaa Leu Ile Tyr Xaa Val Ser Xaa Xaa Xaa Ser Gly Val Pro
    50                  55                  60

Asp Arg Phe Xaa Gly Ser Gly Ser Gly Thr Asp Phe Thr Leu Lys Ile
65                  70                  75                  80

Xaa Xaa Xaa Glu Ala Glu Asp Leu Gly Xaa Tyr Tyr Cys Xaa Gln Xaa
                85                  90                  95

Xaa His Xaa Pro Xaa Thr Phe Gly Xaa Gly Thr Lys Leu Glu Xaa Xaa
            100                 105                 110

<210> SEQ ID NO 8
<211> LENGTH: 120
<212> TYPE: PRT
<213> ORGANISM: Mus sp.

<400> SEQUENCE: 8

Gln Val Thr Leu Lys Glu Ser Gly Pro Gly Ile Leu Lys Pro Ser Gln
 1               5                  10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Thr Thr Thr Ala Asp Tyr Phe Ala Tyr Trp Gly Gln
            100                 105                 110

Gly Thr Thr Leu Thr Val Ser Ser
        115                 120

<210> SEQ ID NO 9
<211> LENGTH: 123
<212> TYPE: PRT
<213> ORGANISM: Mus sp.

<400> SEQUENCE: 9

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Asn
            20                  25                  30

Gly Met Gly Val Ser Trp Ile Arg Gln Pro Ser Gly Lys Gly Leu Glu
```

```
                35                  40                  45
Trp Leu Ala His Ile Tyr Trp Asp Glu Asp Lys Arg Tyr Asn Pro Ser
 50                  55                  60
Leu Lys Ser Arg Leu Thr Ile Ser Lys Asp Thr Ser Asn Asn Gln Val
65                  70                  75                  80
Phe Leu Lys Ile Thr Asn Val Asp Thr Ala Asp Thr Ala Thr Tyr Tyr
                 85                  90                  95
Cys Ala Arg Arg Arg Ile Ile Tyr Asp Val Glu Asp Tyr Phe Asp Tyr
                100                 105                 110
Trp Gly Gln Gly Thr Thr Leu Thr Val Ser Ser
            115                 120
```

<210> SEQ ID NO 10
<211> LENGTH: 123
<212> TYPE: PRT
<213> ORGANISM: Mus sp.

<400> SEQUENCE: 10

```
Gln Ala Thr Leu Lys Glu Ser Gly Pro Gly Ile Leu Gln Ser Ser Gln
1               5                   10                  15
Thr Leu Ser Leu Thr Cys Ser Phe Ser Gly Phe Ser Leu Ser Thr Ser
                 20                  25                  30
Gly Met Gly Val Ser Trp Ile Arg Gln Pro Ser Gly Lys Gly Leu Glu
            35                  40                  45
Trp Leu Ala His Ile Tyr Trp Asp Asp Asp Lys Arg Tyr Asn Pro Ser
 50                  55                  60
Leu Lys Ser Arg Leu Thr Ile Ser Lys Asp Thr Ser Arg Lys Gln Val
65                  70                  75                  80
Phe Leu Lys Ile Thr Ser Val Asp Pro Ala Asp Thr Ala Thr Tyr Tyr
                 85                  90                  95
Cys Val Arg Arg Pro Ile Thr Pro Val Leu Val Asp Ala Met Asp Tyr
                100                 105                 110
Trp Gly Gln Gly Thr Ser Val Thr Val Ser Ser
            115                 120
```

<210> SEQ ID NO 11
<211> LENGTH: 119
<212> TYPE: PRT
<213> ORGANISM: Mus sp.

<400> SEQUENCE: 11

```
Glu Val Lys Leu Val Glu Ser Gly Gly Gly Leu Val Lys Pro Gly Ala
1               5                   10                  15
Ser Leu Lys Leu Ser Cys Ala Ala Ser Gly Phe Thr Phe Ser Asn Tyr
                 20                  25                  30
Gly Met Ser Trp Val Arg Gln Asn Ser Asp Lys Arg Leu Glu Trp Val
            35                  40                  45
Ala Ser Ile Arg Ser Gly Gly Arg Thr Tyr Tyr Ser Asp Asn Val
 50                  55                  60
Lys Gly Arg Phe Thr Ile Ser Arg Glu Asn Ala Lys Asn Thr Leu Tyr
65                  70                  75                  80
Leu Gln Met Ser Ser Leu Lys Ser Glu Asp Thr Ala Leu Tyr Tyr Cys
                 85                  90                  95
Val Arg Tyr Asp His Tyr Ser Gly Ser Ser Asp Tyr Trp Gly Gln Gly
                100                 105                 110
Thr Thr Ile Thr Val Ser Ser
```

```
                                115

<210> SEQ ID NO 12
<211> LENGTH: 122
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Gln or Glu
<220> FEATURE:
<221> NAME/KEY: MOD_RES
<222> LOCATION: (2)..(2)
<223> OTHER INFORMATION: Ala or Val
<220> FEATURE:
<221> NAME/KEY: MOD_RES
<222> LOCATION: (3)..(3)
<223> OTHER INFORMATION: Thr or Lys
<220> FEATURE:
<221> NAME/KEY: MOD_RES
<222> LOCATION: (5)..(5)
<223> OTHER INFORMATION: Lys or Val
<220> FEATURE:
<221> NAME/KEY: MOD_RES
<222> LOCATION: (9)..(9)
<223> OTHER INFORMATION: Pro or Gly
<220> FEATURE:
<221> NAME/KEY: MOD_RES
<222> LOCATION: (11)..(11)
<223> OTHER INFORMATION: Ile or Leu
<220> FEATURE:
<221> NAME/KEY: MOD_RES
<222> LOCATION: (12)..(12)
<223> OTHER INFORMATION: Leu or Val
<220> FEATURE:
<221> NAME/KEY: MOD_RES
<222> LOCATION: (13)..(13)
<223> OTHER INFORMATION: Lys or Gln
<220> FEATURE:
<221> NAME/KEY: MOD_RES
<222> LOCATION: (14)..(14)
<223> OTHER INFORMATION: Pro or Ser
<220> FEATURE:
<221> NAME/KEY: MOD_RES
<222> LOCATION: (15)..(15)
<223> OTHER INFORMATION: Ser or Gly
<220> FEATURE:
<221> NAME/KEY: MOD_RES
<222> LOCATION: (16)..(16)
<223> OTHER INFORMATION: Ala or Gln
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Ser or Lys
<220> FEATURE:
<221> NAME/KEY: MOD_RES
<222> LOCATION: (21)..(21)
<223> OTHER INFORMATION: Thr or Ser
<220> FEATURE:
<221> NAME/KEY: MOD_RES
<222> LOCATION: (23)..(23)
<223> OTHER INFORMATION: Ser or Ala
<220> FEATURE:
<221> NAME/KEY: MOD_RES
<222> LOCATION: (24)..(24)
<223> OTHER INFORMATION: Phe or Ala
<220> FEATURE:
<221> NAME/KEY: MOD_RES
<222> LOCATION: (28)..(28)
<223> OTHER INFORMATION: Ser or Thr
<220> FEATURE:
```

```
<221> NAME/KEY: MOD_RES
<222> LOCATION: (29)..(29)
<223> OTHER INFORMATION: Leu or Phe
<220> FEATURE:
<221> NAME/KEY: MOD_RES
<222> LOCATION: (31)..(31)
<223> OTHER INFORMATION: Thr or Asn
<220> FEATURE:
<221> NAME/KEY: MOD_RES
<222> LOCATION: (32)..(32)
<223> OTHER INFORMATION: Ser or Asn
<220> FEATURE:
<221> NAME/KEY: MOD_RES
<222> LOCATION: (35)..(35)
<223> OTHER INFORMATION: Ser, Gly or absent
<220> FEATURE:
<221> NAME/KEY: MOD_RES
<222> LOCATION: (36)..(36)
<223> OTHER INFORMATION: May or may not be present
<220> FEATURE:
<221> NAME/KEY: MOD_RES
<222> LOCATION: (37)..(37)
<223> OTHER INFORMATION: Ser or Gly
<220> FEATURE:
<221> NAME/KEY: MOD_RES
<222> LOCATION: (39)..(39)
<223> OTHER INFORMATION: Ile or Val
<220> FEATURE:
<221> NAME/KEY: MOD_RES
<222> LOCATION: (42)..(42)
<223> OTHER INFORMATION: Pro or Asn
<220> FEATURE:
<221> NAME/KEY: MOD_RES
<222> LOCATION: (44)..(44)
<223> OTHER INFORMATION: Gly or Asp
<220> FEATURE:
<221> NAME/KEY: MOD_RES
<222> LOCATION: (46)..(46)
<223> OTHER INFORMATION: Gly or Arg
<220> FEATURE:
<221> NAME/KEY: MOD_RES
<222> LOCATION: (50)..(50)
<223> OTHER INFORMATION: Leu or Val
<220> FEATURE:
<221> NAME/KEY: MOD_RES
<222> LOCATION: (52)..(52)
<223> OTHER INFORMATION: His or Ser
<220> FEATURE:
<221> NAME/KEY: MOD_RES
<222> LOCATION: (53)..(53)
<223> OTHER INFORMATION: Trp, Tyr or Arg
<220> FEATURE:
<221> NAME/KEY: MOD_RES
<222> LOCATION: (54)..(54)
<223> OTHER INFORMATION: Trp or Ser
<220> FEATURE:
<221> NAME/KEY: MOD_RES
<222> LOCATION: (55)..(55)
<223> OTHER INFORMATION: Asp or Gly
<220> FEATURE:
<221> NAME/KEY: MOD_RES
<222> LOCATION: (56)..(56)
<223> OTHER INFORMATION: Asp, Glu or Gly
<220> FEATURE:
<221> NAME/KEY: MOD_RES
<222> LOCATION: (57)..(57)
<223> OTHER INFORMATION: Asp or Gly
<220> FEATURE:
<221> NAME/KEY: MOD_RES
<222> LOCATION: (58)..(58)
<223> OTHER INFORMATION: Lys or Arg
<220> FEATURE:
<221> NAME/KEY: MOD_RES
<222> LOCATION: (59)..(59)
<223> OTHER INFORMATION: May or may not be present
<220> FEATURE:
<221> NAME/KEY: MOD_RES
<222> LOCATION: (61)..(61)
<223> OTHER INFORMATION: Tyr or Arg
```

-continued

```
<220> FEATURE:
<221> NAME/KEY: MOD_RES
<222> LOCATION: (62)..(62)
<223> OTHER INFORMATION: Asn or Ser
<220> FEATURE:
<221> NAME/KEY: MOD_RES
<222> LOCATION: (63)..(63)
<223> OTHER INFORMATION: Pro or Asp
<220> FEATURE:
<221> NAME/KEY: MOD_RES
<222> LOCATION: (64)..(64)
<223> OTHER INFORMATION: Ser or Asn
<220> FEATURE:
<221> NAME/KEY: MOD_RES
<222> LOCATION: (66)..(66)
<223> OTHER INFORMATION: Leu or Val
<220> FEATURE:
<221> NAME/KEY: MOD_RES
<222> LOCATION: (68)..(68)
<223> OTHER INFORMATION: Ser or Gly
<220> FEATURE:
<221> NAME/KEY: MOD_RES
<222> LOCATION: (72)..(72)
<223> OTHER INFORMATION: Leu or Phe
<220> FEATURE:
<221> NAME/KEY: MOD_RES
<222> LOCATION: (73)..(73)
<223> OTHER INFORMATION: Lys or Arg
<220> FEATURE:
<221> NAME/KEY: MOD_RES
<222> LOCATION: (74)..(74)
<223> OTHER INFORMATION: Asp or Glu
<220> FEATURE:
<221> NAME/KEY: MOD_RES
<222> LOCATION: (75)..(75)
<223> OTHER INFORMATION: Thr or Asn
<220> FEATURE:
<221> NAME/KEY: MOD_RES
<222> LOCATION: (76)..(76)
<223> OTHER INFORMATION: Ser or Ala
<220> FEATURE:
<221> NAME/KEY: MOD_RES
<222> LOCATION: (77)..(77)
<223> OTHER INFORMATION: Arg, Asn or Lys
<220> FEATURE:
<221> NAME/KEY: MOD_RES
<222> LOCATION: (78)..(78)
<223> OTHER INFORMATION: Asn or Lys
<220> FEATURE:
<221> NAME/KEY: MOD_RES
<222> LOCATION: (79)..(79)
<223> OTHER INFORMATION: Gln or Thr
<220> FEATURE:
<221> NAME/KEY: MOD_RES
<222> LOCATION: (80)..(80)
<223> OTHER INFORMATION: Val or Leu
<220> FEATURE:
<221> NAME/KEY: MOD_RES
<222> LOCATION: (82)..(82)
<223> OTHER INFORMATION: Phe or Tyr
<220> FEATURE:
<221> NAME/KEY: MOD_RES
<222> LOCATION: (83)..(83)
<223> OTHER INFORMATION: Lys or Gln
<220> FEATURE:
<221> NAME/KEY: MOD_RES
<222> LOCATION: (84)..(84)
<223> OTHER INFORMATION: Ile or Met
<220> FEATURE:
<221> NAME/KEY: MOD_RES
<222> LOCATION: (85)..(85)
<223> OTHER INFORMATION: Ser or Thr
<220> FEATURE:
<221> NAME/KEY: MOD_RES
<222> LOCATION: (86)..(86)
<223> OTHER INFORMATION: Ser or Asn
<220> FEATURE:
<221> NAME/KEY: MOD_RES
<222> LOCATION: (87)..(87)
```

```
<223> OTHER INFORMATION: Val or Leu
<220> FEATURE:
<221> NAME/KEY: MOD_RES
<222> LOCATION: (88)..(88)
<223> OTHER INFORMATION: Asp or Lys
<220> FEATURE:
<221> NAME/KEY: MOD_RES
<222> LOCATION: (89)..(89)
<223> OTHER INFORMATION: Thr, Pro or Ser
<220> FEATURE:
<221> NAME/KEY: MOD_RES
<222> LOCATION: (93)..(93)
<223> OTHER INFORMATION: Ala or Glu
<220> FEATURE:
<221> NAME/KEY: MOD_RES
<222> LOCATION: (97)..(97)
<223> OTHER INFORMATION: Thr or Leu
<220> FEATURE:
<221> NAME/KEY: MOD_RES
<222> LOCATION: (99)..(99)
<223> OTHER INFORMATION: Ala or Val
<220> FEATURE:
<221> NAME/KEY: MOD_RES
<222> LOCATION: (100)..(100)
<223> OTHER INFORMATION: Tyr or Arg
<220> FEATURE:
<221> NAME/KEY: MOD_RES
<222> LOCATION: (101)..(101)
<223> OTHER INFORMATION: Arg, Pro or absent
<220> FEATURE:
<221> NAME/KEY: MOD_RES
<222> LOCATION: (102)..(102)
<223> OTHER INFORMATION: May or may not be present
<220> FEATURE:
<221> NAME/KEY: MOD_RES
<222> LOCATION: (103)..(103)
<223> OTHER INFORMATION: Thr, Tyr, Pro or Asp
<220> FEATURE:
<221> NAME/KEY: MOD_RES
<222> LOCATION: (104)..(104)
<223> OTHER INFORMATION: Thr, Asp, Val or His
<220> FEATURE:
<221> NAME/KEY: MOD_RES
<222> LOCATION: (105)..(105)
<223> OTHER INFORMATION: Thr, Val, Leu or Tyr
<220> FEATURE:
<221> NAME/KEY: MOD_RES
<222> LOCATION: (106)..(106)
<223> OTHER INFORMATION: Ala, Glu, Val or Ser
<220> FEATURE:
<221> NAME/KEY: MOD_RES
<222> LOCATION: (107)..(107)
<223> OTHER INFORMATION: Asp or Gly
<220> FEATURE:
<221> NAME/KEY: MOD_RES
<222> LOCATION: (108)..(108)
<223> OTHER INFORMATION: Tyr, Ala or Ser
<220> FEATURE:
<221> NAME/KEY: MOD_RES
<222> LOCATION: (109)..(109)
<223> OTHER INFORMATION: Phe, Met or Ser
<220> FEATURE:
<221> NAME/KEY: MOD_RES
<222> LOCATION: (110)..(110)
<223> OTHER INFORMATION: Ala or Asp
<220> FEATURE:
<221> NAME/KEY: MOD_RES
<222> LOCATION: (117)..(117)
<223> OTHER INFORMATION: Thr or Ser
<220> FEATURE:
<221> NAME/KEY: MOD_RES
<222> LOCATION: (118)..(118)
<223> OTHER INFORMATION: Leu or Val

<400> SEQUENCE: 12

Xaa Xaa Xaa Leu Xaa Glu Ser Gly Xaa Gly Xaa Xaa Xaa Xaa Xaa Xaa
1               5                   10                  15
```

Xaa Leu Xaa Leu Xaa Cys Xaa Xaa Ser Gly Phe Xaa Ser Xaa Xaa
        20                  25                  30

Gly Met Xaa Val Xaa Trp Xaa Arg Gln Xaa Ser Xaa Lys Xaa Leu Glu
            35                  40                  45

Trp Xaa Ile Xaa Xaa Xaa Xaa Xaa Xaa Thr Tyr Xaa Xaa Xaa Xaa
    50                  55                  60

Lys Xaa Arg Xaa Thr Ile Ser Xaa Xaa Xaa Xaa Xaa Xaa Xaa Xaa
65                  70                  75                  80

Leu Xaa Xaa Xaa Xaa Xaa Xaa Asp Thr Ala Xaa Tyr Tyr Cys
            85                  90                  95

Xaa Arg Xaa Xaa Xaa Ile Xaa Xaa Xaa Xaa Xaa Xaa Xaa Tyr Trp
        100                 105                 110

Gly Gln Gly Thr Xaa Xaa Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Val or Ala
<220> FEATURE:
<221> NAME/KEY: MOD_RES
<222> LOCATION: (13)..(13)
<223> OTHER INFORMATION: Lys or Gln
<220> FEATURE:
<221> NAME/KEY: MOD_RES
<222> LOCATION: (14)..(14)
<223> OTHER INFORMATION: Pro or Ser
<220> FEATURE:
<221> NAME/KEY: MOD_RES
<222> LOCATION: (32)..(32)
<223> OTHER INFORMATION: Ser or Asn
<220> FEATURE:
<221> NAME/KEY: MOD_RES
<222> LOCATION: (35)..(35)
<223> OTHER INFORMATION: Ser or Gly
<220> FEATURE:
<221> NAME/KEY: MOD_RES
<222> LOCATION: (37)..(37)
<223> OTHER INFORMATION: Ser or Gly
<220> FEATURE:
<221> NAME/KEY: MOD_RES
<222> LOCATION: (54)..(54)
<223> OTHER INFORMATION: Tyr or Trp
<220> FEATURE:
<221> NAME/KEY: MOD_RES
<222> LOCATION: (57)..(57)
<223> OTHER INFORMATION: Asp or Glu
<220> FEATURE:
<221> NAME/KEY: MOD_RES
<222> LOCATION: (60)..(60)
<223> OTHER INFORMATION: Tyr or Arg
<220> FEATURE:
<221> NAME/KEY: MOD_RES
<222> LOCATION: (77)..(77)
<223> OTHER INFORMATION: Arg or Asn
<220> FEATURE:
<221> NAME/KEY: MOD_RES
<222> LOCATION: (78)..(78)
<223> OTHER INFORMATION: Asn or Lys
<220> FEATURE:
<221> NAME/KEY: MOD_RES
<222> LOCATION: (86)..(86)
<223> OTHER INFORMATION: Ser or Asn
<220> FEATURE:
<221> NAME/KEY: MOD_RES

```
<222> LOCATION: (89)..(89)
<223> OTHER INFORMATION: Thr or Pro
<220> FEATURE:
<221> NAME/KEY: MOD_RES
<222> LOCATION: (98)..(98)
<223> OTHER INFORMATION: Ala or Val
<220> FEATURE:
<221> NAME/KEY: MOD_RES
<222> LOCATION: (101)..(101)
<223> OTHER INFORMATION: Arg, Pro or absent
<220> FEATURE:
<221> NAME/KEY: MOD_RES
<222> LOCATION: (102)..(102)
<223> OTHER INFORMATION: May or may not be present
<220> FEATURE:
<221> NAME/KEY: MOD_RES
<222> LOCATION: (103)..(103)
<223> OTHER INFORMATION: Ile, Thr or absent
<220> FEATURE:
<221> NAME/KEY: MOD_RES
<222> LOCATION: (104)..(104)
<223> OTHER INFORMATION: Thr, Tyr or Pro
<220> FEATURE:
<221> NAME/KEY: MOD_RES
<222> LOCATION: (105)..(105)
<223> OTHER INFORMATION: Thr, Asp or Val
<220> FEATURE:
<221> NAME/KEY: MOD_RES
<222> LOCATION: (106)..(106)
<223> OTHER INFORMATION: Thr, Val or Leu
<220> FEATURE:
<221> NAME/KEY: MOD_RES
<222> LOCATION: (107)..(107)
<223> OTHER INFORMATION: Ala, Glu or Val
<220> FEATURE:
<221> NAME/KEY: MOD_RES
<222> LOCATION: (109)..(109)
<223> OTHER INFORMATION: Tyr or Ala
<220> FEATURE:
<221> NAME/KEY: MOD_RES
<222> LOCATION: (110)..(110)
<223> OTHER INFORMATION: Phe or Met
<220> FEATURE:
<221> NAME/KEY: MOD_RES
<222> LOCATION: (111)..(111)
<223> OTHER INFORMATION: Ala or Asp
<220> FEATURE:
<221> NAME/KEY: MOD_RES
<222> LOCATION: (118)..(118)
<223> OTHER INFORMATION: Thr or Ser
<220> FEATURE:
<221> NAME/KEY: MOD_RES
<222> LOCATION: (119)..(119)
<223> OTHER INFORMATION: Leu or Val

<400> SEQUENCE: 13

Gln Xaa Thr Leu Lys Glu Ser Gly Pro Gly Ile Leu Xaa Xaa Ser Gln
1               5                   10                  15

Thr Leu Ser Leu Thr Cys Ser Phe Ser Gly Phe Ser Leu Ser Thr Xaa
            20                  25                  30

Gly Met Xaa Val Xaa Trp Ile Arg Gln Pro Ser Gly Lys Gly Leu Glu
        35                  40                  45

Trp Leu Ala His Ile Xaa Trp Asp Xaa Asp Lys Xaa Tyr Asn Pro Ser
50                  55                  60

Leu Lys Ser Arg Leu Thr Ile Ser Lys Asp Thr Ser Xaa Xaa Gln Val
65                  70                  75                  80

Phe Leu Lys Ile Thr Xaa Val Asp Xaa Ala Asp Thr Ala Thr Tyr Tyr
                85                  90                  95

Cys Xaa Arg Arg Xaa Ile Xaa Xaa Xaa Xaa Asp Xaa Xaa Xaa Tyr
            100                 105                 110

Trp Gly Gln Gly Thr Xaa Xaa Thr Val Ser Ser
```

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
    consensus sequence
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(6)
<223> OTHER INFORMATION: Ile or Leu
<220> FEATURE:
<221> NAME/KEY: MOD_RES
<222> LOCATION: (7)..(7)
<223> OTHER INFORMATION: Val, Ile or Leu
<220> FEATURE:
<221> NAME/KEY: MOD_RES
<222> LOCATION: (8)..(8)
<223> OTHER INFORMATION: His or Asp
<220> FEATURE:
<221> NAME/KEY: MOD_RES
<222> LOCATION: (10)..(10)
<223> OTHER INFORMATION: Asn or Asp
<220> FEATURE:
<221> NAME/KEY: MOD_RES
<222> LOCATION: (12)..(12)
<223> OTHER INFORMATION: Asn or Lys
<220> FEATURE:
<221> NAME/KEY: MOD_RES
<222> LOCATION: (16)..(16)
<223> OTHER INFORMATION: Glu or Asn

<400> SEQUENCE: 14

Xaa Ser Ser Gln Xaa Xaa Xaa Xaa Ser Xaa Gly Xaa Thr Tyr Leu Xaa
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
    consensus sequence
<220> FEATURE:
<221> NAME/KEY: MOD_RES
<222> LOCATION: (1)..(1)
<223> OTHER INFORMATION: Lys or Leu
<220> FEATURE:
<221> NAME/KEY: MOD_RES
<222> LOCATION: (4)..(4)
<223> OTHER INFORMATION: Asn or Lys
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Phe or Asp

<400> SEQUENCE: 15

Xaa Val Ser Xaa Xaa Xaa Ser
1               5

```
<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Phe or Trp
<220> FEATURE:
<221> NAME/KEY: MOD_RES
<222> LOCATION: (3)..(3)
<223> OTHER INFORMATION: Gly or Ser
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Val or Phe
<220> FEATURE:
<221> NAME/KEY: MOD_RES
<222> LOCATION: (8)..(8)
<223> OTHER INFORMATION: Leu or Arg

<400> SEQUENCE: 16

Xaa Gln Xaa Xaa His Xaa Pro Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Thr or Asn
<220> FEATURE:
<221> NAME/KEY: MOD_RES
<222> LOCATION: (2)..(2)
<223> OTHER INFORMATION: Ser, Asn or Tyr
<220> FEATURE:
<221> NAME/KEY: MOD_RES
<222> LOCATION: (5)..(5)
<223> OTHER INFORMATION: Ser, Gly or absent
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (7)..(7)
<223> OTHER INFORMATION: Gly or Ser

<400> SEQUENCE: 17

Xaa Xaa Gly Met Xaa Val Xaa
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: His or Ser
```

```
<220> FEATURE:
<221> NAME/KEY: MOD_RES
<222> LOCATION: (3)..(3)
<223> OTHER INFORMATION: Trp, Tyr or Arg
<220> FEATURE:
<221> NAME/KEY: MOD_RES
<222> LOCATION: (4)..(4)
<223> OTHER INFORMATION: Trp or Ser
<220> FEATURE:
<221> NAME/KEY: MOD_RES
<222> LOCATION: (5)..(5)
<223> OTHER INFORMATION: Asp or Gly
<220> FEATURE:
<221> NAME/KEY: MOD_RES
<222> LOCATION: (6)..(6)
<223> OTHER INFORMATION: Asp, Glu or Gly
<220> FEATURE:
<221> NAME/KEY: MOD_RES
<222> LOCATION: (7)..(7)
<223> OTHER INFORMATION: Asp or Gly
<220> FEATURE:
<221> NAME/KEY: MOD_RES
<222> LOCATION: (8)..(8)
<223> OTHER INFORMATION: Lys or Arg
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Tyr or Arg
<220> FEATURE:
<221> NAME/KEY: MOD_RES
<222> LOCATION: (12)..(12)
<223> OTHER INFORMATION: Asn or Ser
<220> FEATURE:
<221> NAME/KEY: MOD_RES
<222> LOCATION: (13)..(13)
<223> OTHER INFORMATION: Pro or Asp
<220> FEATURE:
<221> NAME/KEY: MOD_RES
<222> LOCATION: (14)..(14)
<223> OTHER INFORMATION: Ser or Asn
<220> FEATURE:
<221> NAME/KEY: MOD_RES
<222> LOCATION: (15)..(15)
<223> OTHER INFORMATION: Leu or Val
<220> FEATURE:
<221> NAME/KEY: MOD_RES
<222> LOCATION: (17)..(17)
<223> OTHER INFORMATION: Ser or Gly

<400> SEQUENCE: 18

Xaa Ile Xaa Xaa Xaa Xaa Xaa Xaa Thr Xaa Tyr Xaa Xaa Xaa Xaa Lys
1               5                   10                  15

Xaa

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Arg or Tyr
<220> FEATURE:
<221> NAME/KEY: MOD_RES
<222> LOCATION: (2)..(2)
<223> OTHER INFORMATION: Arg, Pro or absent
<220> FEATURE:
<221> NAME/KEY: MOD_RES
<222> LOCATION: (3)..(3)
```

```
<223> OTHER INFORMATION: May or may not be present
<220> FEATURE:
<221> NAME/KEY: MOD_RES
<222> LOCATION: (4)..(4)
<223> OTHER INFORMATION: Ile, Thr or absent
<220> FEATURE:
<221> NAME/KEY: MOD_RES
<222> LOCATION: (5)..(5)
<223> OTHER INFORMATION: Thr, Tyr, Pro or Asp
<220> FEATURE:
<221> NAME/KEY: MOD_RES
<222> LOCATION: (6)..(6)
<223> OTHER INFORMATION: Thr, Asp, Val or His
<220> FEATURE:
<221> NAME/KEY: MOD_RES
<222> LOCATION: (7)..(7)
<223> OTHER INFORMATION: Thr, Val, Leu or Tyr
<220> FEATURE:
<221> NAME/KEY: MOD_RES
<222> LOCATION: (8)..(8)
<223> OTHER INFORMATION: Ala, Glu, Val or Ser
<220> FEATURE:
<221> NAME/KEY: MOD_RES
<222> LOCATION: (9)..(9)
<223> OTHER INFORMATION: Asp or Gly
<220> FEATURE:
<221> NAME/KEY: MOD_RES
<222> LOCATION: (10)..(10)
<223> OTHER INFORMATION: Tyr, Ala or Ser
<220> FEATURE:
<221> NAME/KEY: MOD_RES
<222> LOCATION: (11)..(11)
<223> OTHER INFORMATION: Phe, Met or Ser
<220> FEATURE:
<221> NAME/KEY: MOD_RES
<222> LOCATION: (12)..(12)
<223> OTHER INFORMATION: Ala or Asp

<400> SEQUENCE: 19

Xaa Xaa Ile Xaa Xaa Xaa Xaa Xaa Xaa Xaa Xaa Xaa Tyr
1               5                   10

<210> SEQ ID NO 20
<211> LENGTH: 10
<212> TYPE: PRT
<213> ORGANISM: Mus sp.

<400> SEQUENCE: 20

Arg Thr Thr Thr Ala Asp Tyr Phe Ala Tyr
1               5                   10

<210> SEQ ID NO 21
<211> LENGTH: 10
<212> TYPE: PRT
<213> ORGANISM: Mus sp.

<400> SEQUENCE: 21

Tyr Asp His Tyr Ser Gly Ser Ser Asp Tyr
1               5                   10

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (28)..(28)
<223> OTHER INFORMATION: Asn or Ser
<220> FEATURE:
<221> NAME/KEY: MOD_RES
```

```
<222> LOCATION: (30)..(30)
<223> OTHER INFORMATION: Ile or Val
<220> FEATURE:
<221> NAME/KEY: MOD_RES
<222> LOCATION: (81)..(81)
<223> OTHER INFORMATION: Ser or Lys
<220> FEATURE:
<221> NAME/KEY: MOD_RES
<222> LOCATION: (82)..(82)
<223> OTHER INFORMATION: Arg or Lys
<220> FEATURE:
<221> NAME/KEY: MOD_RES
<222> LOCATION: (90)..(90)
<223> OTHER INFORMATION: Ile or Val
<220> FEATURE:
<221> NAME/KEY: MOD_RES
<222> LOCATION: (96)..(96)
<223> OTHER INFORMATION: Gly or Ser
<220> FEATURE:
<221> NAME/KEY: MOD_RES
<222> LOCATION: (112)..(112)
<223> OTHER INFORMATION: Glu or Lys

<400> SEQUENCE: 22

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Xaa Ile Xaa His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Xaa Xaa Val Glu Ala Glu Asp Leu Gly Xaa Tyr Tyr Cys Phe Gln Xaa
                85                  90                  95

Ser His Val Pro Leu Thr Phe Gly Ala Gly Thr Lys Leu Glu Leu Xaa
            100                 105                 110

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (7)..(7)
<223> OTHER INFORMATION: Ile or Val

<400> SEQUENCE: 23

Arg Ser Ser Gln Xaa Ile Xaa His Ser Asn Gly Asn Thr Tyr Leu Glu
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 24
```

Lys Val Ser Asn Arg Phe Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Gly or Ser

<400> SEQUENCE: 25

Phe Gln Xaa Ser His Val Pro Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asn or Ser
<220> FEATURE:
<221> NAME/KEY: MOD_RES
<222> LOCATION: (5)..(5)
<223> OTHER INFORMATION: Ser or Gly
<220> FEATURE:
<221> NAME/KEY: MOD_RES
<222> LOCATION: (7)..(7)
<223> OTHER INFORMATION: Gly or Ser

<400> SEQUENCE: 26

Thr Xaa Gly Met Xaa Val Xaa
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Trp or Tyr
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (9)..(9)
<223> OTHER INFORMATION: Arg or Tyr

<400> SEQUENCE: 27

His Ile Xaa Trp Asp Xaa Asp Lys Xaa Tyr Asn Pro Ser Leu Lys Ser
1               5                   10                  15

<210> SEQ ID NO 28
<211> LENGTH: 13
<212> TYPE: PRT
<213> ORGANISM: Artificial Sequence
<220> FEATURE:

```
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Arg, Pro or absent
<220> FEATURE:
<221> NAME/KEY: MOD_RES
<222> LOCATION: (3)..(3)
<223> OTHER INFORMATION: Ile or absent
<220> FEATURE:
<221> NAME/KEY: MOD_RES
<222> LOCATION: (4)..(4)
<223> OTHER INFORMATION: Ile, Thr or absent
<220> FEATURE:
<221> NAME/KEY: MOD_RES
<222> LOCATION: (5)..(5)
<223> OTHER INFORMATION: Thr, Tyr or Pro
<220> FEATURE:
<221> NAME/KEY: MOD_RES
<222> LOCATION: (6)..(6)
<223> OTHER INFORMATION: Thr, Asp or Val
<220> FEATURE:
<221> NAME/KEY: MOD_RES
<222> LOCATION: (7)..(7)
<223> OTHER INFORMATION: Thr, Val or Leu
<220> FEATURE:
<221> NAME/KEY: MOD_RES
<222> LOCATION: (8)..(8)
<223> OTHER INFORMATION: Ala, Glu or Val
<220> FEATURE:
<221> NAME/KEY: MOD_RES
<222> LOCATION: (10)..(10)
<223> OTHER INFORMATION: Tyr or Ala
<220> FEATURE:
<221> NAME/KEY: MOD_RES
<222> LOCATION: (11)..(11)
<223> OTHER INFORMATION: Phe or Met
<220> FEATURE:
<221> NAME/KEY: MOD_RES
<222> LOCATION: (12)..(12)
<223> OTHER INFORMATION: Ala or Asp

<400> SEQUENCE: 28

Arg Xaa Xaa Xaa Xaa Xaa Xaa Xaa Asp Xaa Xaa Xaa Tyr
1               5                   10

<210> SEQ ID NO 29
<211> LENGTH: 11
<212> TYPE: PRT
<213> ORGANISM: Mus sp.

<400> SEQUENCE: 29

Gln Ser Ile Val His Ser Asn Gly Asn Thr Tyr
1               5                   10

<210> SEQ ID NO 30
<211> LENGTH: 3
<212> TYPE: PRT
<213> ORGANISM: Mus sp.

<400> SEQUENCE: 30

Lys Val Ser
1

<210> SEQ ID NO 31
<211> LENGTH: 10
<212> TYPE: PRT
<213> ORGANISM: Mus sp.

<400> SEQUENCE: 31

Phe Gln Gly Ser His Val Pro Leu Thr Phe
```

```
1               5                    10
```

<210> SEQ ID NO 32
<211> LENGTH: 11
<212> TYPE: PRT
<213> ORGANISM: Mus sp.

<400> SEQUENCE: 32

```
Gln Ser Ile Val His Ser Asn Gly Asn Thr Tyr
1               5                   10
```

<210> SEQ ID NO 33
<211> LENGTH: 3
<212> TYPE: PRT
<213> ORGANISM: Mus sp.

<400> SEQUENCE: 33

```
Lys Val Ser
1
```

<210> SEQ ID NO 34
<211> LENGTH: 10
<212> TYPE: PRT
<213> ORGANISM: Mus sp.

<400> SEQUENCE: 34

```
Phe Gln Gly Ser His Val Pro Leu Thr Phe
1               5                   10
```

<210> SEQ ID NO 35
<211> LENGTH: 5
<212> TYPE: PRT
<213> ORGANISM: Mus sp.

<400> SEQUENCE: 35

```
Thr Ser Gly Met Gly
1               5
```

<210> SEQ ID NO 36
<211> LENGTH: 7
<212> TYPE: PRT
<213> ORGANISM: Mus sp.

<400> SEQUENCE: 36

```
Ile Trp Trp Asp Asp Asp Arg
1               5
```

<210> SEQ ID NO 37
<211> LENGTH: 13
<212> TYPE: PRT
<213> ORGANISM: Mus sp.

<400> SEQUENCE: 37

```
Arg Ala His Thr Thr Val Leu Gly Asp Trp Phe Ala Tyr
1               5                   10
```

<210> SEQ ID NO 38
<211> LENGTH: 5
<212> TYPE: PRT
<213> ORGANISM: Mus sp.

<400> SEQUENCE: 38

```
Thr Ser Gly Met Gly
1               5
```

```
<210> SEQ ID NO 39
<211> LENGTH: 7
<212> TYPE: PRT
<213> ORGANISM: Mus sp.

<400> SEQUENCE: 39

Ile Trp Trp Asp Asp Asp Lys
1               5

<210> SEQ ID NO 40
<211> LENGTH: 13
<212> TYPE: PRT
<213> ORGANISM: Mus sp.

<400> SEQUENCE: 40

Arg Ala His Asn Val Val Leu Gly Asp Trp Phe Ala Tyr
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 41

Asp Ala Glu Phe Arg His Asp
1               5

<210> SEQ ID NO 42
<211> LENGTH: 112
<212> TYPE: PRT
<213> ORGANISM: Mus sp.

<400> SEQUENCE: 42

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Val Met Thr Gln Ser Pro Leu Ser Leu Pro Val Thr Pro Gly
1               5                   10                  15
```

```
Glu Pro Ala Ser Ile Ser Cys Arg Ser Ser Gln Asn Ile Val His Ser
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
            100                 105                 110
```

<210> SEQ ID NO 44
<211> LENGTH: 112
<212> TYPE: PRT
<213> ORGANISM: Homo sapiens

<400> SEQUENCE: 44

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Arg
             20                  25                  30

Tyr Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
            100                 105                 110
```

<210> SEQ ID NO 45
<211> LENGTH: 100
<212> TYPE: PRT
<213> ORGANISM: Homo sapiens

<400> SEQUENCE: 45

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100
```

<210> SEQ ID NO 46
<211> LENGTH: 123

<212> TYPE: PRT
<213> ORGANISM: Mus sp.

<400> SEQUENCE: 46

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Asn
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Glu Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Asn Val Asp Thr Ala Asp Thr Ala Thr Tyr Tyr
                85                  90                  95

Cys Ala Arg Arg Arg Ile Ile Tyr Asp Val Glu Asp Tyr Phe Asp Tyr
            100                 105                 110

Trp Gly Gln Gly Thr Thr Leu Thr Val Ser Ser
        115                 120

<210> SEQ ID NO 47
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Ser Thr Asn
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Glu Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Ser Leu Lys Leu Ser Ser Val Thr Ala Ala Asp Thr Ala Val Tyr Tyr
                85                  90                  95

Cys Ala Arg Arg Arg Ile Ile Tyr Asp Val Glu Asp Tyr Phe Asp Tyr
            100                 105                 110

Trp Gly Gln Gly Thr Thr Val Thr Val Ser Ser
        115                 120

<210> SEQ ID NO 48
<211> LENGTH: 123
<212> TYPE: PRT
<213> ORGANISM: Homo sapiens

<400> SEQUENCE: 48

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Gly
            20                  25                  30

Ser His Tyr Trp Gly Trp Ile Arg Gln Pro Pro Gly Lys Gly Leu Glu

-continued

```
                35                  40                  45

Trp Ile Gly Ser Ile Tyr Tyr Ser Gly Asn Thr Tyr Phe Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Leu Gly Pro Asp Asp Tyr Thr Leu Asp Gly Met Asp Val
            100                 105                 110

Trp Gly Gln Gly Thr Thr Val Thr Val Ser Ser
            115                 120

<210> SEQ ID NO 49
<211> LENGTH: 99
<212> TYPE: PRT
<213> ORGANISM: Homo sapiens

<400> SEQUENCE: 49

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly Ser Ile Tyr Tyr Ser Gly Ser Thr Tyr Tyr Asn Pro Ser
         50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 50
<211> LENGTH: 112
<212> TYPE: PRT
<213> ORGANISM: Mus sp.

<400> SEQUENCE: 50

Tyr Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
         50                  55                  60

Asp Arg Phe Thr Gly Ser Gly Ser Gly Thr Asp Phe Thr Leu Lys Ile
 65                  70                  75                  80

Ser Arg Ile Glu Ala Glu Asp Leu Gly Leu Tyr Tyr Cys Trp Gln Gly
                 85                  90                  95

Thr His Phe Pro Arg Thr Phe Gly Gly Gly Thr Lys Leu Glu Ile Lys
            100                 105                 110

<210> SEQ ID NO 51
<211> LENGTH: 112
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 51

Tyr Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

<210> SEQ ID NO 52
<211> LENGTH: 112
<212> TYPE: PRT
<213> ORGANISM: Homo sapiens

<400> SEQUENCE: 52

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 53
<211> LENGTH: 100
<212> TYPE: PRT
<213> ORGANISM: Homo sapiens

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Ala
                85                  90                  95

Leu Gln Thr Pro
            100

<210> SEQ ID NO 54
<211> LENGTH: 119
<212> TYPE: PRT
<213> ORGANISM: Mus sp.

<400> SEQUENCE: 54

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Asn Ser Asp Lys Arg Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Thr Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser
        115

<210> SEQ ID NO 56
<211> LENGTH: 121
<212> TYPE: PRT
<213> ORGANISM: Homo sapiens
```

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Val Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Tyr Asp Phe Trp Ser Gly Thr Phe Asp Tyr Trp Gly
            100                 105                 110

Gln Gly Thr Leu Val Thr Val Ser Ser
            115                 120

<210> SEQ ID NO 57
<211> LENGTH: 98
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 58
<211> LENGTH: 112
<212> TYPE: PRT
<213> ORGANISM: Mus sp.

<400> SEQUENCE: 58

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Ser
                85                  90                  95

-continued

```
Ser His Val Pro Leu Thr Phe Gly Ala Gly Thr Lys Leu Glu Leu Lys
                100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Ser His Val Pro Leu Thr Phe Gly Gln Gly Thr Lys Leu Glu Ile Lys
                100                 105                 110

<210> SEQ ID NO 60
<211> LENGTH: 112
<212> TYPE: PRT
<213> ORGANISM: Homo sapiens

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
                100                 105                 110

<210> SEQ ID NO 61
<211> LENGTH: 100
<212> TYPE: PRT
<213> ORGANISM: Homo sapiens

<400> SEQUENCE: 61

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro
            100

<210> SEQ ID NO 62
<211> LENGTH: 120
<212> TYPE: PRT
<213> ORGANISM: Mus sp.

<400> SEQUENCE: 62

Gln Val Thr Leu Lys Glu Ser Gly Pro Gly Ile Leu Lys Pro Ser Gln
 1               5                   10                  15

Thr Leu Ser Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Thr Thr Thr Ala Asp Tyr Phe Ala Tyr Trp Gly Gln
            100                 105                 110

Gly Thr Thr Leu Thr Val Ser Ser
            115                 120

<210> SEQ ID NO 63
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Glu Ser Gly Gly Gly Val Val Gln Pro Gly Arg
 1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Leu Thr Ile Ser Lys Asp Thr Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Thr Thr Thr Ala Asp Tyr Phe Ala Tyr Trp Gly Gln
            100                 105                 110
```

```
Gly Thr Thr Val Thr Val Ser Ser
        115                 120
```

<210> SEQ ID NO 64
<211> LENGTH: 122
<212> TYPE: PRT
<213> ORGANISM: Homo sapiens

<400> SEQUENCE: 64

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Ser Ser Trp Tyr Tyr Gly Met Asp Val Trp
            100                 105                 110

Gly Gln Gly Thr Thr Val Thr Val Ser Ser
        115                 120
```

<210> SEQ ID NO 65
<211> LENGTH: 118
<212> TYPE: PRT
<213> ORGANISM: Homo sapiens

<400> SEQUENCE: 65

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Lys Leu Leu Met Leu Leu Ile Ser Gly Ala Lys Gly
            100                 105                 110

Gln Trp Ser Pro Ser Leu
        115
```

<210> SEQ ID NO 66
<211> LENGTH: 16
<212> TYPE: PRT
<213> ORGANISM: Mus sp.

<400> SEQUENCE: 66

```
Arg Ser Ser Gln Ser Ile Val His Ser Asn Gly Asn Thr Tyr Leu Glu
1               5                   10                  15
```

```
<210> SEQ ID NO 67
<211> LENGTH: 9
<212> TYPE: PRT
<213> ORGANISM: Mus sp.

<400> SEQUENCE: 67

Phe Gln Gly Ser His Val Pro Leu Thr
1               5

<210> SEQ ID NO 68
<211> LENGTH: 16
<212> TYPE: PRT
<213> ORGANISM: Mus sp.

<400> SEQUENCE: 68

Arg Ser Ser Gln Asn Ile Val His Ser Asn Gly Asn Thr Tyr Leu Glu
1               5                   10                  15

<210> SEQ ID NO 69
<211> LENGTH: 16
<212> TYPE: PRT
<213> ORGANISM: Mus sp.

<400> SEQUENCE: 69

Arg Ser Ser Gln Asn Ile Ile His Ser Asn Gly Asn Thr Tyr Leu Glu
1               5                   10                  15

<210> SEQ ID NO 70
<211> LENGTH: 7
<212> TYPE: PRT
<213> ORGANISM: Mus sp.

<400> SEQUENCE: 70

Thr Ser Gly Met Ser Val Gly
1               5

<210> SEQ ID NO 71
<211> LENGTH: 16
<212> TYPE: PRT
<213> ORGANISM: Mus sp.

<400> SEQUENCE: 71

His Ile Trp Trp Asp Asp Asp Lys Tyr Tyr Asn Pro Ser Leu Lys Ser
1               5                   10                  15

<210> SEQ ID NO 72
<211> LENGTH: 7
<212> TYPE: PRT
<213> ORGANISM: Mus sp.

<400> SEQUENCE: 72

Thr Asn Gly Met Gly Val Ser
1               5

<210> SEQ ID NO 73
<211> LENGTH: 16
<212> TYPE: PRT
<213> ORGANISM: Mus sp.

<400> SEQUENCE: 73

His Ile Tyr Trp Asp Glu Asp Lys Arg Tyr Asn Pro Ser Leu Lys Ser
1               5                   10                  15

<210> SEQ ID NO 74
<211> LENGTH: 13
```

```
<212> TYPE: PRT
<213> ORGANISM: Mus sp.

<400> SEQUENCE: 74

Arg Arg Ile Ile Tyr Asp Val Glu Asp Tyr Phe Asp Tyr
1               5                   10

<210> SEQ ID NO 75
<211> LENGTH: 7
<212> TYPE: PRT
<213> ORGANISM: Mus sp.

<400> SEQUENCE: 75

Thr Ser Gly Met Gly Val Ser
1               5

<210> SEQ ID NO 76
<211> LENGTH: 16
<212> TYPE: PRT
<213> ORGANISM: Mus sp.

<400> SEQUENCE: 76

His Ile Tyr Trp Asp Asp Asp Lys Arg Tyr Asn Pro Ser Leu Lys Leu
1               5                   10                  15

<210> SEQ ID NO 77
<211> LENGTH: 13
<212> TYPE: PRT
<213> ORGANISM: Mus sp.

<400> SEQUENCE: 77

Arg Pro Ile Thr Pro Val Leu Val Asp Ala Met Asp Tyr
1               5                   10

<210> SEQ ID NO 78
<211> LENGTH: 9
<212> TYPE: PRT
<213> ORGANISM: Mus sp.

<400> SEQUENCE: 78

Arg Pro Ile Thr Pro Val Leu Val Asp
1               5

<210> SEQ ID NO 79
<211> LENGTH: 9
<212> TYPE: PRT
<213> ORGANISM: Mus sp.

<400> SEQUENCE: 79

Arg Arg Ile Ile Tyr Asp Val Glu Asp
1               5

<210> SEQ ID NO 80
<211> LENGTH: 6
<212> TYPE: PRT
<213> ORGANISM: Mus sp.

<400> SEQUENCE: 80

Arg Thr Thr Thr Ala Asp
1               5

<210> SEQ ID NO 81
<211> LENGTH: 99
<212> TYPE: PRT
<213> ORGANISM: Homo sapiens
```

```
<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg
```